(12) United States Patent
Fraser

(10) Patent No.: US 7,083,793 B2
(45) Date of Patent: Aug. 1, 2006

(54) TANGO 243 POLYPEPTIDES AND USES THEREOF

(75) Inventor: Christopher C. Fraser, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 279 days.

(21) Appl. No.: 10/107,857

(22) Filed: Mar. 26, 2002

(65) Prior Publication Data

US 2003/0170784 A1    Sep. 11, 2003

Related U.S. Application Data

(63) Continuation of application No. 09/928,788, filed on Aug. 13, 2001, now abandoned, which is a continuation of application No. 09/514,009, filed on Feb. 25, 2000, now abandoned, which is a continuation-in-part of application No. 09/259,387, filed on Feb. 26, 1999, now abandoned.

(51) Int. Cl.
*A61K 39/00* (2006.01)
*C07K 19/00* (2006.01)
*C07K 14/435* (2006.01)

(52) U.S. Cl. .................. 424/192.1; 530/350; 536/23.2; 536/23.4

(58) Field of Classification Search ................ 530/350; 536/23.5
See application file for complete search history.

(56) References Cited

U.S. PATENT DOCUMENTS

| | | | | |
|---|---|---|---|---|
| 5,194,596 A | * | 3/1993 | Tischer et al. | ............... 530/399 |
| 5,350,836 A | * | 9/1994 | Kopchick et al. | ........... 530/399 |
| 2003/0166548 A1 | * | 9/2003 | Peterson et al. | ............... 514/12 |

FOREIGN PATENT DOCUMENTS

| | | | |
|---|---|---|---|
| WO | WO 91/10683 | | 7/1991 |
| WO | WO 94/01548 | | 1/1994 |
| WO | WO 98/56400 | * | 12/1998 |
| WO | WO 99/33982 | | 7/1999 |

OTHER PUBLICATIONS

Wang et al., Database GenEmbl, Accession No. U17901, Oct. 22, 1995.*
Janknecht et al., PNAS (USA), Viol. 88, pp. 8972-8976, Oct. 1991.*
Vukicevic et al., 1996, PNAS USA 93:9021-9026.*
U.S. Appl. No. 60/049,316.*
Cross et al., "Purification of CpG islands using a methylated DNA binding column" Nature Genetics 6:236-244, Mar. 1994.
MacDonald et al., Accession No. Z62057, Oct. 1995.
Birren et al., Accession No. AC009994, Dec. 7, 1999.
Chopra et al., Accession No. AF083395, Mar., 4, 1999.
Cole et al., Accession No. Z84395, Jun. 17, 1998.
Pirozzi et al., Accession No. U39546, Dec. 28, 1995.
Peterson, J. W., et al., "Cholera Toxin Induces Synthesis of Phospholipase $A_2$-Activating Protein," *Infect. Immun.*, 64(6):2137-2143 (1996).
Chopra, A. K., et al., "Molecular Characterization of cDNA for Phospholipase $A_2$-Activating Protein," *Biochim. Biophys. Acta*, 1444:125-130 (1999).
Bomalaski, J. S., et al., "Phospholipase $A_2$-Activating Protein Induces the Synthesis of IL-1 and TNF in Human Monocytes," *J. Immunol.*, 154(8):4027-4031 (1995).
Wang, H., et al., "Cloning of a Rat cDNA Encoding a Protein with High Homology to Mouse Phospholipase A2-Activating Protein," *Gene*, 161:237-241 (1995).

* cited by examiner

*Primary Examiner*—Eileen B. O'Hara
(74) *Attorney, Agent, or Firm*—Millennium Pharmaceuticals, Inc.

(57) ABSTRACT

The invention provides isolated nucleic acid molecules, designated TANGO 228 nucleic acid molecules, which encode secreted proteins with homology to the rat MCA-32 protein, isolated nucleic acid molecules, designated TANGO 240 nucleic acid molecules, which encode secreted proteins with homology to the *Mycobacterium tuberculosis* hypothetical protein Rv0712, and isolated nucleic acid molecules, designated TANGO 243 nucleic acid molecules, which encode proteins with homology to human PLAP (phospholipase A2-activating protein). The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening and therapeutic methods utilizing compositions of the invention are also described/disclosed.

7 Claims, 56 Drawing Sheets

```
                                                       M   W   S   H   L   S   R   L   L   F   W    11
CTTCTGACCCCGTCTTGGACTTCAACTG GAGA ATG TGG AGC CAT TTG AGC AGG CTC CTC TTC TGG    66

S   I   F   S   S   V   T       K   A   V   L   D   C   E   A   M   K   T    31
AGC ATA TTT TCT TCT GTC ACT TGT AGA AAA GCT GTA TTG GAT TGT GAG GCA ATG AAA ACA  126

N   E   F   P   S   P   C   L   D   S   K   T   K   V   V   M   K   G   Q   N    51
AAT GAA TTC CCT TCT CCA TGT TTG GAC TCA AAG ACT AAG GTG GTT ATG AAG GGT CAA AAT  186

V   S   M   F   C   S   H   K   N   K   S   L   Q   I   T   Y   S   L   F   R    71
GTA TCT ATG TTT TGT TCC CAT AAG AAC AAA TCA CTG CAG ATC ACC TAT TCA TTG TTT CGA  246

R   K   T   H   L   G   T   Q   D   G   K   G   E   P   A   I   F   N   L   S    91
CGT AAG ACA CAC CTG GGA ACC CAG GAT GGA AAA GGT GAA CCT GCG ATT TTT AAC CTA AGC  306

I   T   E   A   H   E   S   G   P   Y   K   C   K   A   Q   V   T   S   C   S   111
ATC ACA GAA GCC CAT GAA TCA GGC CCC TAC AAA TGC AAA GCC CAA GTT ACC AGC TGT TCA  366

K   Y   S   R   D   F   S   F   T   I   V   D   P   V   T   S   P   V   L   N   131
AAA TAC AGT CGT GAC TTC AGC TTC ACG ATT GTC GAC CCG GTG ACT TCC CCA GTG CTG AAC  426

I   M   V   I   Q   T   E   T   D   R   H   I   T   L   H   C   L   S   V   N   151
ATT ATG GTC ATT CAA ACA GAA ACA GAC CGA CAT ATA ACA TTA CAT TGC CTC TCA GTC AAT  486

G   S   L   P   I   N   Y   T   F   F   E   N   H   V   A   I   S   P   A   I   171
GGC TCG CTG CCC ATC AAT TAC ACT TTC TTT GAA AAC CAT GTT GCC ATA TCA CCA GCT ATT  546

S   K   Y   D   R   E   P   A   E   F   N   L   T   K   K   N   P   G   E   E   191
TCC AAG TAT GAC AGG GAG CCT GCT GAA TTT AAC TTA ACC AAG AAG AAT CCT GGA GAA GAG  606

E   E   Y   R   C   E   A   K   N   R   L   P   N   Y   A   T   Y   S   H   P   211
GAA GAG TAT AGG TGT GAA GCT AAA AAC AGA TTG CCT AAC TAT GCA ACA TAC AGT CAC CCT  666

V   T   M   P   S   T   G   G   D   S   C   P   F   C   L   K   L   L   L   P   231
GTC ACC ATG CCC TCA ACA GGC GGA GAC AGC TGT CCT TTC TGT CTG AAG CTA CTA CTT CCA  726

G   L   L   L   L   L   V   V   I   I   L   I   L   A   F   W   V   L   P   K   251
GGG TTA TTA CTG TTG CTG TG GTG ATA ATC CTA ATT CTG GCT TTT TGG GTA CTG CCC AAA  786

Y   K   T   R   K   A   M   R   N   N   V   P   R   D   R   G   D   T   A   M   271
TAC AAA ACA AGA AAA GCT ATG AGA AAT AAT GTG CCC AGG GAC CGT GGA GAC ACA GCC ATG  846

E   V   G   I   Y   A   N   I   L   E   K   Q   A   K   E   E   S   V   P   E   291
GAA GTT GGA ATC TAT GCA AAT ATC CTT GAA AAA CAA GCA AAG GAG GAA TCT GTG CCA GAA  906

V   G   S   R   P   C   V   S   T   A   Q   D   E   A   K   H   S   Q   E   L   311
GTG GGA TCC AGG CCG TGT GTT TCC ACA GCC CAA GAT GAG GCC AAA CAC TCC CAG GAG CTA  966

Q   Y   A   T   P   V   F   Q   E   V   A   P   R   E   Q   E   A   C   D   S   331
CAG TAT GCC ACC CCC GTG TTC CAG GAG GTG GCA CCA AGA GAG CAA GAA GCC TGT GAT TCT 1026
```

FIG. 1A

```
                Y   K   S   G   Y   V   Y   S   E   L   N   F   *   344
                TAT AAA TCT GGA TAT GTC TAT TCT GAA CTC AAC TTC TGA 1065
```

AATTTACAGAAACAAACTACATCTCAGGTAGAGACAGGGTTTTGCCATGTTGGCCAGGCTGGTCTTCAACTCCTGACCT 1144

CAAGTGATCCGCCCACCTCGGACTCCCAGGGTGCTGGGATTACAGGCGTGAGCCACCTCGCCTGGCCCTCCATTTCCTG 1223

ATCTAGTCTTATATCCACGCTCACCACCTCAGCACGCTCAGACCCACGCTGCTGTGGGCTCCTCTGGCTCCTGGAAGAG 1302

TGCGTCCGCAGATGCTGCAGTCTTTGTGTGGCTCAGCAATTGCCACTCACATCAGGAACTGCCTTTACCCTGTCAGGCT 1381

CTACTGAGACCCGACCCTGGTTATTAAGCTATAGGGGAGACAAGGATGGATCTTAAAGAAGACAAGCAAAATATAGTGA 1460

AGCAAATAGAATGGTGGTTCCTGGGGGATGGGGGCAGGGGACAACGAGGAGTGACTGGCTAACAGATACAGCGTTTCAG 1539

TTTGGAAAGACAAAAAAGTTCTGGAAAAAAGATGGAAGGTGGTGATGGTTGCACAATAATATGAGTTTTGTTGTTGTTG 1618

TTTTTTGAGACAGGGTCTCTCTCTGTTGCCCAGGCTGGAGTGCAGGGGCACGATTTCGGCTCACTGCAACCTCTGCCTC 1697

CCGGGTTCGGGCGATTCTTGTGCCTCAGCCTCCCAGGTAGCTGGGATTGCAGGCGCCCACCACCGTGCCCAGCTAATTT 1776

TTGTATTTTTAGTGGGGATGGGGTTTCACCATGTTGGCCAGGCTGGTCTCGAACTCCTGACCTCAAGTGATTGGCCTGC 1855

CTTGGCCTCCCAAAGTGCTGGGATTACAGGCATGAGCTATTGCGCCCGGCAATATGAATGAATGTTTTAATACCATTG 1934

AATTACACACCTAAAATTGGTTAAAATGGTAAAAAATTTTATGTTATGTATAACTTACCACAATAATTTAAAAAATATT 2013

GTGAAGCGCCTGCCTCATGTGAGGTCTTCTAATAAGAGGGGCTGTTCTCCTTCTCAAGAGCGCTCGCGGGCATTGGGAG 2092

TTTCTTATTCTCAAATGTCCACATCCCAAGGCCTACCCCGTCCCTGTCAGTGTCAGAAGTTAGCAGAGCAGAACTGCTA 2171

GATGTGCTCACTCCATCTCCTCCATGGTTGGCCCACCCTTTCGATCAGATCCTGGAATTGGCTTTCAGCACAGCCTTCC 2250

AGCTGGCTGTGATAAATGAGAGTGGCTTAAACCCTGTCATCAGGGTTTCACAGCTTGCCCTGAACCGTAGCTTCTCATT 2329

TTCTCCTTGCAAATCTTCTAAGGCAGCTAAGAGAAGCCAATTAACTTCACAATCCACATAATTAGCATTGCCCCAAACC 2408

TTTCAAGTGCTGGAATGCTGGCGTCCACTAGTGCCTCGTTTCTTTCTAAACCTCATTCCACATGGCAGGGAAGGTCTT 2487

AGGAATTGTGGAGCTGTGGCGTTCTAAGGGTTCTCACTGCCTACCTATCACCAGCAAGGGAGTCCTTGTTGCCATCCAT 2566

CCCTAGGGGGTAATTTTGTTCCCTGAGGCTGCTTTCTAGGGACTTCTGGTCGCTTGTTTTATCCTGGACCAGACCTGAA 2645

AGCAGAGCCTGAAATAAGGCCTTCTATGCACATCATTTATGTAGGAGGTGGCCCTAGGAAGCAGGCCCAATGCGCCATG 2724

GGAAAAACCAGTACCAGGGTGTTTTGCTGAGTTGAGCACTGTGGTGGGCAGCTGGACATGAGCCCACTGGAATCTTCTG 2803

AAGAGCCCAAGAGCCTCTTCTCAGTATTGTCCACTTGAGGATTGATAGTGAGAGGCATTTATCCACTGGTGTCCAACGC 2882

TCACTGGTTGAGGATCACCCCAGAAAGCGACACCTCCCCCACTTCTAGACTAGCATGTGGGTATTCCAAGCAGGCTTAC 2961

FIG. 1B

```
CTCAGTGTCTCACCCCAGGCACTGCAAACACCCCAGGACAGAAGTGAACATGTGTATTGTGCAATTGAAGCAAGACAC  3040
TATCAGTGCAAAGTGAGTAGACCCTCAGATGCTGCTGGGTCAGAGGGAAGGCCCAGGATATGACACAGGACACAGAGG  3119
TGGCAGATACACCACCTCCCAACATTTCCTCTCTATCACAGCAACTAGAACAATGGCAACAATAGGGGTGGTGTGTGGC  3198
TCGCGCCTGTGGTCCCAATACCCTGGGAGGCCAGGGCAGAAGGATTGCTTGAGCCCAGGAGTTCAAGACTAGCCTGGGC  3277
AACTTGGCGAAACCCTGTCTCTACAAACATATTTGTATGTGATTGAACAAGTAGAACAATGAACGAAAGTCCAGATG  3356
TAGTTCTAAATATGTACAGGAACTTAGTATAGGATAAATATGGCATCTTAAATCAATGGGGAAAAGATGGATTATTCAA  3435
CATATTGTAAAAACTTGAGAATCACATTAAAAAAGTTGGACTCCTCATTCTTTACAACAAATTAATTCTGATAG  3514
ATGTAGTCACAGAAGAGCTAGAAGAATATGCCAGGGGATTTAAAAATAATCTTGAAGTGGGGAGGACTTTTATAGGTATG  3593
ACTCACAACCCAGAAAACATAAAGGATTGTTAAATTTAATTAGATAAATCATTAATTAGATGAAACATTTAAAAATTA  3672
CATTTAGAAATCATAAACTAAATCCAAAGAATAACTAGGGGCCGGGCGCAGTGGCTCACGTCTGTAATCCCATGGGCA  3751
GGTGGATCACCTGAGGTTGGGAGTTTGGGACCAGCCTGTCCAGCACGGTGAGGCCCCGTCTCCTACTAAAATACAAAA  3830
TTAGTTGGTGTGGTGGCACATACCTGTGGTCCCTGCTACTGGGAGGCTGAGGCATGAGAATTGCTTGAACCTGGGAGG  3909
TGGAGGTTGCAGTGAGCCAAGATCGCGCCACTGCATTCCAGCCTGGGCGACAGAGCAAGACTCCATCTCAAAAAAAAA  3988
AAAAAAAAAAAAAAAAAAAAAAAAAAAAAAAAAAAAAAAAAAAAAAAAAAAAAAA  4043
```

FIG. 1C

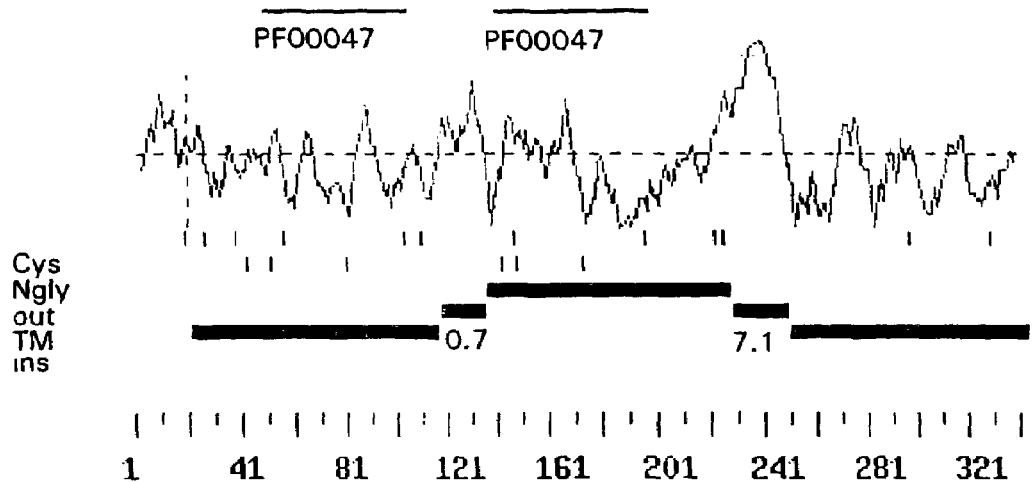

MWSHLSRLLFWSIFSSVTCRKAVLDCEAMKTNEFPSPCLDSKTKVV
MKGQNVSMFCSHKNKSLQITYSLFRRKTHLGTQDGKGEPAIFNLSIT
EAHESGPYKCKAQVTSCSKYSRDFSFTIVDPVTSPVLNIMVIQTETDR
HITLHCLSVNGSLPINYTFFENHVAISPAISKYDREPAEFNLTKKNPGE
EEEYRCEAKNRLPNYATYSHPVTMPSTGGDSCPFCLKLLLPGLLLLL
VVIILILAFWVLPKYKTRKAMRNNVPRDRGDTAMEVGIYANILEKQ
AKEESVPEVGSRPCVSTAQDEAKHSQELQYATPVFQEVAPREQEAC
DSYKSGYVYSELNF

FIG. 2

```
MCA-32  -------CTAAATCCTCT-------CAT---TTC--CTG---CATGTGGT---------T
        ....  :::::     :::     :::  :::    :.::::.:.          :
        ATTTGAGCAGGCTCCTCTTCTGGAGCATATTTTCTTCTGTCACTTGTAGAAAAGCTGTAT
                70        90       100      110      120
                          80

30        40        50            60        70
MCA-32  GGGAAGAGGAATCTTAGAAGACGAG------CCCCACTC--TGTAGCAGCTCAA---CTA
        :::. . ::. :...:::.::.:.       ::: .::: :::.  ..::::: :::
        TGGATTGTGAGGCAATGAAAACAAATGAATTCCCTTCTCCATGTTTGGACTCAAAGACTA
                130       140       150      160      170      180

80
MCA-32  A-------------------------------------CCATGGG-------------
        :                                     :::::...:
        AGGTGGTTATGAAGGGTCAAAATGTATCTATGTTTTGTTCCCATAAGAACAAATCACTGC
                190       200       210      220      230      240

90             100
MCA-32  -----------CGATGAT---------GACACCCCTGTGTGCC----------------
                   :...::.:         ::::: :::: :...::
        AGATCACCTATTCATTGTTTCGACGTAAGACACACCTGGGAACCCAGGATGGAAAAGGTG
                250       260       270      280      290      300

110       120                 130
MCA-32  ------------------------TCTCTGTCGCC------TCATGC-------AAGGGA
                                ::.:.:. :::     ::: ::       :: : :
        AACCTGCGATTTTTAACCTAAGCATCACAGAAGCCCATGAATCAGGCCCCTACAAATGCA
                310       320       330      340      350      360

140       150
MCA-32  GTG----AGTTGCTGGCTGGACAAA-----------CT-------------------
        ..:    :::::.: .:::: .::::              ::
        AAGCCCAAGTTACCAGCTGTTCAAAATACAGTCGTGACTTCAGCTTCACGATTGTCGACC
                370       380       390      400      410      420

160                                               170
MCA-32  ------CTTACTCTGGGCT--------------------------------CTTA---
              :::  : ..: :::                                     
        CGGTGACTTCCCCAGTGCTGAACATTATGGTCATTCAAACAGAAACAGACGGACATATAA
                430       440       450      460      470      480
```

FIG. 3A

```
                       180         190
MCA-32    -----------CTCTGTCTAT--CACACTTC------GAAACAC--------------
                     :::,:::,::  :.:.::  :        ...::::
          CATTACATTGCCTCTCAGTCAATGGCTCGCTGCCCATCAATTACACTTTCTTTGAAAACC
          490       500       510       520       530       540

200         210       220         230
MCA-32    -----------CGCCGTGGATT-----GTAGGA-GGGTGGACAGAAATGGATTGCTTTC
                      ...  .::       ::  .:  ...:  ..  ...  ....  ......::.
          ATGTTGCCATATCACCAGCTATTTCCAAGTATGACAGGGAGCCTGCTGAATTTAACTTA-
                    550       560       570       580       590

240         250       260                         270
MCA-32    TCCAAAT------CTGAACTCAAGTATGAGTGTGG--------------TCAGGATG---
           .:::::..     :::.:  . .::  :.:::::.:.:              .:::..::
          ACCAAGAAGAATCCTGGAGAAGAGGAAGAGTATAGGTGTGAAGCTAAAAACAGATTGCCT
          600       610       620       630       640       650

280       290       300           310
MCA-32    -----GGC--CAAAATGTATCTCTGTCTT-GTTCC-------AGCAAGAACA-CA-TCCA
              ::   ::.:  .::  .:  ::::::.   .:  ::       .::.....::  :.  :::.
          AACTATGCAACATACAGTCACCCTGTCACCATGCCCTCAACAGGCGGAGACAGCTGTCCT
          660       670       680       690       700       710

320             330
MCA-32    T-------AGACATCA----CCTA------TTC----GCT--------------------
          :       :..:..:.    ::..      :.:    :::
          TTCTGTCTGAAGCTACTACTTCCAGGGTTATTACTGTTGCTGGTGGTGATAATCCTAATT
          720       730       740       750       760       770

340                                             350
MCA-32    ----CTTTTTGGGTA-------------------------AGAGATA--------
              ::::::::::::                         :::.:::
          CTGGCTTTTTGGGTACTGCCCAAATACAAAACAAGAAAAGCTATGAGAAATAATGTGCCC
          780       790       800       810       820       830

360
MCA-32    ---------------------------------------CCTAGAAA-----
                                                  :::.::::
          AGGGACCGTGGAGACACAGCCATGGAAGTTGGAATCTATGCAAATATCCTTGAAAAACAA
          840       850       860       870       880       890

370       380               390                400
MCA-32    GCAA--GAGGA----------GAAGAGGGG---GAGCTGTGGATTTCCAC--C------T
          ::::   :::::          ::::.:::.        ..:: :::  .::::::: :         :
          GCAAAGGAGGAATCTGTGCCAGAAGTGGGATCCAGGCCGTGTGTTTCCACAGCCCAAGAT
          900       910       920       930       940       950

410         420                 430
MCA-32    GAGGA-----TCTCC-----------AATGCCAAC---GAGT--CAGG------CCCCT
          ::::     .::::            .::::::::  :   :.::   ::::       :  :::.
          GAGGCCAAACACTCCCAGGAGCTACAGTATGCCACCCCCGTGTTCCAGGAGGTGGCACCA
          960       970       980       990       1000      1010
```

FIG. 3B

```
                       440                                  450
MCA-32  A-----CAAGT-GC---------------------AAAGTCAAT---------------
            :  ::::. ::                    .:.::!:.::
        AGAGAGCAAGAAGCCTGTGATTCTTATAAATCTGGATATGTCTATTCTGAACTCAACTTC
        1020      1030      1040      1050      1060      1070

460            470
MCA-32  -----------GATTC------CAACTC-------GTCGAAATA-------------CAG
                    :..     .:.:::         ........                .:
        TGAAATTTACAGAAACAAACTACATCTCAGGTAGAGACAGGGTTTTGCCATGTTGGCCAG
        1080      1090      1100      1110      1120      1130

480             490                 500
MCA-32  TCAGAATTTCAACT-------TCA---------------CAATCATCCAGGATG-----
         :.:.. :::::::         :::              :.....:. :::::::.::
        GCTGGTCTTCAACTCCTGACCTCAAGTGATCCGCCCACCTCGGACTCCCAGGGTGCTGGG
        1140      1150      1160      1170      1180      1190

510                 520
MCA-32  ---------AGAGC----------TG---CTC---------TTCTTGTCTA---------
                 .::::           ::   :::          .:::.::::.
        ATTACAGGCGTGAGCCACCTCGCCTGGCCCTCCATTTCCTGATCTAGTCTTATATCCACG
        1200      1210      1220      1230      1240      1250

530             540
MCA-32  -------------------CTGTC-------GCTGTTG-CTCC-CAGG----------GG
                            :.:.:       :::::  : :::: :.::           .:
        CTCACCACCTCAGCACGCTCAGACCCACGCTGCTGTGGGCTCCTCTGGCTCCTGGAAGAG
        1260      1270      1280      1290      1300      1310

555        560
MCA-32  TG-------------------TTATTGGGGCT-----AATAC-----------------
         ::                   ::. :: ::::     :.:.:
        TGCGTCCGCAGATGCTGCAGTCTTTGTGTGGCTCAGCAATTGCCACTCACATCAGGAACT
        1320      1330      1340      1350      1360      1370

570               580       590       600
MCA-32  ------TCCC---------------AGGCCTGGCC----TTTTTGATTTATTTGAAATAC
              .:::                 ::.:: :.::     ::.::.:  :::. :...: ::
        GCCTTTACCCTGTCAGGCTCTACTGAGACCCGACCCTGGTTATTAAGCTATAGGGGAGAC
        1380      1390      1400      1410      1420      1430

610                620               630       640
MCA-32  AAAAAAGGGT---------GCA--CAGGAAA----GACTCTGAAAGAGAA-TGAGTCCA
        : :...:.::.:        .::  ::...:.:   ::   :...:.::::... ::. ::::.
        AAGGATGGATCTTAAAGAAGACAAGCAAAATATAGTGAAGCAAATAGAATGGTGGTTCCT
        1440      1450      1460      1470      1480      1490

650        660                      670       680
MCA-32  AGGGTT------CTGGAGA-TGCGC-------C---CACGCA-----AGGGGAGCTGTAT
        .:::  .       :.:.:.:: ..::      :    :. .::    :: : . :.::.:
        GGGGGATGGGGGCAGGGGACAACGAGGAGTGACTGGCTAACAGATACAGCGTTTCAGTTT
        1500      1510      1520      1530      1540      1550
```

FIG. 3C

```
                      690                                    700
MCA-32  G------CGAATA---TCTGTGAAA--------------------CTCAAAAA----
             : .:!.:   :::: .:::                    :..::!.::
        GGAAAGACAAAAAAGTTCTGGAAAAAAGATGGAAGGTGGTGATGGTTGCACAATAATATG
        1560      1570      1580      1590      1600      1610

710       720
MCA-32  -----------------------GGGTCAGAACAACTC--------CAGG--------A
                               :.:.::::..  .:::        ::::         :
        AGTTTTGTTGTTGTTGTTTTTTGAGACAGGGTCTCTCTCTGTTGCCCAGGCTGGAGTGCA
        1620      1630      1640      1650      1660      1670

730       740                   750       760
MCA-32  GATACACTATA-CTACTC---------CAGTCTTCAAAGAGGTGGCA---C-----CCA
        :. .:::  ::. :  .:::        ..: ::  ...:.   :::.    :      ::..
        GGGGCACGATTTCGGCTCACTGCAACCTCTGCCTCCCGGGTTCGGGCGATTCTTGTGCCT
        1680      1690      1700      1710      1720      1730

770       780
MCA-32  CAG----------AACAAGAA----GGC-----------------CT-----------
        :::          :.:..:.:    :::                 ::
        CAGCCTCCCAGGTAGCTGGGATTGCAGGCGCCCACCACCGTGCCCAGCTAATTTTTGTAT
        1740      1750      1760      1770      1780      1790

790       800              810       820
MCA-32  ------TGAGGATAGAA-------AAGATGACTA--CA--TCT---ACTC-TGAACTCA-
              ::.:::::.:..        :..:.::.: :  :.   :::   :::: :::  ::::
        TTTTAGTGGGGATGGGGTTTCACCATGTTGGCCAGGCTGGTCTCGAACTCCTGACCTCAA
        1800      1810      1820      1830      1840      1850

830       840
MCA-32  -------------------CCTACTAAAGTGCGAAGAA-ACTGAC---------------
                            :::  :  ::::::::  ..:::.  ::.:.:
        GTGATTGGCCTGCCTTGGCCTCCCAAAGTGCTGGGATTACAGGCATGAGCTATTGCGCCC
        1860      1870      1880      1890      1900      1910

850                               860
MCA-32  ---------------TGTAT-------------------CCTAATATAAGA-------
                       :::.:                      :::::.::..:.
        GGCAATATGAATGAATGTTTTTAATACCATTGAATTACACACCTAAAATTGGTTAAAATG
        1920      1930      1940      1950      1960      1970

870
MCA-32  ---------------------GACTTTCCA-------------------GT-AAGC--
                             .:::::.:::                    ::  ::::
        GTAAAAAATTTTATGTTATGTATAACTTACCACAATAATTTAAAAAATATTGTGAAGCGC
        1980      1990      2000      2010      2020      2030

880       890       900       910
MCA-32  ---------TGATGCTTACGAAGAAACAGGA-AATTCACCT------GGCACT-----
                 :::.:  :.:: :: ::. .::.  ...:::.:::        .::.::
        CTGCCTCATGTGAGGTCTTCTAATAAGAGGGGCTGTTCTCCTTCTCAAGAGCGCTCGCGG
        2040      2050      2060      2070      2080      2090
```

FIG. 3D

```
              920                      930
MCA-32 TCA----GAGTTTCAT-------------------CCTAGGC---------------TG
        ::    :::::::.:                   ::.:::::               .:
       GCATTGGGAGTTTCTTATTCTCAAATGTCCACATCCCAAGGCCTACCCCGTCCCTGTCAG
       2100      2110      2120      2130      2140      2150

940       950       960
MCA-32 GGGCAGAAGGATCCTGAG------PTCAAGG----------CCAGCT-----------GG
        .  :::        ..  :           :.          :::  ::              :
       TGTCAGAAGTTAGCAGAGCAGAACTGCTAGATGTGCTCACTCCATCTCCTCCATGGTTGG
       2160      2170      2180      2190      2200      2210

970       980           990      1000
MCA-32 CACTACATAGCAA---GACCCTGT------CTTAAAACACAAAGATC------------A
        : :.   :. ..:   ::  ::::        :::.  :..:::::.    ..::               :
       CCCACCCTTTCGATCAGATCCTGGAATTGGCTTTCAGCACAGCCTTCCAGCTGGCTGTGA
       2220      2230      2240      2250      2260      2270

1010       1020                      1030
MCA-32 AAAAAGA-------TTTAACCTGGTCA-------------------CCGAAA--GTGAAT
        .:::.::       .:.:::: ::::                            :: .::  :::.. :
       TAAATGAGAGTGGCTTAAACCCTGTCATCAGGGTTTCACAGCTTGCCCTGAACCGTAGCT
       2280      2290      2300      2310      2320      2330

1040      1050          1060      1070
MCA-32 G-TATTTTTCAC-------ATCT----GGACA-CTATTATT--CCT-TTGGCTA------
         :  .:::::::.:           ::::     .:.:::  :::.  :    ::.   ::..::.
       TCTCATTTTCTCCTTGCAAATCTTCTAAGGCAGCTAAGAGAAGCCAATTAACTTCACAAT
       2340      2350      2360      2370      2380      2390

1080         1090                 1100
MCA-32 --ACTTGG---GCAT----CTAATCTTGTCA------------------CCAAAGTAGC
         ::::..    ::::      : :::.: : :::                    ::: .. .::
       CCACATAATTAGCATTGCCCCAAACCTTTCAAGTGCTGGAATGCTGGCGTCCACTAGTGC
       2400      2410      2420      2430      2440      2450

1110      1120          1130      1140      1150
MCA-32 CAGG---CTTGATAA------------GGGTTAAAAAATACTTCGGTTTTGTGGC-CT
        :. :    :::   :::            ::  ...::. .:::  ::..:::::::   ::
       CTCGTTTCTTTCTAAACCTCATTCCACATGGCAGGGGAAGGTCTTAGGAATTGTGGAGCT
       2460      2470      2480      2490      2500      2510

1160         1170              1180
MCA-32 TCAGC---C-----GTTCTCACTT----------TCCAAC--------CCAATTT-----
        .::   :      :::::::::           .:::.:           :::.. ::
       GTGGCGTTCTAAGGGTTCTCACTGCCTACCTATCACCAGCAAGGGAGTCCTTGTTGCCAT
       2520      2530      2540      2550      2560      2570

1190       1200       1210
MCA-32 -------TAAATGGAATTAT-----CCTGGGGCTGCAGA--AGTGGCT-CAG--------
        :::.. ::::.:.:            :::::.:::::::. .   ::  :.::: :.:
       CCATCCCTAGGGGGTAATTTTGTTCCCTGAGGCTGCTTTCTAGGGACTTCTGGTCGCTTG
       2580      2590      2600      2610      2620      2630
```

FIG. 3E

```
              1220        1230                        1240
MCA-32 ----------CAG--CTAAGAGCAGA---------------CACTGCTCT-----
                 ::: ::.:.::::::                  :. ::::..
       TTTTATCCTGGACCAGACCTGAAAGCAGAGCCTGAAATAAGGCCTTCTATGCACATCATT
       2640      2650      2660      2670      2680      2690

1250
MCA-32 --------------CCCAAAGGA-----------------------------TGG
                     :::::::.:                              ..:
       TATGTAGGAGGTGGCCCTAGGAAGCAGGCCCAATGCGCCATGGGAAAAACCAGTACCAGG
       2700      2710      2720      2730      2740      2750

1260          1270
MCA-32 GAGTTT-----------------------------GAGCCCA---GAGTCTAC-
       :.:::::                            :::::::   ::.:::..
       GTGTTTTGCTGAGTTGAGCACTGTGGTGGGCAGCTGGACATGAGCCCACTGGAATCTTCT
       2760      2770      2780      2790      2800      2810

1280         1290                           1300
MCA-32 ----ATCCCATAA--CTCA---CAGT--TG-CCA----------------ATAACATT
           : :::::..:  :::.   ::::  ::  :::                ....::::
       GAAGAGCCCAAGAGCCTCTTCTCAGTATTGTCCACTTGAGGATTGATAGTGAGAGGCATT
       2820      2830      2840      2850      2860      2870

1310                                    1320
MCA-32 ---------GTTTCCGA-----------AGGATC---------------CATCGCCC
                :: ::::.:           ::::::                : :: :::
       TATCCACTGGTGTCCAACGCTCACTGGTTGAGGATCACCCCAGAAAGCGACACCTCCCCC
       2880      2890      2900      2910      2920      2930

1330              1340       1350              1360
MCA-32 TCTTCTGG-----CA----------CCT-GCAGGC--ACTACA----CTCAT---GTGCA
       .:::::.:     ::          ::. ::::::  :: .::    ::::    . :::
       ACTTCTAGACTAGCATGTGGGTATTCCAAGCAGGCTTACCTCAGTGTCTCACCCCAGGCA
       2940      2950      2960      2970      2980      2990

1370                                1380
MCA-32 CAG---ACACACCTAAACG---------CAT-----------AATT--------------
       ..:   ::::.::......         :::           ::::
       CTGCAAACACCCCAGGACAGAAAGTGAACATGTGTATTGTGCAATTGAAGCAAGACACTA
       3000      3010      3020      3030      3040      3050

1390                 1400      1410
MCA-32 --------AAGTAAGTTGG--------GGCTG--------GAGAGATGGCTCAGTGGTTA
               :::::.::.:.        ::::        :::::.::.::: :::.:..
       TCAGTGCAAAGTGAGTAGACCCTCAGATGCTGCTGGGTCAGAGGGAAGGCCCAGGGATAT
       3060      3070      3080      3090      3100      3110

1420       1430
MCA-32 -----AGAGCAC-----TGACTG----------CTC-------TTCC-------------
            ::...:::     ::..:.:          :::       ::::
       GACACAGGACACAGAGGTGGCAGATACACCACCTCCCAACATTTCCTCTATCACAGCAAC
       3120      3130      3140      3150      3160      3170
```

FIG. 3F

```
                              1440                    1450         1460
MCA-32  ----------------AGAGGT----------------CCTGAGTTC--AATACCC-
                        ::.:::                :::::.: ::  :::::::
        TAGAACAATGGCAACAATAGGGGTGGGTGTGGTGGCTCGCGCCTGTGGTCCCAATACCCT
        3180      3190      3200      3210      3220      3230

1470
MCA-32  -----------------------------AGC---------------AACC------ACAT
                                     :::                :.::      ::.:
        GGGAGGCCAGGGCAGAAGGATTGCTTGAGCCCAGGAGTTCAAGACTAGCCTGGGCAACTT
        3240      3250      3260      3270      3280      3290

1480
MCA-32  GG--------TGGCTC-ACAAACAT--------------------------------
        ::        :: :::  ::::::::
        GGCGAAACCCTGTCTCTACAAACATATTTGTATGTGATTGAACAAGTAGAACAATGGAAC
        3300      3310      3320      3330      3340      3350

1490                                    1500
MCA-32  -----------------CTATA---------------------------ATGGGAT
                         :::.:                          :::: ::
        GGAAAGTCCAGATGTAGTTCTAAATATGTACAGGAACTTAGTATAGGATAAATATGGCAT
        3360      3370      3380      3390      3400      3410

MCA-32  C------CGATG-----------------C-------------------------
        :      :.:::                 :
        CTTAAATCAATGGGGAAAAGATGGATTATTCAACATATTGTAAAAACTTGAGAATCACAT
        3420      3430      3440      3450      3460      3470

1510        1520          1530
MCA-32  -------------------CCTCTT------CTGC-----TGTGTCTGA-------AGAC
                           :::::.:      :...:     :.. ::::::        ::.:
        TAAAAAAGTTGGACTCCTACCTCATTCTTTACAACAAAATTAATTCTGATAGATGTAGTC
        3480      3490      3500      3510      3520      3530

1540
MCA-32  A-------GCTATA-----------------------------------GTGTACTT
        :       :::: :                                   :.: ::::
        ACAGAAGAGCTAGAAGAATATGCAGGGGATTTAAAAATAATCTTGAAGTGGGGAGGACTT
        3540      3550      3560      3570      3580      3590

1550                                    1560
MCA-32  ATGTA-----------------CATAAAA---------------TAAATAAAT
        .:.::                 ::::::.                ::.:::::::
        TTATAGGTATGACTCACAACCCAGAAAACATAAAGGATTGTTAAATTTAATTAGATAAAT
        3600      3610      3620      3630      3640      3650

1570      1580
MCA-32  CTTTAAAATAAATAAA------------------------------TAAGTC------
        :.::.::.::.::.::                              :::.::
        CATTTAATTAGATGAAACATTTAAAAATTACATTTAGAAATCATAAACTAAATCCAAAGA
        3660      3670      3680      3690      3700      3710
```

FIG. 3G

```
MCA-32  ------------------------------------------------------------
        ATAACTAGGGGCCGGGCGCAGTGGCTCACGTCTGTAATCCCATGGGGCAGGTGGATCACC
        3720      3730      3740      3750      3760      3770

1590
MCA-32  ----------TATGGG--------------------------------------------
                  ..:::
        TGAGGTTGGGAGTTTGGGACCAGCCTGTCCAGCACGGTGAGGCCCCGTCTCTACTAAAAA
        3780      3790      3800      3810      3820      3830

1600
MCA-32  ------------------------CATACCA-----CCCTG-------------------
                                :::::: .    :::::
        TACAAAAATTAGTTGGTGTGGTGGCACATACCTGTGGTCCCTGCTACTGGGGAGGCTGAG
        3840      3850      3860      3870      3880      3890

MCA-32  ----------------------------------------------------------TA
                                                                  :.
        GCATGAGAATTGCTTGAACCTGGGAGGTGGAGGTTGCAGTGAGCCAAGATCGCGCCACTG
        3900      3910      3920      3930      3940      3950

1610                    1620
MCA-32  CATGCC---------------CAAG-CTC-ATCT---------------------------
        ::: ::                :::: :::  ::::
        CATTCCAGCCTGGGCGACAGAGCAAGACTCCATCTCAAAAAAAAAAAAAAAAAAAAAAAA
        3960      3970      3980      3990      4000      4010

1630      1640      1650
MCA-32  -------AGAAGTAAATAATAAAATAAAAAAGTTAATCTTA
               :.::..:::.::.:::::.::::::::...:::
        AAAAAAAAAAAAAAAAAAAAAAAAAAAAAAAAAAAAAAAAAA
        4020      4030      4040      4050      4060
```

FIG. 3H

```
              10         20         30         40         50         60
T228    ATGTGGAGCCATTTGAGCAGGCTCCTCTTCTGGAGCATATTTTCTTCTGTCACTTGTAGA
        ::::::     ::::.: ::.     ::::      ........    :   :.   :.::  ::::
        ATGTGG------TTGGGAAGAGGAATCTTAGAAGACGAG----CCCCA--CTCT-GTAGC
                   10         20         30             40

70         80         90        100        110
T228    AAAGCTGTATTGGATTGTGAGGCAATGAAAACAAA--TGAATTCCCTTCTCCATGTTTGG
        ::::  .: :.   :  .:: :::..::::::::     :::::: ::  ::::  :::     :
        --AGCTCAACTA-ACCATG-GGCGATGATGACACCCCTGTGTGCC--TCTC--TGTC--G
              50         60         70         80         90

120        130        140        150        160        170
T228    ACTCAAAGACTAAGGTGGTTATGAAGGGTCAAAATGTATCTATGTTTTGTTCCCATAAGA
        ::::.   .:.:.::.:    :...:..:    :....  ::   ..:.:.  :  ::.  ::     :...:
        CCTCAT--GCAAGGGAG--TGAGTTG---CTGGCTG-GACAAACTCTTACTC---TGGGC
           100        110        120        130        140

180        190        200        210        220        230
T228    ACAAATCACTGCAGATCACCTATTCATTGTTTCGACGTAAGACACACCTGGGAACCCAGG
        .:..: :.::: ::::        .: .::.:: :: :.::  :::.         :
        TCTTA-CTCTGTCTATCAC----------ACTTCGAAACAC-CGCCGTGGAT----TG
           150        160                     170        180

240        250        260        270        280        290
T228    ATGGAAAAGGTGAACCTGCGATTTTTAACCTAAGCATCACAGAAGCCCATGAATCAGGCC
        ..:::   .::::.: .:  .::   .:..: :        ::.:  .::  :   :::::   :
        TAGGA--GGGTGGAC-AGAAATGGATTGCTT-----TCTCCAAATC---TGAA-----CT
           190        200        210             220              230

300        310        320        330        340        350
T228    CCTACAAATGCAAAGCCCAAGTTACCAGCTGTTCAAAATACAGTCGTGACTTCAGCTTCA
        :  .. :....:   ...: :   ....: . :  :...... ..:.::: ::  :::  :.  ::
        CAAGTATGAGTGTGGTCAGGATGGGC--CAAAATGTATCTCTGTCTTG--TTC--CAGCA
           240        250        260        270        280

360        370        380        390        400        410
T228    CGATTGTCGACCCGGTGACTTCCCCAGTGCTGAACATTATGGTCATTCAAACAGAAACAG
        ::. .  . :::.::  ::::.::      ..:.:::.: :          :           ::::.:
        AGAACA-CATCC-ATAGACATCACCTATTC-GCTCTTTTTGGGTA------AGAGA--T
             290        300        310        320               330

420        430        440        450        460        470
T228    ACCGACATATAACATTACATTGCCTCTCAGTCAATGGCTCGCTGCCCATCAATTACACTT
        :::  :   :.:..::. :      :      ::.  .: ::   ::::     :    .::;.: :
        ACCTA--GAAAGCAAGA---GG------AGAAGAGGGGGAGCTG----TGGATTTC-C--
             340        350              360               370
```

FIG. 4A

```
        480        490        500        510        520        530
T228 TCTTTGAAAACCATGTTGCCATATCACCAGCTATTTCCAAGTATGACAGGGAGCCTGCTG
      .::  ::..  :          :::.:::.      :  ::::   ..:.::::    ::::..
     --------ACC-TGAGG----ATCTCCAA----TGCCAA-CGAGTCAGG-CCCCTACAA
             380         390            400          410

540        550        560        570        580        590
T228 AATTTAACTTAACCAAGAAGAATCCTGGAGAAGAGGAAGAGTATAGGTGTGAAGCTAAAA
      .   ..:...:. ::  :.::.:::                    .: . ::     : :::.
     G----TGCAAAGTCA--ATGATTCC--------------AACTCGT------CGAAAT
          420       430                      440

600        610        620        630        640        650
T228 ACAGATTGCCTAACTATGCAACATACAGTCACCCTGTCACCATGCCCTCAACAGGCGGAG
     ::::  .:   :..:.:   :...::   ::..:::  :::  :::             :. :...
     ACAGTCAGAATTTCAA--CTTCA--CAATCATCCAG---------------GATGAGA
     450       460       470       480

660        670        680        690        700        710
T228 ACAGCTGTCCTT-TCTGTCTGAAGCTACTACTTCCAGGGTTATTACTGTTGCTGGTGGTG
      .:.::: :  :::  :::.  :::.  :::.  :..:: ::::::: :.::: ::   :::.
     GCTGCTCTTCTTGTCTA-CTGTCGCTGTTGCTCCCAGGGGTGTTATTGGGGCTA------
     490       500       510       520       530       540

720        730        740        750        760        770
T228 ATAATCCTAATTCTGGCTTTTTGGGTACTGCCCAAATACAAAACAAGAAAAGCTATGAGA
     :::  :::  :.   :::::  ::::  :.:.       :...  ::.::::::.:::.:
     ATACTCCCAGGCCTGGCCTTTTTGATT-----TATTTGAAATACAAAAAAGG--------
                  550         560         570        580

780        790        800        810        820        830
T228 AATAATGTGCCCAGGGACCGTGGAGACACAGCCATGGAAGTTGGAATCTATGCAAATATC
         ::::  :::::.:          :::::.:.:       ....::..  ::..:  ::::. .:
     ------GTGCACAGGAA------AGACTCTG---AAAGAGAATGAGTC----CAAGGGTT
           590           600            610          620

840        850        860        870        880        890
T228 CTTGAAAAACAAGCAAAGGAGGAATCTGTGCCAGAAGTGGGATCCAGGCCGTGTGTTTCC
     ::  ::.:...:.    ::  . .::::.     :..::  . ..:   :.....  :       ::::..
     CTGGAGATGCGCCCACGCAAGGG----GAGCTGTATGCGAATATC------TGTGA----
     630        640        650             660           670

900        910        920        930        940        950
T228 ACAGCCCAAGATGAGGCCAAACACTCCCAGGAGCTACAGTATGCCACCCCCGTGTTCCAG
      .::  :::::.:..:  :   .::::  :::::::  ::::  :::.: ::  ::  ::  :::  :.
     --AACTCAAAAAGGGTCAGAACAACTCCAGGAGATACACTATACTACTCCAGTCTTCAAA
          680       690         700         710        720        730

960        970        980        990        1000       1010
T228 GAGGTGGCACCAAGAGAGCAAGAAGCCTGTGATTCTTATAAATCTGGATATGTCTATTCT
     :::::::::::  :  :::.::::::.:     :  :::   :...:::  ::. ::  .::::  :::
     GAGGTGGCACCCACAGAACAAGAAGGCCTTGAGGATAGAAAAGATGACTACATCTACTCT
     740        750        760        770        780        790
```

FIG. 4B

```
           1020      1030
T228    GAACTCAACTTCTGA
        : : : : : :   : : . :
        GAACTCACCTAC---
              800
```

FIG. 4C

```
             10           20           30           40
MCA-32  MW--LGRGILEDEPHSVA---AQL---TMGDDDTPV-CLS------VASCKGVS--CWL-D
        ::   ..:  ..    ::      ::    ::.     :     ...::  :    .
        MWSHLSRLLFWSIFSSVTCRKAVLDCEAMKTNEFPSPCLDSKTKVVMKGQNVSMFCSHKN
             10           20           30           40           50           60

50                                              60           70
MCA-32  KLLL--WAL-------------------TLSITL---------RNTAVDCRRVDRN---G
        : :    .:                   .::::          .. ...:. .:.
        KSLQITYSLFRRKTHLGTQDGKGEPAIFNLSITEAHESGPYKCKAQVTSCSKYSRDFSFT
             70           80           90          100          110          120

80           90          100          110          120
MCA-32  LLSPNLNSSMSVVRM----GQNVSLSCSSKNTSIDITYSLFLGKRYLESKRRR--GGAVD
        ...:  .. .....      .....: : : :. :.::..:   . .       ...
        IVDPVTSPVLNIMVIQTETDRHITLHCLSVNGSLPINYTFFENHVAISPAISKYDREPAE
            130          140          150          160          170          180

130          140          150          160          170          180
MCA-32  FHLRISNANESGPYKCKVND--SNSSKYSQNFNFTIIQDESCSSCLLSLLLPGVLLGL--
        : .:   ... ... .: ... ..::. ::  . ..::. ::  :::::.:: :
        FNLTKKNPGEEEEYRCEAKNRLPNYATYSHPVTMPSTGGDSCPFCL-KLLLPGLLLLLVV
            190          200          210          220          230

190          200          210          220
MCA-32  ILPGLAFLIYLKYKKGCTGKTLKENESKGSGDAPTQGELYANI----------------
        :.. :::  .  :::   :   :.....:   :... .  . .::::
        IILILAFWVLPKYK---TRKAMRNNVPRDRGDTAMEVGIYANILEKQAKEESVPEVGSRP
            240          250          260          270          280          290

230          240          250          260
MCA-32  CET--QKGSEQLQEIHYTTPVFKEVAPTEQEGLEDRKDDYIYSELTY
        :  .  :  .. :..:..:.::::.:::  :::. ..  :...:::..
        CVSTAQDEAKHSQELQYATPVFQEVAPREQEACDSYKSGYVYSELNF
            300          310          320          330          340
```

FIG. 5

```
  M   A   A   P   A   L   G   L   V   C   G   R   T   P   E   L   G   L   V    19
1 ATG GCT GCG CCC GCA CTA GGG CTG GTG TGT GGA CGT TGC CCT GAG CTG GGT CTC GTC    58

L   L   L   L   L   L   S   L   L   C   G   A   A   G   S   Q   E   A   G   T    39
  CTC TTG CTG CTG CTG CTC TCG CTG CTG TGT GGA GCG GCA GGG AGC CAG GAG GCC GGG ACC  118

G   A   G   A   G   S   L   A   G   S   C   G   C   G   T   P   Q   R   P   G    59
  GGT GCG GGC GCG GGG TCC CTT GCG GGT TCT TGC GGC TGC GGC ACG CCC CAG CGG CCT GGC  178

A   H   G   N   S   A   A   H   R   Y   S   R   E   A   N   A   P   G   P    79
  GCC CAT GGC AAT TCG GCA GCC GCT CAC CGA TAC TCG CGG GAG GCT AAC GCT CCG GGC CCC  238

V   P   G   E   R   Q   L   A   H   S   K   M   V   P   I   P   V   G   V   F    99
  GTA CCC GGA GAG CGG CAA CTC GCG CAC TCA AAG ATG GTC CCC ATC CCT GTT GGA GTA TTT  298

T   M   G   T   D   D   P   Q   I   K   Q   D   G   E   A   P   A   R   R   V   119
  ACA ATG GGC ACA GAT GAT CCT CAG ATA AAG CAG GAT GGG GAA GCA CCT GCG AGG AGA GTT  358

T   I   D   A   F   Y   M   D   A   Y   E   V   S   N   T   E   F   E   K   F   139
  ACT ATT GAT GCC TTT TAC ATG GAT GCC TAT GAA GTC AGT AAT ACT GAA TTT GAG AAG TTT  418

V   N   S   T   G   Y   L   T   E   A   E   K   F   G   D   S   F   V   F   E   159
  GTG AAC TCA ACT GGC TAT TTG ACA GAG GCT GAG AAG TTT GGC GAC TCC TTT GTC TTT GAA  478

G   M   L   S   E   Q   V   K   T   N   I   Q   Q   A   V   A   A   A   P   W   179
  GGC ATG TTG AGT GAG CAA GTG AAG ACC AAT ATT CAA CAG GCA GTT GCA GCT GCT CCC TGG  538

W   L   P   V   K   G   A   N   W   R   H   P   E   G   P   D   S   T   I   L   199
  TGG TTA CCT GTG AAA GGC GCT AAC TGG AGA CAC CCA GAA GGG CCT GAC TCT ACT ATT CTG  598

H   R   P   D   H   P   V   L   H   V   S   W   N   D   A   V   A   Y   C   T   219
  CAC AGG CCG GAT CAT CCA GTT CTC CAT GTG TCC TGG AAT GAT GCG GTT GCC TAC TGC ACT  658

W   A   G   K   R   L   P   T   E   A   E   W   E   Y   S   C   R   G   G   L   239
  TGG GCA GGG AAG CGG CTG CCC ACG GAA GCT GAG TGG GAA TAC AGC TGT CGA GGA GGC CTG  718

H   N   R   L   F   P   W   G   N   K   L   Q   P   K   G   Q   H   Y   A   N   259
  CAT AAT AGA CTT TTC CCC TGG GGC AAC AAA CTG CAG CCC AAA GGC CAG CAT TAT GCC AAC  778

I   W   Q   G   E   F   P   V   T   N   T   G   E   D   G   F   Q   G   T   A   279
  ATT TGG CAG GGC GAG TTT CCG GTG ACC AAC ACT GGT GAG GAT GGC TTC CAA GGA ACT GCG  838

P   V   D   A   F   P   P   N   G   Y   G   L   Y   N   I   V   G   N   A   W   299
  CCT GTT GAT GCC TTC CCT CCC AAT GGT TAT GGC TTA TAC AAC ATA GTG GGG AAC GCA TGG  898

E   W   T   S   D   W   W   T   V   H   H   S   V   E   E   T   L   N   P   K   319
  GAA TGG ACT TCA GAC TGG TGG ACT GTT CAT CAT TCT GTT GAA GAA ACG CTT AAC CCA AAA  958

G   P   P   S   G   K   D   R   V   K   K   G   G   S   Y   M   C   H   R   S   339
  GGT CCC CCT TCT GGG AAA GAC CGA GTG AAG AAA GGT GGA TCC TAC ATG TGC CAT AGG TCT 1018
```

FIG. 6A

```
Y   C   Y   R   Y   R   C   A   A   R   S   Q   N   T   P   D   S   S   A   S    359
TAT TGT TAC AGG TAT CGC TGT GCT GCT CGG AGC CAG AAC ACA CCT GAT AGC TCT GCT TCG  1078

N   L   G   F   R   C   A   D   R   L   P   T   M   D   *                        375
AAT CTG GGA TTC CGC TGT GCA GCC GAC CGC CTG CCC ACT ATG GAC TGA                  1126

CAACCAAGGAAAGTCTTCCCCAGTCCAAGGAGCAGTCGTGTCTGACCTACATTGGGCTTTTCTCAGAACTTTGAACGAT 1205

CCCATGCAAAGAATTCCCACCCTGAGGTGGGTTACATACCTGCCCAATGGCCAAAGGAACCGCCTTGTGAGACCAAATT 1284

GCTGACCTGGGTCAGTGCATGTGCTTTATGGTGTGGTGCATCTTTGGAGATCATCGCCATATTTTACTTTTGAGAGTCT 1363

TTAAAGAGGAAGGGGAGTGGAGGGAACCCTGAGCTAGGCTTCAGGAGGCCCGCGTCCTACGCAGGCTCTGCCACAGGGG 1442

TTAGACCCCAGGTCCGACGCTTGACCTTCCTGGGCCTCAAGTGCCCTCCCCTATCAAATGAAGGGATGGACAGCATGAC 1521

CTCTGGGTGTCTCTCCAACTCACCAGTTCTAAAAAGGGTATCAGATTCTATTGTGACTTCATAGTGAGAATTTATGATA 1600

GATTATTTTTTAGCTATTTTTTCCATGTGTGAACCTTGAGTGATACTAATCATGTAAAGTAAGAGTTCTCTTATGTATT 1679

ATTTTCGGAAGAGGGGTGTGGTGACTCCTTTATATTCGTACTGCACTTTGTTTTTCCAAGGAAATCAGTGTCTTTTACG 1758

TTGTTATGATGAATCCCACATGGGGCCGGTGATGGTATGCTGCAGTTCAGCCGTTGAACACATAGGAATGTCTGTGGGG 1837

TGACTCTACTGTGCTTTATCTTTTAACATTAAGTGCCTTTGGTTCAGAGGGGCAGTCATAAGCTCTGTTTCCCCCTCTC 1916

CCCAAAGCCTTCAGCGAACGTGAAATGTGCGCTAAACGGGGAAACCTGTTTAATTCTAGATATAGGGAAAAAGGAACGA 1995

GGACCTTGAATGAGCTATATTCAGGGTATCCGGTATTTTGTAATAGGGAATAGGAAACCTTGTTGGCTGTGGAATATCC 2074

GATGCTTTGAATCATGCACTGTGTTGAATAAACGTATCTGCTAAAAAAAAAAAAAAAAAAAAAAAAAAAAAAAAAAAAA 2153

AAAAAAAAA  2165
```

FIG. 6B

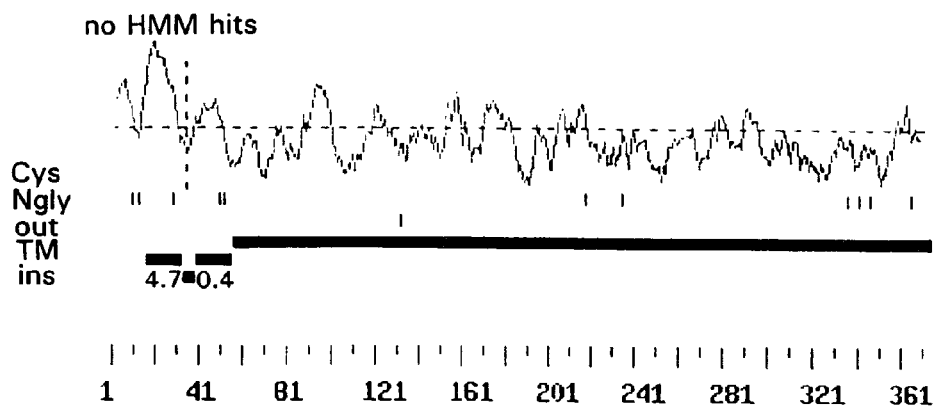

MAAPALGLVCGRCPELGLVLLLLLLSLLCGAAGSQEAGTGAGAGSLAGSC
GCGTPQRPGAHGNSAAAHRYSREANAPGPVPGERQLAHSKMVPIPVGVFT
MGTDDPQIKQDGEAPARRVTIDAFYMDAYEVSNTEFEKFVNSTGYLTEAE
KFGDSFVFEGMLSEQVKTNIQQAVAAAPWWLPVKGANWRHPEGPDSTIL
HRPDHPVLHVSWNDAVAYCTWAGKRLPTEAEWEYSCRGGLHNRLFPWG
NKLQPKGQHYANIWQGEFPVTNTGEDGFQGTAPVDAFPPNGYGLYNIVG
NAWEWTSDWWTVHHSVEETLNPKGPPSGKDRVKKGGSYMCHRSYCYRY
RCAARSQNTPDSSASNLGFRCAADRLPTMD

MAAPALGLVCGRCPELGLVLLLLLLSLLCGAAGSQEAGTGAGAGSLAGSCGCGTPQRPGA
                 10        20        30        40        50        60

10        20        30
rv0712  -----------------------TELVDLPGGSFRMGST--RFYPE-EAPIHTVT
                                 . .:  .: :  ::.    ..  ..  :::  . ::
        HGNSAAAHRYSREANAPGPVPGERQLAHSKMVPIPVGVFTMGTDDPQIKQDGEAPARRVT
           70        80        90       100       110       120

40        50        60        70        80        90
rv0712  VRAFAVERHPVTNAQFAEFVSATGYVTVAEQPLDPGLYPGVDAADLCPGAMVFCPTAGPV
        . ::  ..     :.:..:. ::..::.:  ::.    :.  ..  :. ....    ..   .:.:
        IDAFYMDAYEVSNTEFEKFVNSTGYLTEAEKFGDSFVFEGMLSEQV-KTNIQQAVAAAP-
           130       140       150       160       170

100       110       120       130       140       150
rv0712  DLRDWRQWWDWVPGACWRHPFGRDSDIADRAGHPVVQVAYPDAVAYARWAGRRLPTEAEW
         ::   :  ::  ::::  : ::  ::  . :. .::::..    :::::   :::.::::::::
        -------WWLPVKGANWRHPEGPDSTILHRPDHPVLHVSWNDAVAYCTWAGKRLPTEAEW
                    180       190       200       210       220       230

160       170       180       190       200       210
rv0712  EYAARGGTTAT-YAWGDQEKPGGMLMANTWQGRFPYRNDGALGWVGTSPVGRFPANGFGL
        ::. :::   .    ..:..  .: :    ::.:::  ::    : :.. :   ::..:: ::.:.::
        EYSCRGGLHNRLFPWGNKLQPKGQHYANIWQGEFPVTNTGEDGFQGTAPVDAFPPNGYGL
           240       250       260       270       280       290

220       230       240       250       260       270
rv0712  LDMIGNVWEWTTTEFYPHHRIDPPSTACCAPVKLATAADPTISQTLKGGSHLCAPEYCHR
        ...::.:::::.      ::  ..      ..  .    ...  ::::  .:   ::  :
        YNIVGNAWEWTSDWWTVHHSVEETLNP--------KGPPSGKDRVKKGGSYMCHRSYCYR
           300       310       320       330       340

280       290
rv0712  YRPAARSPQSQDTATTHIGFRCVAD--PV
        ::  ::::::.........::::.::   .  .
        YRCAARSQNTPDSSASNLGFRCAADRLPTMD
           350       360       370
```

FIG. 8

```
CTCGGCCCGCTCGGCGCGCCCCTTCCCAGCCGCCCTTCCGTACCGGCTCTCGGGCTCTTCCGGTCTCCGGCCGCCCCTT    79
ACCTGCAGGCTCTTCTCCCGCCGCGGCCCGGCGCTCTCCGAGTCGCCCCTGCGGACTGGTCTCGCACAGTGCCTGGGCA   158
                              M   T   S   G   A   T   R   Y   R   L   S   C   S    13
CCGGGCGCCAGACAGACACTGGCC ATG ACG AGC GGC GCA ACC AGG TAC CGG CTG AGC TGC TCG        221

L   R   G   H   E   L   D   V   R   G   L   V   C   C   A   Y   P   P   G   A    33
TTC CGG GGC CAC GAG CTG GAC GTA CGG GGC CTG GTG TGC TGC GCC TAT CCG CCG GGA GCC    281

F   V   S   V   S   R   D   R   T   T   R   L   W   A   P   D   S   P   N   R    53
TTT GTG TCC GTG TCC CGA GAC CGC ACC ACC CGC CTC TGG GCC CCA GAC AGT CCA AAC AGG    341

S   F   T   E   M   H   C   M   S   G   H   S   N   F   V   S   C   V   C   I    73
AGC TTT ACA GAA ATG CAC TGT ATG AGT GGC CAT TCC AAT TTT GTA TCT TGT GTA TGC ATC    401

I   P   S   S   D   I   Y   P   H   G   L   I   A   T   G   G   N   D   H   N    93
ATA CCC TCA AGT GAC ATC TAC CCT CAT GGC CTA ATT GCC ACC GGT GGA AAT GAC CAC AAT    461

I   C   I   F   S   L   D   S   P   M   P   L   Y   I   L   K   G   H   K   N   113
ATA TGC ATT TTC TCA CTG GAC AGT CCA ATG CCA CTT TAT ATT CTA AAA GGC CAC AAA AAT    521

T   V   C   S   L   S   S   G   K   F   G   T   L   L   S   G   S   W   D   T   133
ACT GTT TGT AGT CTA TCA TCT GGA AAA TTT GGG ACA TTA CTT AGT GGT TCA TGG GAC ACC    581

T   A   K   V   W   L   N   D   K   C   M   M   T   L   Q   G   H   T   A   A   153
ACT GCT AAA GTC TGG CTG AAT GAC AAG TGC ATG ATG ACC TTG CAG GGT CAT ACA GCT GCA    641

V   W   A   V   K   I   L   P   E   Q   G   L   M   L   T   G   S   A   D   K   173
GTG TGG GCG GTA AAG ATC TTA CCT GAA CAG GGC TTA ATG TTG ACT GGA TCA GCA GAC AAG    701

T   V   K   L   W   K   A   G   R   C   E   R   T   F   S   G   H   E   D   C   193
ACT GTT AAA CTG TGG AAG GCT GGA AGA TGT GAG AGG ACT TTT TCA GGG CAT GAA GAC TGT    761

V   R   G   L   A   I   L   S   E   T   E   F   L   S   C   A   N   D   A   S   213
GTA AGA GGT TTG GCA ATT TTG AGT GAA ACA GAA TTT CTT TCC TGT GCA AAT GAT GCT AGT    821

I   R   R   W   Q   I   T   G   E   C   L   E   V   Y   Y   G   H   T   N   Y   233
ATT AGA AGG TGG CAA ATC ACT GGC GAG TGT CTT GAA GTA TAT TAT GGA CAT ACA AAT TAT    881

I   Y   S   I   S   V   F   P   N   C   R   D   F   V   T   T   A   E   D   R   253
ATT TAT AGC ATA TCC GTT TTT CCA AAT TGT AGA GAC TTT GTG ACA ACA GCA GAG GAC AGA    941

S   L   R   I   W   K   H   G   E   C   A   Q   T   I   R   L   P   A   Q   S   273
TCT CTG AGA ATC TGG AAA CAT GGG GAA TGT GCT CAA ACT ATC CGA CTT CCA GCT CAG TCT   1001

I   W   C   C   C   V   L   D   N   G   D   I   V   V   G   A   S   D   G   I   293
ATA TGG TGC TGC TGT GTG CTC GAC AAT GGT GAC ATT GTG GTT GGT GCG AGT GAT GGC ATT   1061

I   R   V   F   T   E   S   E   D   R   T   A   S   A   E   E   I   K   A   F   313
ATT AGA GTG TTT ACA GAA TCA GAA GAT CGA ACA GCA AGT GCT GAA GAA ATC AAG GCT TTT   1121

E   K   E   L   S   H   A   T   I   D   S   K   T   G   D   L   G   D   I   N   333
GAA AAA GAA CTG TCT CAC GCA ACC ATT GAT TCT AAA ACT GGC GAT TTA GGG GAC ATC AAT   1181
```

FIG. 9A

```
  A   E   Q   L   P   G   R   E   H   L   N   E   P   G   T   R   E   G   Q   T    353
GCT GAG CAG CTT CCT GGG AGG GAA CAT CTT AAT GAA CCT GGT ACT AGA GAA GGA CAG ACT   1241

R   L   I   R   D   G   E   K   V   E   A   Y   Q   W   S   V   S   E   G   R    373
CGT CTA ATC AGA GAT GGG GAG AAA GTC GAA GCC TAT CAG TGG AGT GTT AGT GAA GGG AGG   1301

W   I   K   I   G   D   V   V   G   S   S   G   A   N   Q   Q   T   S   G   K    393
TGG ATA AAA ATT GGT GAT GTT GTT GGC TCA TCT GGT GCT AAT CAG CAA ACA TCT GGA AAA   1361

V   L   Y   E   G   K   E   F   D   Y   V   F   S   I   D   V   N   E   G   G    413
GTT TTA TAT GAA GGG AAA GAA TTT GAT TAT GTT TTC TCA ATT GAT GTC AAT GAA GGT GGA   1421

P   S   Y   K   L   P   Y   N   T   S   D   D   P   W   L   T   A   Y   N   F    433
CCA TCA TAT AAA TTG CCA TAT AAT ACC AGT GAT GAC CCT TGG TTA ACT GCA TAC AAC TTC   1481

L   Q   K   N   D   L   N   P   M   F   L   D   Q   V   A   K   F   I   I   D    453
TTA CAG AAG AAT GAT TTG AAT CCT ATG TTT CTG GAT CAA GTA GCT AAA TTT ATT ATT GAT   1541

N   T   K   G   Q   M   L   G   L   G   N   P   S   F   S   D   P   F   T   G    473
AAC ACA AAA GGT CAA ATG TTG GGA CTT GGG AAT CCC AGC TTT TCA GAT CCA TTT ACA GGT   1601

G   G   R   Y   V   P   G   S   S   G   S   S   N   T   L   P   T   A   D   P    493
GGT GGT CGG TAT GTT CCG GGC TCT TCG GGA TCT TCT AAC ACA CTA CCC ACA GCA GAT CCT   1661

F   T   G   A   G   R   Y   V   P   G   S   A   S   M   G   T   T   M   A   G    513
TTT ACA GGT GCT GGT CGT TAT GTA CCA GGT TCT GCA AGT ATG GGA ACT ACC ATG GCC GGA   1721

V   D   P   F   T   G   N   S   A   Y   R   S   A   A   S   K   T   M   N   I    533
GTT GAT CCA TTT ACA GGG AAT AGT GCC TAC CGA TCA GCT GCA TCT AAA ACA ATG AAT ATT   1781

Y   F   P   K   K   E   A   V   T   F   D   Q   A   N   P   T   Q   I   L   G    553
TAT TTC CCT AAA AAA GAG GCT GTC ACA TTT GAC CAA GCA AAC CCT ACA CAA ATA TTA GGT   1841

K   L   K   E   L   N   G   T   A   P   E   E   K   K   L   T   E   D   D   L    573
AAA CTG AAG GAA CTT AAT GGA ACT GCA CCT GAA GAG AAG AAG TTA ACT GAG GAT GAC TTG   1901

I   L   L   E   K   I   L   S   L   I   C   N   S   S   E   K   P   T   V    593
ATA CTT CTT GAG AAG ATA CTG TCT CTA ATA TGT AAT AGT TCT TCA GAA AAA CCC ACA GTC   1961

Q   Q   L   Q   I   L   W   K   A   I   N   C   P   E   D   I   V   F   P   A    613
CAG CAA CTT CAG ATT TTG TGG AAA GCT ATT AAC TGT CCT GAA GAT ATT GTC TTT CCT GCA   2021

L   D   I   L   R   L   S   I   K   H   P   S   V   N   E   N   F   C   N   E    633
CTT GAC ATT CTT CGG TTG TCA ATT AAA CAC CCC AGT GTG AAT GAG AAC TTC TGC AAT GAA   2081

K   E   G   A   Q   F   S   S   H   L   I   N   L   L   N   P   K   G   K   P    653
AAG GAA GGG GCT CAG TTC AGC AGT CAT CTT ATC AAT CTT CTG AAC CCT AAA GGA AAG CCA   2141

A   N   Q   L   L   A   L   R   T   F   C   N   C   F   V   G   Q   A   G   Q    673
GCA AAC CAG CTG CTT GCT CTC AGG ACT TTT TGC AAT TGT TTT GTT GGC CAG GCA GGA CAA   2201

K   L   M   M   S   Q   R   E   S   L   M   S   H   A   I   E   L   K   S   G    693
AAA CTC ATG ATG TCC CAG AGG GAA TCA CTG ATG TCC CAT GCA ATA GAA CTG AAA TCA GGG   2261

S   N   K   N   I   H   I   A   L   A   T   L   A   L   N   Y   S   V   C   F    713
AGC AAT AAG AAC ATT CAC ATT GCT CTG GCT ACA TTG GCC CTG AAC TAT TCT GTT TGT TTT   2321
```

FIG. 9B

```
H   K   D   H   N   I   E   G   K   A   Q   C   L   S   L   I   S   T   I   L     733
CAT AAA GAC CAT AAC ATT GAA GGG AAA GCC CAA TGT TTG TCA CTA ATT AGC ACA ATC TTG   2381

E   V   Q   D   L   E   A   T   F   R   L   L   V   A   L   G   T   L   I         753
GAA GTA CAA GAC CTA GAA GCC ACT TTT AGA CTT CTT GTG GCT CTT GGA ACA CTT ATC       2441

S   D   D   N   A   V   Q   L   A   K   S   L   G   V   D   S   Q   I   K         773
AGT GAT GAT AAT GCT GTA CAA TTA GCC AAG TCT TTA GGT GTT GAT TCT CAA ATA AAA       2501

K   Y   S   S   V   S   E   P   A   K   V   S   E   C   R   F   I   L   N         793
AAG TAT TCC TCA GTA TCA GAA CCA GCT AAA GTA AGT GAA TGC TGT AGA TTT ATC CTA AAT   2561

L   L   *                                                                         796
TTG CTG TAG                                                                       2570

CAGTGGGGAAGAGAGGACGGATATTTTAATTGATTAGTGTTTTTCCTCACATTGACATGACTGATAACAGATAATT      2649

AAAAAAGAGAATACGGTGATTAAGTAAAATTTTACATCTTGTAAAGTGGTGGGAGGGAAACAGAAATAAAATTTT      2728

TGCACTGCTGAAAAAAAAAAAAAAAAAAAAAAAAAAAAAAAAAAAAAAAAAAAAAAAAAAAAAAAAAAAAAAAAAA      2807

AAAA  2811
```

FIG. 9C

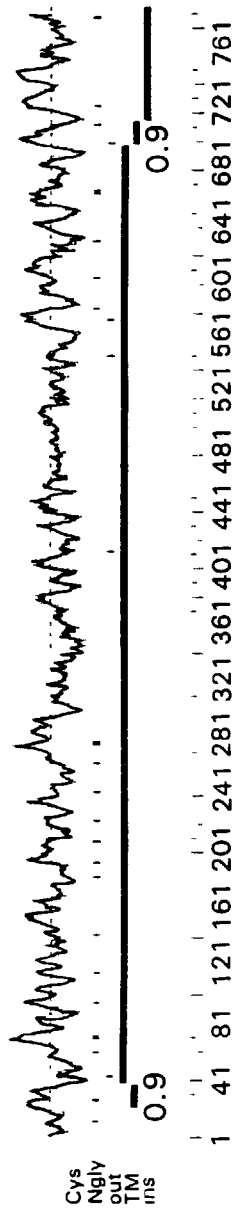

MTSGATRYRLSCSLRGHELDVRGLVCCAYPPGAFVSVSRDRTTRLWAPDS
PNRSFTEMHCMSGHSNFVSCVCIIPSSDIYPHGLIATGGNDHNICIFSLDSPM
PLYILKGHKNTVCSLSSGKFGTLLSGSWDTTAKVWLNDKCMMTLQGHTA
AVWAVKILPEQGLMLTGSADKTVKLWKAGRCERTFSGHEDCVRGLAILSE
TEFLSCANDASIRRWQITGECLEVYYGHTNYIYSISVFPNCRDFVTTAEDRS
LRIWKHGECAQTIRLPAQSIWCCCVLDNGDIVVGASDGIIRVFTESEDRTAS
AEEIKAFEKELSHATIDSKTGDLGDINAEQLPGREHLNEPGTREGQTRLIRD
GEKVEAYQWSVSEGRWIKIGDVVGSSGANQQTSGKVLYEGKEFDYVFSID
VNEGGPSYKLPYNTSDDPWLTAYNFLQKNDLNPMFLDQVAKFIIDNTKGQ
MLGLGNPSFSDPFTGGGRYVPGSSGSSNTLPTADPFTGAGRYVPGSASMGT
TMAGVDPFTGNSAYRSAASKTMNIYFPKKEAVTFDQANPTQILGKLKELN
GTAPEEKKLTEDDLILLEKILSLICNSSSEKPTVQQLQILWKAINCPEDIVFPA
LDILRLSIKHPSVNENFCNEKEGAQFSSHLINLLNPKGKPANQLLALRTFCN
CFVGQAGQKLMMSQRESLMSHAIELKSGSNKNIHIALATLALNYSVCFHK
DHNIEGKAQCLSLISTILEVVQDLEATFRLLVALGTLISDDSNAVQLAKSLG
VDSQIKKYSSVSEPAKVSECCRFLNLL

FIG. 10

```
              10        20        30        40        50        60
T243   CTCGGCCCGCTCGGCGCGCCCCTTCCCAGCCGCCCTTCCGTACCGGCTCTCGGGCTCTTC 70        80        90       100       110       120
T243   CGGTCTCCGGCCGCCCCTTACCTGCAGGCTCTTCTCCCGCCGCGGCCCGGCGCTCTCCGA 130       140       150       160       170       180
T243   GTCGCCCCTGCGGACTGGTCTCGCACAGTGCCTGGGCACCGGGCGCCAGACAGACACTGG 190       200       210       220       230       240
T243   CCATGACGAGCGGCGCAACCAGGTACCGGCTGAGCTGCTCGCTCCGGGGCCACGAGCTGG 250       260       270       280       290       300
T243   ACGTACGGGGCCTGGTGTGCTGCGCCTATCCGCCGGGAGCCTTTGTGTCCGTGTCCCGAG 310       320       330       340       350       360
T243   ACCGCACCACCCGCCTCTGGGCCCCAGACAGTCCAAACAGGAGCTTTACAGAAATGCACT
                                                                 ::::::
                                                           ------ATGCACT 370       380       390       400       410       420
T243   GTATGAGTGGCCATTCCAATTTTGTATCTTGTGTATGCATCATACCCTCAAGTGACATCT
       :::::::  :::::  :::::::::::::::::::::::::::::::::::::::::::
       GTATGAGCGGCCACTCCAATTTTGTATCTTGTGTATGCATCATACCCTCAAGTGACATCT
          10        20        30        40        50        60

430       440       450       460       470       480
T243   ACCCTCATGGCCTAATTGCCACCGGTGGAAATGACCACAATATATGCATTTCTCACTGG
       ::::::::::::::::::::::::::::::::::::::::::::::::::::::::::
       ACCCTCATGGCCTAATTGCCACCGGTGGAAATGACCACAATATATGCATTTCTCACTGG
          70        80        90       100       110       120
```

FIG. 11A

```
          490        500        510        520        530        540
T243  ACAGTCCAATGCCACTTTATATTCTAAAAGGCCACAAAAATACTGTTTGTAGTCTATCAT
      ::::::::::::::::::::::::::::::::::::::::::::::::::::::::::::
      ACAGTCCAATGCCACTTTATATTCTAAAAGGCCACAAAAATACTGTTTGTAGTCTATCAT
      130        140        150        160        170        180

550        560        570        580        590        600
T243  CTGGAAAATTTGGGACATTACTTAGTGGTTCATGGGACACCACTGCTAAAGTCTGGCTGA
      ::::::::::::::::::::::::::::::::::::::::::::::::::::::::::::
      CTGGAAAATTTGGGACATTACTTAGTGGTTCATGGGACACCACTGCTAAAGTCTGGCTGA
      190        200        210        220        230        240

610        620        630        640        650        660
T243  ATGACAAGTGCATGATGACCTTGCAGGGTCATACAGCTGCAGTGTGGGCGGTAAAGATCT
      ::::::::::::::::::::::::::::::::::::::::::::::::::::::::::::
      ATGACAAGTGCATGATGACCTTGCAGGGTCATACAGCTGCAGTGTGGGCGGTAAAGATCT
      250        260        270        280        290        300

670        680        690        700        710        720
T243  TACCTGAACAGGGCTTAATGTTGACTGGATCAGCAGACAAGACTGTTAAACTGTGGAAGG
      ::::::::::::::::::::::::::::::::::::::::::::::::::::::::::::
      TACCTGAACAGGGCTTAATGTTGACTGGATCAGCAGACAAGACTGTTAAACTGTGGAAGG
      310        320        330        340        350        360

730        740        750        760        770        780
T243  CTGGAAGATGTGAGAGGACTTTTTCAGGGCATGAAGACTGTGTAAGAGGTTTGGCAATTT
      ::::::::::::::::::::::::::::::::::::::::::::::::::::::::::::
      CTGGAAGATGTGAGAGGACTTTTTCAGGGCATGAAGACTGTGTAAGAGGTTTGGCAATTT
      370        380        390        400        410        420

790        800        810        820        830        840
T243  TGAGTGAAACAGAATTTCTTTCCTGTGCAAATGATGCTAGTATTAGAAGGTGGCAAATCA
      ::::::::::::::::::::::::::::::::::::::::::::::::::::::::::::
      TGAGTGAAACAGAATTTCTTTCCTGTGCAAATGATGCTAGTATTAGAAGGTGGCAAATCA
      430        440        450        460        470        480

850        860        870        880        890        900
T243  CTGGCGAGTGTCTTGAAGTATATTATGGACATACAAATTATATTTATAGCATATCCGTTT
      ::::::::::::::::::::::::::::::::::::::::::::::::::::::::::::
      CTGGCGAGTGTCTTGAAGTATATTATGGACATACAAATTATATTTATAGCATATCCGTTT
      490        500        510        520        530        540

910        920        930        940        950        960
T243  TTCCAAATTGTAGAGACTTTGTGACAACAGCAGAGGACAGATCTCTGAGAATCTGGAAAC
      ::::::::::::::::::::::::::::::::::::::::::::::::::::::::::::
      TTCCAAATTGTAGAGACTTTGTGACAACAGCAGAGGACAGATCTCTGAGAATCTGGAAAC
      550        560        570        580        590        600

970        980        990       1000       1010       1020
T243  ATGGGGAATGTGCTCAAACTATCCGACTTCCAGCTCAGTCTATATGGTGCTGCTGTGTGC
      ::::::::::::::::::::::::::::::::::::::::::::::::::::::::::::
      ATGGGGAATGTGCTCAAACTATCCGACTTCCAGCTCAGTCTATATGGTGCTGCTGTGTGC
      610        620        630        640        650        660
```

FIG. 11B

```
              1030       1040       1050       1060       1070       1080
T243    TCGACAATGGTGACATTGTGGTTGGTGCGAGTGATGGCATTATTAGAGTGTTTACAGAAT
        ::::::::::::::::::::::::::::::::::::::::::::::::::::::::::::
        TCGACAATGGTGACATTGTGGTTGGTGCGAGTGATGGCATTATTAGAGTGTTTACAGAGT
        670        680        690        700        710        720

1090       1100       1110       1120       1130       1140
T243    CAGAAGATCGAACAGCAAGTGCTGAAGAAATCAAGGCTTTTGAAAAAGAACTGTCTCACG
        ::::::::::::::::::::::::::::::::::::::::::::::::::::::::::::
        CAGAAGATCGAACAGCAAGTGCTGAAGAAATCAAGGCTTTTGAAAAAGAACTGTCTCACG
        730        740        750        760        770        780

1150       1160       1170       1180       1190       1200
T243    CAACCATTGATTCTAAAACTGGCGATTTAGGGGACATCAATGCTGAGCAGCTTCCTGGGA
        ::::::::::::::::::::::::::::::::::::::::::::::::::::::::::::
        CAACCATTGATTCTAAAACTGGCGATTTAGGGGACATCAATGCTGAGCAGCTTCCTGGGA
        790        800        810        820        830        840

1210       1220       1230       1240       1250       1260
T243    GGGAACATCTTAATGAACCTGGTACTAGAGAAGGACAGACTCGTCTAATCAGAGATGGGG
        ::::::::::::::::::::::::::::::::::::::::::::::::::::::::::::
        GGGAACATCTTAATGAACCTGGTACTAGAGAAGGACAGACTCGTCTAATCAGAGATGGGG
        850        860        870        880        890        900

1270       1280       1290       1300       1310       1320
T243    AGAAAGTCGAAGCCTATCAGTGGAGTGTTAGTGAAGGGAGGTGGATAAAAATTGGTGATG
        ::::::::::::::::::::::::::::::::::::::::::::::::::::::::::::
        AGAAAGTCGAAGCCTATCAGTGGAGTGTTAGTGAAGGGAGGTGGATAAAAATTGGTGATG
        910        920        930        940        950        960

1330       1340       1350       1360       1370       1380
T243    TTGTTGGCTCATCTGGTGCTAATCAGCAAACATCTGGAAAAGTTTTATATGAAGGGAAAG
        ::::::::::::::::::::::::::::::::::::::::::::::::::::::::::::
        TTGTTGGCTCATCTGGTGCTAATCAGCAAACATCTGGAAAAGTTTTATATGAAGGGAAAG
        970        980        990        1000       1010       1020

1390       1400       1410       1420       1430       1440
T243    AATTTGATTATGTTTTCTCAATTGATGTCAATGAAGGTGGACCATCATATAAATTGCCAT
        ::::::::::::::::::::::::::::::::::::::::::::::::::::::::::::
        AATTTGATTATGTTTTCTCAATTGATGTCAATGAAGGTGGACCATCATATAAATTGCCAT
        1030       1040       1050       1060       1070       1080

1450       1460       1470       1480       1490       1500
T243    ATAATACCAGTGATGACCCTTGGTTAACTGCATACAACTTCTTACAGAAGAATGATTTGA
        ::::::::::::::::::::::::::::::::::::::::::::::::::::::::::::
        ATAATACCAGTGATGACCCTTGGTTAACTGCATACAACTTCTTACAGAAGAATGATTTGA
        1090       1100       1110       1120       1130       1140

1510       1520       1530       1540       1550       1560
T243    ATCCTATGTTTCTGGATCAAGTAGCTAAATTTATTATTGATAACACAAAAGGTCAAATGT
        ::::::::::::::::::::::::::::::::::::::::::::::::::::::::::::
        ATCCTATGTTTCTGGATCAAGTAGCTAAATTTATTATTGATAACACAAAAGGTCAAATGT
        1150       1160       1170       1180       1190       1200
```

FIG. 11C

```
            1570      1580      1590      1600      1610      1620
T243   TGGGACTTGGGAATCCCAGCTTTTCAGATCCATTTACAGGTGGTGGTCGGTATGTTCCGG
       ::::::::::::::::::::::::::::::::::::::::::::::::::::::::::::
       TGGGACTTGGGAATCCCAGCTTTTCAGATCCATTTACAGGTGGTGGTCGGTATGTTCCGG
       1210      1220      1230      1240      1250      1260

1630      1640      1650      1660      1670      1680
T243   GCTCTTCGGGATCTTCTAACACACTACCCACAGCAGATCCTTTTACAGGTGCTGGTCGTT
       ::::::::::::::::::::::::::::::::::::::::::::::::::::::::::::
       GCTCTTCGGGATCTTCTAACACACTACCCACAGCAGATCCTTTTACAGGTGCTGGTCGTT
       1270      1280      1290      1300      1310      1320

1690      1700      1710      1720      1730      1740
T243   ATGTACCAGGTTCTGCAAGTATGGGAACTACCATGGCCGGAGTTGATCCATTTACAGGGA
       ::::::::::::::::::::::::::::::::::::::::::::::::::::::::::::
       ATGTACCAGGTTCTGCAAGTATGGGAACTACCATGGCCGGAGTTGATCCATTTACAGGGA
       1330      1340      1350      1360      1370      1380

1750      1760      1770      1780      1790      1800
T243   ATAGTGCCTACCGATCAGCTGCATCTAAAACAATGAATATTTATTTCCCTAAAAAAGAGG
       ::::::::::::::::::::::::::::::::::::::::::::::::::::::::::::
       ATAGTGCCTACCGATCAGCTGCATCTAAAACAATGAATATTTATTTCCCTAAAAAAGAGG
       1390      1400      1410      1420      1430      1440

1810      1820      1830      1840      1850      1860
T243   CTGTCACATTTGACCAAGCAAACCCTACACAAATATTAGGTAAACTGAAGGAACTTAATG
       ::::::::::::::::::::::::::::::::::::::::::::::::::::::::::::
       CTGTCACATTTGACCAAGCAAACCCTACACAAATATTAGGTAAACTGAAGGAACTTAATG
       1450      1460      1470      1480      1490      1500

1870      1880      1890      1900      1910      1920
T243   GAACTGCACCTGAAGAGAAGAAGTTAACTGAGGATGACTTGATACTTCTTGAGAAGATAC
       ::::::::::::::::::::::::::::::::::::::::::::::::::::::::::::
       GAACTGCACCTGAAGAGAAGAAGTTAACTGAGGATGACTTGATACTTCTTGAGAAGATAC
       1510      1520      1530      1540      1550      1560

1930      1940      1950      1960      1970      1980
T243   TGTCTCTAATATGTAATAGTTCTTCAGAAAAACCCACAGTCCAGCAACTTCAGATTTTGT
       ::::::::::::::::::::::::::::::::::::::::::::::::::::::::::::
       TGTCTCTAATATGTAATAGTTCTTCAGAAAAACCCACAGTCCAGCAACTTCAGATTTTGT
       1570      1580      1590      1600      1610      1620

1990      2000      2010      2020      2030      2040
T243   GGAAAGCTATTAACTGTCCTGAAGATATTGTCTTTCCTGCACTTGACATTCTTCGGTTGT
       ::::::::::::::::::::::::::::::::::::::::::::::::::::::::::::
       GGAAAGCTATTAACTGTCCTGAAGATATTGTCTTTCCTGCACTTGACATTCTTCGGTTGT
       1630      1640      1650      1660      1670      1680

2050      2060      2070      2080      2090      2100
T243   CAATTAAACACCCCAGTGTGAATGAGAACTTCTGCAATGAAAAGGAAGGGGCTCAGTTCA
       ::::::::::::::::::::::::::::::::::::::::::::::::::::::::::::
       CAATTAAACACCCCAGTGTGAATGAGAACTTCTGCAATGAAAAGGAAGGGGCTCAGTTCA
       1690      1700      1710      1720      1730      1740
```

FIG. 11D

```
              2110      2120      2130      2140      2150      2160
T243    GCAGTCATCTTATCAATCTTCTGAACCCTAAAGGAAAGCCAGCAAACCAGCTGCTTGCTC
        ::::::::::::::::::::::::::::::::::::::::::::::::::::::::::::
        GCAGTCATCTTATCAATCTTCTGAACCCTAAAGGAAAGCCAGCAAACCAGCTGCTTGCTC
        1750      1760      1770      1780      1790      1800

2170      2180      2190      2200      2210      2220
T243    TCAGGACTTTTTGCAATTGTTTTGTTGGCCAGGCAGGACAAAAACTCATGATGTCCCAGA
        ::::::::::::::::::::::::::::::::::::::::::::::::::::::::::::
        TCAGGACTTTTTGCAATTGTTTTGTTGGCCAGGCAGGACAAAAACTCATGATGTCCCAGA
        1810      1820      1830      1840      1850      1860

2230      2240      2250      2260      2270      2280
T243    GGGAATCACTGATGTCCCATGCAATAGAACTGAAATCAGGGAGCAATAAGAACATTCACA
        ::::::::::::::::::::::::::::::::::::::::::::::::::::::::::::
        GGGAATCACTGATGTCCCATGCAATAGAACTGAAATCAGGGAGCAATAAGAACATTCACA
        1870      1880      1890      1900      1910      1920

2290      2300      2310      2320      2330      2340
T243    TTGCTCTGGCTACATTGGCCCTGAACTATTCTGTTTGTTTTCATAAAGACCATAACATTG
        ::::::::::::::::::::::::::::::::::::::::::::::::::::::::::::
        TTGCTCTGGCTACATTGGCCCTGAACTATTCTGTTTGTTTTCATAAAGACCATAACATTG
        1930      1940      1950      1960      1970      1980

2350      2360      2370      2380      2390      2400
T243    AAGGGAAAGCCCAATGTTTGTCACTAATTAGCACAATCTTGGAAGTAGTACAAGACCTAG
        ::::::::::::::::::::::::::::::::::::::::::::::::::::::::::::
        AAGGGAAAGCCCAATGTTTGTCACTAATTAGCACAATCTTGGAAGTAGTACAAGACCTAG
        1990      2000      2010      2020      2030      2040

2410      2420      2430      2440      2450      2460
T243    AAGCCACTTTTAGACTTCTTGTGGCTCTTGGAACACTTATCAGTGATGATTCAAATGCTG
        ::::::::::::::::::::::::::::::::::::::::::::::::::::::::::::
        AAGCCACTTTTAGACTTCTTGTGGCTCTTGGAACACTTATCAGTGATGATTCAAATGCTG
        2050      2060      2070      2080      2090      2100

2470      2480      2490      2500      2510      2520
T243    TACAATTAGCCAAGTCTTTAGGTGTTGATTCTCAAATAAAAAAGTATTCCTCAGTATCAG
        ::::::::::::::::::::::::::::::::::::::::::::::::::::::::::::
        TACAATTAGCCAAGTCTTTAGGTGTTGATTCTCAAATAAAAAAGTATTCCTCAGTATCAG
        2110      2120      2130      2140      2150      2160

2530      2540      2550      2560      2570      2580
T243    AACCAGCTAAAGTAAGTGAATGCTGTAGATTTATCCTAAATTTGCTGTAGCAGTGGGGAA
        ::::::::::::::::::::::::::::::::::::::::::
        AACCAGCTAAAGTAAGTGAATGCTGTAGATTTATCCTAAATTTGCTGT      -----
        2170      2180      2190      2200      2210

2590      2600      2610      2620      2630      2640
T243    GAGGGACGGATATTTTTAATTGATTAGTGTTTTTTTCCTCACATTTGACATGACTGATAA

```
            2650      2660      2670      2680      2690      2700
T243   CAGATAATTAAAAAAAGAGAATACGGTGGATTAAGTAAAATTTTACATCTTGTAAAGTGG

------------------------------------------------------------

2710      2720      2730      2740      2750      2760
T243   TGGGGAGGGGAAACAGAAATAAAATTTTTGCACTGCTGAAAAAAAAAAAAAAAAAAAAAA

------------------------------------------------------------

2770      2780      2790      2800      2810
T243   AAAAAAAAAAAAAAAAAAAAAAAAAAAAAAAAAAAAAAAAAAAAAAAAAA

```
PLAP    ATG---------------------------------------------------------
        :::
        ATGACGAGCGGCGCAACCAGGTACCGGCTGAGCTGCTCGCTCCGGGGCCACGAGCTGGAC
                10        20        30        40        50        60

PLAP    ------------------------------------------------------------
        GTACGGGGCCTGGTGTGCTGCGCCTATCCGCCGGGAGCCTTTGTGTCCGTGTCCCGAGAC
                70        80        90       100       110       120

PLAP    ------------------------------------------------------CACTGT
                                                              ::::::
        CGCACCACCCGCCTCTGGGCCCCAGACAGTCCAAACAGGAGCTTTACAGAAATGCACTGT
               130       140       150       160       170       180

10        20        30        40        50        60
PLAP    ATGAGCGGCCACTCCAATTTTGTATCTTGTGTATGCATCATACCCTCAAGTGACATCTAC
        :::::  :::::  ::::::::::::::::::::::::::::::::::::::::::::::
        ATGAGTGGCCATTCCAATTTTGTATCTTGTGTATGCATCATACCCTCAAGTGACATCTAC
               190       200       210       220       230       240

70        80        90       100       110       120
PLAP    CCTCATGGCCTAATTGCCACCGGTGGAAATGACCACAATATATGCATTTTCTCACTGGAC
        ::::::::::::::::::::::::::::::::::::::::::::::::::::::::::::
        CCTCATGGCCTAATTGCCACCGGTGGAAATGACCACAATATATGCATTTTCTCACTGGAC
               250       260       270       280       290       300

130       140       150       160       170       180
PLAP    AGTCCAATGCCACTTTATATTCTAAAAGGCCACAAAAATACTGTTTGTAGTCTATCATCT
        ::::::::::::::::::::::::::::::::::::::::::::::::::::::::::::
        AGTCCAATGCCACTTTATATTCTAAAAGGCCACAAAAATACTGTTTGTAGTCTATCATCT
               310       320       330       340       350       360

190       200       210       220       230       240
PLAP    GGAAAATTTGGGACATTACTTAGTGGTTCATGGGACACCACTGCTAAAGTCTGGCTGAAT
        ::::::::::::::::::::::::::::::::::::::::::::::::::::::::::::
        GGAAAATTTGGGACATTACTTAGTGGTTCATGGGACACCACTGCTAAAGTCTGGCTGAAT
               370       380       390       400       410       420

250       260       270       280       290       300
PLAP    GACAAGTGCATGATGACCTTGCAGGGTCATACAGCTGCAGTGTGGCGGTAAAGATCTTA
        :::::::::::::::::::::::::::::::::::::::::::::::::::::::::::
        GACAAGTGCATGATGACCTTGCAGGGTCATACAGCTGCAGTGTGGCGGTAAAGATCTTA
               430       440       450       460       470       480
```

FIG. 12A

```
       310        320        330        340        350        360
PLAP   CCTGAACAGGGCTTAATGTTGACTGGATCAGCAGACAAGACTGTTAAACTGTGGAAGGCT
       ::::::::::::::::::::::::::::::::::::::::::::::::::::::::::::
       CCTGAACAGGGCTTAATGTTGACTGGATCAGCAGACAAGACTGTTAAACTGTGGAAGGCT
       490        500        510        520        530        540

370        380        390        400        410        420
PLAP   GGAAGATGTGAGAGGACTTTTTCAGGGCATGAAGACTGTGTAAGAGGTTTGGCAATTTTG
       ::::::::::::::::::::::::::::::::::::::::::::::::::::::::::::
       GGAAGATGTGAGAGGACTTTTTCAGGGCATGAAGACTGTGTAAGAGGTTTGGCAATTTTG
       550        560        570        580        590        600

430        440        450        460        470        480
PLAP   AGTGAAACAGAATTTCTTTCCTGTGCAAATGATGCTAGTATTAGAAGGTGGCAAATCACT
       ::::::::::::::::::::::::::::::::::::::::::::::::::::::::::::
       AGTGAAACAGAATTTCTTTCCTGTGCAAATGATGCTAGTATTAGAAGGTGGCAAATCACT
       610        620        630        640        650        660

490        500        510        520        530        540
PLAP   GGCGAGTGTCTTGAAGTATATTATGGACATACAAATTATATTTATAGCATATCCGTTTTT
       ::::::::::::::::::::::::::::::::::::::::::::::::::::::::::::
       GGCGAGTGTCTTGAAGTATATTATGGACATACAAATTATATTTATAGCATATCCGTTTTT
       670        680        690        700        710        720

550        560        570        580        590        600
PLAP   CCAAATTGTAGAGACTTTGTGACAACAGCAGAGGACAGATCTCTGAGAATCTGGAAACAT
       ::::::::::::::::::::::::::::::::::::::::::::::::::::::::::::
       CCAAATTGTAGAGACTTTGTGACAACAGCAGAGGACAGATCTCTGAGAATCTGGAAACAT
       730        740        750        760        770        780

610        620        630        640        650        660
PLAP   GGGGAATGTGCTCAAACTATCCGACTTCCAGCTCAGTCTATATGGTGCTGCTGTGTGCTC
       ::::::::::::::::::::::::::::::::::::::::::::::::::::::::::::
       GGGGAATGTGCTCAAACTATCCGACTTCCAGCTCAGTCTATATGGTGCTGCTGTGTGCTC
       790        800        810        820        830        840

670        680        690        700        710        720
PLAP   GACAATGGTGACATTGTGGTTGGTGCGAGTGATGGCATTATTAGAGTGTTTACAGAGTCA
       ::::::::::::::::::::::::::::::::::::::::::::::::::::::::.:::
       GACAATGGTGACATTGTGGTTGGTGCGAGTGATGGCATTATTAGAGTGTTTACAGAATCA
       850        860        870        880        890        900

730        740        750        760        770        780
PLAP   GAAGATCGAACAGCAAGTGCTGAAGAAATCAAGGCTTTTGAAAAGAACTGTCTCACGCA
       ::::::::::::::::::::::::::::::::::::::::::::::::::::::::::::
       GAAGATCGAACAGCAAGTGCTGAAGAAATCAAGGCTTTTGAAAAGAACTGTCTCACGCA
       910        920        930        940        950        960

790        800        810        820        830        840
PLAP   ACCATTGATTCTAAAACTGGCGATTTAGGGGACATCAATGCTGAGCAGCTTCCTGGGAGG
       :::::::::::::::::::::::::::::::::::::::::::::::::::::::::::
       ACCATTGATTCTAAAACTGGCGATTTAGGGGACATCAATGCTGAGCAGCTTCCTGGGAGG
       970        980        990        1000       1010       1020
```

FIG. 12B

```
              850         860        870        880         890         900
PLAP    GAACATCTTAATGAACCTGGTACTAGAGAAGGACAGACTCGTCTAATCAGAGATGGGGAG
        ::::::::::::::::::::::::::::::::::::::::::::::::::::::::::::
        GAACATCTTAATGAACCTGGTACTAGAGAAGGACAGACTCGTCTAATCAGAGATGGGGAG
             1030        1040       1050       1060        1070        1080

910         920        930        940         950         960
PLAP    AAAGTCGAAGCCTATCAGTGGAGTGTTAGTGAAGGGAGGTGGATAAAAATTGGTGATGTT
        ::::::::::::::::::::::::::::::::::::::::::::::::::::::::::::
        AAAGTCGAAGCCTATCAGTGGAGTGTTAGTGAAGGGAGGTGGATAAAAATTGGTGATGTT
             1090        1100       1110       1120        1130        1140

970         980        990       1000        1010        1020
PLAP    GTTGGCTCATCTGGTGCTAATCAGCAAACATCTGGAAAAGTTTTATATGAAGGGAAAGAA
        ::::::::::::::::::::::::::::::::::::::::::::::::::::::::::::
        GTTGGCTCATCTGGTGCTAATCAGCAAACATCTGGAAAAGTTTTATATGAAGGGAAAGAA
             1150        1160       1170       1180        1190        1200

1030        1040       1050       1060        1070        1080
PLAP    TTTGATTATGTTTTCTCAATTGATGTCAATGAAGGTGGACCATCATATAAATTGCCATAT
        ::::::::::::::::::::::::::::::::::::::::::::::::::::::::::::
        TTTGATTATGTTTTCTCAATTGATGTCAATGAAGGTGGACCATCATATAAATTGCCATAT
             1210        1220       1230       1240        1250        1260

1090        1100       1110       1120        1130        1140
PLAP    AATACCAGTGATGACCCTTGGTTAACTGCATACAACTTCTTACAGAAGAATGATTTGAAT
        ::::::::::::::::::::::::::::::::::::::::::::::::::::::::::::
        AATACCAGTGATGACCCTTGGTTAACTGCATACAACTTCTTACAGAAGAATGATTTGAAT
             1270        1280       1290       1300        1310        1320

1150        1160       1170       1180        1190        1200
PLAP    CCTATGTTTCTGGATCAAGTAGCTAAATTTATTATTGATAACACAAAAGGTCAAATGTTG
        ::::::::::::::::::::::::::::::::::::::::::::::::::::::::::::
        CCTATGTTTCTGGATCAAGTAGCTAAATTTATTATTGATAACACAAAAGGTCAAATGTTG
             1330        1340       1350       1360        1370        1380

1210        1220       1230       1240        1250        1260
PLAP    GGACTTGGGAATCCCAGCTTTTCAGATCCATTTACAGGTGGTGGTCGGTATGTTCCGGGC
        ::::::::::::::::::::::::::::::::::::::::::::::::::::::::::::
        GGACTTGGGAATCCCAGCTTTTCAGATCCATTTACAGGTGGTGGTCGGTATGTTCCGGGC
             1390        1400       1410       1420        1430        1440

1270        1280       1290       1300        1310        1320
PLAP    TCTTCGGGATCTTCTAACACACTACCCACAGCAGATCCTTTTACAGGTGCTGGTCGTTAT
        ::::::::::::::::::::::::::::::::::::::::::::::::::::::::::::
        TCTTCGGGATCTTCTAACACACTACCCACAGCAGATCCTTTTACAGGTGCTGGTCGTTAT
             1450        1460       1470       1480        1490        1500

1330        1340       1350       1360        1370        1380
PLAP    GTACCAGGTTCTGCAAGTATGGGAACTACCATGGCCGGAGTTGATCCATTTACAGGGAAT
        ::::::::::::::::::::::::::::::::::::::::::::::::::::::::::::
        GTACCAGGTTCTGCAAGTATGGGAACTACCATGGCCGGAGTTGATCCATTTACAGGGAAT
             1510        1520       1530       1540        1550        1560
```

FIG.12C

```
            1390      1400      1410      1420      1430      1440
PLAP    AGTGCCTACCGATCAGCTGCATCTAAAACAATGAATATTTATTTCCCTAAAAAAGAGGCT
        ::::::::::::::::::::::::::::::::::::::::::::::::::::::::::::
        AGTGCCTACCGATCAGCTGCATCTAAAACAATGAATATTTATTTCCCTAAAAAAGAGGCT
            1570      1580      1590      1600      1610      1620

1450      1460      1470      1480      1490      1500
PLAP    GTCACATTTGACCAAGCAAACCCTACACAAATATTAGGTAAACTGAAGGAACTTAATGGA
        ::::::::::::::::::::::::::::::::::::::::::::::::::::::::::::
        GTCACATTTGACCAAGCAAACCCTACACAAATATTAGGTAAACTGAAGGAACTTAATGGA
            1630      1640      1650      1660      1670      1680

1510      1520      1530      1540      1550      1560
PLAP    ACTGCACCTGAAGAGAAGAAGTTAACTGAGGATGACTTGATACTTCTTGAGAAGATACTG
        ::::::::::::::::::::::::::::::::::::::::::::::::::::::::::::
        ACTGCACCTGAAGAGAAGAAGTTAACTGAGGATGACTTGATACTTCTTGAGAAGATACTG
            1690      1700      1710      1720      1730      1740

1570      1580      1590      1600      1610      1620
PLAP    TCTCTAATATGTAATAGTTCTTCAGAAAAACCCACAGTCCAGCAACTTCAGATTTTGTGG
        ::::::::::::::::::::::::::::::::::::::::::::::::::::::::::::
        TCTCTAATATGTAATAGTTCTTCAGAAAAACCCACAGTCCAGCAACTTCAGATTTTGTGG
            1750      1760      1770      1780      1790      1800

1630      1640      1650      1660      1670      1680
PLAP    AAAGCTATTAACTGTCCTGAAGATATTGTCTTTCCTGCACTTGACATTCTTCGGTTGTCA
        ::::::::::::::::::::::::::::::::::::::::::::::::::::::::::::
        AAAGCTATTAACTGTCCTGAAGATATTGTCTTTCCTGCACTTGACATTCTTCGGTTGTCA
            1810      1820      1830      1840      1850      1860

1690      1700      1710      1720      1730      1740
PLAP    ATTAAACACCCCAGTGTGAATGAGAACTTCTGCAATGAAAAGGAAGGGGCTCAGTTCAGC
        ::::::::::::::::::::::::::::::::::::::::::::::::::::::::::::
        ATTAAACACCCCAGTGTGAATGAGAACTTCTGCAATGAAAAGGAAGGGGCTCAGTTCAGC
            1870      1880      1890      1900      1910      1920

1750      1760      1770      1780      1790      1800
PLAP    AGTCATCTTATCAATCTTCTGAACCCTAAAGGAAAGCCAGCAAACCAGCTGCTTGCTCTC
        ::::::::::::::::::::::::::::::::::::::::::::::::::::::::::::
        AGTCATCTTATCAATCTTCTGAACCCTAAAGGAAAGCCAGCAAACCAGCTGCTTGCTCTC
            1930      1940      1950      1960      1970      1980

1810      1820      1830      1840      1850      1860
PLAP    AGGACTTTTTGCAATTGTTTTGTTGGCCAGGCAGGACAAAAACTCATGATGTCCCAGAGG
        ::::::::::::::::::::::::::::::::::::::::::::::::::::::::::::
        AGGACTTTTTGCAATTGTTTTGTTGGCCAGGCAGGACAAAAACTCATGATGTCCCAGAGG
            1990      2000      2010      2020      2030      2040

1870      1880      1890      1900      1910      1920
PLAP    GAATCACTGATGTCCCATGCAATAGAACTGAAATCAGGGAGCAATAAGAACATTCACATT
        ::::::::::::::::::::::::::::::::::::::::::::::::::::::::::::
        GAATCACTGATGTCCCATGCAATAGAACTGAAATCAGGGAGCAATAAGAACATTCACATT
            2050      2060      2070      2080      2090      2100
```

FIG. 12D

```
        1930       1940       1950       1960       1970       1980
PLAP    GCTCTGGCTACATTGGCCCTGAACTATTCTGTTTGTTTTCATAAAGACCATAACATTGAA
        ::::::::::::::::::::::::::::::::::::::::::::::::::::::::::::
        GCTCTGGCTACATTGGCCCTGAACTATTCTGTTTGTTTTCATAAAGACCATAACATTGAA
            2110       2120       2130       2140       2150       2160

1990       2000       2010       2020       2030       2040
PLAP    GGGAAAGCCCAATGTTTGTCACTAATTAGCACAATCTTGGAAGTAGTACAAGACCTAGAA
        ::::::::::::::::::::::::::::::::::::::::::::::::::::::::::::
        GGGAAAGCCCAATGTTTGTCACTAATTAGCACAATCTTGGAAGTAGTACAAGACCTAGAA
            2170       2180       2190       2200       2210       2220

2050       2060       2070       2080       2090       2100
PLAP    GCCACTTTTAGACTTCTTGTGGCTCTTGGAACACTTATCAGTGATGATTCAAATGCTGTA
        ::::::::::::::::::::::::::::::::::::::::::::::::::::::::::::
        GCCACTTTTAGACTTCTTGTGGCTCTTGGAACACTTATCAGTGATGATTCAAATGCTGTA
            2230       2240       2250       2260       2270       2280

2110       2120       2130       2140       2150       2160
PLAP    CAATTAGCCAAGTCTTTAGGTGTTGATTCTCAAATAAAAAAGTATTCCTCAGTATCAGAA
        ::::::::::::::::::::::::::::::::::::::::::::::::::::::::::::
        CAATTAGCCAAGTCTTTAGGTGTTGATTCTCAAATAAAAAAGTATTCCTCAGTATCAGAA
            2290       2300       2310       2320       2330       2340

2170       2180       2190       2200       2210
PLAP    CCAGCTAAAGTAAGTGAATGCTGTAGATTTATCCTAAATTTGCTGTAG
        ::::::::::::::::::::::::::::::::::::::::::::::::
        CCAGCTAAAGTAAGTGAATGCTGTAGATTTATCCTAAATTTGCTGTAG
            2350       2360       2370       2380
```

FIG. 12E

```
           10         20         30         40         50         60
T243  MTSGATRYRLSCSLRGHELDVRGLVCCAYPPGAFVSVSRDRTTRLWAPDSPNRSFTEMHC
      :                                                          ::
      M-----------------------------------------------------------HC 70         80         90        100        110        120
T243  MSGHSNFVSCVCIIPSSDIYPHGLIATGGNDHNICIFSLDSPMPLYILKGHKNTVCSLSS
      ::::::::::::::::::::::::::::::::::::::::::::::::::::::::::::
      MSGHSNFVSCVCIIPSSDIYPHGLIATGGNDHNICIFSLDSPMPLYILKGHKNTVCSLSS
           10         20         30         40         50         60

130        140        150        160        170        180
T243  GKFGTLLSGSWDTTAKVWLNDKCMMTLQGHTAAVWAVKILPEQGLMLTGSADKTVKLWKA
      ::::::::::::::::::::::::::::::::::::::::::::::::::::::::::::
      GKFGTLLSGSWDTTAKVWLNDKCMMTLQGHTAAVWAVKILPEQGLMLTGSADKTVKLWKA
           70         80         90        100        110        120

190        200        210        220        230        240
T243  GRCERTFSGHEDCVRGLAILSETEFLSCANDASIRRWQITGECLEVYYGHTNYIYSISVF
      ::::::::::::::::::::::::::::::::::::::::::::::::::::::::::::
      GRCERTFSGHEDCVRGLAILSETEFLSCANDASIRRWQITGECLEVYYGHTNYIYSISVF
          130        140        150        160        170        180

250        260        270        280        290        300
T243  PNCRDFVTTAEDRSLRIWKHGECAQTIRLPAQSIWCCCVLDNGDIVVGASDGIIRVFTES
      ::::::::::::::::::::::::::::::::::::::::::::::::::::::::::::
      PNCRDFVTTAEDRSLRIWKHGECAQTIRLPAQSIWCCCVLDNGDIVVGASDGIIRVFTES
          190        200        210        220        230        240

310        320        330        340        350        360
T243  EDRTASAEEIKAFEKELSHATIDSKTGDLGDINAEQLPGREHLNEPGTREGQTRLIRDGE
      ::::::::::::::::::::::::::::::::::::::::::::::::::::::::::::
      EDRTASAEEIKAFEKELSHATIDSKTGDLGDINAEQLPGREHLNEPGTREGQTRLIRDGE
          250        260        270        280        290        300

370        380        390        400        410        420
T243  KVEAYQWSVSEGRWIKIGDVVGSSGANQQTSGKVLYEGKEFDYVFSIDVNEGGPSYKLPY
      ::::::::::::::::::::::::::::::::::::::::::::::::::::::::::::
      KVEAYQWSVSEGRWIKIGDVVGSSGANQQTSGKVLYEGKEFDYVFSIDVNEGGPSYKLPY
          310        320        330        340        350        360

430        440        450        460        470        480
T243  NTSDDPWLTAYNFLQKNDLNPMFLDQVAKFIIDNTKGQMLGLGNPSFSDPFTGGGRYVPG
      ::::::::::::::::::::::::::::::::::::::::::::::::::::::::::::
      NTSDDPWLTAYNFLQKNDLNPMFLDQVAKFIIDNTKGQMLGLGNPSFSDPFTGGGRYVPG
          370        380        390        400        410        420
```

FIG. 13A

```
              490        500        510        520        530        540
T243   SSGSSNTLPTADPFTGAGRYVPGSASMGTTMAGVDPFTGNSAYRSAASKTMNIYFPKKEA
       ::::::::::::::::::::::::::::::::::::::::::::::::::::::::::::
       SSGSSNTLPTADPFTGAGRYVPGSASMGTTMAGVDPFTGNSAYRSAASKTMNIYFPKKEA
              430        440        450        460        470        480

550        560        570        580        590        600
T243   VTFDQANPTQILGKLKELNGTAPEEKKLTEDDLILLEKILSLICNSSSEKPTVQQLQILW
       ::::::::::::::::::::::::::::::::::::::::::::::::::::::::::::
       VTFDQANPTQILGKLKELNGTAPEEKKLTEDDLILLEKILSLICNSSSEKPTVQQLQILW
              490        500        510        520        530        540

610        620        630        640        650        660
T243   KAINCPEDIVFPALDILRLSIKHPSVNENFCNEKEGAQFSSHLINLLNPKGKPANQLLAL
       ::::::::::::::::::::::::::::::::::::::::::::::::::::::::::::
       KAINCPEDIVFPALDILRLSIKHPSVNENFCNEKEGAQFSSHLINLLNPKGKPANQLLAL
              550        560        570        580        590        600

670        680        690        700        710        720
T243   RTFCNCFVGQAGQKLMMSQRESLMSHAIELKSGSNKNIHIALATLALNYSVCFHKDHNIE
       ::::::::::::::::::::::::::::::::::::::::::::::::::::::::::::
       RTFCNCFVGQAGQKLMMSQRESLMSHAIELKSGSNKNIHIALATLALNYSVCFHKDHNIE
              610        620        630        640        650        660

730        740        750        760        770        780
T243   GKAQCLSLISTILEVVQDLEATFRLLVALGTLISDDSNAVQLAKSLGVDSQIKKYSSVSE
       ::::::::::::::::::::::::::::::::::::::::::::::::::::::::::::
       GKAQCLSLISTILEVVQDLEATFRLLVALGTLISDDSNAVQLAKSLGVDSQIKKYSSVSE
              670        680        690        700        710        720

790
T243   PAKVSECCRFILNLL
       :::::::::::::::
       PAKVSECCRFILNLL
              730
```

FIG. 13B

```
                                    M   C   L   S   A   V   S   F   K   G   I   R   C    13
CGGCACAGGGCGACGGCCGCTCGCCA ATG TGC CTC TCT GCC GTT TCA TTC AAG GGA ATA AGA TGC   65

W   L   D   K   L   L   L   W   A   L   T   I   S   I   T   L   Q   N   A   A    33
TGG CTG GAC AAA CTG TTA CTT TGG GCT CTT ACA ATT TCT ATC ACA CTT CAG AAT GCT GCA  125

V   D   C   T   R   V   E   N   N   E   L   P   S   P   N   L   N   S   S   M    53
GTG GAT TGT ACG AGG GTG GAA AAT AAC GAA TTA CCT TCT CCA AAT CTG AAC TCA AGT ATG  185

N   V   V   R   M   G   Q   N   V   S   L   S   C   S   T   K   N   T   S   V    73
AAC GTG GTC AGG ATG GGC CAA AAT GTA TCT CTG TCT TGT TCC ACC AAG AAC ACA TCA GTA  245

D   I   T   Y   S   L   F   W   G   T   K   Y   L   E   S   K   R   R   R   G    93
GAC ATC ACC TAT TCG CTC TTC TGG GGT ACA AAA TAT CTA GAA AGC AAG AGA AGA CGA GGG  305

G   A   V   D   F   H   L   R   I   S   N   A   N   E   S   G   P   Y   K   C   113
GGA GCT GTG GAT TTC CAC CTG AGG ATC TCC AAT GCC AAC GAG TCA GGC CCC TAC AAA TGC  365

K   V   N   V   S   N   L   M   K   Y   S   Q   D   F   N   F   T   M   A   K   133
AAA GTC AAT GTT TCC AAC TTG ATG AAA TAC AGT CAG GAT TTC AAC TTC ACA ATG GCC AAA  425

D   E   S   C   P   S   C   R   L   S   L   L   L   P   G   L   L   L   G   I   153
GAT GAG AGC TGC CCT TCA TGC CGG CTG TCA CTG TTG CTC CCA GGG CTG TTA CTG GGG ATA  485

L   V   I   V   L   V   L   A   Y   L   I   H   L   K   Y   K   K   G   K   K   173
CTG GTA ATA GTC CTA GTT CTG GCT TAT TTG ATT CAT CTA AAA TAC AAA AAA GGA AAG AAG  545

T   Q   R   E   D   Q   S   K   G   S   G   D   A   P   A   Q   D   E   L   Y   193
ACT CAG AGA GAG GAC CAG TCC AAG GGT TCT GGA GAT GCG CCT GCA CAG GAC GAG CTG TAT  605

V   N   A   C   K   T   Q   T   E   Q   P   Q   E   I   H   Y   A   T   P   V   213
GTC AAC GCC TGC AAG ACT CAG ACA GAG CAA CCC CAG GAG ATA CAC TAT GCC ACT CCA GTC  665

F   K   E   M   A   P   M   E   E   E   G   G   T   D   G   K   A   D   Y   I   233
TTC AAG GAG ATG GCA CCC ATG GAA GAA GAA GGT GGT ACG GAT GGA AAA GCT GAT TAC ATC  725

Y   S   E   L   T   H   *                                                       240
TAC TCT GAA CTC ACC CAC TGA                                                      746

AGTGTGAAGAAACTGACTGTATCCCAGTGTAAAGACTTTCCAGTAAGCTGGTGTATGAGAAAATAGGAAAACTCACCTG  825

GCACTTAAGAGTTCCATTCTANGCTGANGCAGGAGGATCCTGAGTTTTGANGCCACTTGGGACTACATAGCAAGACCTG  904

GCTTAAA                                                                          911
```

FIG. 14

```
  1 CGGCACAGGGCGACGGCCGCTCGCCAATGTGCCTCTCTGCCGTTTCATTC  50
                     |. || || ||!    ||||
  1 ......................CTTCTGACCCCGTCTTGGACTTCAACT  27

51 AAGGGAATAAGATGCTGGCTGGACAAACTGTTACTTTGGGCTCTTACAAT 100
     | ||||  | ||    || ||   |  ||| || | ||    |
 28 GGGAGAATGTGGAGCCATTTGAGCAGGCTCCT.CTTCTGGAGCATATTTT  76

101 .TTCTATCACACTTCAGAATGCTGCAGTGGATTGTACGAGGGTGGAAAAT 149
     |||| ||||    |  || |||| | ||||||||   |    ||  |||
 77 CTTCTGTCACTTGTAGAAAAGCTGTATTGGATTGTGAGGCAATGAAAACA 126

150 AACGAATTACCTTCTCCAAATCTGAACTCAAGTATGAACGTGGTCAGGAT 199
    || |||||| ||||||||| | || |||||| | :| ||||| | ||
127 AATGAATTCCCTTCTCCATGTTTGGACTCAAAGACTAAGGTGGTTATGAA 176

200 GGGCCAAAATGTATCTCTGTCTTGTTCCACCAAGAACACATCAGTAGACA 249
    |||  |||||||||||| || ||| ||||||   ||||||| |||| | |  | |
177 GGGTCAAAATGTATCTATGTTTTGTTCCCATAAGAACAAATCACTGCAGA 226

250 TCACCTATTCGCTCTTCTGGGGTACAAAATATCTAGAAAGCAAGAGAAGA 299
    |||||||||  | ||  |  | !|!|  ||  |  | || | |  ||
227 TCACCTATTCATTGTTTCGACGTAAGACACACCTGGGAACCCAGGATGGA 276

300 CGAGGGGGAGCTGTGGATTTCCACCTGAGGATCTCCAATGCCAACGAGTC 349
    ||| |  |||  |  ||| |||| || ||| |  | ||| |  | || ||
277 AAAGGTGAACCTGCGATTTTTAACCTAAGCATCACAGAAGCCCATGAATC 326

350 AGGCCCCTACAAATGCAAAGTCAATGTTTCCAACTTGATGAAATACAGTC 399
    |||||||||||||||||||| | | ||| ||| ||    ||||||||||
327 AGGCCCCTACAAATGCAAAGCCCAAGTTACCAGCTGTTCAAAATACAGTC 376

400 AGGATTTCAACTTCACAATGGCCAA...AGATG........AGAGCTGCCC 439
    || |||| ||||||| || | ||    | ||        || |||| |
377 GTGACTTCAGCTTCACGATTGTCGACCCGGTGACTTCCCCAGTGCTGAAC 426

440 TTCATGCCGGCTGTCACTGTTGCTCCCAGGGCTGTTAC......TGGGA 483
    | ||| |  | ||  | |  | |||  |  | | ||  || |  | ||
427 ATTATGGTCATTCAAACAGAAACAGACCGACATATAACATTACATTGCCT 476

484 TACTGGTAATAG.TC.CT.......AGTTCTGGCTTATTTGA........ 516
    | |  ||| || ||  | ||  |     || || |||||
477 CTCAGTCAATGGCTCGCTGCCCATCAATTACACTTTCTTTGAAAACCATG 526

517 TT..CATCTAA......AATACAAAAAGGA.AAGAAGACTCAGAGAGAG 557
    ||  ||| | |       |.| |||| |  ||| | |||| ||    |
527 TTGCCATATCACCAGCTATTTCCAAGTATGACAGGGAGCCTGCTGAATTT 576
```

FIG. 15A

```
558 GACCAGTCC...AAGGGTTCTGGAGATGCG..CCTGCACAGG........ 594
        ||    ||   |||  | |||||||| | |       !  | |||
577 AACTTAACCAAGAAGAATCCTGGAGAAGAGGAAGAGTATAGGTGTGAAGC 626

595 .ACGAGCTGTATGTCAACGCCTGCAAGACTCAGACAGAGCAACCCCAGGA 643
     !  !  | |   !! | |      '|!||| |  !|| ||     ! |||  '
627 TAAAAACAGATTGCCTAACTATGCAACATACAGTCACCCTGTCACCATGC 676

644 GAT..ACACTATGCCAC.....TCCAGTCTTCAAGGAGATGGCAC..CCA 684
        |  |||     |  ||      |||  |||     | ! |    ||  !;!
677 CCTCAACAGGCGGAGACAGCTGTCCTTTCTGTCTGAAGCTACTACTTCCA 726

685 TGGAAGAAGAAGGTGGTACGGATGGAAAAGCTGATTACATC.TACTCTGA 733
    ||         i || |   | ||  ||  || !! |||     | | |  |
727 GGGTTATTACTGTTGCTGGTGGTGATAATCCTAATTCTGGCTTTTTGGGT 776

734 ACTCACCCACT.........GAAGTGTGAAGAAACTGACTGTATCC.... 770
    |||   || | |        |||  |  ! || |    | |||   ||
777 ACTGCCCAAATACAAAACAAGAAAAGCTATGAGAAATAATGTGCCCAGGG 826

771 .CAGTGTAAAGACTTTCCAGTAAGCTGGTGTATGAGAAAATA.....GGA 814
     | ||| | | ||    |   | ||| |||  | |   | |||||        | |
827 ACCGTGGAGACACAGCCATGGAAGTTGGAATCTATGCAAATATCCTTGAA 876

815 AAACTCACCTGGCACTTAAGAGTTCCA.TTCTANGCT.GANGCAG.GAGG 861
    ||||    |    | |   |    || |||        |  :| |   |:||  | | |
877 AAACAAGCAAAGGAGGAATCTGTGCCAGAAGTGGGATCCAGGCCGTGTGT 926

862 ATCCTGAG....TTTTGANGCCA.......CTTGGGACTACA.TA.GCAA 898
    |||   ||       |||:||||         |  ||  ||||||  ||  || | |
927 TTCCACAGCCCAAGATGAGGCCAAACACTCCCAGGAGCTACAGTATGCCA 976

899 GACCTGGCTTAAA............................... 911
        ||  |  ||   |
977 CCCCCGTGTTCCAGGAGGTGGCACCAAGAGAGCAAGAAGCCTGTGATTCT 1026
```

FIG. 15B

```
  1 ATGTGCCTCTCTGCCGTTTCATTCAAGGGAATAAGATGCTGGCTGGACAA  50
                            ||  |  ||    ||   ||
  1 ........................ATGTGGAGCCATTTGAGCAG        20

51 ACTGTTACTTTGGGCTCTTACAAT.TTCTATCACACTTCAGAATGCTGCA  99
    ||  |  |||  ||  |  ||     |  ||||  ||||    |  ||  ||||| |
 21 GCTCCT.CTTCTGGAGCATATTTCTTCTGTCACTTGTAGAAAAGCTGTA   69

100 GTGGATTGTACGAGGGTGGAAAATAACGAATTACCTTCTCCAAATCTGAA 149
    |||||||  |     ||  |||  ||  ||||| |||||||||   |  ||  |
 70 TTGGATTGTGAGGCAATGAAAACAAATGAATTCCCTTCTCCATGTTTGGA 119

150 CTCAAGTATGAACGTGGTCAGGATGGGCCAAAATGTATCTCTGTCTTGTT 199
    |||||   |   ||  ||||||   |  |||  |||||||||||||||| |||  |||||
120 CTCAAAGACTAAGGTGGTTATGAAGGGTCAAAATGTATCTATGTTTTGTT 169

200 CCACCAAGAACACATCAGTAGACATCACCTATTCGCTCTTCTGGGGTACA 249
    ||   ||||||| ||||  |   |  ||||||||||||   |  ||   |||
170 CCCATAAGAACAAATCACTGCAGATCACCTATTCATTGTTTCGACGTAAG 219

250 AAATATCTAGAAAGCAAGAGAAGACGAGGGGGAGCTGTGGATTTCCACCT 299
    |  |  |  |||  |  ||  ||   |||  |  |  |||   |||  |||  ||||
220 ACACACCTGGGAACCCAGGATGGAAAAGGTGAACCTGCGATTTTAACCT  269

300 GAGGATCTCCAATGCCAACGAGTCAGGCCCCTACAAATGCAAAGTCAATG 349
    ||  |||  |   |  |||  |  ||  ||||||||||||||||||||||||| |  | |
270 AAGCATCACAGAAGCCCATGAATCAGGCCCCTACAAATGCAAAGCCCAAG  319

350 TTTCCAACTTGATGAAATACAGTCAGGATTTCAACTTCACAATGGCCAAA 399
    || ||| ||        |||||||||| || |||| ||||||  ||  |  |
320 TTACCAGCTGTTCAAAATACAGTCGTGACTTCAGCTTCACGATTGTCGAC 369

400 GATGAGAGCTGCCCTTCATGCCGGCTGTCACTGT..TGCTCCCAGGGCTG 447
    | ||  |  |||   |||  |   |  ||  || |  |||
370 CCGGTGACTTCCCC..AGTGCTGAACATTATGGTCATTCAAACAGAAACA 417

448 TTACTGGGGATACTGGTA.ATAG..TCCTAGT.TCTGGCTTATTTGATTC 493
     |      |||   ||  || |  ||  |||   |||||     |        |
418 GACCGACATATAACATTACATTGCCTCTCAGTCAATGGCTCGCT...GCCC 465

494 ATCTAAAATACAAAAAGGAAAGAAGACTCAGAGAGAGGACCAG.....T  538
    |||  |  ||       ||||  |     |  | |  |||||  |
466 ATCAATTACACTTTCTTTGAAA.ACCATGTTGCCATATCACCAGCTATTT 514
```

FIG. 16A

```
539 CCAAGGGTTCTGGAGATGCGCCTGCACAGGA......CGAGCTGTAT.GT 581
    |||||  |    | ||  |  |||.|   |        | ||  | ||  |
515 CCAAGTATGACAGGGAGCCTGCTGAATTTAACTTAACCAAGAAGAATCCT 564

582 CAACGCCTGCAAGACTCAGACAGAGCAAC.CCCAGGAGAT....ACACTA 626
       |  ||||| |      ||||    |    ||||        ||||
565 GGAGAAGAGGAAGAGTATAGGTGTGAAGCTAAAAACAGATTGCCTAACTA 614

627 TGCCAC.TCCAGTCTTCAAG..GAGATGGCACCCATGGAAGAAGAAGGTG 673
    ||| || | |||||  |  |       ||| ;  | |  | |  |||  |
615 TGCAACATACAGTCACCCTGTCACCATGCCCTCAACAGGCGGAGACAGCT 664

674 GTACGGATGG..AAAAGCTGATTACATCTACTCTGA..ACTCACCCAC.. 717
    || |    |       |||||| | ||| ||  |  |  |   |||    |
665 GTCCTTTCTGTCTGAAGCT.ACTACTTCCAGGGTTATTACTGTTGCTGGT 713
```

FIG. 16B

```
  1 MCLSAVSFKGIRCWLDKLLLWALTISITLQNAAVDCTRVENNELPSPNLN  50
             . |:|| |.: _|:| . | .||  .. || ||| |.
  1 ..........MWSHLSRLLFWSIFSSVTCRKAVLDCEAMKTNEFPSPCLD  40

51 SSMNVVRMGQNVSLSCSTKNTSVDITYSLFWGTKYLESKRRRGGAVDFHL 100
    |   || |||||: || || |. ||||||    :| .. :|    |.|
 41 SKTKVVMKGQNVSMFCSHKNKSLQITYSLFRRKTHLGTQDGKGEPAIFNL  90

101 RISNANESGPYKCKVNVSNLMKYSQDFNFTMAKDESCPSCRLSLLLPGLL 150
    |. |.|||||||| |..  |||.||.||.   . |   : .:
 91 SITEAHESGPYKCKAQVTSCSKYSRDFSFTIVDPVTSPVLNIMVIQTETD 140

151 LGILVIVLVLAYLIHLKYKKGKKTQREDQSKGSGD.APAQDELYVNACKT 199
        |  . |.  :: |  .     .   |   ||: |
141 RHITLHCLSVNGSLPINYTFFENHVAISPAISKYDREPAEFNLTKKNPGE 190

200 QTEQPQEIHYATPVFKEMAPMEEEGGTDGKADYIYSELTH.......... 239
    :|   |    |:  .       || .    .|
191 EEEYRCEAKNRLPNYATYSHPVTMPSTGGDSCPFCLKLLLPGLLLLLVVI 240
```

FIG. 17

```
        M   A   A   P   A   R   E   P   A   L   R   C   C   I   R   L   A   R   V    19
    C ATG GCT GCG CCC GCG CGA GAG CCG GCT CTC CGC TGC TGC ATC AGA CTG GCG CGA GTC    58

F   L   L   L   V   L   A   C   E   V   A   G   S   D   E   A   E   A   R   E    39
  TTC TTG CTG CTG GTG TTG GCG TGC GAG GTG GCG GGA AGC GAT GAG GCC GAG GCC AGG GAA   118

G   A   A   S   L   A   G   S   C   G   C   G   T   P   Q   R   A   G   A   H    59
  GGT GCG GCG TCC CTT GCG GGC TCG TGC GGC TGC GGA ACG CCC CAG AGG GCC GGG GCC CAT   178

G   S   S   A   A   A   Q   R   Y   S   R   E   A   N   A   P   G   L   T   S    79
  GGC AGC TCG GCG GCG GCG CAG CGC TAC TCC CGG GAG GCG AAC GCC CCG GGC CTG ACC TCA   238

G   P   R   P   L   A   L   T   K   M   V   P   I   P   A   G   V   F   T   M    99
  GGC CCG CGA CCG CTC GCG CTC ACC AAG ATG GTC CCC ATT CCT GCT GGA GTA TTC ACA ATG   298

G   T   D   D   P   Q   I   R   Q   D   G   E   A   P   A   R   R   V   T   V   119
  GGC ACT GAT GAT CCT CAG ATC AGG CAG GAT GGA GAA GCC CCT GCC AGG AGA GTC ACT GTT   358

D   G   F   Y   M   D   A   Y   E   V   S   N   A   D   F   E   K   F   V   N   139
  GAT GGC TTT TAC ATG GAC GCC TAT GAA GTC AGC AAT GCG GAT TTT GAG AAG TTT GTG AAC   418

S   T   G   Y   L   T   E   A   E   K   F   G   D   S   F   V   F   E   G   M   159
  TCG ACT GGC TAT TTG ACA GAG GCT GAG AAG TTT GGA GAC TCT TTC GTC TTT GAA GGC ATG   478

L   S   E   Q   V   K   T   H   I   H   Q   A   V   A   A   A   P   W   W   L   179
  TTG AGC GAG CAA GTG AAA ACG CAT ATC CAC CAG GCA GTT GCA GCT GCT CCA TGG TGG TTG   538

P   V   K   G   A   N   W   R   H   P   E   G   P   D   S   S   I   L   H   R   199
  CCT GTC AAG GGA GCT AAT TGG AGA CAC CCA GAG GGT CCG GAC TCC AGT ATT CTG CAC AGG   598

S   N   H   P   V   L   H   V   S   W   N   D   A   V   A   Y   C   T   W   A   219
  TCA AAT CAT CCG GTT CTC CAT GTT TCC TGG AAC GAT GCT GTT GCC TAC TGC ACA TGG GCG   658

G   K   R   L   P   T   E   A   E   W   E   Y   S   C   R   G   G   L   Q   N   239
  GGC AAG AGG TTG CCT ACT GAG GCA GAG TGG GAA TAC AGC TGT AGA GGA GGC CTG CAG AAC   718

R   L   F   P   W   G   N   K   L   Q   P   K   G   Q   H   Y   A   N   I   W   259
  AGG CTT TTC CCC TGG GGC AAC AAA CTG CAG CCC AAA GGA CAG CAT TAT GCC AAC ATC TGG   778

Q   G   K   F   P   V   S   N   T   G   E   D   G   F   Q   G   T   A   P   V   279
  CAG GGC AAG TTT CCT GTG AGC AAC ACT GGC GAG GAT GGC TTC CAA GGA ACT GCC CCC GTT   838

D   A   F   P   P   N   G   Y   G   L   Y   N   I   V   G   N   V   W   E   W   299
  GAT GCC TTT CCT CCC AAT GGC TAT GGC TTA TAC AAC ATA GTG GGG AAT GTG TGG GAG TGG   898

T   S   D   W   W   T   V   H   H   S   V   E   E   T   F   N   P   K   G   P   319
  ACC TCA GAC TGG TGG ACT GTT CAC CAT TCT GTT GAG GAA ACG TTC AAC CCA AAG GGT CCC   958
```

FIG. 18A

```
  T   S   G   K   D   R   V   K   K   G   S   Y   M   C   H   K   S   Y   C     339
ACT TCT GGG AAA GAC CGA GTG AAG AAG GGT GGA TCC TAC ATG TGC CAT AAG TCC TAT TGC  1018

Y   R   Y   R   C   A   A   R   S   Q   N   T   P   D   S   S   A   S   N   L 359
TAT AGG TAC CGC TGT GCA GCT CGA AGC CAG AAC ACA CCA GAT AGC TCT GCA TCC AAC CTG 1078

G   F   R   C   A   A   D   H   L   P   T   A   D   *                         373
GGA TTC CGA TGT GCA GCC GAC CAC CTG CCC ACC GCA GAC TGA                          1120
```

CAGCCAAGAGGAGCTTTTCCAGATTCAAGAAGGCGTTTCTTACTCGCAGCTGGCCTCCCCTGGAAATCTGAACTGATCT 1199

CATGTAAAGTATTCCCATCTACGGAGGATTCCATGTCCACCCAGTGGCCAAAGGAACTGTCTCGCGTGACCAAATGGCT 1278

GGCGAGTGTCAGCACGTGTGCTTTATTGTGTGGTGTATCTTTGGGGATCATCGCCATGTTTTACTTTGAAAGCCTTTTG 1357

AAGAGGAGAGAGCCGAGAACCAGGAAGTCCTGGCCAGACTCTGCCACAGGGTCAGACCCTGGAGTCCAGCACCTTGTCT 1436

GCCTTGACCTCTGTCTCCTCATGAAATGAGGGATGGTCAACGTGATCTTTGAGGCTCTCTCCAACTCTATTTGAACTAG 1515

CAGATTCTATTCGAACTAGCAGAGTGTATTGTGATTGCATAGTGAGAATTTATGACAGATTATTTTTTAGCTATTTTTT 1594

TGCCATGTGTGAATCTTGAGTAATACTAATCATATAAGGCGAGAGTTATCTTACATATTATTTTCAGAAAAGGGTGGGG 1673

TTTGAGTCTTTTATATTCATACTGCACTTTGTTCTTTCAAGGAAATCAGTGTCTTTTACATTGTTGTGACAAATCCCAT 1752

TGGGACAGCGAGGGGACACTTAAGTTTGGAGTTCTGAACACACAGGAATGCCTGTGGAGTGACTCTACTGTCCTTTTTC 1831

TTTTGACATTAAGTGCCTTTGGCTCAGAGGGACAGTTTGAAGCCTTGTTTCCCCTTTGCCCCCAAGCCTTCAAAGAATG 1910

TGAAATATGTACTAATTAGGGAAACCATTTAATTCTAGGTCTTTGGGTGTTGAGGTTTTGTCAGATGGTATGAATTGTA 1989

TTGTAATGCTAAATCTGGTACCTGAAGGTCTAGGCCTGTGAGTGAATTCTCACATTTACAAGATTTTGTTGTGCAAACC 2068

TTGTTCCTTAATTTAAAACTATTGGTTAAATAAAATTGGCTACAGCCAATTACTGGAGGGATTAGAGGTAGGTGGGTTT 2147

TGAGTGTGGTTGGGTATGGAGAGAGAGAGGAGAGATCAAGGAGAGAAGCAGGAAGAAGAGGATAGGAGGAGCTGCCATG 2226

AAGAAGATGGACCATAAGCCTTTGTCCAGAGGAAACTCCCAAGTATCTGGGAACACCGCTGTGAGGCAACCAGGCCAGC 2305

AGTTAGAAAAGTAGATTAGGGGCTACCCCCAGTAATTGTCAAAGCCAAATAAAATATCAAAAAAAAAAAAAAAAAAAAA 2384

AAAAAAAAAAAAAAAAAAAAAAAAAACAAAAAAAAAAAAAAA                                     2426

FIG. 18B

```
  1 CATGGCTGCGCCCGCGCGAGAGCCGGCTCTCCGCTGCTGCATCAGACTGG  50
    ||||||||||||||| | || || ||       |  | |||    ||||
  1 CATGGCTGCGCCCGCACTAGGGCTGGTGTGTGGACGTTGCCCTGAGCTGG  50

51 CGCGAGTCTTCTTGCTGCTGGT......GTTGGCGTGCGAGGTGGCGGGA  94
       |   ||| ||||||||||| |      | ||  ||| |  | ||| ||
 51 GTCTCGTCCTCTTGCTGCTGCTGCTCTCGCTGCTGTGTGGAGCGGCAGGG  100

95 AGCGATGAGGCCGAGGCCAGGGAAGGTGCGGCGTCCCTTGCGGGCTCGTG  144
    ||| | ||||||| | || | |   ||  |||| ||||||||||| || ||
101 AGCCAGGAGGCCGGGACCGGTGCGGGCGCGGGGTCCCTTGCGGGTTCTTG  150

145 CGGCTGCGGAACGCCCCAGAGGGCCGGGGCCCATGGCAGCTCGGCGGCGG  194
    |||||||||  ||||||||| || |  || |||||||||   !!!!! || |
151 CGGCTGCGGCACGCCCCAGCGGCCTGGCGCCCATGGCAATTCGGCAGCCG  200

195 CGCAGCGCTACTCCCGGGAGGCGAACGCCCCGGGCCTGACCTCAGGCCCG  244
    |  || || ||||| ||||||||| ||||| ||||||| |||      |  ||   |
201 CTCACCGATACTCGCGGGAGGCTAACGCTCCGGGCCCCGTACCCGGAGAG  250

245 CGACCGCTCGCGCTCACCAAGATGGTCCCCATTCCTGCTGGAGTATTCAC  294
    || |    |||||||| | || |||||||||||||.|||| |||  ||||||||||| ||
251 CGGCAACTCGCGCACTCAAAGATGGTCCCCATCCCTGTTGGAGTATTTAC  300

295 AATGGGCACTGATGATCCTCAGATCAGGCAGGATGGAGAAGCCCCTGCCA  344
    |||||||| |||||||||||||||| |  ||||||||| |||||  |||||  |
301 AATGGGCACAGATGATCCTCAGATAAAGCAGGATGGGGAAGCACCTGCGA  350

345 GGAGAGTCACTGTTGATGGCTTTTACATGGACGCCTATGAAGTCAGCAAT  394
    ||||||| ||| |||||| ||||||||||| ||||||||||||||||||| |||
351 GGAGAGTTACTATTGATGCCTTTTACATGGATGCCTATGAAGTCAGTAAT  400

395 GCGGATTTTGAGAAGTTTGTGAACTCGACTGGCTATTTGACAGAGGCTGA  444
    | ||  ||||||||||||||||||||| |||||||||||||||||||||| |
401 ACTGAATTTGAGAAGTTTGTGAACTCAACTGGCTATTTGACAGAGGCTGA  450

445 GAAGTTTGGAGACTCTTTCGTCTTTGAAGGCATGTTGAGCGAGCAAGTGA  494
    |||||||| |||||| ||| || ||||||||||||||||||||| !||||||||| |
451 GAAGTTTGGCGACTCCTTTGTCTTTGAAGGCATGTTGAGTGAGCAAGTGA  500

495 AAACGCATATCCACCAGGCAGTTGCAGCTGCTCCATGGTGGTTGCCTGTC  544
    | ||   ||||  || |||||||||||||||||||| ||||||||  |||||
501 AGACCAATATTCAACAGGCAGTTGCAGCTGCTCCCTGGTGGTTACCTGTG  550

545 AAGGGAGCTAATTGGAGACACCCAGAGGGTCCGGACTCCAGTATTCTGCA  594
    || || |||||| ||||||||||||||| || || |||||  | ||||||||||
551 AAAGGCGCTAACTGGAGACACCCAGAAGGGCCTGACTCTACTATTCTGCA  600
```

FIG. 19A

```
595  CAGGTCAAATCATCCGGTTCTCCATGTTTCCTGGAACGATGCTGTTGCCT  644
     ||||  | ||||||| |||||||||| ||||||||  |||||  |||||||
601  CAGGCCGGATCATCCAGTTCTCCATGTGTCCTGGAATGATGCGGTTGCCT  650

645  ACTGCACATGGGCGGGCAAGAGGTTGCCTACTGAGGCAGAGTGGGAATAC  694
     |||||| |||||| ||| || |||| || || || |||||||||||||
651  ACTGCACTTGGGCAGGGAAGCGGCTGCCCACGGAAGCTGAGTGGGAATAC  700

695  AGCTGTAGAGGAGGCCTGCAGAACAGGCTTTTCCCCTGGGGCAACAAACT  744
     |||||| |||||||||||| || || |||||||||||||||||||||||
701  AGCTGTCGAGGAGGCCTGCATAATAGACTTTTCCCCTGGGGCAACAAACT  750

745  GCAGCCCAAAGGACAGCATTATGCCAACATCTGGCAGGGCAAGTTTCCTG  794
     |||||||||||| |||||||||||||||| ||||||||| |||||||| |
751  GCAGCCCAAAGGCCAGCATTATGCCAACATTTGGCAGGGCGAGTTTCCGG  800

795  TGAGCAACACTGGCGAGGATGGCTTCCAAGGAACTGCCCCCGTTGATGCC  844
     ||| |||||||||| ||||||||||||||||||||||||| || |||||||||
801  TGACCAACACTGGTGAGGATGGCTTCCAAGGAACTGCGCCTGTTGATGCC  850

845  TTTCCTCCCAATGGCTATGGCTTATACAACATAGTGGGGAATGTGTGGGA  894
     || ||||||||||| |||||||||||||||||||||||||  | |||||
851  TTCCCTCCCAATGGTTATGGCTTATACAACATAGTGGGGAACGCATGGGA  900

895  GTGGACCTCAGACTGGTGGACTGTTCACCATTCTGTTGAGGAAACGTTCA  944
     |||||  |||||||||||||||||||| ||||||||||  |||||| |  |
901  ATGGACTTCAGACTGGTGGACTGTTCATCATTCTGTTGAAGAAACGCTTA  950

945  ACCCAAAGGGTCCCACTTCTGGGAAAGACCGAGTGAAGAAGGGTGGATCC  994
     |||||||  ||||||  |||||||||||||||||||||||||||||||||
951  ACCCAAAAGGTCCCCCTTCTGGGAAAGACCGAGTGAAGAAAGGTGGATCC  1000

995  TACATGTGCCATAAGTCCTATTGCTATAGGTACCGCTGTGCAGCTCGAAG  1044
     |||||||||||||| ||| ||||| || ||||| ||||||| || || ||
1001 TACATGTGCCATAGGTCTTATTGTTACAGGTATCGCTGTGCTGCTCGGAG  1050

1045 CCAGAACACACCAGATAGCTCTGCATCCAACCTGGGATTCCGATGTGCAG  1094
     |||||||||||  |||||||||| || || ||||||||||||| ||||||
1051 CCAGAACACACCTGATAGCTCTGCTTCGAATCTGGGATTCCGCTGTGCAG  1100

1095 CCGACCACCTGCCCACCGCAGACTGACAGCCAAGAGGAGCTTTTCCAGAT  1144
     ||||||  ||||||||| |||| |||||  ||||| || || || |    |
1101 CCGACCGCCTGCCCACTATGGACTGACAACCAAGGAAAGTCTTCCCCAGT  1150
```

FIG. 19B

```
1145 TCA...AGAAGGCGTTTCTTACTCGCAGCTGGCCTCCCCTGGAAATCTGA 1191
     ||   || || ||| ||| ||    ||   ||| |   |  ||| | |||
1151 CCAAGGAGCAGTCGTGTCTGACCTACATTGGGCTTTTCTCAGAACTTTGA 1200

1192 ACTGATCTCATGTAAAGTATTCCCA.TCTACGGAGGATTCCATGTCCACC 1240
     || |||| |||| |||| ||||||   || || ||  ||  || |   ||
1201 AC.GATCCATGCAAAGAATTCCCACCCTGAGGTGGGTTACATACCTGCC 1249

1241 CAGTGGCCAAAGGAACTGTCTCGCGTGACCAAATGGCTGGCGAGTGTCAG 1290
     || |||||||||||||| | ||  |  |||||||||| ||| | | |||||
1250 CAATGGCCAAAGGAACCGCCTTGTGAGACCAAATTGCTGACCTGGGTCAG 1299

1291 CACGTGTGCTTTATTGTGTGGTGTATCTTTGGGGATCATCGCCATGTTTT 1340
     |  ||||||||||| ||||||||  ||||||||| ||||||||||| |||| ||||
1300 TGCATGTGCTTTATGGTGTGGTGCATCTTTGGAGATCATCGCCATATTTT 1349

1341 AC.TTTGAAAGCCTTT..........TGAAGAGGAGAGAGCCGAGAAC... 1377
     || |||||| || ||||          | || |||| || ||  ||| |
1350 ACTTTTGAGAGTCTTTAAAGAGGAAGGGGAGTGGAGGGAACCCTGAGCTA 1399

1378 .....CAGGA......AGTCCTGGCCAGACTCTGCCACA.GGGTCAGACC 1415
          |||||       |||||    |||  ||||||||||| |||| |||||
1400 GGCTTCAGGAGGCCCGCGTCCTACGCAGGCTCTGCCACAGGGGTTAGACC 1449

1416 CTGGAGTCCAGCACCTTGTCTGCCTTGACCTC.TGTCTCCTC....ATGA 1460
     |  | |||| ||| |   ||  ||| | |||| ||  ||||       || |
1450 CCAG.GTCCGACGCTTGACCTTCCTGGGCCTCAAGTGCCCTCCCTATCA 1498

1461 AATG.AGGGATGGTCAACGTGATCTTTGAGGCTCTCTCCAACTCTATTTG 1509
     ||||  |||||||| || | ||| || || |    ||||||||||||
1499 AATGAAGGGATGGACAGCATGACCTCTGGGTGTCTCTCCAACTC...... 1542

1510 AACTAGCAGATTCTATTCGAACTAGCAGAGTGTATTGTGATTGCATAGTG 1559
       | ||| |||||           ||  |||| | |||||||||| | |||||||
1543 ....ACCAG.TTCTAAAAGGGTATCAGATTCTATTGTGACTTCATAGTG 1587

1560 AGAATTTATGACAGATTATTTTTAGCTATTTTTTGCCATGTGTGAATC 1609
     ||||||||||| ||||||||||||||||||||||||||   |||||||||| |
1588 AGAATTTATGATAGATTATTTTTAGCTATTTTT...CCATGTGTGAACC 1635

1610 TTGAGTAATACTAATCATATAAGGCGAGAGTTATCTTACATATTATTTTC 1659
     ||||||  ||||||||||| |||       |||||| |||||  ||||||||||
1636 TTGAGTGATACTAATCATGTAAAGTAAGAGTTCTCTTATGTATTATTTTC 1685
```

FIG. 19C

```
1660 AGAAAAGGGTGGGGTTTGAGTCTTTTATATTCATACTGCACTTTGTTCTT 1709
     ||| ||||  |     ||| !! |||||||||| |||||||||||||| ||
1686 GGAAGAGGG.GTGTGGTGACTCCTTTATATTCGTACTGCACTTTGTTTTT 1734

1710 TCAAGGAAATCAGTGTCTTTTACATTGTTGTGACAAATCC...CATTGGGA 1757
     ||||||||||||||||||||||:|| ||||| |||  |||||  ||| |||
1735 CCAAGGAAATCAGTGTCTTTTACGTTGTTATGATGAATCCCACATGGGGC 1784

1758 CAGCGAGGGGACACTTAAGTTTGGAGTTCTGAACACACAGGAATGCCTGT 1807
     |  || ||  |   ||||  |   |  |||||||| |||||| ||||
1785 CGGTGATGGTATGCTGCAGTTCAGCCGT.TGAACACATAGGAATGTCTGT 1833

1808 GGAGTGACTCTACTGTCCTTTTTCTTTTGACATTAAGTGCCTTTGGCTCA 1857
     || |||||||||||| |||| |||||| ||||||||||||||||| |||
1834 GGGGTGACTCTACTGTGCTTTATCTTTTAACATTAAGTGCCTTTGGTTCA 1883

1858 GAGGGACAGTTTGAAGCCTTGTTTCCCCTTTGCCCCCAAGCCTTCAAAGA 1907
     ||||| ||||    ||||  :,!||||||| |  ||| |||||||||| ||
1884 GAGGGCAGTCATAAGCTCTGTTTCCCCTCTCCCCAAAGCCTTCAGCGA 1933

1908 ATGTGAAATATGTACTAATTAGGGAAACC.ATTTAATTCTAGGTCTTTGG 1956
     |  ||||||| ||  ||||   .|||||||  |||||||||||   ||| |
1934 ACGTGAAATGTGCGCTAAACGGGGAAACCTGTTTAATTCTAG...ATATAG 1981

1957 GTGTTGAGGTTTTGTCAGATGGTATGAATTGTATT...GTAATGCTAAAT 2003
     |    |||       |     ||||  |   |   |||   |  |   ||
1982 GGAAAAAGGAACGAGGACCTTGAATGAGCTATATTCAGGGTATCCGGTAT 2031

2004 CTGGTACCTGAAGGTCTAGGCCTGTGAGTGAATTCTCACATTTACAAGAT 2053
     | |||      | ||  ||||   ||        |  |  ||  ||||||
2032 TTTGTA..ATAGGGAATAGGAAACCTTGTTGGCTGTGGAATATCCGATGC 2079

2054 TTTGTTGTGCAAACCTTGTTCCTTAATTTAAAACTATTGGTTAAATAAAA 2103
     ||||           ||  ||  |  || ||||    |||   ||||  ||||
2080 TTTGAATCATGCACTGTGT...TGAA...TAAACGTATCTGCTAAAAAAA 2124

2104 TTGGCTACAGCCAATTACTGGAGGGATTAGAGGTAGGTGGGTTTTGAGTG 2153
     | |  ||  |     |  |   |   |
2125 AAAAAAAAAAAAAAAAAAAAAAAAAAAAAAAAAAAAAAAA......... 2165
```

FIG. 19D

```
  1 ATGGCTGCGCCCGCGCGAGAGCCGGCTCTCCGCTGCTGCATCAGACTGGC  50
    |||||||||||||| | || || ||     |  | |||      ||||
  1 ATGGCTGCGCCCGCACTAGGGCTGGTGTGTGGACGTTGCCCTGAGCTGGG  50

51 GCGAGTCTTCTTGCTGCTGGT......GTTGGCGTGCGAGGTGGCGGGAA  94
      |   ||| |||||||||||| |     | || ||| |  | ||| || |
 51 TCTCGTCCTCTTGCTGCTGCTCTCGCTGCTGTGTGGAGCGGCAGGGA   100

95 GCGATGAGGCCGAGGCCAGGGAAGGTGCGGCGTCCCTTGCGGGCTCGTGC  144
    ;| | ||||||| | || | |  || |||| |||||||||||| || |||
101 GCCAGGAGGCCGGGACCGGTGCGGGCGCGGGTCCCTTGCGGTTCTTGC    150

145 GGCTGCGGAACGCCCCAGAGGGCCGGGGCCCATGGCAGCTCGGCGGCGGC  194
    ||||||||  |||||||||| || | || |||||||||||  ||||| ||
151 GGCTGCGGCACGCCCCAGCGGCCTGGCGCCCATGGCAATTCGGCAGCCGC  200

195 GCAGCGCTACTCCCGGGAGGCGAACGCCCCGGGCCTGACCTCAGGCCCGC  244
    || || |||||  ||||||||  |||||  |||||       |  ||  ||
201 TCACCGATACTCGCGGGAGGCTAACGCTCCGGGCCCCGTACCCGGAGAGC  250

245 GACCGCTCGCGCTCACCAAGATGGTCCCCATTCCTGCTGGAGTATTCACA  294
    ! |  |||||||  | |  |||||||||||| |||| |||||||||| |||
251 GGCAACTCGCGCACTCAAAGATGGTCCCCATCCCTGTTGGAGTATTTACA  300

295 ATGGGCACTGATGATCCTCAGATCAGGCAGGATGGAGAAGCCCCTGCCAG  344
    ||||||||  ||||||||||||||   |  |||||||||||||  ||||| ||
301 ATGGGCACAGATGATCCTCAGATAAAGCAGGATGGGGAAGCACCTGCGAG  350

345 GAGAGTCACTGTTGATGGCTTTTACATGGACGCCTATGAAGTCAGCAATG  394
    |||||| ||| |||||| ||||||||||||  |||||||||||||||||||   |||
351 GAGAGTTACTATTGATGCCTTTTACATGGATGCCTATGAAGTCAGTAATA  400

395 CGGATTTTGAGAAGTTTGTGAACTCGACTGGCTATTTGACAGAGGCTGAG  444
    | || ||||||||||||||||||||| ||||||||||||||||||||||||||||||||
401 CTGAATTTGAGAAGTTTGTGAACTCAACTGGCTATTTGACAGAGGCTGAG  450

445 AAGTTTGGAGACTCTTTCGTCTTTGAAGGCATGTTGAGCGAGCAAGTGAA  494
    ||||||| ||||| || ||||||||||||||||||||||| |||||||||
451 AAGTTTGGCGACTCCTTTGTCTTTGAAGGCATGTTGAGTGAGCAAGTGAA  500

495 AACGCATATCCACCAGGCAGTTGCAGCTGCTCCATGGTGGTTGCCTGTCA  544
    ||   |||| || |||||||||||||||||||||||| ||||||    || |
501 GACCAATATTCAACAGGCAGTTGCAGCTGCTCCCTGGTGGTTACCTGTGA  550
```

FIG. 20A

```
 545 AGGGAGCTAATTGGAGACACCCAGAGGGTCCGGACTCCAGTATTCTGCAC  594
     | || ||||| |||||||||||||| || || ||||| | ||||||||||
 551 AAGGCGCTAACTGGAGACACCCAGAAGGGCCTGACTCTACTATTCTGCAC  600

595 AGGTCAAATCATCCGGTTCTCCATGTTTCCTGGAACGATGCTGTTGCCTA  644
     ||| | |||||||| ||||||||||||| |||||||| ||||| ||||||
 601 AGGCCGGATCATCCAGTTCTCCATGTGTCCTGGAATGATGCGGTTGCCTA  650

645 CTGCACATGGGCGGGCAAGAGGTTGCCTACTGAGGCAGAGTGGGAATACA  694
      ||||| ||||| || || |||| || || || |||||||||||||
 651 CTGCACTTGGGCAGGGAAGCGGCTGCCCACGGAAGCTGAGTGGGAATACA  700

695 GCTGTAGAGGAGGCCTGCAGAACAGGCTTTTCCCCTGGGGCAACAAACTG  744
     ||||| ||||||||||||| || || |||||||||||||||||||||||
 701 GCTGTCGAGGAGGCCTGCATAATAGACTTTTCCCCTGGGGCAACAAACTG  750

745 CAGCCCAAAGGACAGCATTATGCCAACATCTGGCAGGGCAAGTTTCCTGT  794
     |||||||||| |||||||||||||||||| ||||||||| ||||||| ||
 751 CAGCCCAAAGGCCAGCATTATGCCAACATTTGGCAGGGCGAGTTTCCGGT  800

795 GAGCAACACTGGCGAGGATGGCTTCCAAGGAACTGCCCCCGTTGATGCCT  844
     || ||||||||| |||||||||||||||||||||||| || |||||||||
 801 GACCAACACTGGTGAGGATGGCTTCCAAGGAACTGCGCCTGTTGATGCCT  850

845 TTCCTCCCAATGGCTATGGCTTATACAACATAGTGGGGAATGTGTGGGAG  894
     | ||||||||| |||||||||||||||||||||||||||| | |||||
 851 TCCCTCCCAATGGTTATGGCTTATACAACATAGTGGGGAACGCATGGGAA  900

895 TGGACCTCAGACTGGTGGACTGTTCACCATTCTGTTGAGGAAACGTTCAA  944
     ||||| ||||||||||||||||||||| |||||||| |||||| || ||
 901 TGGACTTCAGACTGGTGGACTGTTCATCATTCTGTTGAAGAAACGCTTAA  950

945 CCCAAAGGGTCCCACTTCTGGGAAAGACCGAGTGAAGAAGGGTGGATCCT  994
     |||||| |||||| |||||||||||||||||||||||||| |||||||||
 951 CCCAAAAGGTCCCCCTTCTGGGAAAGACCGAGTGAAGAAAGGTGGATCCT  1000

995 ACATGTGCCATAAGTCCTATTGCTATAGGTACCGCTGTGCAGCTCGAAGC  1044
     |||||||||||| ||| |||| ||||| |||||||||| ||||||| |||
1001 ACATGTGCCATAGGTCTTATTGTTACAGGTATCGCTGTGCTGCTCGGAGC  1050

1045 CAGAACACACCAGATAGCTCTGCATCCAACCTGGGATTCCGATGTGCAGC  1094
     |||||||||| |||||||||| || || |||||||||||| |||||||||
1051 CAGAACACACCTGATAGCTCTGCTTCGAATCTGGGATTCCGCTGTGCAGC  1100

1095 CGACCACCTGCCCACCGCAGAC  1116
     ||||| |||||||||||  |||
1101 CGACCGCCTGCCCACTATGGAC  1122
```

FIG. 20B

```
  1 MAAPAREPALRCCIRLARVFLLLVLA..CEVAGSDEAEAREGAASLAGSC   48
    |||||       |  |  |||·|·   |   |||  ||      ||  ||||||
  1 MAAPALGLVCGRCPELGLVLLLLLLSLLCGAAGSQEAGTGAGAGSLAGSC   50

49 GCGTPQRAGAHGSSAAAQRYSREANAPGLTSGPRPLALTKMVPIPAGVFT   98
    |||||||  ||||·||||  ||||||||||     |  ||  ·|||||| ||||
 51 GCGTPQRPGAHGNSAAAHRYSREANAPGPVPGERQLAHSKMVPIPVGVFT  100

99 MGTDDPQIRQDGEAPARRVTVDGFYMDAYEVSNADFEKFVNSTGYLTEAE  148
    |||||||:||||||||||·|  ||||||||||·||||||||||||||||
101 MGTDDPQIKQDGEAPARRVTIDAFYMDAYEVSNTEFEKFVNSTGYLTEAE  150

149 KFGDSFVFEGMLSEQVKTHIHQAVAAAPWWLPVKGANWRHPEGPDSSILH  198
    |||||||||||||||||||·| |||||||||||||||||||||||||·|||
151 KFGDSFVFEGMLSEQVKTNIQQAVAAAPWWLPVKGANWRHPEGPDSTILH  200

199 RSNHPVLHVSWNDAVAYCTWAGKRLPTEAEWEYSCRGGLQNRLFPWGNKL  248
    | ·|||||||||||||||||||||||||||||||||||| |||||||||
201 RPDHPVLHVSWNDAVAYCTWAGKRLPTEAEWEYSCRGGLHNRLFPWGNKL  250

249 QPKGQHYANIWQGKFPVSNTGEDGFQGTAPVDAFPPNGYGLYNIVGNVWE  298
    ||||||||||·|||·||||||||||||||||||||||||||||||||| ||
251 QPKGQHYANIWQGEFPVTNTGEDGFQGTAPVDAFPPNGYGLYNIVGNAWE  300

299 WTSDWWTVHHSVEETFNPKGPTSGKDRVKKGGSYMCHKSYCYRYRCAARS  348
    |||||||||||||| |||||  |||||||||||||:|||||||||||||
301 WTSDWWTVHHSVEETLNPKGPPSGKDRVKKGGSYMCHRSYCYRYRCAARS  350

349 QNTPDSSASNLGFRCAADHLPTAD  372
    ||||||||||||||||||| ||| |
351 QNTPDSSASNLGFRCAADRLPTMD  374
```

FIG. 21

```
      R   P   A   R   R   A   P   S   Q   P   P   F   R   T   G   S   R   A   L       19
     CT CGG CCC GCT CGG CGC GCC CCT TCC CAG CCG CCC TTC CGT ACC GGC TCT CGG GCT CTT      59

P   V   S   G   R   P   L   P   A   G   S   S   P   A   A   A   R   R   S   P       39
 CCG GTC TCC GGC CGC CCC TTA CCT GCA GGC TCT TCT CCC GCC GCG GCC CGG CGC TCT CCG      119

S   R   P   C   G   L   V   S   H   S   A   W   A   P   G   A   R   Q   T   L       59
 AGT CGC CCC TGC GGA CTG GTC TCG CAC AGT GCC TGG GCA CCG GGC GCC AGA CAG ACA CTG      179

A   M   T   S   G   A   T   R   Y   R   L   S   C   S   L   R   G   H   E   L       79
 GCC ATG ACG AGC GGC GCA ACC AGG TAC CGG CTG AGC TGC TCG CTC CGG GGC CAC GAG CTG      239

D   V   R   G   L   V   C   C   A   Y   P   P   G   A   F   V   S   V   S   R       99
 GAC GTA CGG GGC CTG GTG TGC TGC GCC TAT CCG CCG GGA GCC TTT GTG TCC GTG TCC CGA      299

D   R   T   T   R   L   W   A   P   D   S   P   N   R   S   F   T   E   M   H      119
 GAC CGC ACC ACC CGC CTC TGG GCC CCA GAC AGT CCA AAC AGG AGC TTT ACA GAA ATG CAC      359

C   M   S   G   H   S   N   F   V   S   C   V   C   I   I   P   S   S   D   I      139
 TGT ATG AGT GGC CAT TCC AAT TTT GTA TCT TGT GTA TGC ATC ATA CCC TCA AGT GAC ATC      419

Y   P   H   G   L   I   A   T   G   G   N   D   H   N   I   C   I   F   S   L      159
 TAC CCT CAT GGC CTA ATT GCC ACC GGT GGA AAT GAC CAC AAT ATA TGC ATT TTC TCA CTG      479

D   S   P   M   P   L   Y   I   L   K   G   H   K   N   T   V   C   S   L   S      179
 GAC AGT CCA ATG CCA CTT TAT ATT CTA AAA GGC CAC AAA AAT ACT GTT TGT AGT CTA TCA      539

S   G   K   F   G   T   L   L   S   G   S   W   D   T   T   A   K   V   W   L      199
 TCT GGA AAA TTT GGG ACA TTA CTT AGT GGT TCA TGG GAC ACC ACT GCT AAA GTC TGG CTG      599

N   D   K   C   M   M   T   L   Q   G   H   T   A   A   V   W   A   V   K   I      219
 AAT GAC AAG TGC ATG ATG ACC TTG CAG GGT CAT ACA GCT GCA GTG TGG GCG GTA AAG ATC      659

L   P   E   Q   G   L   M   L   T   G   S   A   D   K   T   V   K   L   W   K      239
 TTA CCT GAA CAG GGC TTA ATG TTG ACT GGA TCA GCA GAC AAG ACT GTT AAA CTG TGG AAG      719

A   G   R   C   E   R   T   F   S   G   H   E   D   C   V   R   G   L   A   I      259
 GCT GGA AGA TGT GAG AGG ACT TTT TCA GGG CAT GAA GAC TGT GTA AGA GGT TTG GCA ATT      779

L   S   E   T   E   F   L   S   C   A   N   D   A   S   I   R   R   W   Q   I      279
 TTG AGT GAA ACA GAA TTT CTT TCC TGT GCA AAT GAT GCT AGT ATT AGA AGG TGG CAA ATC      839

T   G   E   C   L   E   V   Y   Y   G   H   T   N   Y   I   Y   S   I   S   V      299
 ACT GGC GAG TGT CTT GAA GTA TAT TAT GGA CAT ACA AAT TAT ATT TAT AGC ATA TCC GTT      899

F   P   N   C   R   D   F   V   T   T   A   E   D   R   S   L   R   I   W   K      319
 TTT CCA AAT TGT AGA GAC TTT GTG ACA ACA GCA GAG GAC AGA TCT CTG AGA ATC TGG AAA      959

H   G   E   C   A   Q   T   I   R   L   P   A   Q   S   I   W   C   C   C   V      339
 CAT GGG GAA TGT GCT CAA ACT ATC CGA CTT CCA GCT CAG TCT ATA TGG TGC TGC TGT GTG     1019
```

FIG. 22A

```
  L   D   N   G   D   I   V   V   G   A   S   D   G   I   I   R   V   F   T   E   359
 CTC GAC AAT GGT GAC ATT GTG GTT GGT GCG AGT GAT GGC ATT ATT AGA GTG TTT ACA GAA  1079

S   E   D   R   T   A   S   A   E   E   I   K   A   F   E   K   E   L   S   H   379
 TCA GAA GAT CGA ACA GCA AGT GCT GAA GAA ATC AAG GCT TTT GAA AAA GAA CTG TCT CAC  1139

A   T   I   D   S   K   T   G   D   L   G   D   I   N   A   E   Q   L   P   G   399
 GCA ACC ATT GAT TCT AAA ACT GGC GAT TTA GGG GAC ATC AAT GCT GAG CAG CTT CCT GGG  1199

R   E   H   L   N   E   P   G   T   R   E   G   Q   T   R   L   I   R   D   G   419
 AGG GAA CAT CTT AAT GAA CCT GGT ACT AGA GAA GGA CAG ACT CGT CTA ATA AGA GAT GGG  1259

E   K   V   E   A   Y   Q   W   S   V   S   E   G   R   W   I   K   I   G   D   439
 GAG AAA GTC GAA GCC TAT CAG TGG AGT GTT AGT GAA GGG AGG TGG ATA AAA ATT GGT GAT  1319

V   V   G   S   S   G   A   N   Q   Q   T   S   G   K   V   L   Y   E   G   K   459
 GTT GTT GGC TCA TCT GGT GCT AAT CAG CAA ACA TCT GGA AAA GTT TTA TAT GAA GGG AAA  1379

E   F   D   Y   V   F   S   I   D   V   N   E   G   G   P   S   Y   K   L   P   479
 GAA TTT GAT TAT GTT TTC TCA ATT GAT GTC AAT GAA GGT GGA CCA TCA TAT AAA TTG CCA  1439

Y   N   T   S   D   D   P   W   L   T   A   Y   N   F   L   Q   K   N   D   L   499
 TAT AAT ACC AGT GAT GAC CCT TGG TTA ACT GCA TAC AAC TTC TTA CAG AAG AAT GAT TTG  1499

N   P   M   F   L   D   Q   V   A   K   F   I   I   D   N   T   K   G   Q   M   519
 AAT CCT ATG TTT CTG GAT CAA GTA GCT AAA TTT ATT ATT GAT AAC ACA AAA GGT CAA ATG  1559

L   G   L   G   N   P   S   F   S   D   P   F   T   G   G   G   R   Y   V   P   539
 TTG GGA CTT GGG AAT CCC AGC TTT TCA GAT CCA TTT ACA GGT GGT GGT CGG TAT GTT CCG  1619

G   S   S   G   S   S   N   T   L   P   T   A   D   P   F   T   G   A   G   R   559
 GGC TCT TCG GGA TCT TCT AAC ACA CTA CCC ACA GCA GAT CCT TTT ACA GGT GCT GGT CGT  1679

Y   V   P   G   S   A   S   M   G   T   T   M   A   G   V   D   P   F   T   G   579
 TAT GTA CCA GGT TCT GCA AGT ATG GGA ACT ACC ATG GCC GGA GTT GAT CCA TTT ACA GGG  1739

N   S   A   Y   R   S   A   A   S   K   T   M   N   I   Y   F   P   K   K   E   599
 AAT AGT GCC TAC CGA TCA GCT GCA TCT AAA ACA ATG AAT ATT TAT TTC CCT AAA AAA GAG  1799

A   V   T   F   D   Q   A   N   P   T   Q   I   L   G   K   L   K   E   L   N   619
 GCT GTC ACA TTT GAC CAA GCA AAC CCT ACA CAA ATA TTA GGT AAA CTG AAG GAA CTT AAT  1859

G   T   A   P   E   E   K   K   L   T   E   D   D   L   I   L   L   E   K   I   639
 GGA ACT GCA CCT GAA GAG AAG AAG TTA ACT GAG GAT GAC TTG ATA CTT CTT GAG AAG ATA  1919

L   S   L   I   C   N   S   S   S   E   K   P   T   V   Q   Q   L   Q   I   L   659
 CTG TCT CTA ATA TGT AAT AGT TCT TCA GAA AAA CCC ACA GTC CAG CAA CTT CAG ATT TTG  1979

W   K   A   I   N   C   P   E   D   I   V   F   P   A   L   D   I   L   R   L   679
 TGG AAA GCT ATT AAC TGT CCT GAA GAT ATT GTC TTT CCT GCA CTT GAC ATT CTT CGG TTG  2039

S   I   K   H   P   S   V   N   E   N   F   C   N   E   K   E   G   A   Q   F   699
 TCA ATT AAA CAC CCC AGT GTG AAT GAG AAC TTC TGC AAT GAA AAG GAA GGG GCT CAG TTC  2099
```

FIG. 22B

```
  S   S   H   L   I   N   L   L   N   P   K   G   K   P   A   N   Q   L   L   A      719
AGC AGT CAT CTT ATC AAT CTT CTG AAC CCT AAA GGA AAG CCA GCA AAC CAG CTG CTT GCT     2159

L   R   T   F   C   N   C   F   V   G   Q   A   G   Q   K   L   M   M   S   Q      739
TTC AGG ACT TTT TGC AAT TGT TTT GTT GGC CAG GCA GGA CAA AAA CTC ATG ATG TCC CAG     2219

R   E   S   L   M   S   H   A   I   E   L   K   S   G   S   N   K   N   I   H      759
AGG GAA TCA CTG ATG TCC CAT GCA ATA GAA CTG AAA TCA GGG AGC AAT AAG AAC ATT CAC     2279

I   A   L   A   T   L   A   L   N   Y   S   V   C   F   H   K   D   H   N   I      779
ATT GCT CTG GCT ACA TTG GCC CTG AAC TAT TCT GTT TGT TTT CAT AAA GAC CAT AAC ATT     2339

E   G   K   A   Q   C   L   S   L   I   S   T   I   L   E   V   V   Q   D   L      799
GAA GGG AAA GCC CAA TGT TTG TCA CTA ATT AGC ACA ATC TTG GAA GTA GTA CAA GAC CTA     2399

E   A   T   F   R   L   L   V   A   L   G   T   L   I   S   D   D   S   N   A      819
GAA GCC ACT TTT AGA CTT CTT GTG GCT CTT GGA ACA CTT ATC AGT GAT GAT TCA AAT GCT     2459

V   Q   L   A   K   S   L   G   V   D   S   Q   I   K   K   Y   S   S   V   S      839
GTA CAA TTA GCC AAG TCT TTA GGT GTT GAT TCT CAA ATA AAA AAG TAT TCC TCA GTA TCA     2519

E   P   A   K   V   S   E   C   C   R   F   I   L   N   L   *                      856
GAA CCA GCT AAA GTA AGT GAA TGC TGT AGA TTT ATC CTA AAT TTG CTG TAG                 2570

CAGTGGGGAAGAGGGACGGATATTTTTAATTGATTAGTGTTTTTTTCCTCACATTTGACATGACTGATAACAGATAATT    2649

AAAAAAAGAGAATACGGTGGATTAAGTAAAATTTTACATCTTGTAAAGTGGTGGGGAGGGGAAACAGAAATAAAATTTT    2728

TGCACTGCTGAAAAAAAAAAAAAAAAAAAAAAAAAAAAAAAAAAAAAAAAAAAAAAAAAAAAAAAAAAAAAAAAAAAAA    2807

AAAA                                                                                2811
```

FIG. 22C

TANGO 243 POLYPEPTIDES AND USES THEREOF

RELATED APPLICATIONS

This application is a continuation of U.S. application Ser. No. 09/928,788, filed Aug. 13, 2001, now abandoned, which is a continuation of U.S. application Ser. No. 09/514,009, filed Feb. 25, 2000, now abandoned, which is a continuation-in-part of U.S. application Ser. No. 09/259,387, filed Feb. 26, 1999, now abandoned.

BACKGROUND OF THE INVENTION

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted and transmembrane proteins and the genes which encode them.

Many secreted proteins are receptors which bind a ligand and transduce an intracellular signal, leading to a variety of cellular responses. The identification and characterization of such a receptor enables one to identify both the ligands which bind to the receptor and the intracellular molecules and signal transduction pathways associated with the receptor, permitting one to identify or design modulators of receptor activity, e.g., receptor agonists or antagonists and modulators of signal transduction.

SUMMARY OF THE INVENTION

The present invention is based, at least in part, on the discovery of cDNA molecules which encode the TANGO 228, 240, and 243 proteins, all of which are either wholly secreted or transmembrane proteins.

The TANGO 228 proteins are homologous to rat surface protein MCA-32 (mast cell Ag-32), a component of the immunologic pathway.

The TANGO 240 proteins are homologous to the *Mycobacterium tuberculosis* conserved hypothetical protein Rv0712.

The TANGO 243 proteins share significant homology to human PLAP (phospholipase A2-activating protein), a modulator of arthropathic disorders.

The TANGO 228, TANGO 240, and TANGO 243 proteins, fragments, derivatives, and variants thereof are collectively referred to herein as "polypeptides of the invention" or "proteins of the invention." Nucleic acid molecules encoding the polypeptides or proteins of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable for use as primers or hybridization probes for the detection of nucleic acids encoding a polypeptide of the invention.

The invention features nucleic acid molecules which are at least 30% (or 35%, 40%, 45%, 50%, 55%, 65%, 75%, 85%, 95%, or 98%) identical to the nucleotide sequence of SEQ ID NO:1, the nucleotide sequence of the cDNA insert of a clone deposited with ATCC as Accession Number 207116, or a complement thereof.

The invention features nucleic acid molecules which are at least 48% (or 50%, 55%, 60%, 65%, 75%, 85%, 95%, or 98%) identical to the nucleotide sequence of SEQ ID NO:2, the nucleotide sequence of the cDNA insert of a clone deposited with ATCC as Accession Number 207116, or a complement thereof.

The invention features nucleic acid molecules which are at least 30% (or 40%, 45%, 50%, 55%, 65%, 75%, 85%, 95%, or 98%) identical to the nucleotide sequence of SEQ ID NO:13 or 14, the nucleotide sequence of the cDNA insert of a clone deposited with ATCC as Accession Number 207116, or a complement thereof.

The invention features nucleic acid molecules which are at least 80% (or 82%, 85%, 87%, 90%, 92%, 95%, or 98%) identical to the nucleotide sequence of SEQ ID NO:19, the nucleotide sequence of the cDNA insert of a clone deposited with ATCC as Accession Number 207116, or a complement thereof.

The invention features nucleic acid molecules which are at least 93% (or 94%, 95%, 96%, 97%, or 98%) identical to the nucleotide sequence of SEQ ID NO:20, the nucleotide sequence of the cDNA insert of a clone deposited with ATCC as Accession Number 207116, or a complement thereof.

The invention features nucleic acid molecules which include a fragment of at least 310 (400, 500, 600, 800, 1000, 1250, 1500, 1750, 2000, 2250, 2500, 2750, 3000, 3250, 3500, 3750, 4000, or 4020) nucleotides of the nucleotide sequence of SEQ ID NO:1 the nucleotide sequence of the cDNA of ATCC Accession Number 207116, or a complement thereof.

The invention features nucleic acid molecules which are at least 30% (or 40%, 45%, 50%, 55%, 65%, 75%, 85%, 95%, or 98%) identical to the nucleotide sequence of SEQ ID NO:31 or 32, or a complement thereof.

The invention features nucleic acid molecules which are at least 30% (or 40%, 45%, 50%, 55%, 65%, 75%, 85%, 95%, or 98%) identical to the nucleotide sequence of SEQ ID NO:39 or 40, or a complement thereof.

The invention features nucleic acid molecules which include a fragment of at least 515 (530, 550, 600, 700, 800, 900, 1000, 1100, 1200, 1300, 1400, 1500, 1600, 1700, 1800, 1900, 2000, 2100, or 2150) nucleotides of the nucleotide sequence of SEQ ID NO:13, the nucleotide sequence of the cDNA of ATCC Accession Number 207116, or a complement thereof.

The invention features nucleic acid molecules which include a fragment of at least 2220 (2260, 2300, 2340, 2380, 2420, 2460, 2500, 2540, 2580, 2620, 2660, 2700, 2740, 2780, or 2800) nucleotides of the nucleotide sequence of SEQ ID NO:19, the nucleotide sequence of the cDNA of ATCC Accession Number 207116, or a complement thereof.

The invention features nucleic acid molecules which include a fragment of at least 50 (100, 150, 200, 250, 300, 350, 400, 450, 500, 550, 600, 650, 700, 750, 800, or 900) nucleotides of the nucleotide sequence of SEQ ID NO:31 or 32, or a complement thereof.

The invention features nucleic acid molecules which include a fragment of at least 50 (100, 150, 200, 250, 300, 350, 400, 450 500, 550, 600, 700, 800, 900, 1000, 1100, 1200, 1300, 1400, 1500, 1600, 1700, 1800, 1900, 2000, 2100, or 220) nucleotides of the nucleotide sequence of SEQ ID NO:39 or 40, or a complement thereof.

The invention also features nucleic acid molecules which include a nucleotide sequence encoding a protein having an amino acid sequence that is at least 30% (or 35%, 40%, 45%, 50%, 55%, 60%, 65%, 75%, 85%, 95%, or 98%) identical to the amino acid sequence of SEQ ID NO:3, the amino acid sequence encoded by the cDNA of ATCC Accession Number 207116, or a complement thereof.

The invention also features nucleic acid molecules which include a nucleotide sequence encoding a protein having an amino acid sequence that is at least 35% (or 40%, 45%, 50%, 55%, 65%, 75%, 85%, 95%, or 98%) identical to the amino acid sequence of SEQ ID NO:15, the amino acid sequence encoded by the cDNA of ATCC Accession Number 207116, or a complement thereof.

The invention also features nucleic acid molecules which include a nucleotide sequence encoding a protein having an amino acid sequence that is at least 93% (or 94%, 95%, 96%, 97% or 98%) identical to the amino acid sequence of SEQ ID NO:21, the amino acid sequence encoded by the cDNA of ATCC Accession Number 207116, or a complement thereof.

The invention also features nucleic acid molecules which include a nucleotide sequence encoding a protein having an amino acid sequence that is at least 35% (or 40%, 45%, 50%, 55%, 65%, 75%, 85%, 95%, or 98%) identical to the amino acid sequence of SEQ ID NO:33, the amino acid sequence encoded by the cDNA of ATCC Accession Number 207116, or a complement thereof.

The invention also features nucleic acid molecules which include a nucleotide sequence encoding a protein having an amino acid sequence that is at least 35% (or 40%, 45%, 50%, 55%, 65%, 75%, 85%, 95%, or 98%) identical to the amino acid sequence of SEQ ID NO:41, the amino acid sequence encoded by the cDNA of ATCC Accession Number 207116, or a complement thereof.

The invention also features nucleic acid molecules which include a nucleotide sequence encoding a protein having an amino acid sequence that is at least 35% (or 40%, 45%, 50%, 55%, 65%, 75%, 85%, 95%, or 98%) identical to the amino acid sequence of SEQ ID NO:45, the amino acid sequence encoded by the cDNA of ATCC Accession Number 207116, or a complement thereof.

In preferred embodiments, the nucleic acid molecules have the nucleotide sequence of SEQ ID NO:1, 2, 13, 14, 19, 20, 31, 32, 39, 40, 44 or the nucleotide sequence of the cDNA of ATCC Accession Number 207116.

Also within the invention are nucleic acid molecules which encode a fragment of a polypeptide having the amino acid sequence of SEQ ID NO:3, or a fragment including at least 15 (25, 30, 50, 75, 100, 125, 150, 175, 200, 225, 250, 275, 300, or 340) contiguous amino acids of SEQ ID NO:3, or the amino acid sequence encoded by the cDNA of ATCC Accession Number 207116.

Also within the invention are nucleic acid molecules which encode a fragment of a polypeptide having the amino acid sequence of SEQ ID NO:15, or a fragment including at least 15 (25, 30, 50, 75, 100, 125, 150, 175, 200, 225, 250, 275, 300, 325, 350, 360, or 370) contiguous amino acids of SEQ ID NO:15, or the amino acid sequence encoded by the cDNA of ATCC Accession Number 207116.

Also within the invention are nucleic acid molecules which encode a fragment of a polypeptide having the amino acid sequence of SEQ ID NO:21, or a fragment including at least 740 (745, 750, 755, 760, 765, 770, 775, 780, 785, 790) contiguous amino acids of SEQ ID NO:21, or the amino acid sequence encoded by the cDNA of ATCC Accession Number 207116.

Also within the invention are nucleic acid molecules which encode a fragment of a polypeptide having the amino acid sequence of SEQ ID NO:33, or a fragment including at least 15 (25, 30, 50, 75, 100, 125, 150, 175, 200, 225, or 240) contiguous amino acids of SEQ ID NO:33.

Also within the invention are nucleic acid molecules which encode a fragment of a polypeptide having the amino acid sequence of SEQ ID NO:41, or a fragment including at least 15 (25, 30, 50, 75, 100, 125, 150, 175, 200, 250, 300, 350 or 370) contiguous amino acids of SEQ ID NO:41.

Also within the invention are nucleic acid molecules which encode a fragment of a polypeptide having the amino acid sequence of SEQ ID NO:21, or a fragment including at least 740 (745, 750, 755, 760, 765, 770, 775, 780, 785, 790, 800, 825, 850, or 880) contiguous amino acids of SEQ ID NO:21, or the amino acid sequence encoded by the cDNA of ATCC Accession Number 207116.

The invention includes nucleic acid molecules which encode a naturally occurring allelic variant of a polypeptide comprising the amino acid sequence of SEQ ID NO:3, 15, 21, 33, 41, or 45, or the amino acid sequence encoded by the cDNA of ATCC Accession Number 207116, wherein the nucleic acid molecule hybridizes to a nucleic acid molecule consisting of a nucleic acid sequence encoding SEQ ID NO:3, 15, 21, 33, 41, or 45, the amino acid sequence encoded by the cDNA of ATCC Accession Number 207116, or a complement thereof under stringent conditions.

Also within the invention are isolated polypeptides or proteins having an amino acid sequence that is at least about 30%, preferably 35%, 45%, 55%, 65%, 75%, 85%, 95%, or 98% identical to the amino acid sequence of SEQ ID NO:3, or the amino acid sequence encoded by the cDNA of ATCC Accession Number 207116.

Also within the invention are isolated polypeptides or proteins having an amino acid sequence that is at least about 35%, preferably 40%, 45%, 50%, 55%, 65%, 75%, 85%, 95%, or 98% identical to the amino acid sequence of SEQ ID NO:15, or the amino acid sequence encoded by the cDNA of ATCC Accession Number 207116.

Also within the invention are isolated polypeptides or proteins having an amino acid sequence that is at least about 93%, preferably 94%, 95%, 96%, 97% or 98% identical to the amino acid sequence of SEQ ID NO:21, or the amino acid sequence encoded by the cDNA of ATCC Accession Number 207116.

Also within the invention are isolated polypeptides or proteins having an amino acid sequence that is at least about 35%, preferably 40%, 45%, 50%, 55%, 65%, 75%, 85%, 95%, or 98% identical to the amino acid sequence of SEQ ID NO:33.

Also within the invention are isolated polypeptides or proteins having an amino acid sequence that is at least about 35%, preferably 40%, 45%, 50%, 55%, 65%, 75%, 85%, 95%, or 98% identical to the amino acid sequence of SEQ ID NO:41

Also within the invention are isolated polypeptides or proteins having an amino acid sequence that is at least about 35%, preferably 40%, 45%, 50%, 55%, 65%, 75%, 85%, 95%, or 98% identical to the amino acid sequence of SEQ ID NO:45.

Also within the invention are isolated polypeptides or proteins which are encoded by a nucleic acid molecule having a nucleotide sequence that is at least about 48%, preferably 50%, 55%, 60%, 65%, 75%, 85%, or 95% identical to the nucleic acid sequence encoding SEQ ID NO:3, and isolated polypeptides or proteins which are encoded by a nucleic acid molecule having a nucleotide sequence which hybridizes under stringent hybridization conditions to a nucleic acid molecule having the nucleotide sequence of SEQ ID NO:1 or 2, a complement thereof, or the non-coding strand of the cDNA of ATCC Accession Number 207116.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:15, and isolated polypeptides or proteins which are encoded by a nucleic acid molecule having a nucleotide sequence which hybridizes under stringent hybridization conditions to a nucleic acid molecule having the nucleotide sequence of SEQ ID NO:13 or 14, a complement thereof, or the non-coding strand of the cDNA of ATCC Accession Number 207116.

Also within the invention are isolated polypeptides or proteins which are encoded by a nucleic acid molecule having a nucleotide sequence that is at least about 93%, preferably 94%, 95%, 96%, 97%, or 98% identical to the nucleic acid sequence encoding SEQ ID NO:21, and isolated polypeptides or proteins which are encoded by a nucleic acid molecule having a nucleotide sequence which hybridizes under stringent hybridization conditions to a nucleic acid molecule having the nucleotide sequence of SEQ ID NO:19, 20, or 44, a complement thereof, or the non-coding strand of the cDNA of ATCC Accession Number 207116.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:33, and isolated polypeptides or proteins which are encoded by a nucleic acid molecule having a nucleotide sequence which hybridizes under stringent hybridization conditions to a nucleic acid molecule having the nucleotide sequence of SEQ ID NO:31 or 32, a complement thereof.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:41, and isolated polypeptides or proteins which are encoded by a nucleic acid molecule having a nucleotide sequence which hybridizes under stringent hybridization conditions to a nucleic acid molecule having the nucleotide sequence of SEQ ID NO:39 or 40.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:45, and isolated polypeptides or proteins which are encoded by a nucleic acid molecule having a nucleotide sequence which hybridizes under stringent hybridization conditions to a nucleic acid molecule having the nucleotide sequence of SEQ ID NO:19 or 44.

Also within the invention are polypeptides which are naturally occurring allelic variants of a polypeptide that includes the amino acid sequence of SEQ ID NO:3, 15, 21, 33, 41, or 45, or the amino acid sequence encoded by the cDNA of ATCC Accession Number 207116, wherein the polypeptide is encoded by a nucleic acid molecule which hybridizes to a nucleic acid molecule having the sequence of SEQ ID NO:1, 2, 3, 13, 14, 19, 20, 31, 32, 39, 40, or 44 or a complement thereof under stringent conditions.

The invention also features nucleic acid molecules that hybridize under stringent conditions to a nucleic acid molecule having the nucleotide sequence of SEQ ID NO:1 or 2, the cDNA of ATCC Accession Number 207116, or a complement thereof. In other embodiments, the nucleic acid molecules are at least 310 (400, 500, 600, 800, 1000, 1250, 1500, 1750, 2000, 2250, 2500, 2750, 3000, 3250, 3500, 3750, 4000, or 4020) nucleotides in length and hybridize under stringent conditions to a nucleic acid molecule comprising the nucleotide sequence of SEQ ID NO:1 or 2, the cDNA of ATCC Accession Number 207116, or a complement thereof.

The invention also features nucleic acid molecules that hybridize under stringent conditions to a nucleic acid molecule having the nucleotide sequence of SEQ ID NO:13 or 14, the cDNA of ATCC Accession Number 207116, or a complement thereof. In other embodiments, the nucleic acid molecules are at least 515 (530, 550, 600, 700, 800, 900, 1000, 1100, 1200, 1300, 1400, 1500, 1600, 1700, 1800, 1900, 2000, 2100, or 2150) nucleotides in length and hybridize under stringent conditions to a nucleic acid molecule comprising the nucleotide sequence of SEQ ID NO:13 or 14, the cDNA of ATCC Accession Number 207116, or a complement thereof.

The invention also features nucleic acid molecules that hybridize under stringent conditions to a nucleic acid molecule having the nucleotide sequence of SEQ ID NO:19 or 20, or the cDNA of ATCC Accession Number 207116, or a complement thereof. In other embodiments, the nucleic acid molecules are at least 2220 (2260, 2300, 2340, 2380, 2420, 2460, 2500, 2540, 2580, 2620, 2660, 2700, 2740, 2780, or 2800) nucleotides in length and hybridize under stringent conditions to a nucleic acid molecule comprising the nucleotide sequence of SEQ ID NO:19 or 20, the cDNA of ATCC Accession Number 207116, or a complement thereof.

The invention also features nucleic acid molecules that hybridize under stringent conditions to a nucleic acid molecule having the nucleotide sequence of SEQ ID NO:31 or 32, or a complement thereof. In other embodiments, the nucleic acid molecules are at least 100 (150, 200, 250, 300, 350, 400, 500, 600, or 700) nucleotides in length and hybridize under stringent conditions to a nucleic acid molecule comprising the nucleotide sequence of SEQ ID NO:31 or 32, or a complement thereof.

The invention also features nucleic acid molecules that hybridize under stringent conditions to a nucleic acid molecule having the nucleotide sequence of SEQ ID NO:39 or 40, or a complement thereof. In other embodiments, the nucleic acid molecules are at least 515 (530, 550, 600, 700, 800, 900, 1000, 1100, 1200, 1300, 1400, 1500, 1600, 1700, 1800, 1900, 2000, 2100, or 2150) nucleotides in length and hybridize under stringent conditions to a nucleic acid molecule comprising the nucleotide sequence of SEQ ID NO:39 or 40, or a complement thereof.

The invention also features nucleic acid molecules that hybridize under stringent conditions to a nucleic acid molecule having the nucleotide sequence of SEQ ID NO:19 or 44, the cDNA of ATCC Accession Number 207116, or a complement thereof. In other embodiments, the nucleic acid molecules are at least 515 (530, 550, 600, 700, 800, 900, 1000, 1100, 1200, 1300, 1400, 1500, 1600, 1700, 1800, 1900, 2000, 2100, or 2150) nucleotides in length and hybridize under stringent conditions to a nucleic acid molecule comprising the nucleotide sequence of SEQ ID NO:19 or 44, the cDNA of ATCC Accession Number 207116, or a complement thereof.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector or a nucleic acid molecule of the invention. The invention also provides methods for producing a polypeptide of the invention by culturing, in a suitable medium, a host cell of the invention containing a recombinant expression vector such that a polypeptide is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, or a functional activity of a polypeptide or nucleic acid of the invention refers to an activity exerted by a protein, polypeptide or nucleic acid molecule of the invention on a responsive cell as determined in vivo, or in vitro, according to standard techniques. Such activities can be a direct activity, such as an association with or an enzymatic activity on a second protein, or an indirect activity, such as a cellular signaling activity mediated by interaction of the protein with a second protein.

For TANGO 228, biological activities include, e.g., (1) the ability to modulate, e.g., stabilize, protein-protein interactions (e.g., homophilic and/or heterophilic), and protein-ligand interactions, e.g., in receptor-ligand recognition; (2) ability to interact with (e.g., noncovalently bind to) antigens, e.g., the antigens that elicited their formation; (3) the ability to initiate the immune response; and (4) the ability to modulate the activity (e.g., the development and/or activation) of connective tissue cells (e.g., mast cells and/or monocytes).

Other activities of TANGO 228 include: (1) the ability to modulate intracellular signaling cascades (e.g., signal transduction cascade), e.g., by interacting with target peptides (e.g., phosphotyrosine-containing target peptides); and (2) the ability to mediate (e.g., initiate) the allergic response, e.g., by serving as a receptor to antigens and/or a signaling molecule to other immune response mediators (e.g., histamines).

Still other activities of TANGO 228 include: (1) the ability to modulate (e.g., inhibit) lipid associated processes (e.g., exocytosis and/or lipid mediator generation) by, e.g., interacting with (e.g., binding to) a cell surface protein (e.g., a receptor) on a cell type involved in the immune response (e.g., mast cell); and (2) the ability to perform one or more of the functions of rat surface protein MCA-32 described, for example, in Pirozzi et al. (1995) Journal of Immunology. 155:5811–5818, the contents of which are incorporated herein by reference.

For TANGO 240, biological activities include, e.g., (1) the ability to modulate the tuberculosis pathology pathway in the same fashion as *Mycobacterium tuberculosis* conserved hypothetical protein Rv0712; and (2) the ability to modulate the function, migration, proliferation (e.g., suppress cell growth), and/or differentiation of cells, e.g., cells in tissues in which it is expressed (see description of expression data below).

For TANGO 243, biological activities include, e.g., (1) the ability to modulate (e.g., activate) the activity of enzymes (e.g., phospholipases) that hydrolyze lipids (e.g., phospholipids); (2) the ability to modulate (e.g., activate) the activity of enzymes that release precursors (e.g., arachidonic acid) of regulatory molecules (e.g., prostaglandins and/or eicosanoids) associated with the arthropathy pathway; (3) the ability to mediate (e.g., activate) the arthropathy pathway, e.g., through biological activity (1); and (4) the ability to modulate (e.g., induce) the activity (e.g., proliferation) of cell types associated with the arthropathic pathway (e.g., leukocytes, e.g., polymorphonuclear leukocytes, and/or mononuclear inflammatory cells).

Other activities of TANGO 243 include: (1) the ability to modulate, e.g., by causing cells to alter (e.g., increase) the synthesis of, and/or by causing cells (e.g., macrophages) to release, cell mediating molecules, e.g., cytokines (e.g., IL-1 and/or TNF); (2) the ability to modulate (e.g., initiate) an immune and/or inflammatory response, e.g., through biological activity (1); and (3) the ability to modulate (e.g., perpetuate) an immune and/or inflammatory response, e.g., through biological activity (1), whereby TANGO 243 itself is stimulated by the cell mediating molecule that it modulates (e.g., cytokine (e.g., IL-1 and/or TNF)).

Additional activities of TANGO 243 include: (1) the ability to modulate (e.g., initiate) the activity of enzymes (e.g., phospholipases (e.g., phospholipase A2), e.g., by modulating their signal transduction; (2) the ability to modulate (e.g., promote) cell-cell interaction (e.g., chemotaxis) by modulating (e.g., initiating) phospolipase A2 activation and/or signal transduction; (3) the ability to modulate (e.g., increase) cell permeability (e.g., endothelial cell permeability), e.g., via biological activity (2); and (4) the ability to modulate (e.g., promote) cell-cell adhesion (e.g., membrane fusion), e.g., via biological activity (2).

Still other activities of TANGO 243 include: (1) the ability to modulate (e.g., inhibit) cellular functions, e.g., cell division, cell-fate determination, gene transcription, transmembrane signaling, mRNA modification, and/or vesicle fusion; (2) the ability to modulate signal transduction, e.g., that of transmembrane receptors; and (3) the ability to perform one or more of the functions of human PLAP described, for example, in Bomalaski et al. (1990) J Lab Clin Med. 16 (6):814–825, the contents of which are incorporated herein by reference.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 60% identity, preferably 65% identity, more preferably 75%, 85%, 95%, 98% or more identity are defined herein as sufficiently identical.

In one embodiment, a TANGO 228 protein includes at least one or more of the following domains: a signal sequence, an extracellular domain, an Ig domain, a transmembrane domain, and an intracellular domain. In another embodiment, a TANGO 228 protein includes an extracellular domain, two Ig domains, and is wholly secreted. In yet another, a TANGO 228 protein includes an extracellular domain, two Ig domains, a transmembrane domain, and a cytoplasmic domain, and is a transmembrane protein.

In one embodiment, a TANGO 240 protein includes a signal peptide.

In one embodiment, a TANGO 243 protein includes a G-beta domain. In another embodiment, a TANGO 243 protein includes at least about two G-beta domains. In still another embodiment, a TANGO 243 protein includes at least three, four, five, six, or seven G-beta domains.

The polypeptides of the present invention, or biologically active portions thereof, can be operably linked to a heterologous amino acid sequence to form fusion proteins. The invention further features antibodies that specifically bind a polypeptide of the invention such as monoclonal or polyclonal antibodies. In addition, the polypeptides of the invention or biologically active portions thereof can be incorporated into pharmaceutical compositions, which optionally include pharmaceutically acceptable carriers.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIGS. 1A–1C depict the cDNA sequence of human TANGO 228 (SEQ ID NO:1) and the predicted amino acid sequence of TANGO 228 (SEQ ID NO:3). The open reading frame of SEQ ID NO:1 extends from nucleotide 34 to nucleotide 1062 of SEQ ID NO:1 (SEQ ID NO:2).

FIG. 2 depicts a hydropathy plot of human TANGO 228. Relatively hydrophobic regions of the protein are above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. The dashed vertical line separates the signal sequence (amino acids 1 to 19 of SEQ ID NO:3; SEQ ID NO:5) on the left from the mature protein (amino acids 20 to 343 of SEQ ID NO:3; SEQ ID NO:4) on the right. Thicker gray horizontal bars below the dashed horizontal line indicate extracellular ("out"), transmembrane ("TM"), and intracellular ("in") regions of the molecule. Below the hydropathy plot, the amino acid sequence of TANGO 228 is depicted.

FIGS. 3A–3H depict an alignment of the nucleotide sequence of rat surface protein MCA-32 (SEQ ID NO:11; GenBank Accession Number U39546) and the nucleotide sequence of human TANGO 228 (SEQ ID NO:1). The nucleotide sequences of rat MCA-32 and human TANGO 228 are 28.3% identical. This alignment was performed using the ALIGN alignment program with a PAM120 scoring matrix, a gap length penalty of 12, and a gap penalty of 4.

FIGS. 4A–4C depict an alignment of the nucleotide sequence of the open reading frames of rat MCA-32 (nucleotides 8 to 826 of SEQ ID NO:11) and human TANGO 228 (SEQ ID NO:2). The nucleotide sequences of the open reading frames of rat MCA-32 and human TANGO 228 (SEQ ID NO:2) are 45.4% identical. This alignment was performed using the ALIGN alignment program with a PAM120 scoring matrix, a gap length penalty of 12, and a gap penalty of 4.

FIG. 5 depicts an alignment of the amino acid sequence of rat MCA-32 (SEQ ID NO:12) and the amino acid sequence of human TANGO 228 (SEQ ID NO:3). The amino acid sequences of rat MCA-32 and human TANGO 228 are 26.8% identical. This alignment was performed using the ALIGN alignment program with a PAM120 scoring matrix, a gap length penalty of 12, and a gap penalty of 4.

FIGS. 6A–6B depict the cDNA sequence of human TANGO 240 (SEQ ID NO:13) and the predicted amino acid sequence of TANGO 240 (SEQ ID NO:15). The open reading frame of SEQ ID NO:13 extends from nucleotide 2 to nucleotide 1123 of SEQ ID NO:13 (SEQ ID NO:14).

FIG. 7 depicts a hydropathy plot of human TANGO 240. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 34 of SEQ ID NO:15; SEQ ID NO:17) on the left from the mature protein (amino acids 35 to 374 of SEQ ID NO:15; SEQ ID NO:16) on the right. Below the hydropathy plot, the amino acid sequence of TANGO 240 is depicted.

FIG. 8 depicts an alignment of the amino acid sequence of the *Mycobacterium tuberculosis* conserved hypothetical protein Rv0712 (SEQ ID NO:18; GenBank Accession Number Z84395) and the amino acid sequence of human TANGO 240 (SEQ ID NO:15). The amino acid sequences of Rv0712 and human TANGO 240 are 31.2% identical. This alignment was performed using the ALIGN alignment program with a PAM120 scoring matrix, a gap length penalty of 12, and a gap penalty of 4.

FIGS. 9A–9C depict the cDNA sequence of human TANGO 243 (SEQ ID NO:19) and the predicted amino acid sequence of TANGO 243 (SEQ ID NO:21). The open reading frame of SEQ ID NO:19 extends from nucleotide 183 to nucleotide 2567 of SEQ ID NO:19 (SEQ ID NO:20).

FIG. 10 depicts a hydropathy plot of human TANGO 243. Relatively hydrophobic regions of the protein are above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. Below the hydropathy plot, the amino acid sequence of TANGO 243 is depicted.

FIGS. 11A–11F depict an alignment of the nucleotide sequence of human PLAP (SEQ ID NO:29; GenBank Accession Number AF083395) and the nucleotide sequence of human TANGO 243 (SEQ ID NO:19). The nucleotide sequences of human PLAP and human TANGO 243 are 78.8% identical. This alignment was performed using the ALIGN alignment program with a PAM120 scoring matrix, a gap length penalty of 12, and a gap penalty of 4.

FIGS. 12A–12E depict an alignment of the nucleotide sequence of the open reading frames of human PLAP (nucleotides 1 to 2217 of SEQ ID NO:29) and human TANGO 243 (SEQ ID NO:20). The nucleotide sequences of the open reading frames of human PLAP and human TANGO 243 (SEQ ID NO:20) are 92.7% identical. This alignment was performed using the ALIGN alignment program with a PAM120 scoring matrix, a gap length penalty of 12, and a gap penalty of 4.

FIGS. 13A–13B depict an alignment of the amino acid sequence of human PLAP (SEQ ID NO:30) and the amino acid sequence of human TANGO 243 (SEQ ID NO:21). The amino acid sequences of human PLAP and human TANGO 243 are 92.8% identical. This alignment was performed using the ALIGN alignment program with a PAM120 scoring matrix, a gap length penalty of 12, and a gap penalty of 4.

FIG. 14 depicts the cDNA sequence of murine TANGO 228 (SEQ ID NO:31) and the predicted amino acid sequence of murine TANGO 228 (SEQ ID NO:33). The open reading frame of SEQ ID NO:31 extends from nucleotide 27 to nucleotide 743 of SEQ ID NO:31 (SEQ ID NO:33).

FIGS. 15A–15B depict an alignment of the nucleotide sequence of murine TANGO 228 (SEQ ID NO:31; upper line of each pair) and the nucleotide sequence of human TANGO 228 (SEQ ID NO:1; lower line of each pair). The nucleotide sequences of murine TANGO 228 and human TANGO 228 are 58.2% identical, over the length of the murien cDNA. This alignment was performed using the ALIGN alignment program with a PAM120 scoring matrix, a gap length penalty of 12, and a gap penalty of 4.

FIGS. 16A–16B depict an alignment of the nucleotide sequence of the open reading frames of murine TANGO 228 (SEQ ID NO:33; upper line of each pair) and human TANGO 228 (SEQ ID NO:3; lower line of each pair). The nucleotide sequences of the open reading frames of murine TANGO 228 human TANGO 228 are 58.2% identical, over the length of the murine ORF. This alignment was performed using the ALIGN alignment program with a PAM120 scoring matrix, a gap length penalty of 12, and a gap penalty of 4.

FIG. 17 depicts an alignment of the amino acid sequence of murine TANGO 228 (SEQ ID NO:32; upper line of each pair) and human TANGO 228 (SEQ ID NO:3; lower line of each pair). The amino acid sequences of murine TANGO 228 and human TANGO 228 are 30.6% identical, over the length of the murine protein. This alignment was performed using the ALIGN alignment program with a PAM120 scoring matrix, a gap length penalty of 12, and a gap penalty of 4.

FIGS. 18A–18B depict the cDNA sequence of murine TANGO 240 (SEQ ID NO:39) and the predicted amino acid sequence of murine TANGO 240 (SEQ ID NO:41). The open reading frame of SEQ ID NO:41 extends from nucleotide 2 to nucleotide 1117 of SEQ ID NO:41 (SEQ ID NO:40).

FIGS. 19A–19D depict an alignment of the nucleotide sequence of murine TANGO 240 (SEQ ID NO:39; upper line of each pair) and the nucleotide sequence of human TANGO 228 (SEQ ID NO:13; lower line of each pair). In this alignment the sequences are 78.4% identical, over the length of the human cDNA. This alignment was performed using the ALIGN alignment program with a PAM120 scoring matrix, a gap length penalty of 12, and a gap penalty of 4.

FIGS. 20A–20B depict an alignment of the nucleotide sequence of the open reading frames of murine TANGO 240 (SEQ ID NO:40; upper line of each pair) and human TANGO 240 (SEQ ID NO:14; lower line of each pair). The nucleotide sequences of the open reading frames of murine TANGO 240 human TANGO 240 are 84.4% identical. This alignment was performed using the ALIGN alignment program with a PAM120 scoring matrix, a gap length penalty of 12, and a gap penalty of 4.

FIG. 21 depicts an alignment of the amino acid sequence of murine TANGO 240 (SEQ ID NO:41; upper line of each pair) and human TANGO 240 (SEQ ID NO:17; lower line of each pair). The amino acid sequences of murine TANGO 240 and human TANGO 240 are 86% identical. This alignment was performed using the ALIGN alignment program with a PAM120 scoring matrix, a gap length penalty of 12, and a gap penalty of 4.

FIGS. 22A–22C depict the cDNA sequence of human TANGO 243 (SEQ ID NO:19) and the predicted amino acid sequence of a longer form of TANGO 243 (SEQ ID NO:45) arising from an alternative translation of the human TANGO 243 cDNA. In this translation the open reading frame of SEQ ID NO:19 extends from nucleotide 3 to nucleotide 2567 of SEQ ID NO:19 (SEQ ID NO:44).

DETAILED DESCRIPTION OF THE INVENTION

Figure 23:
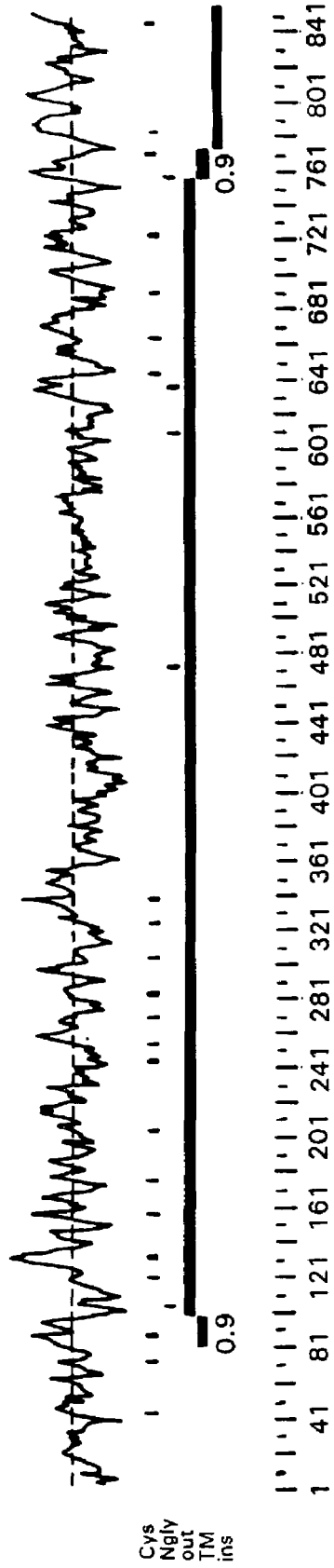
FIG. 23 depicts a hydropathy plot of the longer form of human TANGO 243 arising from the alternative translation of the human TANGO 243 cDNA. Relatively hydrophobic regions of the protein are above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. Below the hydropathy plot, the amino acid sequence of TANGO 243 is depicted.

The TANGO 228, TANGO 240, and TANGO 243 proteins and nucleic acid molecules comprise a family of molecules having certain conserved structural and functional features. As used herein, the term "family" is intended to mean two or more proteins or nucleic acid molecules having a common structural domain and having sufficient amino acid or nucleotide sequence identity as defined herein. Family members can be from either the same or different species. For example, a family can comprises two or more proteins of human origin, or can comprise one or more proteins of human origin and one or more of non-human origin. Members of the same family may also have common structural domains.

For example, TANGO 228 proteins and TANGO 240 proteins of the invention have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer. Thus, in one embodiment, a TANGO 228 protein contains a signal sequence at about amino acids 1 to 19 of SEQ ID NO:3 (SEQ ID NO:5). In another embodiment, a TANGO 240 protein contains a signal sequence at about amino acids 1 to 34 of SEQ ID NO:15 (SEQ ID NO:17). The signal sequence is cleaved during processing of the mature protein.

In another example, a TANGO 228 family member also includes one or more of the following domains: (1) an extracellular domain; (2) a transmembrane domain; and (3) a cytoplasmic domain. Thus, in one embodiment, a TANGO 228 protein contains an extracellular domain at about amino acids 1 to 227 of SEQ ID NO:3 (SEQ ID NO:6). In another embodiment, a TANGO 228 protein contains a transmembrane domain at about amino acids 228 to 249 of SEQ ID NO:3 (SEQ ID NO:7). In another embodiment, a TANGO 228 protein contains a cytoplasmic domain at about amino acids 250 to 343 of SEQ ID NO:3 (SEQ ID NO:10).

In one embodiment, the extracellular domain of TANGO 228 can also include an Ig domain. In another embodiment, the extracellular domain of TANGO 228 includes about 1 to 10, preferably about 3–8, more preferably about 6, N-glycosylation sites, about 1 to 30, preferably about 10 to 20, more preferably about 15 conserved serine residues (not including residues within the Ig domain), and about 1 to 20, preferably about 5 to 15, more preferably about 11 conserved threonine residues (not including residues within the Ig domain).

In a preferred embodiment, a TANGO 228 family member has the amino acid sequence of SEQ ID NO:3 wherein the extracellular domain is located at about amino acids 1 to 227 (SEQ ID NO:6), the N-glycosylation sites are located at about amino acid residue positions 51 to 54, 60 to 63, 89 to 92, 151 to 154, 157 to 160, and 182 to 185, the conserved serine residues are located at about amino acid positions 3, 6, 12, 15, 16, 36, 41, 109, 111, 114, 118, 127, 209, 216, and 221, and the conserved threonine residues are located at about amino acid positions 18, 31, 43, 108, 120, 126, 137, 139, 207, 213, and 217.

TANGO 228 family members can also include an Ig domain contained within the extracellular domain. As used herein, the term "Ig domain" refers to a protein domain bearing homology to immunoglobulin superfamily members. An Ig domain includes about 30–90 amino acid residues, preferably about 40–80 amino acid residues, more preferably about 50–70 amino acid residues, still more preferably about 55–65 amino acid residues, and most preferably about 57 to 59 amino acid residues. Typically, an Ig domain contains a conserved cysteine residue within about 5 to 15 amino acid residues, preferably about 7 to 12 amino acid residues, and most preferably about 8 amino acid residues from its N-terminal end, and another conserved cysteine residue within about 1 to 5 amino acid residues, preferably about 2 to 4 amino acid residues, and most preferably about 3 amino acid residues from its C-terminal end.

An Ig domain typically has the following consensus sequence, beginning about 1 to 15 amino acid residues, more preferably about 3 to 10 amino acid residues, and most preferably about 5 amino acid residues from the domain C terminal end of a protein: (FY)-Xaa-C-Xaa-(VA)-COO-, wherein (FY) is either a phenylalanine or a tyrosine residue (preferably tyrosine), Xaa is any amino acid, C is a cysteine residue, (VA) is either a valine or an alanine residue (preferably alanine), and COO— is the protein C terminus.

In one embodiment, a TANGO 228 family member includes one or more Ig domains having an amino acid sequence that is at least about 55%, preferably at least about 65%, more preferably at least about 75%, yet more preferably at least about 85%, and most preferably at least about 95% identical to amino acids 49 to 105 and/or amino acids 140 to 198 of SEQ ID NO:3, which are the Ig domains of TANGO 228 (these Ig domains are also represented as SEQ ID NO:8 and 9, respectively). In another embodiment, a TANGO 228 family member includes one or more Ig domains having an amino acid sequence that is at least about 55%, preferably at least about 65%, more preferably at least about 75%, yet more preferably at least about 85%, and most preferably at least about 95% identical to amino acids 49 to 105 and/or amino acids 140 to 198 of SEQ ID NO:3 (SEQ ID NO:8 and 9, respectively), includes a conserved cysteine residue about 8 residues downstream from the N-terminus of the Ig domain, and has one or more Ig domain consensus sequences described herein. In another embodiment, a TANGO 228 family member includes one or more Ig domains having an amino acid sequence that is at least 55%, preferably at least about 65%, more preferably at least about 75%, yet more preferably at least about 85%, and most preferably at least about 95% identical to amino acids 49 to 105 and/or amino acids 140 to 198 of SEQ ID NO:3 (SEQ ID NO:8 and 9, respectively), includes a conserved cysteine residue 8 residues downstream from the N-terminus of the Ig domain, has one or more Ig domain consensus sequences described herein, and has a conserved cysteine within the consensus sequence that forms a disulfide both with said first conserved cysteine. In yet another embodiment, a TANGO 228 family member includes one or more Ig domains having an amino acid sequence that is at least 55%, preferably at least about 65%, more preferably at least about 75%, yet more preferably at least about 85%, and most preferably at least about 95% identical to amino acids 49 to 105 and/or amino acids 140 to 198 of SEQ ID NO:3 (SEQ ID NO:8 and 9, respectively), includes a conserved cysteine residue 8 residues downstream from the N-terminus of the Ig domain, has one or more Ig domain consensus sequences described herein, has a conserved cysteine within the consensus sequence that forms a disulfide both with said first conserved cysteine, and has at least one TANGO 228 biological activity as described herein.

In a preferred embodiment, a TANGO 228 family member has the amino acid sequence of SEQ ID NO:3 wherein the aforementioned Ig domain conserved residues are located as follows: the N-terminal conserved cysteine residue is located at about amino acid residue position 56 (within the first Ig domain (SEQ ID NO:8)) and at about amino acid residue position 147 (within the second Ig domain (SEQ ID NO:9)), and the C-terminal conserved cysteine residue is located at about amino acid position 103 (within the first Ig domain (SEQ ID NO:8)) and at about amino acid residue position 196 (within the second Ig domain (SEQ ID NO:9)).

A TANGO 228 family member can also include a cytoplasmic domain. The cytoplasmic domain can include hydrophobic amino acid residues, and can contain several SH2 domain recognition sites, which contain typically begin with a tyrosine residue. This cytoplasmic domain can contain about 1 to 5, more preferably about 2 to 4, and still more preferably about 3 SH2 domain recognition sites.

One type of SH2 domain recognition site typically has the following consensus sequence: Y-Xaa1-Xaa1-(IP), wherein Y is a tyrosine residue, Xaa1 is any hydrophobic amino acid, and (IP) is either an isoleucine or proline residue. Another type of SH2 domain recognition site typically has the following consensus sequence: Y-Xaa1-Xaa-Xaa1, wherein Y is a tyrosine residue, Xaa1 is any hydrophobic amino acid, and Xaa is any amino acid.

In a preferred embodiment, a TANGO 228 family member has the amino acid sequence of SEQ ID NO:3 wherein the cytoplasmic domain is located at about amino acids 250 to 343 (SEQ ID NO:10) and the conserved SH2 domain recognition sites are located at about amino acid positions 276 to 279, 313 to 317, and 338 to 341.

A TANGO 240 family member can include a signal sequence. In a preferred embodiment, a TANGO 240 family member has the amino acid sequence of SEQ ID NO:15, and the signal sequence is located at about amino acids 1 to 34.

A TANGO 243 family member can include one or more G-beta domains. As used herein, a "G-beta domain" refers to a domain which includes about 25 to 55 amino acid residues, preferably about 30 to 50 amino acid residues, more preferably about 35–55 amino acid residues, and most preferably about 38 to 44 amino acid residues. In addition, a G-beta domain contains a conserved glycine residue adjacent to a conserved histidine residue, a conserved aspartic acid residue, and one or more conserved valine or isoleucine residues.

G-beta domains are typically found within the WD-repeat (tryptophan-aspartate repeat) family of proteins. The WD-repeat family of proteins are found in all eukaryotes but not in prokaryotes, and are functionally diverse, in some cases regulating cellular functions, transmembrane signaling, and/or vesicle fusion, among other things.

A G-beta domain typically has the following consensus sequence: G-H-Xaa(n1)-V-Xaa(n2)-[V or L]-Xaa(n3)-D-Xaa(n4)-W, wherein G is glycine, H is histidine, V is valine, D is aspartic acid, L is leucine, W is tryptophan, Xaa is any amino acid, n1 is about 1–8 amino acid residues, more preferably about 2–5 amino acid residues, and more preferably about 3 amino acid residues, n2 is about 1–8 amino acid residues, more preferably about 1–4 amino acid residues, and more preferably about 2 amino acid residues, n3 is about 5–30 amino acid residues, more preferably about 10–25 amino acid residues, and more preferably about 14–19 amino acid residues, and n4 is about 1–8 amino acid residues, more preferably about 3–6 amino acid residues, and more preferably about 5 amino acid residues.

A TANGO 243 family member can also include a G-beta-like domain. As used herein, a "G-beta-like domain" refers to an stretch of amino acid residues, about 25 to 55 residues, preferably about 30 to 50 residues, more preferably about 35–55 amino acid residues, and most preferably about 38 to 44 residues, in length, that is similar in content to a G-beta domain. A G-beta-like domain typically has the following consensus sequence: [V or I]-Xaa(2)-[V or C]-Xaa(n1)-[P or D]-[D or N]-G-Xaa(n2)-G-Xaa(2)-D, wherein V is valine, I is isoleucine, C is cysteine, P is proline, D is aspartic acid, G is glycine, Xaa is any amino acid, n1 is about 1 to 8 amino acid residues, preferably about 2 to 5 amino acid residues, more preferably about 3 amino acid residues, and n2 is about 1 to 8 amino acid residues, preferably about 2 to 5 amino acid residues, more preferably about 4 amino acid residues.

In one embodiment, a TANGO 243 family member includes one or more G-beta domains having an amino acid sequence that is at least about 55%, preferably at least about 65%, more preferably at least about 75%, yet more preferably at least about 85%, and most preferably at least about 95% identical to amino acids 8 to 47, or amino acids 55 to 98, or amino acids 102 to 139, or amino acids 141 to 179, or amino acids 181 to 218, or amino acids 221 to 259 of SEQ ID NO:21, which are the G-beta domains of TANGO 243 (these G-beta domains are also represented as SEQ ID NO:22, 23, 24, 25, 26, and 27, respectively). In another embodiment, a TANGO 243 family member includes one or more G-beta domains having an amino acid sequence that is at least about 55%, preferably at least about 65%, more preferably at least about 75%, yet more preferably at least about 85%, and most preferably at least about 95% identical to amino acids 8 to 47, or amino acids 55 to 98, or amino acids 102 to 139, or amino acids 141 to 179, or amino acids 181 to 218, or amino acids 221 to 259 of SEQ ID NO:21 (SEQ ID NO:22, 23, 24, 25, 26, and 27, respectively), and has a G-beta domain consensus sequence as described herein. In yet another embodiment, a TANGO 243 family member includes one or more G-beta domains having an amino acid sequence that is at least about 55%, preferably at least about 65%, more preferably at least about 75%, yet more preferably at least about 85%, and most preferably at least about 95% identical to amino acids 8 to 47, or amino acids 55 to 98, or amino acids 102 to 139, or amino acids 141 to 179, or amino acids 181 to 218, or amino acids 221 to 259 of SEQ ID NO:21 (SEQ ID NO:22, 23, 24, 25, 26, and 27, respectively), has a G-beta domain consensus sequence as described herein, and has at least one TANGO 243 biological activity as described herein.

In another embodiment, a TANGO 243 family member includes one or more G-beta domains having an amino acid sequence that is at least about 55%, preferably at least about 65%, more preferably at least about 75%, yet more preferably at least about 85%, and most preferably at least about 95% identical to amino acids 8 to 47, or amino acids 55 to 98, or amino acids 102 to 139, or amino acids 141 to 179, or amino acids 181 to 218, or amino acids 221 to 259 of SEQ ID NO:21, amino acids 68 to 107, or amino acids 115 to 158, or amino acids 162 to 199, or amino acids 201 to 139, or amino acids 141 to 278, or amino acids 281 to 219 of SEQ ID NO:45 (SEQ ID NO:22, 23, 24, 25, 26, and 27, respectively), G-beta-like domain having an amino acid sequence that is at least about 55%, preferably at least about 65%, more preferably at least about 75%, yet more preferably at least about 85%, and most preferably at least about 95% identical to amino acids 261 to 298 of SEQ ID NO:21 (SEQ ID NO:28), has a G-beta domain consensus sequence and a G-beta-like domain consensus sequence as described herein, and has at least one TANGO 243 biological activity as described herein.

A TANGO 243 family member can include a PLAP-like domain. A PLAP-like domain 1 can include at least 20, 25, 30, or 40 contiguous amino acids of SEQ ID NO:47. A PLAP-like domain 2 can include at least 20, 25, 30, 40, or 45 contiguous amino acids of SEQ ID NO:48. A PLAP-like domain 3 can include 20, 25, 30, 40, 45, 50, 60, 70, or 80 contiguous amino acids of SEQ ID NO:49. A PLAP-like domain 1 can include at least 20, 25, 30, or 35 contiguous amino acids of SEQ ID NO:50.

In a preferred embodiment, a TANGO 243 family member has the amino acid sequence of SEQ ID NO:21 wherein the G-beta consensus sequences are located from amino acid 16 to 46 (the first G-beta domain (SEQ ID NO:22)), 63 to 97 (the second G-beta domain (SEQ ID NO:23)), 110 to 138 (the third G-beta domain (SEQ ID NO:24)), 149 to 178 (the fourth G-beta domain (SEQ ID NO:25)), 189 to 217 (the fifth G-beta domain (SEQ ID NO:26)), and 229 to 258 (the sixth G-beta domain (SEQ ID NO:27)), and the G-beta-like consensus sequence is located from amino acid 261 to 298 (SEQ ID NO:28).

Various features of human TANGO 228, murine TANGO 228, human TANGO 240, and human TANGO 243 are summarized below.

Human TANGO 228

A cDNA encoding human TANGO 228 was identified by analyzing the sequences of clones present in a fetal spleen cDNA library. This analysis led to the identification of a clone, jthsa055f08, encoding full-length human TANGO 228. The human TANGO 228 cDNA of this clone is 4043 nucleotides long (FIGS. 1A–1C; SEQ ID NO:1). The open reading frame of this cDNA, nucleotides 34 to 1062 of SEQ ID NO:1 (SEQ ID NO:2), encodes a 343 amino acid transmembrane protein (FIGS. 1A–1C; SEQ ID NO:3).

The signal peptide prediction program SIGNALP (Nielsen et al. (1997) Protein Engineering 10:1–6) predicted that human TANGO 228 includes a 19 amino acid signal peptide (amino acid 1 to about amino acid 19 of SEQ ID NO:3)(SEQ ID NO:5) preceding the mature TANGO 228 protein (corresponding to about amino acid 20 to amino acid 343 of SEQ ID NO:3)(SEQ ID NO:4). The TANGO 228 protein molecular weight is 38.7 kDa prior to the cleavage of the signal peptide, 36.4 kDa after cleavage of the signal peptide.

TANGO 228 includes a extracellular domain (about amino acids 1 to 227 of SEQ ID NO:3; SEQ ID NO:6), a transmembrane domain (about amino acids 228 to 249 of SEQ ID NO:3; SEQ ID NO:7), two Ig domains (about amino acids 49 to 105, and about amino acids 140 to 198, of SEQ ID NO:3; SEQ ID NO:8 and 9), and a cytoplasmic domain (about amino acids 250 to 343 of SEQ ID NO:3; SEQ ID NO:10).

An N-glycosylation site having the sequence NVSM is found from amino acids 51 to 54 of SEQ ID NO:3. A second N-glycosylation site having the sequence NKSL is found from amino acids 60 to 63. A third N-glycosylation site having the sequence NLSI is found from amino acids 89 to 92. A fourth N-glycosylation site having the sequence NGSL is found from amino acids 151 to 154. A fifth N-glycosylation site having the sequence NYTF is found from amino acids 157 to 160. A sixth N-glycosylation site having the sequence NLTK is found from amino acids 182 to 185. A cAMP and cGMP-dependent protein kinase phosphorylation site having the sequence RRKT is found from amino acids 71 to 74. A protein kinase C phosphorylation site having the sequence TCR is found from amino acids 18 to 20. A second protein kinase C phosphorylation site having the sequence SHK is found from amino acids 57 to 59. A third protein kinase C phosphorylation site having the sequence TDR is found from amino acids 139 to 141. A fourth protein kinase C phosphorylation site having the sequence TKK is found from amino acids 184 to 186. A fifth protein kinase C phosphorylation site having the sequence TRK is found from amino acids 254 to 256. A sixth protein kinase C phosphorylation site having the sequence SYK is found from amino acids 331 to 333. A casein kinase II phosphorylation site having the sequence SITE is found from amino acids 91 to 94. A second casein kinase II phosphorylation site having the sequence TIVD is found from amino acids 120 to 123. A third casein kinase II phosphorylation site having the sequence TETD is found from amino acids 137 to 140. A fourth casein kinase II phosphorylation site having the sequence TFFE is found from amino acids 159 to 162. A fifth casein kinase II phosphorylation site having the sequence SKYD is found from amino acids 172 to 175. A sixth casein kinase II phosphorylation site having the sequence TGGD is found from amino acids 217 to 220. A seventh casein kinase II phosphorylation site having the sequence TAME is found from amino acids 269 to 272. An eighth casein kinase II phosphorylation site having the sequence SVPE is found from amino acids 288 to 291. A ninth casein kinase II phosphorylation site having the sequence TAQD is found from amino acids 300 to 303. A tyrosine kinase phosphorylation site having the sequence KNPGEEEEY is found from amino acids 186 to 194. A second tyrosine kinase phosphorylation site having the sequence KHSQELQY is found from amino acids 306 to 313. An N-myristoylation site having the sequence GQNVSM is found from amino acids 49 to 54. A second N-myristoylation site having the sequence GTQDGK is found from amino acids 77 to 82. A third N-myristoylation site having the sequence GIYANI is found from amino acids 274 to 279. A fourth N-myristoylation site having the sequence GSRPCV is found from amino acids 293 to 298. A cell attachment sequence having the sequence RGD is found from amino acids 266 to 268. A leucine zipper pattern having the sequence LLLPGLLLLLVVIILILAFWVL is found from amino acids 228 to 249.

TANGO 228 is homologous to rat MCA-32, which is known to exist in two forms, one of which has a transmembrane domain, and the other which does not. Thus TANGO 228, like rat MCA-32, is likely to exist in two forms, one having domains as follows and is wholly secreted: an extracellular domain (SEQ ID NO:6) containing one or more Ig domains (SEQ ID NO:8 and 9), and the other having the following domains and is a transmembrane, e.g., a cell surface, protein: an extracellular domain (SEQ ID NO:6) containing one or more Ig domains (SEQ ID NO:8 and 9), a transmembrane domain (SEQ ID NO:7), and cytoplasmic domain (SEQ ID NO:10).

FIGS. 3A–3H show an alignment of the human TANGO 228 full length nucleic acid sequence (SEQ ID NO:1) with the rat MCA-32 full length nucleic acid sequence (SEQ ID NO:11). FIGS. 4A–4C show an alignment of the human TANGO 228 coding region (SEQ ID NO:2) with the rat MCA-32 coding region. FIG. 5 shows an alignment of the human TANGO 228 protein sequence (SEQ ID NO:3) with the rat MCA-32 protein sequence (SEQ ID NO:12). As shown in FIG. 5, the human TANGO 228 signal sequence is represented by amino acids 1–19 (and encoded by nucleotides 34 to 90 of SEQ ID NO:1). Though the rat MCA-32 gene structure suggests it can function as a secreted protein or cell surface protein, depending on the splice variant, it does not exhibit the characteristic hydrophobic signal sequence generally found in secretory and transmembrane proteins. The human TANGO 228 extracellular domain sequence (SEQ ID NO:6) is represented by amino acids 1 to 227 (and encoded by nucleotides 34 to 714 of SEQ ID NO:1), and the rat MCA-32 extracellular domain sequence is represented by amino acids 1 to 177 (and encoded by nucleotides 8 to 523 of SEQ ID NO:11). The human TANGO 228 Ig domains (SEQ ID NO:8 and 9) are represented by amino acids 49 to 105, and 140 to 198 (and encoded by nucleotides 178 to 348, and 451 to 627 of SEQ ID NO:1), and the rat MCA-32 Ig domain is represented by amino acids 99 to 153 (and encoded by nucleotides 287 to 451 of SEQ ID NO:11). The human TANGO 228 transmembrane domain (SEQ ID NO:7) is represented by amino acids 228 to 249 (and encoded by nucleotides 715 to 780 of SEQ ID NO:1), and the rat MCA-32 transmembrane domain is represented by amino acids 178 to 199 (and encoded by nucleotides 524 to 589 of SEQ ID NO:11). The human TANGO 228 cytoplasmic domain (SEQ ID NO:10) is represented by amino acids 250 to 343 (and encoded by nucleotides 781 to 1065 of SEQ ID NO:1), and the rat MCA-32 cytoplasmic domain is represented by amino acids 200 to 278 (and encoded by nucleotides 590 to 829 of SEQ ID NO:11).

FIGS. 3A–3H and FIGS. 4A–4C show that there is an overall 28.3% identity between the full length human TANGO 228 nucleic acid molecule and the full length rat MCA-32 nucleic acid molecule, and an overall 45.5% identity between the open reading frame of human TANGO 228 nucleic acid molecule and the open reading frame of the rat MCA-32 nucleic acid molecule, respectively. The amino acid alignment in FIG. 5 shows a 26.8% overall amino acid sequence identity between human TANGO 228 and rat MCA-32.

Clone EpT228, which encodes human TANGO 228, was deposited with the American Type Culture Collection (10801 University Boulevard, Manassas, Va. 20110-2209) on Feb. 18, 1999 and assigned Accession Number 207116. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIG. 2 depicts a hydropathy plot of human TANGO 228. Relatively hydrophobic regions of the protein are shown above the horizontal line, and relatively hydrophilic regions of the protein are below the horizontal line. The cysteine residues (cys) and N-glycosylation sites are indicated by short vertical lines just below the hydropathy trace. The dashed vertical line separates the signal sequence (amino acids 1 to 19 of SEQ ID NO:3; SEQ ID NO:5) on the left from the mature protein (amino acids 20 to 343 of SEQ ID NO:3; SEQ ID NO:4) on the right. The TANGO 228 transmembrane domain is indicated by the section of the plot under which the number 7.1 can be seen, which represents a score assigned to the predicted transmembrane domain. The extracellular domain (SEQ ID NO:6) and cytoplasmic domain (SEQ ID NO:10) are similarly indicated by gray horizontal bars, labeled as "out" and "in", respectively.

Human TANGO 228 was mapped to h17q23. The nearby flanking markers include: WI-4118 and WI-5110. The known nearby loci include: JPD (periodontitis, juvenile) and DGI1 (dentinogenesis imperfecta). Nearby known human genes include: COIL (coilin P80), TNFAIP1 (tumor necrosis factor), GH1 (growth hormone1, 2), ICAM2 (intercellular adhesion molecule), APOH (apolipoprotein H), PEPE (peptidase E), MPO (myeloperoxidase), and CDK3 (cyclin dependent kinase3). Thus, human TANGO 228 nucleic acid molecules can be used to map these loci and genes.

The syntenic mouse chromosomal location is mo11. Nearby mouse loci include: rimy (rimy), al (alopecia), nog (noggin), and bda (baldarthritic). Near known mouse genes include: rimy (rimy), al (alopecia), hlf (hepatic leukemia factor), chad (ahondroadherin), re (rex), mpo (myeloperoxidase), nog (noggin), bda (bald arthritic), gip (gastric inhibitory polypeptide), and ngfr (nerve growth factor receptor).

Murine TANGO 228

A cDNA encoding murine TANGO 228 was identified by analyzing the sequences of clones present in a bone marrow stromal cell cDNA library. This analysis led to the identification of a clone, jtmMa107f05, encoding full-length murine TANGO 228. The murine TANGO 228 cDNA of this clone is 911 nucleotides long (FIG. 14; SEQ ID NO:31). The open reading frame of this cDNA, nucleotides 27 to 743 of SEQ ID NO:31 (SEQ ID NO:32), encodes a 239 amino acid transmembrane protein (FIG. 14; SEQ ID NO:33).

The signal peptide prediction program SIGNALP (Nielsen et al. (1997) Protein Engineering 10:1–6) predicted that murine TANGO 228 includes a 34 amino acid signal peptide (amino acid 1 to about amino acid 34 of SEQ ID NO:33; SEQ ID NO:35) preceding the mature murine TANGO 228 protein (corresponding to about amino acid 35 to amino acid 239 of SEQ ID NO:33; SEQ ID NO:34). The murine TANGO 228 protein molecular weight is 26.7 kDa prior to the cleavage of the signal peptide, 22.9 kDa after cleavage of the signal peptide.

Mature murine TANGO 228 includes an extracellular domain (about amino acids 35 to 141 of SEQ ID NO:33; SEQ ID NO:36), a transmembrane domain (about amino acids 142 to 164 of SEQ ID NO:33; SEQ ID NO:37), and a cytoplasmic domain (about amino acids 165 to 239 of SEQ ID NO:33; SEQ ID NO:8). Murine TANGO 228 also includes an Ig domain (about amino acids 59 to 115 of SEQ ID NO:33; SEQ ID NO:46).

FIGS. 15A–15B show an alignment of the murine TANGO 228 full length nucleic acid sequence (upper line of each pair; SEQ ID NO:31) with the human TANGO 228 full length nucleic acid sequence (lower line of each pair; SEQ ID NO:1). FIGS. 16A–16B show an alignment of the murine TANGO 228 coding region (upper line of each pair; SEQ ID NO:32) with the human TANGO 228 coding region (lower line of each pair; SEQ ID NO:2). FIG. 17 shows an alignment of the murine TANGO 228 protein sequence (upper line of each pair; SEQ ID NO:33) with the human TANGO 228 protein sequence (lower line of each pair; SEQ ID NO:3).

FIGS. 15A–15B and FIGS. 16A–4B show that there is an overall 58.2% identity between the full length murine TANGO 228 nucleic acid molecule and the full length human TANGO 228 nucleic acid molecule over the length of the murine molecule and an overall 58.2% identity between the open reading frame of murine TANGO 228 nucleic acid molecule and the open reading frame of the human TANGO 228 nucleic acid molecule over the length of the murine molecule, respectively. The amino acid alignment in FIG. 17 shows a 30.6% overall amino acid sequence identity between murine TANGO 228 and human TANGO 228 over the length of the murine moleceule Uses of TANGO 228 Nucleic Acids, Polypeptides, and Modulators Thereof As TANGO 228 was originally found in a fetal spleen library, TANGO 228 nucleic acids, proteins, and modulators thereof can be used to modulate the proliferation, differentiation, and/or function of cells that form the spleen, e.g., cells of the splenic connective tissue, e.g., splenic smooth muscle cells and/or endothelial cells of the splenic blood vessels. TANGO 228 nucleic acids, proteins, and modulators thereof can also be used to modulate the proliferation, differentiation, and/or function of cells that are processed, e.g., regenerated or phagocytized within the spleen, e.g., erythrocytes and/or B and T lymphocytes and macrophages. Thus TANGO 228 nucleic acids, proteins, and modulators thereof can be used to treat spleen, e.g., the fetal spleen, associated diseases and disorders. Examples of splenic diseases and disorders include e.g., splenic lymphoma and/or splenomegaly, and/or phagocytotic disorders, e.g., those inhibiting macrophage engulfment of bacteria and viruses in the bloodstream.

Due to TANGO 228's homology to rat MCA-32, which is a cell surface antigen gene up-regulated in activated mast cells, TANGO 228 nucleic acids, proteins, and modulators thereof can be used to modulate mast cell function and thus to treat immunologic diseases and disorders. Examples of immunologic diseases and disorders include allergic disorders, e.g., anaphylaxis and allergic asthma, and inflammatory disorders, e.g., atopic dermatitis.

Because TANGO 228 is homologous to rat MCA-32, which is expressed in monocyte and macrophage cell lines, TANGO 228 nucleic acids, proteins, and modulators thereof can be used to protect the body from antigenic invaders, e.g., by modulating the activity of macrophages, and can be used to treat allergies, e.g., anaphylactic shock and/or allergic rhinitis.

In addition, as TANGO 228 includes one or more Ig domains, TANGO 228 nucleic acids, proteins, and modulators thereof can be used to modulate immunologic function, e.g., by the modulation of immunoglobulins and the formation of antibodies. For the same reason, TANGO 228 nucleic acids, proteins, and modulators thereof can be used to modulate Type I immunologic disorders, e.g., anaphylaxis and/or rhinitis, by modulating, e.g., stabilizing, the interaction between antigens and mast cell receptors, e.g., high affinity IgE receptors.

Due to its mapping in the same region as TNFAIP1, a tumor necrosis factor, TANGO 228 nucleic acids, proteins, and modulators thereof can be sued to treat TNF related disorders (e.g., acute myocarditis, myocardial infarction, congestive heart failure, T cell disorders (e.g., dermatitis, fibrosis)), differentiative and apoptotic disorders, and disorders related to angiogenesis (e.g., tumor formation and/or metastasis, cancer). Modulators of TANGO 228 expression and/or activity can be used to treat such disorders.

Human TANGO 240

A cDNA encoding human TANGO 240 was identified by analyzing the sequences of clones present in an osteoblast cDNA library. This analysis led to the identification of a clone, jthoc087d01, encoding full-length human TANGO 240. The human TANGO 240 cDNA of this clone is 2165 nucleotides long (FIG. 6; SEQ ID NO:13). The open reading frame of this cDNA, nucleotides 2 to 1126 of SEQ ID NO:13 (SEQ ID NO:14), encodes a 374 amino acid secreted protein (FIG. 6; SEQ ID NO:15).

The signal peptide prediction program SIGNALP (Nielsen, et al. (1997) Protein Engineering 10:1–6) predicted that human TANGO 240 includes an 34 amino acid signal peptide (amino acid 1 to about amino acid 34 of SEQ ID NO:15)(SEQ ID NO:17) preceding the mature TANGO 240 protein (corresponding to about amino acid 35 to amino acid 374 of SEQ ID NO:15; SEQ ID NO:16). The TANGO 240 protein molecular weight is 40.6 kDa prior to the cleavage of the signal peptide, 37.2 kDa after cleavage of the signal peptide.

An N-glycosylation site having the sequence NSTG is found from amino acids 141 to 144 of SEQ ID NO:15. A cAMP and cGMP-dependent protein kinase phosphorylation site having the sequence RRVT is found from amino acids 117 to 120. A protein kinase C phosphorylation site having the sequence SCR is found from amino acids 234 to 236. A second protein kinase C phosphorylation site having the sequence SGK is found from amino acids 323 to 325. A casein kinase II phosphorylation site having the sequence SNTE is found from amino acids 132 to 135. A second casein kinase II phosphorylation site having the sequence TEAE is found from amino acids 147 to 150. A third casein kinase II phosphorylation site having the sequence SWND is found from amino acids 210 to 213. A fourth casein kinase II phosphorylation site having the sequence TEAE is found from amino acids 227 to 230. A fifth casein kinase II phosphorylation site having the sequence TGED is found from amino acids 270 to 273. A sixth casein kinase II phosphorylation site having the sequence SVEE is found from amino acids 311 to 314. A seventh casein kinase II phosphorylation site having the sequence SGKD is found from amino acids 323 to 326. A tyrosine kinase phosphorylation site having the sequence RVTIDAFY is found from amino acids 118 to 125. An N-myristoylation site having the sequence GLVCGR is found from amino acids 7 to 12. A second N-myristoylation site having the sequence GAAGSQ is found from amino acids 30 to 35. A third N-myristoylation site having the sequence GTGAGA is found from amino acids 38 to 43. A fourth N-myristoylation site having the sequence GSLAGS is found from amino acids 44 to 49. A fifth N-myristoylation site having the sequence GAHGNS is found from amino acids 59 to 64. A sixth N-myristoylation site having the sequence GGLHNR is found from amino acids 237 to 242. A seventh N-myristoylation site having the sequence GQHYAN is found from amino acids 254 to 259. An eighth N-myristoylation site having the sequence GSYMCH is found from amino acids 332 to 337. An amidation site having the sequence AGKR is found from amino acids 221 to 224. A prokaryotic membrane lipoprotein lipid attachment site having the sequence GAGAGSLAGSC is found from amino acids 40 to 50.

Clone EpT240, which encodes human TANGO 240, was deposited with the American Type Culture Collection (10801 University Boulevard, Manassas, Va. 20110-2209) on Feb. 18, 1999 and assigned Accession Number 207116. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIG. 7 depicts a hydropathy plot of human TANGO 240. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 34 of SEQ ID NO:15; SEQ ID NO:17) on the left from the mature protein (amino acids 35 to 374 of SEQ ID NO:15; SEQ ID NO:16) on the right.

Northern analysis of TANGO 240 expression in human tissues showed that an approximately 2.2 kB transcript is weakly expressed in skeletal muscle, brain, colon, thymus, spleen, and small intestine, moderately expressed in heart, liver, lung, and peripheral blood leukocytes, and strongly expressed in kidney and placenta.

Secretion assays indicate that the polypeptide encoded by human TANGO 240 is a secreted protein, as the presence of a 48 kD and a 42 kD protein was detected by performing the assays. The secretion assays were performed essentially as follows: 8×10$^5$ 293T cells were plated per well in a 6-well plate and the cells were incubated in growth medium (DMEM, 10% fetal bovine serum, penicillin/streptomycin) at 37° C., 5% $CO_2$ overnight. 293T cells were transfected with 2 g of full-length TANGO 240 inserted in the pMET7 vector/well and 10 g LipofectAMINE (GIBCO/BRL Cat. #18324-012)/well according to the protocol for GIBCO/BRL LipofectAMINE. The transfectant was removed 5 hours later and fresh growth medium was added to allow the cells to recover overnight. The medium was removed and each well was gently washed twice with DMEM without methionine and cysteine (ICN Cat. #16-424-54). Next, 1 ml DMEM without methionine and cysteine with 50 Ci Trans-$^{35}$S (ICN Cat. #51006) was added to each well and the cells were incubated at 37° C., 5% $CO_2$ for the appropriate time period. A 150 l aliquot of conditioned medium was obtained and 150 l of 2×SDS sample buffer was added to the aliquot. The sample was heat-activated and loaded on a 4–20% SDS-PAGE gel. The gel was fixed and the presence of secreted protein was detected by autoradiography.

Murine TANGO 240

A cDNA encoding murine TANGO 240 was identified by analyzing the sequences of clones present in a mouse bone marrow stromal cell cDNA library. This analysis led to the identification of a clone, jtmMa100b11, encoding full-length murine TANGO 240. The murine TANGO 240 cDNA of this clone is 2426 nucleotides long (FIGS. 18A–18B; SEQ ID NO:39). The open reading frame of this cDNA, nucleotides 2 to 1117 of SEQ ID NO:39 (SEQ ID NO:40), encodes a 372 amino acid secreted protein (FIGS. 18A–18B; SEQ ID NO:41).

The signal peptide prediction program SIGNALP (Nielsen, et al. (1997) Protein Engineering 10:1–6) predicted that murine TANGO 240 includes a 31 amino acid signal peptide (amino acid 1 to about amino acid 31 of SEQ ID NO:41; SEQ ID NO:43) preceding the mature murine TANGO 240 protein (corresponding to about amino acid 32 to amino acid 372 of SEQ ID NO:11; SEQ ID NO:42). The murine TANGO 240 protein molecular weight is 40.7 kDa prior to the cleavage of the signal peptide, 37.3 kDa after cleavage of the signal peptide.

FIGS. 19A–19D show an alignment of the murine TANGO 240 full length nucleic acid sequence (upper line of each pair; SEQ ID NO:39) with the human TANGO—240 full length nucleic acid sequence (lower line of each pair; SEQ ID NO:13). FIGS. 20A–20B show an alignment of the murine TANGO 240 coding region (upper line of each pair; SEQ ID NO:40) with the human TANGO 240 coding region (lower line of each pair; SEQ ID NO:14). FIG. 21 shows an alignment of the murine TANGO 240 protein sequence (upper line of each pair; SEQ ID NO:41) with the human TANGO 240 protein sequence (lower line of each pair; SEQ ID NO:15).

FIGS. 19A–19D and FIGS. 20A–20B show that there is an overall 78.4% identity between the full length murine TANGO 240 nucleic acid molecule and the full length human TANGO 240 nucleic acid molecule, over the length of the human molecule, and an overall 84.4% identity between the open reading frame of murine TANGO 240 nucleic acid molecule and the open reading frame of the human TANGO 240 nucleic acid molecule, respectively. The amino acid alignment in FIG. 21 shows an 86% overall amino acid sequence identity between murine TANGO 240 and human TANGO 240.

Northern analysis of TANGO 240 expression in mouse tissues showed that an approximately 2.2 kB transcript is weakly expressed in spleen and skeletal muscle, moderately expressed in testis, and strongly expressed in heart, brain, lung, liver, and kidney.

Uses of TANGO 240 Nucleic Acids, Polypeptides, and Modulators Thereof

As TANGO 240 was originally found in an osteoblast library, TANGO 240 nucleic acids, proteins, and modulators thereof can be used to modulate the proliferation, differentiation, and/or function of bone and cartilage cells, e.g., chondrocytes and osteoblasts, and to treat bone and/or cartilage associated diseases or disorders. Examples of bone and/or cartilage diseases and disorders include bone and/or cartilage injury due to for example, trauma (e.g., bone breakage, cartilage tearing), degeneration (e.g., osteoporosis), degeneration of joints, e.g., arthritis, e.g., osteoarthritis, and bone wearing.

As TANGO 240 is homologous to *Mycobacterium tuberculosis* conserved hypothetical protein Rv0712, TANGO 240 nucleic acids, proteins, and modulators thereof can be used to treat diseases associated with bacterial infection, e.g., tuberculosis, e.g., pulmonary tuberculosis. In addition, TANGO 240 can be used to modulate, e.g., trigger, the immune response and can be used to treat immunologic disease and disorders, e.g., those associated with the respiratory system, e.g., asthma.

TANGO 240 nucleic acids, proteins, and modulators thereof can also be used to treat disorders of the cells and tissues in which it is expressed. As TANGO 240 is expressed in heart, brain, spleen, lung, liver, skeletal muscle, kidney, testis, colon, thymus, peripheral blood leukocytes, small intestine, and placenta, TANGO 240 nucleic acids, proteins, and modulators thereof can be used to treat disorders of these cells, tissues, or organs, e.g., ischemic heart disease or atherosclerosis, head trauma, brain cancer, splenic lymphoma, splenomegaly, lung cancer, cystic fibrosis, rheumatoid lung disease, liver cirrhosis, hepatitis, muscular dystrophy, stroke, muscular atrophy, glomerulonephritis, end stage renal disease, uremia, testicular cancer, colon cancer and colonic volvulus, DiGeorge syndrome, thymoma, autoimmune disorders, atresia, Crohns disease, and various placental disorders.

Human TANGO 243

A cDNA encoding human TANGO 243 was identified by analyzing the sequences of clones present in a fetal spleen cDNA library. This analysis led to the identification of a clone, jthsa049g04, encoding potentially full-length human TANGO 243. The human TANGO 243 cDNA of this clone is 2811 nucleotides long (FIG. 9; SEQ ID NO:19). The open reading frame of this cDNA, nucleotides 183 to 2567 of SEQ ID NO:19 (SEQ ID NO:20), encodes a 795 amino acid protein (FIG. 9; SEQ ID NO:21). The TANGO 243 protein molecular weight is 87.1 kDa.

Like TANGO 243, proteins with a WD domain contain a number of conserved G-beta repeats and are intracellular. The functions associated with WD domains and G-beta repeats, e.g., signal transduction, cell division control, transcriptional regulation, vesicular trafficking, are performed within the cell.

TANGO 243 includes 6 G-beta domains and one G-beta-like domain. G-beta domain 1 is located at about amino acids 8 to 47 of SEQ ID NO:21 (SEQ ID NO:22). G-beta domain 2 is located at about amino acids 55 to 98 of SEQ ID NO:21 (SEQ ID NO:23). G-beta domain 3 is located at about amino acids 102 to 139 of SEQ ID NO:21 (SEQ ID NO:24). G-beta domain 4 is located at about amino acids 141 to 179 of SEQ ID NO:21 (SEQ ID NO:25). G-beta domain 5 is located at about amino acids 181 to 218 of SEQ ID NO:21 (SEQ ID NO:26). G-beta domain 6 is located at about amino acids 221 to 259 of SEQ ID NO:21 (SEQ ID NO:27). The G-beta-like domain is located at about amino acids 261 to 298 of SEQ ID NO:21 (SEQ ID NO:28).

An N-glycosylation site having the sequence NRSF is found from amino acids 52 to 55 of SEQ ID NO:21. A second N-glycosylation site having the sequence NTSD is found from amino acids 421 to 424. A third N-glycosylation site having the sequence NGTA is found from amino acids 559 to 562. A fourth N-glycosylation site having the sequence NSSS is found from amino acids 585 to 588. A fifth N-glycosylation site having the sequence NYSV is found from amino acids 708 to 711. A cAMP and cGMP-dependent protein kinase phosphorylation site having the sequence KKLT is found from amino acids 566 to 569. A second cAMP and cGMP-dependent protein kinase phosphorylation site having the sequence KKYS is found from amino acids 773 to 776. A protein kinase C phosphorylation site having the sequence SLR is found from amino acids 13 to 15. A second protein kinase C phosphorylation site having the sequence TTR is found from amino acids 42 to 44. A third protein kinase C phosphorylation site having the sequence SGK is found from amino acids 120 to 122. A fourth protein kinase C phosphorylation site having the sequence TAK is found from amino acids 134 to 136. A fifth protein kinase C phosphorylation site having the sequence TVK is found from amino acids 174 to 176. A sixth protein kinase C phosphorylation site having the sequence SIR is found from amino acids 213 to 215. A seventh protein kinase C phosphorylation site having the sequence SLR is found from amino acids 254 to 256. An eighth protein kinase C phosphorylation site having the sequence TIR is found from amino acids 266 to 268. A ninth protein kinase C phosphorylation site having the sequence SGK is found from amino acids 391 to 393. A tenth protein kinase C phosphorylation site having the sequence SYK is found from amino acids 415 to 417. An eleventh protein kinase C phosphorylation site having the sequence SEK is found from amino acids 588 to 590. A twelfth protein kinase C phosphorylation site having the sequence SIK is found from amino acids 620 to 622. A thirteenth protein kinase C phosphorylation site having the sequence SQR is found from amino acids 678 to 680. A fourteenth protein kinase C phosphorylation site having the sequence SNK is found from amino acids 694 to 696. A fifteenth protein kinase C phosphorylation site having the sequence TFR is found from amino acids 742 to 744. A casein kinase II phosphorylation site having the sequence SFTE is found from amino acids 54 to 57. A second casein kinase II phosphorylation site having the sequence SGHE is found from amino acids 188 to 191. A third casein kinase II phosphorylation site having the sequence SETE is found from amino acids 201 to 204. A fourth casein kinase II phosphorylation site having the sequence TTAE is found from amino acids 248 to 251. A fifth casein kinase II phosphorylation site having the sequence TESE is found from amino acids 298 to 301. A sixth casein kinase II phosphorylation site having the sequence SAEE is found from amino acids 306 to 309. A seventh casein kinase II phosphorylation site having the sequence SVSE is found from amino acids 368 to 371. An eighth casein kinase II phosphorylation site having the sequence TSDD is found from amino acids 422 to 425. A ninth casein kinase II phosphorylation site having the sequence SFSD is found from amino acids 466 to 469. A tenth casein kinase II phosphorylation site having the sequence TAPE is found from amino acids 561 to 564. An eleventh casein kinase II phosphorylation site having the sequence TEDD is found from amino acids 569 to 572. A twelfth casein kinase II phosphorylation site having the sequence SSSE is found from amino acids 586 to 589. A thirteenth casein kinase II phosphorylation site having the sequence SVNE is found from amino acids 625 to 628. A fourteenth casein kinase II phosphorylation site having the sequence SQRE is found from amino acids 678 to 681. A fifteenth casein kinase II phosphorylation site having the sequence TILE is found from amino acids 731 to 734. A sixteenth casein kinase II phosphorylation site having the sequence SVSE is found from amino acids 777 to 780. An N-myristoylation site having the sequence GLVCCA is found from amino acids 23 to 28. A second N-myristoylation site having the sequence GAFVSV is found from amino acids 32 to 37. A third N-myristoylation site having the sequence GLIATG is found from amino acids 83 to 88. A fourth N-myristoylation site having the sequence GNDHNI is found from amino acids 89 to 94. A fifth N-myristoylation site having the sequence GTLLSG is found from amino acids 124 to 129. A sixth N-myristoylation site having the sequence GLMLTG is found from amino acids 164 to 169. A seventh N-myristoylation site having the sequence GASDGI is found from amino acids 288 to 293. An eighth N-myristoylation site having the sequence GTREGQ is found from amino acids 347 to 352. A ninth N-myristoylation site having the sequence GSSGAN is found from amino acids 382 to 387. A tenth N-myristoylation site having the sequence GQMLGL is found from amino acids 457 to 462. An eleventh N-myristoylation site having the sequence GSSGSS is found from amino acids 480 to 485. A twelfth N-myristoylation site having the sequence GTTMAG is found from amino acids 508 to 513. A thirteenth N-myristoylation site having the sequence GAQFSS is found from amino acids 636 to 641. A fourteenth N-myristoylation site having the sequence GSNKNI is found from amino acids 693 to 698. A fifteenth N-myristoylation site having the sequence GTLISD is found from amino acids 750 to 755.

Clone EpT243, which encodes human TANGO 243, was deposited with the American Type Culture Collection (10801 University Boulevard, Manassas, Va. 20110–2209) on Feb. 18, 1999 and assigned Accession Number 207116. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIG. 10 depicts a hydropathy plot of human TANGO 243. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathytrace.

TANGO 243 bears some similarity to human PLAP (GenBank Accession Number AF083395). An alignment of the nucleotide sequence of human PLAP (SEQ ID NO:29; GenBank Accession Number AF083395) and the nucleotide sequence of human TANGO 243 (SEQ ID NO:19) is depicted in FIGS. 11A–11F. In this alignment, the nucleotide sequences of human PLAP and human TANGO 243 are 78.8% identical. This alignment was performed using the ALIGN alignment program with a PAM120 scoring matrix, a gap length penalty of 12, and a gap penalty of 4. FIGS. 12A–12E depict an alignment of the nucleotide sequence of the open reading frames of human PLAP (nucleotides 1 to 2217 of SEQ ID NO:29) and human TANGO 243 (SEQ ID NO:20). The nucleotide sequences of the open reading frames of human PLAP and human TANGO 243 (SEQ ID NO:20) are 92.7% identical. This alignment was performed using the ALIGN alignment program with a PAM120 scoring matrix, a gap length penalty of 12, and a gap penalty of 4. An alignment of the amino acid sequence of human PLAP (SEQ ID NO:30) and the amino acid sequence of human TANGO 243 (SEQ ID NO:21) is depicted in FIGS. 13A–13B. The amino acid sequences of human PLAP and human TANGO 243 are 92.8% identical. This alignment was performed using the ALIGN alignment program with a PAM120 scoring matrix, a gap length penalty of 12, and a gap penalty of 4.

It is possible that the human TANGO 243 clone described above, jthsa049g04, is a less than full-length clone and encodes a portion of human TANGO 243. If so, the start site of translation is located upstream of the 5' end of this clone. FIG. 22 depicts an alternative translation of the 2811 nucleotide long human TANGO 243 cDNA clone described above. In this translation, the open reading frame of the cDNA, nucleotides 3 to 2567 of SEQ ID NO: 19 (SEQ ID NO: 44), encodes a 855 amino acid protein (FIG. 22; SEQ ID NO: 45). The molecular weight of this TANGO 243 protein is 93.7 kDa.

In this alternative translation of the human TANGO 243, G-beta domain 1 is located at about amino acids 68 to 107 of SEQ ID NO:45 (SEQ ID NO:22), G-beta domain 2 is located at about amino acids 115 to 158 of SEQ ID NO:45 (SEQ ID NO:23), G-beta domain 3 is located at about amino acids 162 to 199 of SEQ ID NO:45 (SEQ ID NO:24), G-beta domain 4 is located at about amino acids 201 to 239 of SEQ ID NO:45 (SEQ ID NO:25), G-beta domain 5 is located at about amino acids 241 to 278 of SEQ ID NO:45 (SEQ ID NO:26), G-beta domain 6 is located at about amino acids 281 to 319 of SEQ ID NO:45 (SEQ ID NO:27), and the G-beta-like domain is located at about amino acids 321 to 358 of SEQ ID NO:45 (SEQ ID NO:28).

Within this longer form of TANGO 243, there are regions with considerable similarity to human PLAP. For example, a region of human TANGO 243 from amino acids 358 to 609 of SEQ ID NO:45 (SEQ ID NO:47) constitute PLAP-like domain 1. A region of human TANGO 243 from amino acids 528 to 758 of SEQ ID NO:45 (SEQ ID NO:48) constitute PLAP-like domain 2. A region of human TANGO 243 from amino acids 118 to 205 of SEQ ID NO:45 (SEQ ID NO:49) constitute PLAP-like domain 3. A region of human TANGO 243 from amino acids 239 to 273 of SEQ ID NO:45 (SEQ ID NO:50) constitute PLAP-like domain 4.

In this alternative translation of the TANGO 243 clone the following sites are present. An N-glycosylation site having the sequence NRSF is found from amino acids 112 to 115 of SEQ ID NO:45. A second N-glycosylation site having the sequence NTSD is found from amino acids 481 to 484. A third N-glycosylation site having the sequence NGTA is found from amino acids 619 to 622. A fourth N-glycosylation site having the sequence NSSS is found from amino acids 645 to 648. A fifth N-glycosylation site having the sequence NYSV is found from amino acids 768 to 771. A cAMP and cGMP-dependent protein kinase phosphorylation site having the sequence KKLT is found from amino acids 626 to 629. A second cAMP and cGMP-dependent protein kinase phosphorylation site having the sequence KKYS is found from amino acids 833 to 836. A protein kinase C phosphorlyation site having the sequence SGR is found from amino acids 22 to 24. A second protein kinase C phosphorylation site having the sequence SLR is found from amino acids 73 to 75. A third protein kinase C phosphorylation site having the sequence TTR is found from amino acids 102 to 104. A fourth protein kinase C phosphorylation site having the sequence SGK is found from amino acids 180 to 182. A fifth protein kinase C phosphorylation site having the sequence TAK is found from amino acids 194 to 196. A sixth protein kinase C phosphorylation site having the sequence TVK is found from amino acids 234 to 236. A seventh protein kinase C phosphorylation site having the sequence SIR is found from amino acids 273 to 275. An eighth protein kinase C phosphorylation site having the sequence SLR is found from amino acids 314 to 316. A ninth protein kinase C phosphorylation site having the sequence TIR is found from amino acids 326 to 328. A tenth protein kinase C phosphorylation site having the sequence SGK is found from amino acids 451 to 453. An eleventh protein kinase C phosphorylation site having the sequence SYK is found from amino acids 475 to 477. A twelfth protein kinase C phosphorylation site having the sequence SEK is found from amino acids 648 to 650. A thirteenth protein kinase C phosphorylation site having the sequence SIK is found from amino acids 680 to 682. A fourteenth protein kinase C phosphorylation site having the sequence SQR is found from amino acids 738 to 740. A fifteenth protein kinase C phosphorylation site having the sequence SNK is found from amino acids 754 to 756. A sixteenth protein kinase C phosphorylation site having the sequence TFR is found from amino acids 802 to 804. A casein kinase II phosphorylation site having the sequence SFTE is found from amino acids 114 to 117. A second casein kinase II phosphorylation site having the sequence SGHE is found from amino acids 248 to 252. A third casein kinase II phosphorylation site having the sequence SETE is found from amino acids 261 to 264. A fourth casein kinase II phosphorylation site having the sequence TTAE is found from amino acids 308 to 331. A fifth casein kinase II phosphorylation site having the sequence TESE is found from amino acids 358 to 361. A sixth casein kinase II phosphorylation site having the sequence SAEE is found from amino acids 366 to 369. A seventh casein kinase II phosphorylation site having the sequence SVSE is found from amino acids 428 to 431. An eighth casein kinase II phosphorylation site having the sequence TSDD is found from amino acids 482 to 485. A ninth casein kinase II phosphorylation site having the sequence SFSD is found from amino acids 526 to 529. A tenth casein kinase II phosphorylation site having the sequence TAPE is found from amino acids 621 to 624. An eleventh casein kinase II phosphorylation site having the sequence TEDD is found from amino acids 629 to 632. A twelfth casein kinase II phosphorylation site having the sequence SSSE is found from amino acids 646 to 649. A thirteenth casein kinase II phosphorylation site having the sequence SVNE is found from amino acids 685 to 688. A fourteenth casein kinase II phosphorylation site having the sequence SQRE is found from amino acids 738 to 741. A fifteenth casein kinase II phosphorylation site having the sequence TILE is found from amino acids 791 to 794. A sixteenth casein kinase II phosphorylation site having the sequence SVSE is found from amino acids 837 to 840. An N-myristoylation site having the sequence GSSPAA is found from amino acids 29 to 34. A second N-myristoylation site having the sequence GARQTL is found from amino acids 54 to 59. A third N-myristoylation site having the sequence GLVCCA is found from amino acids 83 to 88. A fourth N-myristoylation site having the sequence GAFVSV is found from amino acids 92 to 97. A fifth N-myristoylation site having the sequence GLIATG is found from amino acids 83 to 88. A sixth N-myristoylation site having the sequence GNDHNI is found from amino acids 149 to 154. A seventh N-myristoylation site having the sequence GTLLSG is found from amino acids 184 to 189. An eighth N-myristoylation site having the sequence GLMLTG is found from amino acids 224 to 229. A ninth N-myristoylation site having the sequence GASDGI is found from amino acids 348 to 353. An tenth N-myristoylation site having the sequence GTREGQ is found from amino acids 407 to 412. A eleventh N-myristoylation site having the sequence GSSGAN is found from amino acids 442 to 447. A twelfth N-myristoylation site having the sequence GQMLGL is found from amino acids 517 to 522. A thirteenth N-myristoylation site having the sequence GSSGSS is found from amino acids 540 to 545. A fourteenth N-myristoylation site having the sequence GTTMAG is found from amino acids 568 to 573. A fifteenth N-myristoylation site having the sequence GAQFSS is found from amino acids 696 to 701. A sixteenth N-myristoylation site having the sequence GSNKNI is found from amino acids 753 to 758. A seventeenth N-myristoylation site having the sequence GTLISD is found from amino acids 810 to 815.

FIG. 23 depicts a hydropathy plot of the 855 amino acid human TANGO 243 protein arising from the alternative translation. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace.

Uses of TANGO 243 Nucleic Acids, Polypeptides, and Modulators Thereof

As TANGO 243 was originally found in a fetal spleen library, TANGO 243 nucleic acids, proteins, and modulators thereof can be used to modulate the proliferation, differentiation, and/or function of cells that form the spleen, e.g., cells of the splenic connective tissue, e.g., splenic smooth muscle cells and/or endothelial cells of the splenic blood vessels. TANGO 243 nucleic acids, proteins, and modulators thereof can also be used to modulate the proliferation, differentiation, and/or function of cells that are processed, e.g., regenerated or phagocytized within the spleen, e.g., erythrocytes and/or B and T lymphocytes and macrophages. Thus TANGO 243 nucleic acids, proteins, and modulators thereof can be used to treat spleen, e.g., the fetal spleen, associated diseases and disorders. Examples of splenic diseases and disorders include e.g., splenic lymphoma and/or splenomegaly, and/or phagocytotic disorders, e.g., those inhibiting macrophage engulfment of bacteria and viruses in the bloodstream.

Since TANGO 243 is homologous to human PLAP, which is up-regulated in patients with rheumatoid arthritis, and which activates molecules involved in the arthropathy pathway, TANGO 243 nucleic acids, proteins, and modulators thereof can be used to treat inflammatory arthropathy, and in bone and cartilage diseases and disorders, e.g., bone and cartilage degenerative diseases and disorders, e.g., arthritis, e.g., rheumatoid arthritis.

Because both TANGO 243 and PLAP hydrolyze phospholipids into lysophospholipids, which are known to modulate chemotaxis, regulate blood vessel permeability, and promote membrane fusion, and can cause monocytes to secrete IL-1 (interleukin 1), in turn modulating T-cell-mediated immunity, TANGO 243 nucleic acids, proteins and modulators thereof can be used to modulate chemotaxis, regulate blood vessel permeability, and promote membrane fusion, and can cause monocytes to secrete IL-1 (interleukin 1), in turn modulating T-cell-mediated immunity.

TANGO 243 and PLAP can also be used to modulate IL-1 and TNF (tumor necrosis factor) synthesis and release (e.g., by modulating, e.g., activating PLA2 (phospholipase A2), which releases arachidonic acid as a byproduct of hydrolysis, which regulates IL-1 and TNF transcription). As IL-1 and TNF are involved in immunologic processes, TANGO 243 nucleic acids, proteins, and modulators thereof can be used to modulate such processes and to treat immunologic disorders.

By activating PLA2, TANGO 243 nucleic acids, proteins, and modulators thereof can modulate levels of arachidonic acid, and thus control levels of eicosanoids and prostaglandins. By controlling the levels of eicosanoids and prostaglandins, TANGO 243 nucleic acids, proteins, and modulators thereof can modulate the immunologic pathway.

The presence of one or more G-beta domain suggests that TANGO 228 functions in a manner similar to other G-beta-containing proteins, such as members of the WD-repeat family. For example, members of WD-repeat family typically have biological functions that include, but are not limited to, signal transduction, cell divisional control, transcription regulation, and vesicular trafficking.

Tables 1 and 2 below provide a summary of the sequence information for human TANGO 228, human TANGO 240, and human TANGO 243. Tables 3 and 4 below provide a summary of the sequence information for murine TANGO 228 and murine TANGO 240.

TABLE 1

Summary of Human TANGO 228, TANGO 240 and TANGO 243 Sequence Information

| Gene | cDNA | ORF | Figure | Accession Number |
|---|---|---|---|---|
| TANGO 228 | SEQ ID NO: 1 | SEQ ID NO: 2 | FIGS. 1A–1C | 207116 |
| TANGO 240 | SEQ ID NO: 13 | SEQ ID NO: 14 | FIGS. 6A–6B | 207116 |
| TANGO 243 | SEQ ID NO: 19 | SEQ ID NO: 20 | FIGS. 9A–9C | 207116 |
| TANGO 243 Alternative translation | SEQ ID NO: 19 | SEQ ID NO: 44 | FIGS. 22A–22C | 207116 |

TABLE 2

Summary of Domains of Human TANGO 228, TANGO 240, and TANGO 243 Proteins

| Protein | Signal Sequence | Mature Protein | Extracellular | Ig | Transmembrane | Cytoplasmic | G-beta |
|---|---|---|---|---|---|---|---|
| TANGO 228 | aa 1–19 of SEQ ID NO: 3 (SEQ ID NO: 5) | aa 20–343 of SEQ ID NO: 3 (SEQ ID NO: 4) | aa 1–227 of SEQ ID NO: 3 (SEQ ID NO: 6) | aa 49–105 and 140–198 of SEQ ID NO: 3 (SEQ ID NO: 8 and 9) | aa 228–249 of SEQ ID NO: 3 (SEQ ID NO: 7) | aa 250–343 of SEQ ID NO: 3 (SEQ ID NO: 10) | |
| TANGO 240 | aa 1–34 of SEQ ID NO: 13 (SEQ ID NO: 17) | aa 35–374 of SEQ ID NO: 13 (SEQ ID NO: 16) | | | | | |
| TANGO 243 | | | | | | | aa 8–47, 55–98, 102–139, 141–179, 181–218, 221–259, and 261–298 of SEQ ID NO: 19 (SEQ ID NO: 22–28) |
| TANGO 243 Alternative Translation | | | | | | | aa 68–107, 115–158, 162–199, 201–239, 241–278, 281–319, and 321–358 of SEQ ID NO: 45 (SEQ ID NO: 22–28) |

TABLE 3

Summary of Murine TANGO 228 and Murine TANGO 240 Sequence Information

| Gene | cDNA | ORF | Figure | Accession Number |
|---|---|---|---|---|
| TANGO 228 | SEQ ID NO: 31 | SEQ ID NO: 32 | FIG. 14 | |
| TANGO 240 | SEQ ID NO: 43 | SEQ ID NO: 44 | FIG. 18 | |

Various aspects of the invention are described in further detail in the following subsections:

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or

TABLE 4

Summary of Domains of Murine TANGO 228 and TANGO 240 Proteins

| Protein | Signal Sequence | Mature Protein | Extracellular | Transmembrane | Cytoplasmic |
|---|---|---|---|---|---|
| TANGO 228 | aa 1–34 of SEQ ID NO: 33 (SEQ ID NO: 35) | aa 35–239 of SEQ ID NO: 33 (SEQ ID NO: 34) | aa 35–141 of SEQ ID NO: 33 (SEQ ID NO: 36) | aa 142–164 of SEQ ID NO: 33 (SEQ ID NO: 37) | aa 165–239 of SEQ ID NO: 33 (SEQ ID NO: 38) |
| TANGO 240 | aa 1–31 of SEQ ID NO: 41 (SEQ ID NO: 43) | aa 32–372 of SEQ ID NO: 41 (SEQ ID NO: 42) | | | | mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

A nucleic acid molecule of the present invention, e.g., a nucleic acid molecule having the nucleotide sequence of SEQ ID NO:1, 2, 3, 13, 14, 19, 20, 31, 32, 39, 40, or 44, or a complement thereof, can be isolated using standard molecular biology techniques and the sequence information provided herein. Using all or a portion of the nucleic acid sequences of SEQ ID NO:1, 2, 3, 13, 14, 19, 20, 31, 32, 39, 40, or 44 as a hybridization probe, nucleic acid molecules of the invention can be isolated using standard hybridization and cloning techniques (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 2, 3, 13, 14, 19, 20, 31, 32, 39, 40, or 44, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, 2, 3, 13, 14, 19, 20, 31, 32, 39, 40, or 44 or of a naturally occurring mutant of SEQ ID NO:1, 2, 3, 13, 14, 19, 20, 31, 32, 39, 40, or 44.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a "biologically active portion" of a polypeptide of the invention can be prepared by isolating a portion of any of SEQ ID NO:2, 14, or 20, expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 2, 3, 13, 14, 19, 20, 31, 32, 39, 40, or 44, due to degeneracy of the genetic code and thus encode the same protein as that encoded by the nucleotide sequence of SEQ ID NO:2, 14, or 20.

In addition to the nucleotide sequences of SEQ ID NO:2, 14, and 20, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologues), which have a nucleotide sequence which differs from that of the human protein described herein are intended to be within the scope of the invention. Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 300 (325, 350, 375, 400, 425, 450, 500, 550, 600, 650, 700, 800, 900, or 1000) nucleotides in length and hybridizes under stringent conditions to the nucleic acid molecule comprising the nucleotide sequence, preferably the coding sequence, of SEQ ID NO:1 or 13, or a complement thereof.

Accordingly, in another embodiment, an isolated nucleic acid molecule of the invention is at least 600 (650, 700, 800, 900, 1000, 1200, 1400, 1600, 1800, 2000, or 2200) nucleotides in length and hybridizes under stringent conditions to the nucleic acid molecule comprising the nucleotide sequence, preferably the coding sequence, of SEQ ID NO:19, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, 2, 3, 13, 14, 19, 20, 31, 32, 39, 40, or 44, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:3, yet retain biological activity. In one embodiment, the isolated nucleic acid molecule includes a nucleotide sequence encoding a protein that includes an amino acid sequence that is at least about 30% identical, 35%, 40%, 45%, 50%, 55%, 60%, 65%, 75%, 85%, 95%, or 98% identical to the amino acid sequence of SEQ ID NO:3.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:15, yet retain biological activity. In one embodiment, the isolated nucleic acid molecule includes a nucleotide sequence encoding a protein that includes an amino acid sequence that is at least about 35% identical, 40%, 45%, 50%, 55%, 65%, 75%, 85%, 95%, or 98% identical to the amino acid sequence of SEQ ID NO:15.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:21, yet retain biological activity. In one embodiment, the isolated nucleic acid molecule includes a nucleotide sequence encoding a protein that includes an amino acid sequence that is at least about 93% identical, 94%, 95%, 96%, 97% or 98% identical to the amino acid sequence of SEQ ID NO:21.

An isolated nucleic acid molecule encoding a variant protein can be created by introducing one or more nucleotide substitutions, additions or deletions into the nucleotide sequence of SEQ ID NO:1, 2, 3, 13, 14, 19, 20, 31, 32, 39, 40, or 44 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein:protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation, cellular migration or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an -anomeric nucleic acid molecule. An -anomeric nucleic acid molecule forms specific double-stranded hybrids with complementary RNA in which, contrary to the usual, β-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) Science 261: 1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) Anticancer Drug Des. 6(6):569–84; Helene (1992) Ann. N.Y. Acad. Sci. 660:27–36; and Maher (1992) Bioassays 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) Proc. Natl. Acad. Sci. USA 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) Nucleic Acids Res. 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) Nucleic Acids Res. 17:5973–88). PNA monomers are then coupled in a stepwise manner to produce a chimeric molecule with a 5' PNA segment and a 3' DNA segment (Finn et al. (1996) Nucleic Acids Res. 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al.(1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NO:3, 4, 15, 16, 21, 22, 33, 34, 41, 42, or 45), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:3, 4, 15, 16, 21, 22, 33, 34, 41, 42, or 45. Other useful proteins are substantially identical (e.g., at least about 45%, preferably 55%, 65%, 75%, 85%, 95%, or 99%) to any of SEQ ID NO: 3, 4, 15, 16, 21, 22, 33, 34, 41, 42, or 45, or substantially identical (e.g., at least about 93%, preferably 94%, 95%, 96%, or 99%) to any of SEQ ID NO:21 or 22, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:5 and 19) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811–7815; Delgrave et al. (1993) Protein Engineering 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:3, 15, 21, or 45, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 2, 7, and 10 are hydropathy plots of the proteins of the invention. These plots or similar analyses can be used to identify hydrophilic regions.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77–96) or trioma techniques. The technology for producing hybridomas is well known (see generally Current Protocols in Immunology (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al. (1994) Bio/technology 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, Gene Expression Technology: Methods in Enzymology 185, Academic Press San Diego, Calif. (1990) 119–428). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoidspecific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the beta-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental-influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the-preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283, 317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) Science 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) Proc. Natl. Acad. Sci. USA 87:6223–27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 13, or 19 can comfortably provide positive individual identification with a panel of perhaps 10 to 1,000 primers which each yield a noncoding amplified sequence of 100 bases. If predicted coding sequences, such as those in SEQ ID NO:2, 14, 20, or 44 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 2, 3, 13, 14, 19, 20, 31, 32, 39, 40, or 44, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., a proliferative disorder, e.g., psoriasis or cancer). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., an immunologic disorder, e.g., asthma, anaphylaxis, or atopic dermatitis. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al. (1985) Science 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) Proc. Natl. Acad. Sci. USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) Proc. Natl. Acad. Sci. USA 86:2766; see also Cotton (1993) Mutat. Res. 285:125–144; Hayashi (1992) Genet. Anal. Tech. Appl. 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., chondrocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention. For example, disorders characterized by aberrant expression or activity of the polypeptides of the invention include immunologic disorders. In addition, the nucleic acids, polypeptides, and modulators thereof of the invention can be used to treat immunologic diseases and disorders, including but not limited to, allergic disorders (e.g., anaphylaxis and allergic asthma) and inflammatory disorders (e.g., atopic dermatitis). Polypeptides of the invention can also treat diseases associated with bacterial infection (e.g., tuberculosis, e.g., pulmonary tuberculosis), inflammatory arthropathy, and bone and cartilage degenerative diseases and disorders (e.g., arthritis, e.g., rheumatoid arthritis), as well as other disorders described herein.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of a TANGO 240 protein may be used to treat an arthropathic disorder, e.g., rheumatoid arthritis. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

This invention is further illustrated by the following examples which should not be construed as limiting. The contents of all references, patents and published patent applications cited throughout this application are hereby incorporated by reference.

Deposit of Clones

Clones containing cDNA molecules encoding TANGO 228, (clone EpT228), TANGO 240 (EpT240) and TANGO 243 (clone EpT243) were deposited with the American Type Culture Collection, 10801 University Boulevard, Manassas, Va., 20110-2209, on Feb. 18, 1999 as Accession Number 207116, as part of a composite deposit representing a mixture of three strains, each carrying one recombinant plasmid harboring a particular cDNA clone.

To distinguish the strains and isolate a strain harboring a particular cDNA clone, an aliquot of the mixture can be streaked out to single colonies on nutrient medium (e.g., LB plates) supplemented with 100 µg/ml ampicillin, single colonies grown, and then plasmid DNA extracted using a standard minipreparation procedure. Next, a sample of the DNA minipreparation can be digested with a combination of the restriction enzymes Sal I and Not I and the resultant products resolved on a 0.8% agarose gel using standard DNA electrophoresis conditions. The digest liberates fragments as follows:

TANGO 228: 4.1 kb
TANGO 240: 2.2 kb
TANGO 243: 2.8 kb

The identity of the strains can be inferred from the fragments liberated.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 51

<210> SEQ ID NO 1
<211> LENGTH: 4043
<212> TYPE: DNA
<213> ORGANISM: Homo sapiens
<220> FEATURE:
<221> NAME/KEY: CDS
<222> LOCATION: (34)...(1062)

<400> SEQUENCE: 1

```
cttctgaccc cgtcttggac ttcaactggg aga atg tgg agc cat ttg agc agg      54
                                    Met Trp Ser His Leu Ser Arg
                                     1               5 ctc ctc ttc tgg agc ata ttt tct tct gtc act tgt aga aaa gct gta     102
Leu Leu Phe Trp Ser Ile Phe Ser Ser Val Thr Cys Arg Lys Ala Val
```

-continued

```
              10                  15                  20
ttg gat tgt gag gca atg aaa aca aat gaa ttc cct tct cca tgt ttg        150
Leu Asp Cys Glu Ala Met Lys Thr Asn Glu Phe Pro Ser Pro Cys Leu
    25                  30                  35 gac tca aag act aag gtg gtt atg aag ggt caa aat gta tct atg ttt        198
Asp Ser Lys Thr Lys Val Val Met Lys Gly Gln Asn Val Ser Met Phe
40                  45                  50                  55 tgt tcc cat aag aac aaa tca ctg cag atc acc tat tca ttg ttt cga        246
Cys Ser His Lys Asn Lys Ser Leu Gln Ile Thr Tyr Ser Leu Phe Arg
            60                  65                  70 cgt aag aca cac ctg gga acc cag gat gga aaa ggt gaa cct gcg att        294
Arg Lys Thr His Leu Gly Thr Gln Asp Gly Lys Gly Glu Pro Ala Ile
        75                  80                  85 ttt aac cta agc atc aca gaa gcc cat gaa tca ggc ccc tac aaa tgc        342
Phe Asn Leu Ser Ile Thr Glu Ala His Glu Ser Gly Pro Tyr Lys Cys
            90                  95                 100 aaa gcc caa gtt acc agc tgt tca aaa tac agt cgt gac ttc agc ttc        390
Lys Ala Gln Val Thr Ser Cys Ser Lys Tyr Ser Arg Asp Phe Ser Phe
        105                 110                 115 acg att gtc gac ccg gtg act tcc cca gtg ctg aac att atg gtc att        438
Thr Ile Val Asp Pro Val Thr Ser Pro Val Leu Asn Ile Met Val Ile
120                 125                 130                 135 caa aca gaa aca gac cga cat ata aca tta cat tgc ctc tca gtc aat        486
Gln Thr Glu Thr Asp Arg His Ile Thr Leu His Cys Leu Ser Val Asn
            140                 145                 150 ggc tcg ctg ccc atc aat tac act ttc ttt gaa aac cat gtt gcc ata        534
Gly Ser Leu Pro Ile Asn Tyr Thr Phe Phe Glu Asn His Val Ala Ile
        155                 160                 165 tca cca gct att tcc aag tat gac agg gag cct gct gaa ttt aac tta        582
Ser Pro Ala Ile Ser Lys Tyr Asp Arg Glu Pro Ala Glu Phe Asn Leu
    170                 175                 180 acc aag aag aat cct gga gaa gag gaa gag tat agg tgt gaa gct aaa        630
Thr Lys Lys Asn Pro Gly Glu Glu Glu Glu Tyr Arg Cys Glu Ala Lys
185                 190                 195 aac aga ttg cct aac tat gca aca tac agt cac cct gtc acc atg ccc        678
Asn Arg Leu Pro Asn Tyr Ala Thr Tyr Ser His Pro Val Thr Met Pro
200                 205                 210                 215 tca aca ggc gga gac agc tgt cct ttc tgt ctg aag cta cta ctt cca        726
Ser Thr Gly Gly Asp Ser Cys Pro Phe Cys Leu Lys Leu Leu Leu Pro
            220                 225                 230 ggg tta tta ctg ttg ctg gtg gtg ata atc cta att ctg gct ttt tgg        774
Gly Leu Leu Leu Leu Leu Val Val Ile Ile Leu Ile Leu Ala Phe Trp
        235                 240                 245 gta ctg ccc aaa tac aaa aca aga aaa gct atg aga aat aat gtg ccc        822
Val Leu Pro Lys Tyr Lys Thr Arg Lys Ala Met Arg Asn Asn Val Pro
    250                 255                 260 agg gac cgt gga gac aca gcc atg gaa gtt gga atc tat gca aat atc        870
Arg Asp Arg Gly Asp Thr Ala Met Glu Val Gly Ile Tyr Ala Asn Ile
265                 270                 275 ctt gaa aaa caa gca aag gag gaa tct gtg cca gaa gtg gga tcc agg        918
Leu Glu Lys Gln Ala Lys Glu Glu Ser Val Pro Glu Val Gly Ser Arg
280                 285                 290                 295 ccg tgt gtt tcc aca gcc caa gat gag gcc aaa cac tcc cag gag cta        966
Pro Cys Val Ser Thr Ala Gln Asp Glu Ala Lys His Ser Gln Glu Leu
            300                 305                 310 cag tat gcc acc ccc gtg ttc cag gag gtg gca cca aga gag caa gaa       1014
Gln Tyr Ala Thr Pro Val Phe Gln Glu Val Ala Pro Arg Glu Gln Glu
        315                 320                 325 gcc tgt gat tct tat aaa tct gga tat gtc tat tct gaa ctc aac ttc       1062
```

Ala Cys Asp Ser Tyr Lys Ser Gly Tyr Val Tyr Ser Glu Leu Asn Phe
       330                 335                 340 tgaaatttac agaaacaaac tacatctcag gtagagacag ggttttgcca tgttggccag      1122
gctggtcttc aactcctgac ctcaagtgat ccgcccacct cggactccca gggtgctggg      1182
attacaggcg tgagccacct cgcctggccc tccatttcct gatctagtct tatatccacg      1242
ctcaccacct cagcacgctc agacccacgc tgctgtgggc tcctctggct cctggaagag      1302
tgcgtccgca gatgctgcag tctttgtgtg gctcagcaat tgccactcac atcaggaact      1362
gcctttaccc tgtcaggctc tactgagacc cgaccctggt tattaagcta taggggagac      1422
aaggatggat cttaaagaag acaagcaaaa tatagtgaag caaatagaat ggtggttcct      1482
gggggatggg ggcaggggac aacgaggagt gactggctaa cagatacagc gtttcagttt      1542
ggaaagacaa aaaagttctg gaaaaagat ggaaggtggt gatggttgca caataatatg       1602
agttttgttg ttgttgtttt ttgagacagg gtctctctct gttgcccagg ctggagtgca      1662
ggggcacgat ttcggctcac tgcaacctct gcctcccggg ttcgggcgat tcttgtgcct      1722
cagcctccca ggtagctggg attgcaggcg cccaccaccg tgcccagcta atttttgtat      1782
ttttagtggg gatggggttt caccatgttg gccaggctgg tctcgaactc ctgacctcaa      1842
gtgattggcc tgccttggcc tcccaaagtg ctgggattac aggcatgagc tattgcgccc      1902
ggcaatatga atgaatgttt ttaataccat tgaattacac acctaaaatt ggttaaaatg      1962
gtaaaaaatt ttatgttatg tataacttac cacaataatt taaaaaatat tgtgaagcgc      2022
ctgcctcatg tgaggtcttc taataagagg ggctgttctc cttctcaaga gcgctcgcgg      2082
gcattgggag tttcttattc tcaaatgtcc acatcccaag gcctaccccg tccctgtcag      2142
tgtcagaagt tagcagagca gaactgctag atgtgctcac tccatctcct ccatggttgg      2202 cccaccctt cgatcagatc ctggaattgg cttccagcac agccttccag ctggctgtga       2262
taaatgagag tggcttaaac cctgtcatca gggtttcaca gcttgccctg aaccgtagct      2322 tctcatttc tccttgcaaa tcttctaagg cagctaagag aagccaatta acttcacaat       2382
ccacataatt agcattgccc caaacctttc aagtgctgga atgctggcgt ccactagtgc      2442
ctcgtttctt tctaaacctc attccacatg gcagggaag gtcttaggaa ttgtggagct       2502
gtggcgttct aagggttctc actgcctacc tatcaccagc aagggagtcc ttgttgccat      2562
ccatccctag ggggtaattt tgttccctga ggctgctttc tagggacttc tggtcgcttg      2622
ttttatcctg gaccagacct gaaagcagag cctgaaataa ggccttctat gcacatcatt      2682
tatgtaggag gtggccctag gaagcaggcc caatgcgcca tgggaaaaac cagtaccagg      2742
gtgttttgct gagttgagca ctgtggtggg cagctggaca tgagcccact ggaatcttct      2802
gaagagccca agagcctctt ctcagtattg tccacttgag gattgatagt gagaggcatt      2862
tatccactgg tgtccaacgc tcactggttg aggatcaccc cagaaagcga cacctccccc      2922
acttctagac tagcatgtgg gtattccaag caggcttacc tcagtgtctc accccaggca      2982
ctgcaaacac cccaggacag aaagtgaaca tgtgtattgt gcaattgaag caagacacta      3042
tcagtgcaaa gtgagtagac cctcagatgc tgctgggtca gagggaaggc ccagggatat      3102
gacacaggac acagaggtgg cagatacacc acctcccaac atttcctcta tcacagcaac      3162
tagaacaatg gcaacaatag gggtgggtgt ggtggctcgc gcctgtggtc ccaataccct      3222 ggaggccag ggcagaagga ttgcttgagc ccaggagttc aagactagcc tgggcaactt       3282
ggcgaaaccc tgtctctaca acatatttg tatgtgattg aacaagtaga acaatggaac       3342

| | | | | |
|---|---|---|---|---|
| ggaaagtcca | gatgtagttc | taaatatgta | caggaactta | gtataggata aatatgcat | 3402 |
| cttaaatcaa | tggggaaaag | atggattatt | caacatattg | taaaaacttg agaatcacat | 3462 |
| taaaaaagtt | ggactcctac | ctcattcttt | acaacaaaat | taattctgat agatgtagtc | 3522 |
| acagaagagc | tagaagaata | tgcaggggat | ttaaaaataa | tcttgaagtg gggaggactt | 3582 |
| ttataggtat | gactcacaac | ccagaaaaca | taaaggattg | ttaaatttaa ttagataaat | 3642 |
| catttaatta | gatgaaacat | ttaaaaatta | catttagaaa | tcataaacta aatccaaaga | 3702 |
| ataactaggg | gccgggcgca | gtggctcacg | tctgtaatcc | catggggcag gtggatcacc | 3762 |
| tgaggttggg | agtttgggac | cagcctgtcc | agcacggtga | ggccccgtct ctactaaaaa | 3822 |
| tacaaaaatt | agttggtgtg | gtggcacata | cctgtggtcc | ctgctactgg ggaggctgag | 3882 |
| gcatgagaat | tgcttgaacc | tgggaggtgg | aggttgcagt | gagccaagat cgcgccactg | 3942 |
| cattccagcc | tgggcgacag | agcaagactc | catctcaaaa | aaaaaaaaa aaaaaaaaa | 4002 |
| aaaaaaaaaa | aaaaaaaaaa | aaaaaaaaaa | aaaaaaaaaa | a | 4043 |

<210> SEQ ID NO 2
<211> LENGTH: 1029
<212> TYPE: DNA
<213> ORGANISM: Homo sapiens

<400> SEQUENCE: 2

| | | | | |
|---|---|---|---|---|
| atgtggagcc | atttgagcag | gctcctcttc | tggagcatat | tttcttctgt cacttgtaga | 60 |
| aaagctgtat | tggattgtga | ggcaatgaaa | acaaatgaat | tcccttctcc atgtttggac | 120 |
| tcaaagacta | aggtggttat | gaagggtcaa | aatgtatcta | tgttttgttc ccataagaac | 180 |
| aaatcactgc | agatcaccta | ttcattgttt | cgacgtaaga | cacacctggg aacccaggat | 240 |
| ggaaaaggtg | aacctgcgat | ttttaaccta | agcatcacag | aagcccatga atcaggcccc | 300 |
| tacaaatgca | aagcccaagt | taccagctgt | tcaaaataca | gtcgtgactt cagcttcacg | 360 |
| attgtcgacc | cggtgacttc | cccagtgctg | aacattatgg | tcattcaaac agaaacagac | 420 |
| cgacatataa | cattcattg | cctctcagtc | aatggctcgc | tgcccatcaa ttacactttc | 480 |
| tttgaaaacc | atgttgccat | atcaccagct | atttccaagt | atgacaggga gcctgctgaa | 540 |
| tttaacttaa | ccaagaagaa | tcctggagaa | gaggaagagt | ataggtgtga agctaaaaac | 600 |
| agattgccta | actatgcaac | atacagtcac | cctgtcacca | tgccctcaac aggcggagac | 660 |
| agctgtcctt | tctgtctgaa | gctactactt | ccagggttat | tactgttgct ggtggtgata | 720 |
| atcctaattc | tggcttttg | ggtactgccc | aaatacaaaa | caagaaaagc tatgagaaat | 780 |
| aatgtgccca | gggaccgtgg | agacacagcc | atgaagttg | gaatctatgc aaatatcctt | 840 |
| gaaaaacaag | caaggagga | atctgtgcca | gaagtgggat | ccaggccgtg tgtttccaca | 900 |
| gcccaagatg | aggccaaaca | ctcccaggag | ctacagtatg | ccaccccgt gttccaggag | 960 |
| gtggcaccaa | gagagcaaga | agcctgtgat | tcttataaat | ctggatatgt ctattctgaa | 1020 |
| ctcaacttc | | | | | 1029 |

<210> SEQ ID NO 3
<211> LENGTH: 343
<212> TYPE: PRT
<213> ORGANISM: Homo sapiens
<220> FEATURE:
<221> NAME/KEY: SIGNAL
<222> LOCATION: (1)...(19)

<400> SEQUENCE: 3

-continued

```
Met Trp Ser His Leu Ser Arg Leu Leu Phe Trp Ser Ile Phe Ser Ser
        -15                 -10                 -5
Val Thr Cys Arg Lys Ala Val Leu Asp Cys Glu Ala Met Lys Thr Asn
            1               5                   10
Glu Phe Pro Ser Pro Cys Leu Asp Ser Lys Thr Lys Val Val Met Lys
        15                  20                  25
Gly Gln Asn Val Ser Met Phe Cys Ser His Lys Asn Lys Ser Leu Gln
 30              35                  40                  45
Ile Thr Tyr Ser Leu Phe Arg Arg Lys Thr His Leu Gly Thr Gln Asp
                50                  55                  60
Gly Lys Gly Glu Pro Ala Ile Phe Asn Leu Ser Ile Thr Glu Ala His
             65                  70                  75
Glu Ser Gly Pro Tyr Lys Cys Lys Ala Gln Val Thr Ser Cys Ser Lys
         80                  85                  90
Tyr Ser Arg Asp Phe Ser Phe Thr Ile Val Asp Pro Val Thr Ser Pro
 95                  100                 105
Val Leu Asn Ile Met Val Ile Gln Thr Glu Thr Asp Arg His Ile Thr
110             115                 120                 125
Leu His Cys Leu Ser Val Asn Gly Ser Leu Pro Ile Asn Tyr Thr Phe
                130                 135                 140
Phe Glu Asn His Val Ala Ile Ser Pro Ala Ile Ser Lys Tyr Asp Arg
            145                 150                 155
Glu Pro Ala Glu Phe Asn Leu Thr Lys Lys Asn Pro Gly Glu Glu Glu
        160                 165                 170
Glu Tyr Arg Cys Glu Ala Lys Asn Arg Leu Pro Asn Tyr Ala Thr Tyr
        175                 180                 185
Ser His Pro Val Thr Met Pro Ser Thr Gly Gly Asp Ser Cys Pro Phe
190                 195                 200                 205
Cys Leu Lys Leu Leu Leu Pro Gly Leu Leu Leu Leu Val Val Ile
                210                 215                 220
Ile Leu Ile Leu Ala Phe Trp Val Leu Pro Lys Tyr Lys Thr Arg Lys
                225                 230                 235
Ala Met Arg Asn Asn Val Pro Arg Asp Arg Gly Asp Thr Ala Met Glu
        240                 245                 250
Val Gly Ile Tyr Ala Asn Ile Leu Glu Lys Gln Ala Lys Glu Glu Ser
        255                 260                 265
Val Pro Glu Val Gly Ser Arg Pro Cys Val Ser Thr Ala Gln Asp Glu
270                 275                 280                 285
Ala Lys His Ser Gln Glu Leu Gln Tyr Ala Thr Pro Val Phe Gln Glu
            290                 295                 300
Val Ala Pro Arg Glu Gln Glu Ala Cys Asp Ser Tyr Lys Ser Gly Tyr
            305                 310                 315
Val Tyr Ser Glu Leu Asn Phe
        320

<210> SEQ ID NO 4
<211> LENGTH: 324
<212> TYPE: PRT
<213> ORGANISM: Homo sapiens

<400> SEQUENCE: 4

Arg Lys Ala Val Leu Asp Cys Glu Ala Met Lys Thr Asn Glu Phe Pro
 1               5                   10                  15
Ser Pro Cys Leu Asp Ser Lys Thr Lys Val Val Met Lys Gly Gln Asn
            20                  25                  30
```

```
Val Ser Met Phe Cys Ser His Lys Asn Lys Ser Leu Gln Ile Thr Tyr
         35                  40                  45
Ser Leu Phe Arg Arg Lys Thr His Leu Gly Thr Gln Asp Gly Lys Gly
 50                  55                  60
Glu Pro Ala Ile Phe Asn Leu Ser Ile Thr Glu Ala His Glu Ser Gly
 65                  70                  75                  80
Pro Tyr Lys Cys Lys Ala Gln Val Thr Ser Cys Ser Lys Tyr Ser Arg
                 85                  90                  95
Asp Phe Ser Phe Thr Ile Val Asp Pro Val Thr Ser Pro Val Leu Asn
                100                 105                 110
Ile Met Val Ile Gln Thr Glu Thr Asp Arg His Ile Thr Leu His Cys
                115                 120                 125
Leu Ser Val Asn Gly Ser Leu Pro Ile Asn Tyr Thr Phe Phe Glu Asn
    130                 135                 140
His Val Ala Ile Ser Pro Ala Ile Ser Lys Tyr Asp Arg Glu Pro Ala
145                 150                 155                 160
Glu Phe Asn Leu Thr Lys Lys Asn Pro Gly Glu Glu Glu Tyr Arg
                165                 170                 175
Cys Glu Ala Lys Asn Arg Leu Pro Asn Tyr Ala Thr Tyr Ser His Pro
                180                 185                 190
Val Thr Met Pro Ser Thr Gly Gly Asp Ser Cys Pro Phe Cys Leu Lys
                195                 200                 205
Leu Leu Leu Pro Gly Leu Leu Leu Leu Val Ile Ile Leu Ile
    210                 215                 220
Leu Ala Phe Trp Val Leu Pro Lys Tyr Lys Thr Arg Lys Ala Met Arg
225                 230                 235                 240
Asn Asn Val Pro Arg Asp Arg Gly Asp Thr Ala Met Glu Val Gly Ile
                245                 250                 255
Tyr Ala Asn Ile Leu Glu Lys Gln Ala Lys Glu Glu Ser Val Pro Glu
                260                 265                 270
Val Gly Ser Arg Pro Cys Val Ser Thr Ala Gln Asp Glu Ala Lys His
                275                 280                 285
Ser Gln Glu Leu Gln Tyr Ala Thr Pro Val Phe Gln Glu Val Ala Pro
    290                 295                 300
Arg Glu Gln Glu Ala Cys Asp Ser Tyr Lys Ser Gly Tyr Val Tyr Ser
305                 310                 315                 320
Glu Leu Asn Phe

<210> SEQ ID NO 5
<211> LENGTH: 19
<212> TYPE: PRT
<213> ORGANISM: Homo sapiens
<220> FEATURE:
<221> NAME/KEY: SIGNAL
<222> LOCATION: (1)...(19)

<400> SEQUENCE: 5

Met Trp Ser His Leu Ser Arg Leu Leu Phe Trp Ser Ile Phe Ser Ser
                -15                 -10                  -5
Val Thr Cys

<210> SEQ ID NO 6
<211> LENGTH: 227
<212> TYPE: PRT
<213> ORGANISM: Homo sapiens
```

```
<400> SEQUENCE: 6

Met Trp Ser His Leu Ser Arg Leu Leu Phe Trp Ser Ile Phe Ser Ser
 1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
 65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110

Tyr Ser Arg Asp Phe Ser Phe Thr Ile Val Asp Pro Val Thr Ser Pro
        115                 120                 125

Val Leu Asn Ile Met Val Ile Gln Thr Glu Thr Asp Arg His Ile Thr
130                 135                 140

Leu His Cys Leu Ser Val Asn Gly Ser Leu Pro Ile Asn Tyr Thr Phe
145                 150                 155                 160

Phe Glu Asn His Val Ala Ile Ser Pro Ala Ile Ser Lys Tyr Asp Arg
                165                 170                 175

Glu Pro Ala Glu Phe Asn Leu Thr Lys Lys Asn Pro Gly Glu Glu Glu
            180                 185                 190

Glu Tyr Arg Cys Glu Ala Lys Asn Arg Leu Pro Asn Tyr Ala Thr Tyr
        195                 200                 205

Ser His Pro Val Thr Met Pro Ser Thr Gly Gly Asp Ser Cys Pro Phe
    210                 215                 220

Cys Leu Lys
225

<210> SEQ ID NO 7
<211> LENGTH: 22
<212> TYPE: PRT
<213> ORGANISM: Homo sapiens

<400> SEQUENCE: 7

Leu Leu Leu Pro Gly Leu Leu Leu Leu Val Val Ile Ile Leu Ile
 1               5                   10                  15

Leu Ala Phe Trp Val Leu
            20

<210> SEQ ID NO 8
<211> LENGTH: 57
<212> TYPE: PRT
<213> ORGANISM: Homo sapiens

<400> SEQUENCE: 8

Gly Gln Asn Val Ser Met Phe Cys Ser His Lys Asn Lys Ser Leu Gln
 1               5                   10                  15

Ile Thr Tyr Ser Leu Phe Arg Arg Lys Thr His Leu Gly Thr Gln Asp
            20                  25                  30

Gly Lys Gly Glu Pro Ala Ile Phe Asn Leu Ser Ile Thr Glu Ala His
        35                  40                  45

Glu Ser Gly Pro Tyr Lys Cys Lys Ala
```

<210> SEQ ID NO 9
<211> LENGTH: 59
<212> TYPE: PRT
<213> ORGANISM: Homo sapiens

<400> SEQUENCE: 9

Asp Arg His Ile Thr Leu His Cys Leu Ser Val Asn Gly Ser Leu Pro
1               5                   10                  15

Ile Asn Tyr Thr Phe Phe Glu Asn His Val Ala Ile Ser Pro Ala Ile
            20                  25                  30

Ser Lys Tyr Asp Arg Glu Pro Ala Glu Phe Asn Leu Thr Lys Lys Asn
        35                  40                  45

Pro Gly Glu Glu Glu Glu Tyr Arg Cys Glu Ala
    50                  55

<210> SEQ ID NO 10
<211> LENGTH: 94
<212> TYPE: PRT
<213> ORGANISM: Homo sapiens

<400> SEQUENCE: 10

Pro Lys Tyr Lys Thr Arg Lys Ala Met Arg Asn Asn Val Pro Arg Asp
1               5                   10                  15

Arg Gly Asp Thr Ala Met Glu Val Gly Ile Tyr Ala Asn Ile Leu Glu
            20                  25                  30

Lys Gln Ala Lys Glu Glu Ser Val Pro Glu Val Gly Ser Arg Pro Cys
        35                  40                  45

Val Ser Thr Ala Gln Asp Glu Ala Lys His Ser Gln Glu Leu Gln Tyr
    50                  55                  60

Ala Thr Pro Val Phe Gln Glu Val Ala Pro Arg Glu Gln Glu Ala Cys
65                  70                  75                  80

Asp Ser Tyr Lys Ser Gly Tyr Val Tyr Ser Glu Leu Asn Phe
                85                  90

<210> SEQ ID NO 11
<211> LENGTH: 1659
<212> TYPE: DNA
<213> ORGANISM: Rattus norvegicus

<400> SEQUENCE: 11
ctaaatcctc tcatttcctg catgtggttg ggaagaggaa tcttagaaga cgagccccac      60
tctgtagcag ctcaactaac catgggcgat gatgacaccc tgtgtgcct ctctgtcgcc     120
tcatgcaagg gagtgagttg ctggctggac aaactcttac tctgggctct tactctgtct     180
atcacacttc gaaacaccgc cgtggattgt aggagggtgg acagaaatgg attgctttct     240
ccaaatctga actcaagtat gagtgtggtc aggatgggcc aaaatgtatc tctgtcttgt     300
tccagcaaga acacatccat agacatcacc tattcgctct ttttgggtaa gagataccta     360
gaaagcaaga ggagaagagg gggagctgtg gatttccacc tgaggatctc caatgccaac     420
gagtcaggcc cctacaagtg caaagtcaat gattccaact cgtcgaaata cagtcagaat     480
ttcaacttca caatcatcca ggatgagagc tgctcttctt gtctactgtc gctgttgctc     540
ccaggggtgt tattggggct aatactccca ggcctggcct ttttgattta tttgaaatac     600
aaaaaagggt gcacaggaaa gactctgaaa gagaatgagt ccaagggttc tggagatgcg     660
cccacgcaag gggagctgta tgcgaatatc tgtgaaactc aaaaagggtc agaacaactc     720

```
caggagatac actatactac tccagtcttc aaagaggtgg cacccacaga acaagaaggc      780
cttgaggata gaaagatga ctacatctac tctgaactca cctactaaag tgcgaagaaa       840
ctgactgtat cctaatataa gagactttcc agtaagctga tgcttacgaa gaaacaggaa     900
attcacctgg cacttcagag tttcatccta ggctggggca gaaggatcct gagttcaagg      960
ccagctggca ctacatagca agaccctgtc ttaaaacaca agatcaaaa aagatttaac      1020 ctggtcaccg aaagtgaatg tatttttcac atctggacac tattattcct ttggctaact    1080
tgggcatcta atcttgtcac caaagtagcc aggcttgata agggttaaaa atacttcgg      1140 ttttgtggcc ttcagccgtt ctcactttcc aacccaattt taaatggaat tatcctgggg    1200
ctgcagaagt ggctcagcag ctaagagcag acactgctct cccaaaggat gggagtttga    1260
gcccagagtc tacatcccat aactcacagt tgccaataac attgtttccg aaggatccat    1320
cgccctcttc tggcacctgc aggcactaca ctcatgtgca cagacacacc taaacgcata    1380
attaagtaag ttggggctgg agagatggct cagtggttaa gagcactgac tgctcttcca    1440
gaggtcctga gttcaatacc cagcaaccac atggtggctc acaaacatct ataatgggat    1500
ccgatgccct cttctgctgt gtctgaagac agctatagtg tacttatgta cataaaataa    1560
ataaatcttt aaaataaata aataagtcta tgggcatacc accctgtaca tgcccaagct    1620
catctagaag taaataataa aataaaaaag ttaatctta                           1659
```

<210> SEQ ID NO 12
<211> LENGTH: 268
<212> TYPE: PRT
<213> ORGANISM: Rattus norvegicus

<400> SEQUENCE: 12

```
Met Trp Leu Gly Arg Gly Ile Leu Glu Asp Glu Pro His Ser Val Ala
 1               5                  10                  15

Ala Gln Leu Thr Met Gly Asp Asp Thr Pro Val Cys Leu Ser Val
            20                  25                  30

Ala Ser Cys Lys Gly Val Ser Cys Trp Leu Asp Lys Leu Leu Leu Trp
        35                  40                  45

Ala Leu Thr Leu Ser Ile Thr Leu Arg Asn Thr Ala Val Asp Cys Arg
    50                  55                  60

Arg Val Asp Arg Asn Gly Leu Leu Ser Pro Asn Leu Asn Ser Ser Met
65                  70                  75                  80

Ser Val Val Arg Met Gly Gln Asn Val Ser Leu Ser Cys Ser Ser Lys
                85                  90                  95

Asn Thr Ser Ile Asp Ile Thr Tyr Ser Leu Phe Leu Gly Lys Arg Tyr
            100                 105                 110

Leu Glu Ser Lys Arg Arg Arg Gly Gly Ala Val Asp Phe His Leu Arg
        115                 120                 125

Ile Ser Asn Ala Asn Glu Ser Gly Pro Tyr Lys Cys Lys Val Asn Asp
    130                 135                 140

Ser Asn Ser Ser Lys Tyr Ser Gln Asn Phe Asn Phe Thr Ile Ile Gln
145                 150                 155                 160

Asp Glu Ser Cys Ser Ser Cys Leu Leu Ser Leu Leu Pro Gly Val
                165                 170                 175

Leu Leu Gly Leu Ile Leu Pro Gly Leu Ala Phe Leu Ile Tyr Leu Lys
            180                 185                 190

Tyr Lys Lys Gly Cys Thr Gly Lys Thr Leu Lys Glu Asn Glu Ser Lys
        195                 200                 205
```

```
Gly Ser Gly Asp Ala Pro Thr Gln Gly Glu Leu Tyr Ala Asn Ile Cys
    210                 215                 220

Glu Thr Gln Lys Gly Ser Gln Leu Gln Glu Ile His Tyr Thr Thr
225                 230                 235                 240

Pro Val Phe Lys Glu Val Ala Pro Thr Glu Gln Gly Leu Glu Asp
                245                 250                 255

Arg Lys Asp Asp Tyr Ile Tyr Ser Glu Leu Thr Tyr
            260                 265

<210> SEQ ID NO 13
<211> LENGTH: 2165
<212> TYPE: DNA
<213> ORGANISM: Homo sapiens
<220> FEATURE:
<221> NAME/KEY: CDS
<222> LOCATION: (2)...(1123)

<400> SEQUENCE: 13 c atg gct gcg ccc gca cta ggg ctg gtg tgt gga cgt tgc cct gag ctg      49
  Met Ala Ala Pro Ala Leu Gly Leu Val Cys Gly Arg Cys Pro Glu Leu
    1               5                  10                  15 ggt ctc gtc ctc ttg ctg ctg ctc tcg ctg ctg tgt gga gcg gca           97
Gly Leu Val Leu Leu Leu Leu Leu Ser Leu Leu Cys Gly Ala Ala
             20                  25                  30 ggg agc cag gag gcc ggg acc ggt gcg ggc gcg ggg tcc ctt gcg ggt      145
Gly Ser Gln Glu Ala Gly Thr Gly Ala Gly Ala Gly Ser Leu Ala Gly
         35                  40                  45 tct tgc ggc tgc ggc acg ccc cag cgg cct ggc gcc cat ggc aat tcg      193
Ser Cys Gly Cys Gly Thr Pro Gln Arg Pro Gly Ala His Gly Asn Ser
 50                  55                  60 gca gcc gct cac cga tac tcg cgg gag gct aac gct ccg ggc ccc gta      241
Ala Ala Ala His Arg Tyr Ser Arg Glu Ala Asn Ala Pro Gly Pro Val
 65                  70                  75                  80 ccc gga gag cgg caa ctc gcg cac tca aag atg gtc ccc atc cct gtt      289
Pro Gly Glu Arg Gln Leu Ala His Ser Lys Met Val Pro Ile Pro Val
                 85                  90                  95 gga gta ttt aca atg ggc aca gat gat cct cag ata aag cag gat ggg      337
Gly Val Phe Thr Met Gly Thr Asp Asp Pro Gln Ile Lys Gln Asp Gly
            100                 105                 110 gaa gca cct gcg agg aga gtt act att gat gcc ttt tac atg gat gcc      385
Glu Ala Pro Ala Arg Arg Val Thr Ile Asp Ala Phe Tyr Met Asp Ala
        115                 120                 125 tat gaa gtc agt aat act gaa ttt gag aag ttt gtg aac tca act ggc      433
Tyr Glu Val Ser Asn Thr Glu Phe Glu Lys Phe Val Asn Ser Thr Gly
130                 135                 140 tat ttg aca gag gct gag aag ttt ggc gac tcc ttt gtc ttt gaa ggc      481
Tyr Leu Thr Glu Ala Glu Lys Phe Gly Asp Ser Phe Val Phe Glu Gly
145                 150                 155                 160 atg ttg agt gag caa gtg aag acc aat att caa cag gca gtt gca gct      529
Met Leu Ser Glu Gln Val Lys Thr Asn Ile Gln Gln Ala Val Ala Ala
                165                 170                 175 gct ccc tgg tgg tta cct gtg aaa ggc gct aac tgg aga cac cca gaa      577
Ala Pro Trp Trp Leu Pro Val Lys Gly Ala Asn Trp Arg His Pro Glu
            180                 185                 190 ggg cct gac tct act att ctg cac agg ccg gat cat cca gtt ctc cat      625
Gly Pro Asp Ser Thr Ile Leu His Arg Pro Asp His Pro Val Leu His
        195                 200                 205 gtg tcc tgg aat gat gcg gtt gcc tac tgc act tgg gca ggg aag cgg      673
Val Ser Trp Asn Asp Ala Val Ala Tyr Cys Thr Trp Ala Gly Lys Arg
210                 215                 220
```

-continued

```
ctg ccc acg gaa gct gag tgg gaa tac agc tgt cga gga ggc ctg cat       721
Leu Pro Thr Glu Ala Glu Trp Glu Tyr Ser Cys Arg Gly Gly Leu His
225                 230                 235                 240 aat aga ctt ttc ccc tgg ggc aac aaa ctg cag ccc aaa ggc cag cat       769
Asn Arg Leu Phe Pro Trp Gly Asn Lys Leu Gln Pro Lys Gly Gln His
            245                 250                 255 tat gcc aac att tgg cag ggc gag ttt ccg gtg acc aac act ggt gag       817
Tyr Ala Asn Ile Trp Gln Gly Glu Phe Pro Val Thr Asn Thr Gly Glu
        260                 265                 270 gat ggc ttc caa gga act gcg cct gtt gat gcc ttc cct ccc aat ggt       865
Asp Gly Phe Gln Gly Thr Ala Pro Val Asp Ala Phe Pro Pro Asn Gly
    275                 280                 285 tat ggc tta tac aac ata gtg ggg aac gca tgg gaa tgg act tca gac       913
Tyr Gly Leu Tyr Asn Ile Val Gly Asn Ala Trp Glu Trp Thr Ser Asp
290                 295                 300 tgg tgg act gtt cat cat tct gtt gaa gaa acg ctt aac cca aaa ggt       961
Trp Trp Thr Val His His Ser Val Glu Glu Thr Leu Asn Pro Lys Gly
305                 310                 315                 320 ccc cct tct ggg aaa gac cga gtg aag aaa ggt gga tcc tac atg tgc      1009
Pro Pro Ser Gly Lys Asp Arg Val Lys Lys Gly Gly Ser Tyr Met Cys
                325                 330                 335 cat agg tct tat tgt tac agg tat cgc tgt gct gct cgg agc cag aac      1057
His Arg Ser Tyr Cys Tyr Arg Tyr Arg Cys Ala Ala Arg Ser Gln Asn
            340                 345                 350 aca cct gat agc tct gct tcg aat ctg gga ttc cgc tgt gca gcc gac      1105
Thr Pro Asp Ser Ser Ala Ser Asn Leu Gly Phe Arg Cys Ala Ala Asp
        355                 360                 365 cgc ctg ccc act atg gac tgacaaccaa ggaaagtctt ccccagtcca             1153
Arg Leu Pro Thr Met Asp
    370 aggagcagtc gtgtctgacc tacattgggc ttttctcaga actttgaacg atcccatgca    1213 aagaattccc accctgaggt gggttacata cctgcccaat ggccaaagga accgccttgt    1273 gagaccaaat tgctgacctg gtcagtgca tgtgctttat ggtgtggtgc atctttggag     1333 atcatcgcca tattttactt ttgagagtct ttaaagagga aggggagtgg agggaaccct    1393 gagctaggct tcaggaggcc cgcgtcctac gcaggctctg ccacaggggt tagaccccag    1453 gtccgacgct tgaccttcct gggcctcaag tgccctcccc tatcaaatga agggatggac    1513 agcatgacct ctgggtgtct ctccaactca ccagttctaa aagggtatc agattctatt    1573 gtgacttcat agtgagaatt tatgatagat tattttttag ctattttttc catgtgtgaa    1633 ccttgagtga tactaatcat gtaaagtaag agttctctta tgtattattt tcggaagagg    1693 ggtgtggtga ctccttttata ttcgtactgc actttgtttt tccaaggaaa tcagtgtctt    1753 ttacgttgtt atgatgaatc ccacatgggg ccggtgatgg tatgctgcag ttcagccgtt    1813 gaacacatag gaatgtctgt ggggtgactc tactgtgctt tatcttttaa cattaagtgc    1873 ctttggttca gaggggcagt cataagctct gtttccccct ctccccaaag ccttcagcga    1933 acgtgaaatg tgcgctaaac ggggaaacct gtttaattct agatataggg aaaaaggaac    1993 gaggaccttg aatgagctat attcagggta tccggtattt tgtaataggg aataggaaac    2053 cttgttggct gtggaatatc cgatgctttg aatcatgcac tgtgttgaat aaacgtatct    2113 gctaaaaaaa aaaaaaaaaa aaaaaaaaaa aaaaaaaaaa aaaaaaaaaa aa            2165
```

<210> SEQ ID NO 14
<211> LENGTH: 1122
<212> TYPE: DNA

-continued

<213> ORGANISM: Homo sapiens

<400> SEQUENCE: 14

```
atggctgcgc cgcactagg gctggtgtgt ggacgttgcc ctgagctggg tctcgtcctc      60
ttgctgctgc tgctctcgct gctgtgtgga gcggcaggga gccaggaggc cgggaccggt    120
gcgggcgcgg ggtcccttgc gggttcttgc ggctgcggca cgccccagcg gcctggcgcc    180
catggcaatt cggcagccgc tcaccgatac tcgcgggagg ctaacgctcc gggccccgta    240
cccggagagc ggcaactcgc gcactcaaag atggtcccca tccctgttgg agtatttaca    300
atgggcacag atgatcctca gataaagcag gatggggaag cacctgcgag agagttact     360
attgatgcct tttacatgga tgcctatgaa gtcagtaata ctgaatttga agtttgtg     420
aactcaactg ctatttgac agaggctgag aagtttggcg actcctttgt ctttgaaggc    480
atgttgagtg agcaagtgaa gaccaatatt caacaggcag ttgcagctgc tccctggtgg    540
ttacctgtga aggcgctaa ctggagacac ccagaagggc ctgactctac tattctgcac    600
aggccggatc atccagttct ccatgtgtcc tggaatgatg cggttgccta ctgcacttgg    660
gcagggaagc ggctgcccac ggaagctgag tgggaataca gctgtcgagg aggcctgcat    720
aatagacttt tcccctgggg caacaaactg cagcccaaag ccagcatta tgccaacatt    780
tggcagggcg agtttccggt gaccaacact ggtgaggatg gcttccaagg aactgcgcct    840
gttgatgcct tccctcccaa tggttatggc ttatacaaca tagtggggaa cgcatgggaa    900
tggacttcag actggtggac tgttcatcat tctgttgaag aaacgcttaa cccaaaaggt    960
ccccttctg ggaaagaccg agtgaagaaa ggtggatcct acatgtgcca taggtcttat   1020
tgttacaggt atcgctgtgc tgctcggagc cagaacacac ctgatagctc tgcttcgaat   1080
ctgggattcc gctgtgcagc cgaccgcctg cccactatgg ac                     1122
```

<210> SEQ ID NO 15
<211> LENGTH: 374
<212> TYPE: PRT
<213> ORGANISM: Homo sapiens

<400> SEQUENCE: 15

```
Met Ala Ala Pro Ala Leu Gly Leu Val Cys Gly Arg Cys Pro Glu Leu
 1               5                  10                  15

Gly Leu Val Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
            35                  40                  45

Ser Cys Gly Cys Gly Thr Pro Gln Arg Pro Gly Ala His Gly Asn Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Val
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160
```

```
Met Leu Ser Glu Gln Val Lys Thr Asn Ile Gln Gln Ala Val Ala Ala
            165                 170                 175

Ala Pro Trp Trp Leu Pro Val Lys Gly Ala Asn Trp Arg His Pro Glu
        180                 185                 190

Gly Pro Asp Ser Thr Ile Leu His Arg Pro Asp His Pro Val Leu His
            195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370

<210> SEQ ID NO 16
<211> LENGTH: 340
<212> TYPE: PRT
<213> ORGANISM: Homo sapiens

<400> SEQUENCE: 16

Gln Glu Ala Gly Thr Gly Ala Gly Ala Gly Ser Leu Ala Gly Ser Cys
1               5                   10                  15

Gly Cys Gly Thr Pro Gln Arg Pro Gly Ala His Gly Asn Ser Ala Ala
            20                  25                  30

Ala His Arg Tyr Ser Arg Glu Ala Asn Ala Pro Gly Pro Val Pro Gly
        35                  40                  45

Glu Arg Gln Leu Ala His Ser Lys Met Val Pro Ile Pro Val Gly Val
    50                  55                  60

Phe Thr Met Gly Thr Asp Asp Pro Gln Ile Lys Gln Asp Gly Glu Ala
65                  70                  75                  80

Pro Ala Arg Arg Val Thr Ile Asp Ala Phe Tyr Met Asp Ala Tyr Glu
                85                  90                  95

Val Ser Asn Thr Glu Phe Glu Lys Phe Val Asn Ser Thr Gly Tyr Leu
            100                 105                 110

Thr Glu Ala Glu Lys Phe Gly Asp Ser Phe Val Phe Glu Gly Met Leu
        115                 120                 125

Ser Glu Gln Val Lys Thr Asn Ile Gln Gln Ala Val Ala Ala Ala Pro
    130                 135                 140

Trp Trp Leu Pro Val Lys Gly Ala Asn Trp Arg His Pro Glu Gly Pro
```

```
                145                 150                 155                 160
Asp Ser Thr Ile Leu His Arg Pro Asp His Pro Val Leu His Val Ser
                    165                 170                 175
Trp Asn Asp Ala Val Ala Tyr Cys Thr Trp Ala Gly Lys Arg Leu Pro
                180                 185                 190
Thr Glu Ala Glu Trp Glu Tyr Ser Cys Arg Gly Gly Leu His Asn Arg
            195                 200                 205
Leu Phe Pro Trp Gly Asn Lys Leu Gln Pro Lys Gly Gln His Tyr Ala
        210                 215                 220
Asn Ile Trp Gln Gly Glu Phe Pro Val Thr Asn Thr Gly Glu Asp Gly
225                 230                 235                 240
Phe Gln Gly Thr Ala Pro Val Asp Ala Phe Pro Pro Asn Gly Tyr Gly
                245                 250                 255
Leu Tyr Asn Ile Val Gly Asn Ala Trp Glu Trp Thr Ser Asp Trp Trp
                260                 265                 270
Thr Val His His Ser Val Glu Thr Leu Asn Pro Lys Gly Pro Pro
                275                 280                 285
Ser Gly Lys Asp Arg Val Lys Lys Gly Gly Ser Tyr Met Cys His Arg
290                 295                 300
Ser Tyr Cys Tyr Arg Tyr Arg Cys Ala Ala Arg Ser Gln Asn Thr Pro
305                 310                 315                 320
Asp Ser Ser Ala Ser Asn Leu Gly Phe Arg Cys Ala Ala Asp Arg Leu
                325                 330                 335
Pro Thr Met Asp
            340

<210> SEQ ID NO 17
<211> LENGTH: 34
<212> TYPE: PRT
<213> ORGANISM: Homo sapiens
<220> FEATURE:
<221> NAME/KEY: SIGNAL
<222> LOCATION: (1)...(34)

<400> SEQUENCE: 17

Met Ala Ala Pro Ala Leu Gly Leu Val Cys Gly Arg Cys Pro Glu Leu
                -30                 -25                 -20
Gly Leu Val Leu Leu Leu Leu Leu Ser Leu Leu Cys Gly Ala Ala
            -15                 -10                  -5
Gly Ser

<210> SEQ ID NO 18
<211> LENGTH: 299
<212> TYPE: PRT
<213> ORGANISM: Mycobacterium tuberculosis

<400> SEQUENCE: 18

Met Leu Thr Glu Leu Val Asp Leu Pro Gly Ser Phe Arg Met Gly
 1               5                  10                  15
Ser Thr Arg Phe Tyr Pro Glu Glu Ala Pro Ile His Thr Val Thr Val
                20                  25                  30
Arg Ala Phe Ala Val Glu Arg His Pro Val Thr Asn Ala Gln Phe Ala
            35                  40                  45
Glu Phe Val Ser Ala Thr Gly Tyr Val Thr Val Ala Glu Gln Pro Leu
        50                  55                  60
Asp Pro Gly Leu Tyr Pro Gly Val Asp Ala Ala Asp Leu Cys Pro Gly
65                  70                  75                  80
```

```
Ala Met Val Phe Cys Pro Thr Ala Gly Pro Val Asp Leu Arg Asp Trp
             85                  90                  95

Arg Gln Trp Trp Asp Trp Val Pro Gly Ala Cys Trp Arg His Pro Phe
            100                 105                 110

Gly Arg Asp Ser Asp Ile Ala Asp Arg Ala Gly His Pro Val Val Gln
            115                 120                 125

Val Ala Tyr Pro Asp Ala Val Ala Tyr Ala Arg Trp Ala Gly Arg Arg
        130                 135                 140

Leu Pro Thr Glu Ala Glu Trp Glu Tyr Ala Ala Arg Gly Gly Thr Thr
145                 150                 155                 160

Ala Thr Tyr Ala Trp Gly Asp Gln Glu Lys Pro Gly Gly Met Leu Met
                165                 170                 175

Ala Asn Thr Trp Gln Gly Arg Phe Pro Tyr Arg Asn Asp Gly Ala Leu
            180                 185                 190

Gly Trp Val Gly Thr Ser Pro Val Gly Arg Phe Pro Ala Asn Gly Phe
        195                 200                 205

Gly Leu Leu Asp Met Ile Gly Asn Val Trp Glu Trp Thr Thr Thr Glu
    210                 215                 220

Phe Tyr Pro His His Arg Ile Asp Pro Pro Ser Thr Ala Cys Cys Ala
225                 230                 235                 240

Pro Val Lys Leu Ala Thr Ala Ala Asp Pro Thr Ile Ser Gln Thr Leu
                245                 250                 255

Lys Gly Gly Ser His Leu Cys Ala Pro Glu Tyr Cys His Arg Tyr Arg
            260                 265                 270

Pro Ala Ala Arg Ser Pro Gln Ser Gln Asp Thr Ala Thr Thr His Ile
        275                 280                 285

Gly Phe Arg Cys Val Ala Asp Pro Val Ser Gly
    290                 295

<210> SEQ ID NO 19
<211> LENGTH: 2811
<212> TYPE: DNA
<213> ORGANISM: Homo sapiens
<220> FEATURE:
<221> NAME/KEY: CDS
<222> LOCATION: (183)...(2567)

<400> SEQUENCE: 19
ctcggcccgc tcggcgcgcc ccttcccagc cgcccttccg taccggctct cgggctcttc      60
cggtctccgg ccgccccta actgcaggct cttctcccgc cgcggccgg cgctctccga      120 gtcgccctg cggactggtc tcgcacagtg cctgggcacc gggcgccaga cagacactgg     180 cc atg acg agc ggc gca acc agg tac cgg ctg agc tgc tcg ctc cgg      227
   Met Thr Ser Gly Ala Thr Arg Tyr Arg Leu Ser Cys Ser Leu Arg
    1               5                  10                  15 ggc cac gag ctg gac gta cgg ggc ctg gtg tgc tgc gcc tat ccg ccg      275
Gly His Glu Leu Asp Val Arg Gly Leu Val Cys Cys Ala Tyr Pro Pro
                20                  25                  30 gga gcc ttt gtg tcc gtg tcc cga gac cgc acc acc cgc ctc tgg gcc      323
Gly Ala Phe Val Ser Val Ser Arg Asp Arg Thr Thr Arg Leu Trp Ala
            35                  40                  45 cca gac agt cca aac agg agc ttt aca gaa atg cac tgt atg agt ggc      371
Pro Asp Ser Pro Asn Arg Ser Phe Thr Glu Met His Cys Met Ser Gly
        50                  55                  60 cat tcc aat ttt gta tct tgt gta tgc atc ata ccc tca agt gac atc      419
His Ser Asn Phe Val Ser Cys Val Cys Ile Ile Pro Ser Ser Asp Ile
    65                  70                  75
```

```
                                                             -continued tac cct cat ggc cta att gcc acc ggt gga aat gac cac aat ata tgc      467
Tyr Pro His Gly Leu Ile Ala Thr Gly Gly Asn Asp His Asn Ile Cys
 80              85                  90                  95 att ttc tca ctg gac agt cca atg cca ctt tat att cta aaa ggc cac      515
Ile Phe Ser Leu Asp Ser Pro Met Pro Leu Tyr Ile Leu Lys Gly His
                100                 105                 110 aaa aat act gtt tgt agt cta tca tct gga aaa ttt ggg aca tta ctt      563
Lys Asn Thr Val Cys Ser Leu Ser Ser Gly Lys Phe Gly Thr Leu Leu
            115                 120                 125 agt ggt tca tgg gac acc act gct aaa gtc tgg ctg aat gac aag tgc      611
Ser Gly Ser Trp Asp Thr Thr Ala Lys Val Trp Leu Asn Asp Lys Cys
        130                 135                 140 atg atg acc ttg cag ggt cat aca gct gca gtg tgg gcg gta aag atc      659
Met Met Thr Leu Gln Gly His Thr Ala Ala Val Trp Ala Val Lys Ile
    145                 150                 155 tta cct gaa cag ggc tta atg ttg act gga tca gca gac aag act gtt      707
Leu Pro Glu Gln Gly Leu Met Leu Thr Gly Ser Ala Asp Lys Thr Val
160                 165                 170                 175 aaa ctg tgg aag gct gga aga tgt gag agg act ttt tca ggg cat gaa      755
Lys Leu Trp Lys Ala Gly Arg Cys Glu Arg Thr Phe Ser Gly His Glu
                180                 185                 190 gac tgt gta aga ggt ttg gca att ttg agt gaa aca gaa ttt ctt tcc      803
Asp Cys Val Arg Gly Leu Ala Ile Leu Ser Glu Thr Glu Phe Leu Ser
            195                 200                 205 tgt gca aat gat gct agt att aga agg tgg caa atc act ggc gag tgt      851
Cys Ala Asn Asp Ala Ser Ile Arg Arg Trp Gln Ile Thr Gly Glu Cys
        210                 215                 220 ctt gaa gta tat tat gga cat aca aat tat att tat agc ata tcc gtt      899
Leu Glu Val Tyr Tyr Gly His Thr Asn Tyr Ile Tyr Ser Ile Ser Val
    225                 230                 235 ttt cca aat tgt aga gac ttt gtg aca aca gca gag gac aga tct ctg      947
Phe Pro Asn Cys Arg Asp Phe Val Thr Thr Ala Glu Asp Arg Ser Leu
240                 245                 250                 255 aga atc tgg aaa cat ggg gaa tgt gct caa act atc cga ctt cca gct      995
Arg Ile Trp Lys His Gly Glu Cys Ala Gln Thr Ile Arg Leu Pro Ala
                260                 265                 270 cag tct ata tgg tgc tgc tgt gtg ctc gac aat ggt gac att gtg gtt     1043
Gln Ser Ile Trp Cys Cys Cys Val Leu Asp Asn Gly Asp Ile Val Val
            275                 280                 285 ggt gcg agt gat ggc att att aga gtg ttt aca gaa tca gaa gat cga     1091
Gly Ala Ser Asp Gly Ile Ile Arg Val Phe Thr Glu Ser Glu Asp Arg
        290                 295                 300 aca gca agt gct gaa gaa atc aag gct ttt gaa aaa gaa ctg tct cac     1139
Thr Ala Ser Ala Glu Glu Ile Lys Ala Phe Glu Lys Glu Leu Ser His
    305                 310                 315 gca acc att gat tct aaa act ggc gat tta ggg gac atc aat gct gag     1187
Ala Thr Ile Asp Ser Lys Thr Gly Asp Leu Gly Asp Ile Asn Ala Glu
320                 325                 330                 335 cag ctt cct ggg agg gaa cat ctt aat gaa cct ggt act aga gaa gga     1235
Gln Leu Pro Gly Arg Glu His Leu Asn Glu Pro Gly Thr Arg Glu Gly
                340                 345                 350 cag act cgt cta atc aga gat ggg gag aaa gtc gaa gcc tat cag tgg     1283
Gln Thr Arg Leu Ile Arg Asp Gly Glu Lys Val Glu Ala Tyr Gln Trp
            355                 360                 365 agt gtt agt gaa ggg agg tgg ata aaa att ggt gat gtt gtt ggc tca     1331
Ser Val Ser Glu Gly Arg Trp Ile Lys Ile Gly Asp Val Val Gly Ser
        370                 375                 380 tct ggt gct aat cag caa aca tct gga aaa gtt tta tat gaa ggg aaa     1379
Ser Gly Ala Asn Gln Gln Thr Ser Gly Lys Val Leu Tyr Glu Gly Lys
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 385 |     |     |     |     | 390 |     |     |     |     | 395 |     |     |      |
| gaa | ttt | gat | tat | gtt | ttc | tca | att | gat | gtc | aat | gaa | ggt | gga | cca | tca | 1427 |
| Glu | Phe | Asp | Tyr | Val | Phe | Ser | Ile | Asp | Val | Asn | Glu | Gly | Gly | Pro | Ser |      |
| 400 |     |     |     |     | 405 |     |     |     |     | 410 |     |     |     |     | 415 |      |
| tat | aaa | ttg | cca | tat | aat | acc | agt | gat | gac | cct | tgg | tta | act | gca | tac | 1475 |
| Tyr | Lys | Leu | Pro | Tyr | Asn | Thr | Ser | Asp | Asp | Pro | Trp | Leu | Thr | Ala | Tyr |      |
|     |     |     |     | 420 |     |     |     |     | 425 |     |     |     |     | 430 |     |      |
| aac | ttc | tta | cag | aag | aat | gat | ttg | aat | cct | atg | ttt | ctg | gat | caa | gta | 1523 |
| Asn | Phe | Leu | Gln | Lys | Asn | Asp | Leu | Asn | Pro | Met | Phe | Leu | Asp | Gln | Val |      |
|     |     |     | 435 |     |     |     |     | 440 |     |     |     |     | 445 |     |     |      |
| gct | aaa | ttt | att | att | gat | aac | aca | aaa | ggt | caa | atg | ttg | gga | ctt | ggg | 1571 |
| Ala | Lys | Phe | Ile | Ile | Asp | Asn | Thr | Lys | Gly | Gln | Met | Leu | Gly | Leu | Gly |      |
|     |     | 450 |     |     |     |     | 455 |     |     |     |     | 460 |     |     |     |      |
| aat | ccc | agc | ttt | tca | gat | cca | ttt | aca | ggt | ggt | ggt | cgg | tat | gtt | ccg | 1619 |
| Asn | Pro | Ser | Phe | Ser | Asp | Pro | Phe | Thr | Gly | Gly | Gly | Arg | Tyr | Val | Pro |      |
|     | 465 |     |     |     |     | 470 |     |     |     |     | 475 |     |     |     |     |      |
| ggc | tct | tcg | gga | tct | tct | aac | aca | cta | ccc | aca | gca | gat | cct | ttt | aca | 1667 |
| Gly | Ser | Ser | Gly | Ser | Ser | Asn | Thr | Leu | Pro | Thr | Ala | Asp | Pro | Phe | Thr |      |
| 480 |     |     |     |     | 485 |     |     |     |     | 490 |     |     |     |     | 495 |      |
| ggt | gct | ggt | cgt | tat | gta | cca | ggt | tct | gca | agt | atg | gga | act | acc | atg | 1715 |
| Gly | Ala | Gly | Arg | Tyr | Val | Pro | Gly | Ser | Ala | Ser | Met | Gly | Thr | Thr | Met |      |
|     |     |     |     | 500 |     |     |     |     | 505 |     |     |     |     | 510 |     |      |
| gcc | gga | gtt | gat | cca | ttt | aca | ggg | aat | agt | gcc | tac | cga | tca | gct | gca | 1763 |
| Ala | Gly | Val | Asp | Pro | Phe | Thr | Gly | Asn | Ser | Ala | Tyr | Arg | Ser | Ala | Ala |      |
|     |     |     | 515 |     |     |     |     | 520 |     |     |     |     | 525 |     |     |      |
| tct | aaa | aca | atg | aat | att | tat | ttc | cct | aaa | aaa | gag | gct | gtc | aca | ttt | 1811 |
| Ser | Lys | Thr | Met | Asn | Ile | Tyr | Phe | Pro | Lys | Lys | Glu | Ala | Val | Thr | Phe |      |
|     |     | 530 |     |     |     |     | 535 |     |     |     |     | 540 |     |     |     |      |
| gac | caa | gca | aac | cct | aca | caa | ata | tta | ggt | aaa | ctg | aag | gaa | ctt | aat | 1859 |
| Asp | Gln | Ala | Asn | Pro | Thr | Gln | Ile | Leu | Gly | Lys | Leu | Lys | Glu | Leu | Asn |      |
| 545 |     |     |     |     | 550 |     |     |     |     | 555 |     |     |     |     |     |      |
| gga | act | gca | cct | gaa | gag | aag | aag | tta | act | gag | gat | gac | ttg | ata | ctt | 1907 |
| Gly | Thr | Ala | Pro | Glu | Glu | Lys | Lys | Leu | Thr | Glu | Asp | Asp | Leu | Ile | Leu |      |
| 560 |     |     |     |     | 565 |     |     |     |     | 570 |     |     |     |     | 575 |      |
| ctt | gag | aag | ata | ctg | tct | cta | ata | tgt | aat | agt | tct | tca | gaa | aaa | ccc | 1955 |
| Leu | Glu | Lys | Ile | Leu | Ser | Leu | Ile | Cys | Asn | Ser | Ser | Ser | Glu | Lys | Pro |      |
|     |     |     |     | 580 |     |     |     |     | 585 |     |     |     |     | 590 |     |      |
| aca | gtc | cag | caa | ctt | cag | att | ttg | tgg | aaa | gct | att | aac | tgt | cct | gaa | 2003 |
| Thr | Val | Gln | Gln | Leu | Gln | Ile | Leu | Trp | Lys | Ala | Ile | Asn | Cys | Pro | Glu |      |
|     |     |     | 595 |     |     |     |     | 600 |     |     |     |     | 605 |     |     |      |
| gat | att | gtc | ttt | cct | gca | ctt | gac | att | ctt | cgg | ttg | tca | att | aaa | cac | 2051 |
| Asp | Ile | Val | Phe | Pro | Ala | Leu | Asp | Ile | Leu | Arg | Leu | Ser | Ile | Lys | His |      |
|     |     | 610 |     |     |     |     | 615 |     |     |     |     | 620 |     |     |     |      |
| ccc | agt | gtg | aat | gag | aac | ttc | tgc | aat | gaa | aag | gaa | ggg | gct | cag | ttc | 2099 |
| Pro | Ser | Val | Asn | Glu | Asn | Phe | Cys | Asn | Glu | Lys | Glu | Gly | Ala | Gln | Phe |      |
|     | 625 |     |     |     |     | 630 |     |     |     |     | 635 |     |     |     |     |      |
| agc | agt | cat | ctt | atc | aat | ctt | ctg | aac | cct | aaa | gga | aag | cca | gca | aac | 2147 |
| Ser | Ser | His | Leu | Ile | Asn | Leu | Leu | Asn | Pro | Lys | Gly | Lys | Pro | Ala | Asn |      |
| 640 |     |     |     |     | 645 |     |     |     |     | 650 |     |     |     |     | 655 |      |
| cag | ctg | ctt | gct | ctc | agg | act | ttt | tgc | aat | tgt | ttt | gtt | ggc | cag | gca | 2195 |
| Gln | Leu | Leu | Ala | Leu | Arg | Thr | Phe | Cys | Asn | Cys | Phe | Val | Gly | Gln | Ala |      |
|     |     |     |     | 660 |     |     |     |     | 665 |     |     |     |     | 670 |     |      |
| gga | caa | aaa | ctc | atg | atg | tcc | cag | agg | gaa | tca | ctg | atg | tcc | cat | gca | 2243 |
| Gly | Gln | Lys | Leu | Met | Met | Ser | Gln | Arg | Glu | Ser | Leu | Met | Ser | His | Ala |      |
|     |     |     | 675 |     |     |     |     | 680 |     |     |     |     | 685 |     |     |      |
| ata | gaa | ctg | aaa | tca | ggg | agc | aat | aag | aac | att | cac | att | gct | ctg | gct | 2291 |
| Ile | Glu | Leu | Lys | Ser | Gly | Ser | Asn | Lys | Asn | Ile | His | Ile | Ala | Leu | Ala |      |
|     |     | 690 |     |     |     |     | 695 |     |     |     |     | 700 |     |     |     |      |
| aca | ttg | gcc | ctg | aac | tat | tct | gtt | tgt | ttt | cat | aaa | gac | cat | aac | att | 2339 |

```
Thr Leu Ala Leu Asn Tyr Ser Val Cys Phe His Lys Asp His Asn Ile
    705                 710                 715 gaa ggg aaa gcc caa tgt ttg tca cta att agc aca atc ttg gaa gta      2387
Glu Gly Lys Ala Gln Cys Leu Ser Leu Ile Ser Thr Ile Leu Glu Val
720                 725                 730                 735 gta caa gac cta gaa gcc act ttt aga ctt ctt gtg gct ctt gga aca      2435
Val Gln Asp Leu Glu Ala Thr Phe Arg Leu Leu Val Ala Leu Gly Thr
                740                 745                 750 ctt atc agt gat gat tca aat gct gta caa tta gcc aag tct tta ggt      2483
Leu Ile Ser Asp Asp Ser Asn Ala Val Gln Leu Ala Lys Ser Leu Gly
            755                 760                 765 gtt gat tct caa ata aaa aag tat tcc tca gta tca gaa cca gct aaa      2531
Val Asp Ser Gln Ile Lys Lys Tyr Ser Ser Val Ser Glu Pro Ala Lys
        770                 775                 780 gta agt gaa tgc tgt aga ttt atc cta aat ttg ctg tagcagtggg           2577
Val Ser Glu Cys Cys Arg Phe Ile Leu Asn Leu
    785                 790                 795 gaagagggac ggatatttttt aattgattag tgttttttc ctcacatttg acatgactga     2637
taacagataa ttaaaaaaag agaatacggt ggattaagta aaattttaca tcttgtaaag    2697
tggtggggag gggaaacaga aataaaattt ttgcactgct gaaaaaaaaa aaaaaaaaa     2757 aaaaaaaaaa aaaaaaaaaa aaaaaaaaaa aaaaaaaaa aaaaaaaaa aaaa            2811

<210> SEQ ID NO 20
<211> LENGTH: 2385
<212> TYPE: DNA
<213> ORGANISM: Homo sapiens

<400> SEQUENCE: 20
atgacgagcg gcgcaaccag gtaccggctg agctgctcgc tccggggcca cgagctggac      60
gtacggggcc tggtgtgctg cgcctatccg ccgggagcct tgtgtccgt gtcccgagac     120 cgcaccaccc gcctctgggc cccagacagt ccaaacagga gctttacaga aatgcactgt    180
atgagtggcc attccaattt gtatcttgt gtatgcatca taccctcaag tgacatctac    240
cctcatggcc taattgccac cggtggaaat gaccacaata tatgcatttt ctcactggac    300
agtccaatgc cactttatat tctaaaaggc cacaaaaata ctgtttgtag tctatcatct    360
ggaaaatttg gacattact tagtggttca tgggacacca ctgctaaagt ctggctgaat    420
gacaagtgca tgatgacctt gcagggtcat acagctgcag tgtgggcggt aaagatctta    480
cctgaacagg gcttaatgtt gactggatca gcagacaaga ctgttaaact gtggaaggct    540
ggaagatgtg agaggacttt tcagggcat gaagactgtg taagaggttt ggcaattttg    600
agtgaaacag aatttctttc ctgtgcaaat gatgctagta ttagaaggtg gcaaatcact    660
ggcgagtgtc ttgaagtata ttatggacat acaaattata tttatagcat atccgttttt    720
ccaaattgta gagctttgt gacaacagca gaggacagat ctctgagaat ctggaaacat    780
ggggaatgtg ctcaaactat ccgacttcca gctcagtcta tatggtgctg ctgtgtgctc    840
gacaatggtg acattgtggt tggtgcgagt gatggcatta ttagagtgtt tacagaatca    900
gaagatcgaa cagcaagtgc tgaagaaatc aaggcttttg aaaaagaact gtctcacgca    960
accattgatt ctaaaactgg cgatttaggg gacatcaatg ctgagcagct tcctgggagg   1020
gaacatctta atgaacctgg tactagagaa ggacagactc gtctaatcag agatggggag   1080
aaagtcgaag cctatcagtg gagtgttagt gaagggaggt ggataaaat tggtgatgtt   1140 gttggctcat ctggtgctaa tcagcaaaca tctggaaaag ttttatatga agggaaagaa   1200
```

```
tttgattatg ttttctcaat tgatgtcaat gaaggtggac catcatataa attgccatat    1260
aataccagtg atgacccttg gttaactgca tacaacttct tacagaagaa tgatttgaat    1320
cctatgtttc tggatcaagt agctaaattt attattgata acacaaaagg tcaaatgttg    1380
ggacttggga atcccagctt ttcagatcca tttacaggtg gtggtcggta tgttccgggc    1440
tcttcgggat cttctaacac actacccaca gcagatcctt ttacaggtgc tggtcgttat    1500
gtaccaggtt ctgcaagtat gggaactacc atggccggag ttgatccatt tacagggaat    1560
agtgcctacc gatcagctgc atctaaaaca atgaatattt atttccctaa aaaagaggct    1620
gtcacatttg accaagcaaa ccctacacaa atattaggta aactgaagga acttaatgga    1680
actgcacctg aagagaagaa gttaactgag gatgacttga tacttcttga agatactg     1740 tctctaatat gtaatagttc ttcagaaaaa cccacagtcc agcaacttca gattttgtgg    1800
aaagctatta actgtcctga agatattgtc tttcctgcac ttgacattct tcggttgtca    1860
attaaacacc ccagtgtgaa tgagaacttc tgcaatgaaa aggaagggc tcagttcagc     1920 agtcatctta tcaatcttct gaaccctaaa ggaaagccag caaaccagct gcttgctctc    1980 aggactttt gcaattgttt tgttggccag gcaggacaaa aactcatgat gtcccagagg      2040
gaatcactga tgtcccatgc aatagaactg aaatcaggga gcaataagaa cattcacatt    2100
gctctggcta cattggccct gaactattct gtttgttttc ataaagacca taacattgaa    2160
gggaaagccc aatgtttgtc actaattagc acaatcttgg aagtagtaca agacctagaa    2220 gccacttta gacttcttgt ggctcttgga acacttatca gtgatgattc aaatgctgta      2280
caattagcca agtctttagg tgttgattct caaataaaaa agtattcctc agtatcagaa    2340
ccagctaaag taagtgaatg ctgtagattt atcctaaatt tgctg                    2385
```

<210> SEQ ID NO 21
<211> LENGTH: 795
<212> TYPE: PRT
<213> ORGANISM: Homo sapiens

<400> SEQUENCE: 21

```
Met Thr Ser Gly Ala Thr Arg Tyr Arg Leu Ser Cys Ser Leu Arg Gly
  1               5                  10                  15

His Glu Leu Asp Val Arg Gly Leu Val Cys Cys Ala Tyr Pro Pro Gly
                 20                  25                  30

Ala Phe Val Ser Val Ser Arg Asp Arg Thr Thr Arg Leu Trp Ala Pro
             35                  40                  45

Asp Ser Pro Asn Arg Ser Phe Thr Glu Met His Cys Met Ser Gly His
         50                  55                  60

Ser Asn Phe Val Ser Cys Val Cys Ile Ile Pro Ser Ser Asp Ile Tyr
 65                  70                  75                  80

Pro His Gly Leu Ile Ala Thr Gly Gly Asn Asp His Asn Ile Cys Ile
                 85                  90                  95

Phe Ser Leu Asp Ser Pro Met Pro Leu Tyr Ile Leu Lys Gly His Lys
            100                 105                 110

Asn Thr Val Cys Ser Leu Ser Ser Gly Lys Phe Gly Thr Leu Leu Ser
            115                 120                 125

Gly Ser Trp Asp Thr Thr Ala Lys Val Trp Leu Asn Asp Lys Cys Met
        130                 135                 140

Met Thr Leu Gln Gly His Thr Ala Ala Val Trp Ala Val Lys Ile Leu
145                 150                 155                 160

Pro Glu Gln Gly Leu Met Leu Thr Gly Ser Ala Asp Lys Thr Val Lys
```

-continued

```
                165                 170                 175
Leu Trp Lys Ala Gly Arg Cys Glu Arg Thr Phe Ser Gly His Glu Asp
            180                 185                 190
Cys Val Arg Gly Leu Ala Ile Leu Ser Glu Thr Glu Phe Leu Ser Cys
        195                 200                 205
Ala Asn Asp Ala Ser Ile Arg Arg Trp Gln Ile Thr Gly Glu Cys Leu
    210                 215                 220
Glu Val Tyr Tyr Gly His Thr Asn Tyr Ile Tyr Ser Ile Ser Val Phe
225                 230                 235                 240
Pro Asn Cys Arg Asp Phe Val Thr Thr Ala Glu Asp Arg Ser Leu Arg
            245                 250                 255
Ile Trp Lys His Gly Glu Cys Ala Gln Thr Ile Arg Leu Pro Ala Gln
            260                 265                 270
Ser Ile Trp Cys Cys Val Leu Asp Asn Gly Asp Ile Val Val Gly
        275                 280                 285
Ala Ser Asp Gly Ile Ile Arg Val Phe Thr Glu Ser Glu Asp Arg Thr
    290                 295                 300
Ala Ser Ala Glu Glu Ile Lys Ala Phe Glu Lys Glu Leu Ser His Ala
305                 310                 315                 320
Thr Ile Asp Ser Lys Thr Gly Asp Leu Gly Asp Ile Asn Ala Glu Gln
            325                 330                 335
Leu Pro Gly Arg Glu His Leu Asn Glu Pro Gly Thr Arg Glu Gly Gln
            340                 345                 350
Thr Arg Leu Ile Arg Asp Gly Glu Lys Val Glu Ala Tyr Gln Trp Ser
        355                 360                 365
Val Ser Glu Gly Arg Trp Ile Lys Ile Gly Asp Val Val Gly Ser Ser
    370                 375                 380
Gly Ala Asn Gln Gln Thr Ser Gly Lys Val Leu Tyr Glu Gly Lys Glu
385                 390                 395                 400
Phe Asp Tyr Val Phe Ser Ile Asp Val Asn Glu Gly Gly Pro Ser Tyr
            405                 410                 415
Lys Leu Pro Tyr Asn Thr Ser Asp Asp Pro Trp Leu Thr Ala Tyr Asn
            420                 425                 430
Phe Leu Gln Lys Asn Asp Leu Asn Pro Met Phe Leu Asp Gln Val Ala
        435                 440                 445
Lys Phe Ile Ile Asp Asn Thr Lys Gly Gln Met Leu Gly Leu Gly Asn
    450                 455                 460
Pro Ser Phe Ser Asp Pro Phe Thr Gly Gly Arg Tyr Val Pro Gly
465                 470                 475                 480
Ser Ser Gly Ser Ser Asn Thr Leu Pro Thr Ala Asp Pro Phe Thr Gly
            485                 490                 495
Ala Gly Arg Tyr Val Pro Gly Ser Ala Ser Met Gly Thr Thr Met Ala
            500                 505                 510
Gly Val Asp Pro Phe Thr Gly Asn Ser Ala Tyr Arg Ser Ala Ala Ser
        515                 520                 525
Lys Thr Met Asn Ile Tyr Phe Pro Lys Lys Glu Ala Val Thr Phe Asp
    530                 535                 540
Gln Ala Asn Pro Thr Gln Ile Leu Gly Lys Leu Lys Glu Leu Asn Gly
545                 550                 555                 560
Thr Ala Pro Glu Glu Lys Lys Leu Thr Glu Asp Asp Leu Ile Leu Leu
            565                 570                 575
Glu Lys Ile Leu Ser Leu Ile Cys Asn Ser Ser Ser Glu Lys Pro Thr
            580                 585                 590
```

Val Gln Gln Leu Gln Ile Leu Trp Lys Ala Ile Asn Cys Pro Glu Asp
            595                 600                 605

Ile Val Phe Pro Ala Leu Asp Ile Leu Arg Leu Ser Ile Lys His Pro
    610                 615                 620

Ser Val Asn Glu Asn Phe Cys Asn Glu Lys Glu Gly Ala Gln Phe Ser
625                 630                 635                 640

Ser His Leu Ile Asn Leu Asn Pro Lys Gly Lys Pro Ala Asn Gln
                645                 650                 655

Leu Leu Ala Leu Arg Thr Phe Cys Asn Cys Phe Val Gly Gln Ala Gly
                660                 665                 670

Gln Lys Leu Met Met Ser Gln Arg Glu Ser Leu Met Ser His Ala Ile
            675                 680                 685

Glu Leu Lys Ser Gly Ser Asn Lys Asn Ile His Ile Ala Leu Ala Thr
            690                 695                 700

Leu Ala Leu Asn Tyr Ser Val Cys Phe His Lys Asp His Asn Ile Glu
705                 710                 715                 720

Gly Lys Ala Gln Cys Leu Ser Leu Ile Ser Thr Ile Leu Glu Val Val
                725                 730                 735

Gln Asp Leu Glu Ala Thr Phe Arg Leu Leu Val Ala Leu Gly Thr Leu
                740                 745                 750

Ile Ser Asp Asp Ser Asn Ala Val Gln Leu Ala Lys Ser Leu Gly Val
            755                 760                 765

Asp Ser Gln Ile Lys Lys Tyr Ser Ser Val Ser Glu Pro Ala Lys Val
770                 775                 780

Ser Glu Cys Cys Arg Phe Ile Leu Asn Leu Leu
785                 790                 795

<210> SEQ ID NO 22
<211> LENGTH: 31
<212> TYPE: PRT
<213> ORGANISM: Homo sapiens

<400> SEQUENCE: 22

Gly His Glu Leu Asp Val Arg Gly Leu Val Cys Cys Ala Tyr Pro Pro
1               5                   10                  15

Gly Ala Phe Val Ser Val Ser Arg Asp Arg Thr Thr Arg Leu Trp
            20                  25                  30

<210> SEQ ID NO 23
<211> LENGTH: 35
<212> TYPE: PRT
<213> ORGANISM: Homo sapiens

<400> SEQUENCE: 23

Gly His Ser Asn Phe Val Ser Cys Val Cys Ile Ile Pro Ser Ser Asp
1               5                   10                  15

Ile Tyr Pro His Gly Leu Ile Ala Thr Gly Gly Asn Asp His Asn Ile
            20                  25                  30

Cys Ile Phe
        35

<210> SEQ ID NO 24
<211> LENGTH: 29
<212> TYPE: PRT
<213> ORGANISM: Homo sapiens

<400> SEQUENCE: 24

```
Gly His Lys Asn Thr Val Cys Ser Leu Ser Ser Gly Lys Phe Gly Thr
 1               5                  10                  15
Leu Leu Ser Gly Ser Trp Asp Thr Thr Ala Lys Val Trp
            20                  25
```

<210> SEQ ID NO 25
<211> LENGTH: 30
<212> TYPE: PRT
<213> ORGANISM: Homo sapiens

<400> SEQUENCE: 25

```
Gly His Thr Ala Ala Val Trp Ala Val Lys Ile Leu Pro Glu Gln Gly
 1               5                  10                  15
Leu Met Leu Thr Gly Ser Ala Asp Lys Thr Val Lys Leu Trp
            20                  25                  30
```

<210> SEQ ID NO 26
<211> LENGTH: 29
<212> TYPE: PRT
<213> ORGANISM: Homo sapiens

<400> SEQUENCE: 26

```
Gly His Glu Asp Cys Val Arg Gly Leu Ala Ile Leu Ser Glu Thr Glu
 1               5                  10                  15
Phe Leu Ser Cys Ala Asn Asp Ala Ser Ile Arg Arg Trp
            20                  25
```

<210> SEQ ID NO 27
<211> LENGTH: 30
<212> TYPE: PRT
<213> ORGANISM: Homo sapiens

<400> SEQUENCE: 27

```
Gly His Thr Asn Tyr Ile Tyr Ser Ile Ser Val Phe Pro Asn Cys Arg
 1               5                  10                  15
Asp Phe Val Thr Thr Ala Glu Asp Arg Ser Leu Arg Ile Trp
            20                  25                  30
```

<210> SEQ ID NO 28
<211> LENGTH: 37
<212> TYPE: PRT
<213> ORGANISM: Homo sapiens

<400> SEQUENCE: 28

```
Gly Glu Cys Ala Gln Thr Ile Arg Leu Pro Ala Gln Ser Ile Trp Cys
 1               5                  10                  15
Cys Cys Val Leu Asp Asn Gly Asp Ile Val Val Gly Ala Ser Asp Gly
            20                  25                  30
Ile Ile Arg Val Phe
        35
```

<210> SEQ ID NO 29
<211> LENGTH: 2217
<212> TYPE: DNA
<213> ORGANISM: Homo sapiens
<220> FEATURE:
<221> NAME/KEY: CDS
<222> LOCATION: (1)...(2214)

<400> SEQUENCE: 29

```
atg cac tgt atg agc ggc cac tcc aat ttt gta tct tgt gta tgc atc      48
Met His Cys Met Ser Gly His Ser Asn Phe Val Ser Cys Val Cys Ile
 1               5                  10                  15
```

-continued

| | |
|---|---|
| ata ccc tca agt gac atc tac cct cat ggc cta att gcc acc ggt gga<br>Ile Pro Ser Ser Asp Ile Tyr Pro His Gly Leu Ile Ala Thr Gly Gly<br>            20                  25                  30 | 96 |
| aat gac cac aat ata tgc att ttc tca ctg gac agt cca atg cca ctt<br>Asn Asp His Asn Ile Cys Ile Phe Ser Leu Asp Ser Pro Met Pro Leu<br>        35                  40                  45 | 144 |
| tat att cta aaa ggc cac aaa aat act gtt tgt agt cta tca tct gga<br>Tyr Ile Leu Lys Gly His Lys Asn Thr Val Cys Ser Leu Ser Ser Gly<br>            50                  55                  60 | 192 |
| aaa ttt ggg aca tta ctt agt ggt tca tgg gac acc act gct aaa gtc<br>Lys Phe Gly Thr Leu Leu Ser Gly Ser Trp Asp Thr Thr Ala Lys Val<br>65                  70                  75                  80 | 240 |
| tgg ctg aat gac aag tgc atg atg acc ttg cag ggt cat aca gct gca<br>Trp Leu Asn Asp Lys Cys Met Met Thr Leu Gln Gly His Thr Ala Ala<br>                  85                  90                  95 | 288 |
| gtg tgg gcg gta aag atc tta cct gaa cag ggc tta atg ttg act gga<br>Val Trp Ala Val Lys Ile Leu Pro Glu Gln Gly Leu Met Leu Thr Gly<br>            100                 105              110 | 336 |
| tca gca gac aag act gtt aaa ctg tgg aag gct gga aga tgt gag agg<br>Ser Ala Asp Lys Thr Val Lys Leu Trp Lys Ala Gly Arg Cys Glu Arg<br>            115                 120              125 | 384 |
| act ttt tca ggg cat gaa gac tgt gta aga ggt ttg gca att ttg agt<br>Thr Phe Ser Gly His Glu Asp Cys Val Arg Gly Leu Ala Ile Leu Ser<br>130                  135                 140 | 432 |
| gaa aca gaa ttt ctt tcc tgt gca aat gat gct agt att aga agg tgg<br>Glu Thr Glu Phe Leu Ser Cys Ala Asn Asp Ala Ser Ile Arg Arg Trp<br>145                  150               155              160 | 480 |
| caa atc act ggc gag tgt ctt gaa gta tat tat gga cat aca aat tat<br>Gln Ile Thr Gly Glu Cys Leu Glu Val Tyr Tyr Gly His Thr Asn Tyr<br>                  165               170              175 | 528 |
| att tat agc ata tcc gtt ttt cca aat tgt aga gac ttt gtg aca aca<br>Ile Tyr Ser Ile Ser Val Phe Pro Asn Cys Arg Asp Phe Val Thr Thr<br>            180                 185              190 | 576 |
| gca gag gac aga tct ctg aga atc tgg aaa cat ggg gaa tgt gct caa<br>Ala Glu Asp Arg Ser Leu Arg Ile Trp Lys His Gly Glu Cys Ala Gln<br>            195                 200              205 | 624 |
| act atc cga ctt cca gct cag tct ata tgg tgc tgc tgt gtg ctc gac<br>Thr Ile Arg Leu Pro Ala Gln Ser Ile Trp Cys Cys Cys Val Leu Asp<br>210                  215                 220 | 672 |
| aat ggt gac att gtg gtt ggt gcg agt gat ggc att att aga gtg ttt<br>Asn Gly Asp Ile Val Val Gly Ala Ser Asp Gly Ile Ile Arg Val Phe<br>225                  230               235              240 | 720 |
| aca gag tca gaa gat cga aca gca agt gct gaa gaa atc aag gct ttt<br>Thr Glu Ser Glu Asp Arg Thr Ala Ser Ala Glu Glu Ile Lys Ala Phe<br>                  245               250              255 | 768 |
| gaa aaa gaa ctg tct cac gca acc att gat tct aaa act ggc gat tta<br>Glu Lys Glu Leu Ser His Ala Thr Ile Asp Ser Lys Thr Gly Asp Leu<br>            260                 265              270 | 816 |
| ggg gac atc aat gct gag cag ctt cct ggg agg gaa cat ctt aat gaa<br>Gly Asp Ile Asn Ala Glu Gln Leu Pro Gly Arg Glu His Leu Asn Glu<br>            275                 280              285 | 864 |
| cct ggt act aga gaa gga cag act cgt cta atc aga gat ggg gag aaa<br>Pro Gly Thr Arg Glu Gly Gln Thr Arg Leu Ile Arg Asp Gly Glu Lys<br>        290                 295              300 | 912 |
| gtc gaa gcc tat cag tgg agt gtt agt gaa ggg agg tgg ata aaa att<br>Val Glu Ala Tyr Gln Trp Ser Val Ser Glu Gly Arg Trp Ile Lys Ile<br>305                  310               315              320 | 960 |
| ggt gat gtt gtt ggc tca tct ggt gct aat cag caa aca tct gga aaa<br>Gly Asp Val Val Gly Ser Ser Gly Ala Asn Gln Gln Thr Ser Gly Lys | 1008 |

```
                325                 330                 335
gtt tta tat gaa ggg aaa gaa ttt gat tat gtt ttc tca att gat gtc    1056
Val Leu Tyr Glu Gly Lys Glu Phe Asp Tyr Val Phe Ser Ile Asp Val
            340                 345                 350 aat gaa ggt gga cca tca tat aaa ttg cca tat aat acc agt gat gac    1104
Asn Glu Gly Gly Pro Ser Tyr Lys Leu Pro Tyr Asn Thr Ser Asp Asp
        355                 360                 365 cct tgg tta act gca tac aac ttc tta cag aag aat gat ttg aat cct    1152
Pro Trp Leu Thr Ala Tyr Asn Phe Leu Gln Lys Asn Asp Leu Asn Pro
370                 375                 380 atg ttt ctg gat caa gta gct aaa ttt att att gat aac aca aaa ggt    1200
Met Phe Leu Asp Gln Val Ala Lys Phe Ile Ile Asp Asn Thr Lys Gly
385                 390                 395                 400 caa atg ttg gga ctt ggg aat ccc agc ttt tca gat cca ttt aca ggt    1248
Gln Met Leu Gly Leu Gly Asn Pro Ser Phe Ser Asp Pro Phe Thr Gly
                405                 410                 415 ggt ggt cgg tat gtt ccg ggc tct tcg gga tct tct aac aca cta ccc    1296
Gly Gly Arg Tyr Val Pro Gly Ser Ser Gly Ser Ser Asn Thr Leu Pro
            420                 425                 430 aca gca gat cct ttt aca ggt gct ggt cgt tat gta cca ggt tct gca    1344
Thr Ala Asp Pro Phe Thr Gly Ala Gly Arg Tyr Val Pro Gly Ser Ala
        435                 440                 445 agt atg gga act acc atg gcc gga gtt gat cca ttt aca ggg aat agt    1392
Ser Met Gly Thr Thr Met Ala Gly Val Asp Pro Phe Thr Gly Asn Ser
450                 455                 460 gcc tac cga tca gct gca tct aaa aca atg aat att tat ttc cct aaa    1440
Ala Tyr Arg Ser Ala Ala Ser Lys Thr Met Asn Ile Tyr Phe Pro Lys
465                 470                 475                 480 aaa gag gct gtc aca ttt gac caa gca aac cct aca caa ata tta ggt    1488
Lys Glu Ala Val Thr Phe Asp Gln Ala Asn Pro Thr Gln Ile Leu Gly
                485                 490                 495 aaa ctg aag gaa ctt aat gga act gca cct gaa gag aag aag tta act    1536
Lys Leu Lys Glu Leu Asn Gly Thr Ala Pro Glu Glu Lys Lys Leu Thr
            500                 505                 510 gag gat gac ttg ata ctt ctt gag aag ata ctg tct cta ata tgt aat    1584
Glu Asp Asp Leu Ile Leu Leu Glu Lys Ile Leu Ser Leu Ile Cys Asn
        515                 520                 525 agt tct tca gaa aaa ccc aca gtc cag caa ctt cag att tgg aaa       1632
Ser Ser Ser Glu Lys Pro Thr Val Gln Gln Leu Gln Ile Leu Trp Lys
530                 535                 540 gct att aac tgt cct gaa gat att gtc ttt cct gca ctt gac att ctt    1680
Ala Ile Asn Cys Pro Glu Asp Ile Val Phe Pro Ala Leu Asp Ile Leu
545                 550                 555                 560 cgg ttg tca att aaa cac ccc agt gtg aat gag aac ttc tgc aat gaa    1728
Arg Leu Ser Ile Lys His Pro Ser Val Asn Glu Asn Phe Cys Asn Glu
                565                 570                 575 aag gaa ggg gct cag ttc agc agt cat ctt atc aat ctt ctg aac cct    1776
Lys Glu Gly Ala Gln Phe Ser Ser His Leu Ile Asn Leu Leu Asn Pro
            580                 585                 590 aaa gga aag cca gca aac cag ctg ctt gct ctc agg act ttt tgc aat    1824
Lys Gly Lys Pro Ala Asn Gln Leu Leu Ala Leu Arg Thr Phe Cys Asn
        595                 600                 605 tgt ttt gtt ggc cag gca gga caa aaa ctc atg atg tcc cag agg gaa    1872
Cys Phe Val Gly Gln Ala Gly Gln Lys Leu Met Met Ser Gln Arg Glu
610                 615                 620 tca ctg atg tcc cat gca ata gaa ctg aaa tca ggg agc aat aag aac    1920
Ser Leu Met Ser His Ala Ile Glu Leu Lys Ser Gly Ser Asn Lys Asn
625                 630                 635                 640 att cac att gct ctg gct aca ttg gcc ctg aac tat tct gtt tgt ttt    1968
```

```
Ile His Ile Ala Leu Ala Thr Leu Ala Leu Asn Tyr Ser Val Cys Phe
              645                 650                 655 cat aaa gac cat aac att gaa ggg aaa gcc caa tgt ttg tca cta att      2016
His Lys Asp His Asn Ile Glu Gly Lys Ala Gln Cys Leu Ser Leu Ile
              660                 665                 670 agc aca atc ttg gaa gta gta caa gac cta gaa gcc act ttt aga ctt      2064
Ser Thr Ile Leu Glu Val Val Gln Asp Leu Glu Ala Thr Phe Arg Leu
              675                 680                 685 ctt gtg gct ctt gga aca ctt atc agt gat gat tca aat gct gta caa      2112
Leu Val Ala Leu Gly Thr Leu Ile Ser Asp Asp Ser Asn Ala Val Gln
              690                 695                 700 tta gcc aag tct tta ggt gtt gat tct caa ata aaa aag tat tcc tca      2160
Leu Ala Lys Ser Leu Gly Val Asp Ser Gln Ile Lys Lys Tyr Ser Ser
705                 710                 715                 720 gta tca gaa cca gct aaa gta agt gaa tgc tgt aga ttt atc cta aat      2208
Val Ser Glu Pro Ala Lys Val Ser Glu Cys Cys Arg Phe Ile Leu Asn
                    725                 730                 735 ttg ctg tag                                                          2217
Leu Leu <210> SEQ ID NO 30
<211> LENGTH: 738
<212> TYPE: PRT
<213> ORGANISM: Homo sapiens

<400> SEQUENCE: 30

Met His Cys Met Ser Gly His Ser Asn Phe Val Ser Cys Val Cys Ile
1               5                   10                  15

Ile Pro Ser Ser Asp Ile Tyr Pro His Gly Leu Ile Ala Thr Gly Gly
                20                  25                  30

Asn Asp His Asn Ile Cys Ile Phe Ser Leu Asp Ser Pro Met Pro Leu
            35                  40                  45

Tyr Ile Leu Lys Gly His Lys Asn Thr Val Cys Ser Leu Ser Ser Gly
        50                  55                  60

Lys Phe Gly Thr Leu Leu Ser Gly Ser Trp Asp Thr Thr Ala Lys Val
65                  70                  75                  80

Trp Leu Asn Asp Lys Cys Met Met Thr Leu Gln Gly His Thr Ala Ala
                85                  90                  95

Val Trp Ala Val Lys Ile Leu Pro Glu Gln Gly Leu Met Leu Thr Gly
            100                 105                 110

Ser Ala Asp Lys Thr Val Lys Leu Trp Lys Ala Gly Arg Cys Glu Arg
        115                 120                 125

Thr Phe Ser Gly His Glu Asp Cys Val Arg Gly Leu Ala Ile Leu Ser
    130                 135                 140

Glu Thr Glu Phe Leu Ser Cys Ala Asn Asp Ala Ser Ile Arg Arg Trp
145                 150                 155                 160

Gln Ile Thr Gly Glu Cys Leu Glu Val Tyr Tyr Gly His Thr Asn Tyr
                165                 170                 175

Ile Tyr Ser Ile Ser Val Phe Pro Asn Cys Arg Asp Phe Val Thr Thr
            180                 185                 190

Ala Glu Asp Arg Ser Leu Arg Ile Trp Lys His Gly Glu Cys Ala Gln
        195                 200                 205

Thr Ile Arg Leu Pro Ala Gln Ser Ile Trp Cys Cys Cys Val Leu Asp
    210                 215                 220

Asn Gly Asp Ile Val Val Gly Ala Ser Asp Gly Ile Ile Arg Val Phe
225                 230                 235                 240
```

-continued

```
Thr Glu Ser Glu Asp Arg Thr Ala Ser Ala Glu Glu Ile Lys Ala Phe
            245                 250                 255
Glu Lys Glu Leu Ser His Ala Thr Ile Asp Ser Lys Thr Gly Asp Leu
            260                 265                 270
Gly Asp Ile Asn Ala Glu Gln Leu Pro Gly Arg Glu His Leu Asn Glu
            275                 280                 285
Pro Gly Thr Arg Glu Gly Gln Thr Arg Leu Ile Arg Asp Gly Glu Lys
            290                 295                 300
Val Glu Ala Tyr Gln Trp Ser Val Ser Glu Gly Arg Trp Ile Lys Ile
305                 310                 315                 320
Gly Asp Val Val Gly Ser Ser Gly Ala Asn Gln Gln Thr Ser Gly Lys
            325                 330                 335
Val Leu Tyr Glu Gly Lys Glu Phe Asp Tyr Val Phe Ser Ile Asp Val
            340                 345                 350
Asn Glu Gly Gly Pro Ser Tyr Lys Leu Pro Tyr Asn Thr Ser Asp Asp
            355                 360                 365
Pro Trp Leu Thr Ala Tyr Asn Phe Leu Gln Lys Asn Asp Leu Asn Pro
            370                 375                 380
Met Phe Leu Asp Gln Val Ala Lys Phe Ile Asp Asn Thr Lys Gly
385                 390                 395                 400
Gln Met Leu Gly Leu Gly Asn Pro Ser Phe Ser Asp Pro Phe Thr Gly
            405                 410                 415
Gly Gly Arg Tyr Val Pro Gly Ser Ser Gly Ser Ser Asn Thr Leu Pro
            420                 425                 430
Thr Ala Asp Pro Phe Thr Gly Ala Gly Arg Tyr Val Pro Gly Ser Ala
            435                 440                 445
Ser Met Gly Thr Thr Met Ala Gly Val Asp Pro Phe Thr Gly Asn Ser
            450                 455                 460
Ala Tyr Arg Ser Ala Ala Ser Lys Thr Met Asn Ile Tyr Phe Pro Lys
465                 470                 475                 480
Lys Glu Ala Val Thr Phe Asp Gln Ala Asn Pro Thr Gln Ile Leu Gly
            485                 490                 495
Lys Leu Lys Glu Leu Asn Gly Thr Ala Pro Glu Glu Lys Lys Leu Thr
            500                 505                 510
Glu Asp Asp Leu Ile Leu Leu Glu Lys Ile Leu Ser Leu Ile Cys Asn
            515                 520                 525
Ser Ser Ser Glu Lys Pro Thr Val Gln Gln Leu Gln Ile Leu Trp Lys
            530                 535                 540
Ala Ile Asn Cys Pro Glu Asp Ile Val Phe Pro Ala Leu Asp Ile Leu
545                 550                 555                 560
Arg Leu Ser Ile Lys His Pro Ser Val Asn Glu Asn Phe Cys Asn Glu
            565                 570                 575
Lys Glu Gly Ala Gln Phe Ser Ser His Leu Ile Asn Leu Leu Asn Pro
            580                 585                 590
Lys Gly Lys Pro Ala Asn Gln Leu Leu Ala Leu Arg Thr Phe Cys Asn
            595                 600                 605
Cys Phe Val Gly Gln Ala Gly Gln Lys Leu Met Met Ser Gln Arg Glu
            610                 615                 620
Ser Leu Met Ser His Ala Ile Glu Leu Lys Ser Gly Ser Asn Lys Asn
625                 630                 635                 640
Ile His Ile Ala Leu Ala Thr Leu Ala Leu Asn Tyr Ser Val Cys Phe
            645                 650                 655
His Lys Asp His Asn Ile Glu Gly Lys Ala Gln Cys Leu Ser Leu Ile
```

-continued

```
                    660                 665                 670
Ser Thr Ile Leu Glu Val Val Gln Asp Leu Glu Ala Thr Phe Arg Leu
                675                 680                 685

Leu Val Ala Leu Gly Thr Leu Ile Ser Asp Ser Asn Ala Val Gln
            690                 695                 700

Leu Ala Lys Ser Leu Gly Val Asp Ser Gln Ile Lys Lys Tyr Ser Ser
705                 710                 715                 720

Val Ser Glu Pro Ala Lys Val Ser Glu Cys Cys Arg Phe Ile Leu Asn
                725                 730                 735

Leu Leu
```

<210> SEQ ID NO 31
<211> LENGTH: 911
<212> TYPE: DNA
<213> ORGANISM: Mus musculus
<220> FEATURE:
<221> NAME/KEY: CDS
<222> LOCATION: (27)...(743)
<221> NAME/KEY: misc_feature
<222> LOCATION: (1)...(911)
<223> OTHER INFORMATION: n = A,T,C or G

<400> SEQUENCE: 31

```
cggcacaggg cgacggccgc tcgcca atg tgc ctc tct gcc gtt tca ttc aag      53
                              Met Cys Leu Ser Ala Val Ser Phe Lys
                                1               5 gga ata aga tgc tgg ctg gac aaa ctg tta ctt tgg gct ctt aca att     101
Gly Ile Arg Cys Trp Leu Asp Lys Leu Leu Leu Trp Ala Leu Thr Ile
 10              15                  20                  25 tct atc aca ctt cag aat gct gca gtg gat tgt acg agg gtg gaa aat     149
Ser Ile Thr Leu Gln Asn Ala Ala Val Asp Cys Thr Arg Val Glu Asn
                 30                  35                  40 aac gaa tta cct tct cca aat ctg aac tca agt atg aac gtg gtc agg     197
Asn Glu Leu Pro Ser Pro Asn Leu Asn Ser Ser Met Asn Val Val Arg
             45                  50                  55 atg ggc caa aat gta tct ctg tct tgt tcc acc aag aac aca tca gta     245
Met Gly Gln Asn Val Ser Leu Ser Cys Ser Thr Lys Asn Thr Ser Val
         60                  65                  70 gac atc acc tat tcg ctc ttc tgg ggt aca aaa tat cta gaa agc aag     293
Asp Ile Thr Tyr Ser Leu Phe Trp Gly Thr Lys Tyr Leu Glu Ser Lys
 75                  80                  85 aga aga cga ggg gga gct gtg gat ttc cac ctg agg atc tcc aat gcc     341
Arg Arg Arg Gly Gly Ala Val Asp Phe His Leu Arg Ile Ser Asn Ala
 90                  95                 100                 105 aac gag tca ggc ccc tac aaa tgc aaa gtc aat gtt tcc aac ttg atg     389
Asn Glu Ser Gly Pro Tyr Lys Cys Lys Val Asn Val Ser Asn Leu Met
             110                 115                 120 aaa tac agt cag gat ttc aac ttc aca atg gcc aaa gat gag agc tgc     437
Lys Tyr Ser Gln Asp Phe Asn Phe Thr Met Ala Lys Asp Glu Ser Cys
         125                 130                 135 cct tca tgc cgg ctg tca ctg ttg ctc cca ggg ctg tta ctg gga ata     485
Pro Ser Cys Arg Leu Ser Leu Leu Leu Pro Gly Leu Leu Leu Gly Ile
     140                 145                 150 ctg gta ata gtc cta gtt ctg gct tat ttg att cat cta aaa tac aaa     533
Leu Val Ile Val Leu Val Leu Ala Tyr Leu Ile His Leu Lys Tyr Lys
 155                 160                 165 aaa gga aag aag act cag aga gag gac cag tcc aag ggt tct gga gat     581
Lys Gly Lys Lys Thr Gln Arg Glu Asp Gln Ser Lys Gly Ser Gly Asp
170                 175                 180                 185 gcg cct gca cag gac gag ctg tat gtc aac gcc tgc aag act cag aca     629
```

```
Ala Pro Ala Gln Asp Glu Leu Tyr Val Asn Ala Cys Lys Thr Gln Thr
                190                 195                 200 gag caa ccc cag gag ata cac tat gcc act cca gtc ttc aag gag atg      677
Glu Gln Pro Gln Glu Ile His Tyr Ala Thr Pro Val Phe Lys Glu Met
            205                 210                 215 gca ccc atg gaa gaa gaa ggt ggt acg gat gga aaa gct gat tac atc      725
Ala Pro Met Glu Glu Glu Gly Gly Thr Asp Gly Lys Ala Asp Tyr Ile
        220                 225                 230 tac tct gaa ctc acc cac tgaagtgtga agaaactgac tgtatcccag             773
Tyr Ser Glu Leu Thr His
    235 tgtaaagact ttccagtaag ctggtgtatg agaaaatagg aaaactcacc tggcacttaa    833 gagttccatt ctangctgan gcaggaggat cctgagtttt gangccactt gggactacat    893 agcaagacct ggcttaaa                                                  911

<210> SEQ ID NO 32
<211> LENGTH: 720
<212> TYPE: DNA
<213> ORGANISM: Mus musculus

<400> SEQUENCE: 32
atgtgcctct ctgccgtttc attcaaggga ataagatgct ggctggacaa actgttactt     60
tgggctctta caatttctat cacacttcag aatgctgcag tggattgtac gagggtggaa    120 ataacgaat taccttctcc aaatctgaac tcaagtatga acgtggtcag gatgggccaa    180
aatgtatctc tgtcttgttc caccaagaac acatcagtag acatcaccta ttcgctcttc    240
tggggtacaa atatctaga agcaagaga agacgagggg gagctgtgga tttccacctg    300
aggatctcca atgccaacga gtcaggcccc tacaaatgca agtcaatgt ttccaacttg    360 atgaaataca gtcaggattt caacttcaca atggccaaag atgagagctg cccttcatgc    420
cggctgtcac tgttgctccc agggctgtta ctggggatac tggtaatagt cctagttctg    480
gcttatttga ttcatctaaa atacaaaaaa ggaagaaga ctcagagaga ggaccagtcc    540
aagggttctg gagatgcgcc tgcacaggac gagctgtatg tcaacgcctg caagactcag    600
acagagcaac cccaggagat acactatgcc actccagtct tcaaggagat ggcacccatg    660
gaagaagaag gtgacgga tggaaaagct gattacatct actctgaact cacccactga    720

<210> SEQ ID NO 33
<211> LENGTH: 239
<212> TYPE: PRT
<213> ORGANISM: Mus musculus
<220> FEATURE:
<221> NAME/KEY: SIGNAL
<222> LOCATION: (1)...(34)

<400> SEQUENCE: 33

Met Cys Leu Ser Ala Val Ser Phe Lys Gly Ile Arg Cys Trp Leu Asp
                -30                 -25                 -20

Lys Leu Leu Leu Trp Ala Leu Thr Ile Ser Ile Thr Leu Gln Asn Ala
            -15                 -10                  -5

Ala Val Asp Cys Thr Arg Val Glu Asn Asn Glu Leu Pro Ser Pro Asn
          1               5                  10

Leu Asn Ser Ser Met Asn Val Val Arg Met Gly Gln Asn Val Ser Leu
 15                  20                  25                  30

Ser Cys Ser Thr Lys Asn Thr Ser Val Asp Ile Thr Tyr Ser Leu Phe
                 35                  40                  45
```

```
Trp Gly Thr Lys Tyr Leu Glu Ser Lys Arg Arg Gly Gly Ala Val
            50                  55                  60

Asp Phe His Leu Arg Ile Ser Asn Ala Asn Glu Ser Gly Pro Tyr Lys
        65                  70                  75

Cys Lys Val Asn Val Ser Asn Leu Met Lys Tyr Ser Gln Asp Phe Asn
 80                  85                  90

Phe Thr Met Ala Lys Asp Glu Ser Cys Pro Ser Cys Arg Leu Ser Leu
 95                 100                 105                 110

Leu Leu Pro Gly Leu Leu Leu Gly Ile Leu Val Ile Val Leu Val Leu
            115                 120                 125

Ala Tyr Leu Ile His Leu Lys Tyr Lys Lys Gly Lys Lys Thr Gln Arg
            130                 135                 140

Glu Asp Gln Ser Lys Gly Ser Gly Asp Ala Pro Ala Gln Asp Glu Leu
            145                 150                 155

Tyr Val Asn Ala Cys Lys Thr Gln Thr Glu Gln Pro Gln Glu Ile His
        160                 165                 170

Tyr Ala Thr Pro Val Phe Lys Glu Met Ala Pro Met Glu Glu Glu Gly
175                 180                 185                 190

Gly Thr Asp Gly Lys Ala Asp Tyr Ile Tyr Ser Glu Leu Thr His
                195                 200                 205

<210> SEQ ID NO 34
<211> LENGTH: 205
<212> TYPE: PRT
<213> ORGANISM: Mus musculus

<400> SEQUENCE: 34

Asp Cys Thr Arg Val Glu Asn Asn Glu Leu Pro Ser Pro Asn Leu Asn
 1               5                  10                  15

Ser Ser Met Asn Val Val Arg Met Gly Gln Asn Val Ser Leu Ser Cys
            20                  25                  30

Ser Thr Lys Asn Thr Ser Val Asp Ile Thr Tyr Ser Leu Phe Trp Gly
        35                  40                  45

Thr Lys Tyr Leu Glu Ser Lys Arg Arg Gly Gly Ala Val Asp Phe
 50                  55                  60

His Leu Arg Ile Ser Asn Ala Asn Glu Ser Gly Pro Tyr Lys Cys Lys
 65                  70                  75                  80

Val Asn Val Ser Asn Leu Met Lys Tyr Ser Gln Asp Phe Asn Phe Thr
            85                  90                  95

Met Ala Lys Asp Glu Ser Cys Pro Ser Cys Arg Leu Ser Leu Leu
        100                 105                 110

Pro Gly Leu Leu Leu Gly Ile Leu Val Ile Val Leu Val Leu Ala Tyr
            115                 120                 125

Leu Ile His Leu Lys Tyr Lys Lys Gly Lys Lys Thr Gln Arg Glu Asp
130                 135                 140

Gln Ser Lys Gly Ser Gly Asp Ala Pro Ala Gln Asp Glu Leu Tyr Val
145                 150                 155                 160

Asn Ala Cys Lys Thr Gln Thr Glu Gln Pro Gln Glu Ile His Tyr Ala
            165                 170                 175

Thr Pro Val Phe Lys Glu Met Ala Pro Met Glu Glu Glu Gly Gly Thr
        180                 185                 190

Asp Gly Lys Ala Asp Tyr Ile Tyr Ser Glu Leu Thr His
            195                 200                 205

<210> SEQ ID NO 35
```

```
<211> LENGTH: 34
<212> TYPE: PRT
<213> ORGANISM: Mus musculus
<220> FEATURE:
<221> NAME/KEY: SIGNAL
<222> LOCATION: (1)...(34)

<400> SEQUENCE: 35
```

Met Cys Leu Ser Ala Val Ser Phe Lys Gly Ile Arg Cys Trp Leu Asp
                -30                 -25                 -20

Lys Leu Leu Leu Trp Ala Leu Thr Ile Ser Ile Thr Leu Gln Asn Ala
            -15                 -10                  -5

Ala Val

```
<210> SEQ ID NO 36
<211> LENGTH: 107
<212> TYPE: PRT
<213> ORGANISM: Mus musculus

<400> SEQUENCE: 36
```

Asp Cys Thr Arg Val Glu Asn Asn Glu Leu Pro Ser Pro Asn Leu Asn
 1               5                  10                  15

Ser Ser Met Asn Val Val Arg Met Gly Gln Asn Val Ser Leu Ser Cys
                20                  25                  30

Ser Thr Lys Asn Thr Ser Val Asp Ile Thr Tyr Ser Leu Phe Trp Gly
            35                  40                  45

Thr Lys Tyr Leu Glu Ser Lys Arg Arg Arg Gly Gly Ala Val Asp Phe
        50                  55                  60

His Leu Arg Ile Ser Asn Ala Asn Glu Ser Gly Pro Tyr Lys Cys Lys
 65                 70                  75                  80

Val Asn Val Ser Asn Leu Met Lys Tyr Ser Gln Asp Phe Asn Phe Thr
                85                  90                  95

Met Ala Lys Asp Glu Ser Cys Pro Ser Cys Arg
            100                 105

```
<210> SEQ ID NO 37
<211> LENGTH: 23
<212> TYPE: PRT
<213> ORGANISM: Mus musculus

<400> SEQUENCE: 37
```

Leu Ser Leu Leu Leu Pro Gly Leu Leu Gly Ile Leu Val Ile Val
 1               5                  10                  15

Leu Val Leu Ala Tyr Leu Ile
            20

```
<210> SEQ ID NO 38
<211> LENGTH: 75
<212> TYPE: PRT
<213> ORGANISM: Mus musculus

<400> SEQUENCE: 38
```

His Leu Lys Tyr Lys Lys Gly Lys Lys Thr Gln Arg Glu Asp Gln Ser
 1               5                  10                  15

Lys Gly Ser Gly Asp Ala Pro Ala Gln Asp Glu Leu Tyr Val Asn Ala
                20                  25                  30

Cys Lys Thr Gln Thr Glu Gln Pro Gln Glu Ile His Tyr Ala Thr Pro
            35                  40                  45

Val Phe Lys Glu Met Ala Pro Met Glu Glu Glu Gly Gly Thr Asp Gly
        50                  55                  60

```
Lys Ala Asp Tyr Ile Tyr Ser Glu Leu Thr His
 65                  70                  75

<210> SEQ ID NO 39
<211> LENGTH: 2426
<212> TYPE: DNA
<213> ORGANISM: Mus musculus
<220> FEATURE:
<221> NAME/KEY: CDS
<222> LOCATION: (2)...(1117)

<400> SEQUENCE: 39 c atg gct gcg ccc gcg cga gag ccg gct ctc cgc tgc tgc atc aga ctg       49
  Met Ala Ala Pro Ala Arg Glu Pro Ala Leu Arg Cys Cys Ile Arg Leu
    1               5                  10                  15 gcg cga gtc ttc ttg ctg ctg gtg ttg gcg tgc gag gtg gcg gga agc        97
Ala Arg Val Phe Leu Leu Leu Val Leu Ala Cys Glu Val Ala Gly Ser
             20                  25                  30 gat gag gcc gag gcc agg gaa ggt gcg gcg tcc ctt gcg ggc tcg tgc       145
Asp Glu Ala Glu Ala Arg Glu Gly Ala Ala Ser Leu Ala Gly Ser Cys
         35                  40                  45 ggc tgc gga acg ccc cag agg gcc ggg gcc cat ggc agc tcg gcg gcg       193
Gly Cys Gly Thr Pro Gln Arg Ala Gly Ala His Gly Ser Ser Ala Ala
 50                  55                  60 gcg cag cgc tac tcc cgg gag gcg aac gcc ccg ggc ctg acc tca ggc       241
Ala Gln Arg Tyr Ser Arg Glu Ala Asn Ala Pro Gly Leu Thr Ser Gly
 65                  70                  75                  80 ccg cga ccg ctc gcg ctc acc aag atg gtc ccc att cct gct gga gta       289
Pro Arg Pro Leu Ala Leu Thr Lys Met Val Pro Ile Pro Ala Gly Val
                 85                  90                  95 ttc aca atg ggc act gat gat cct cag atc agg cag gat gga gaa gcc       337
Phe Thr Met Gly Thr Asp Asp Pro Gln Ile Arg Gln Asp Gly Glu Ala
            100                 105                 110 cct gcc agg aga gtc act gtt gat ggc ttt tac atg gac gcc tat gaa       385
Pro Ala Arg Arg Val Thr Val Asp Gly Phe Tyr Met Asp Ala Tyr Glu
        115                 120                 125 gtc agc aat gcg gat ttt gag aag ttt gtg aac tcg act ggc tat ttg       433
Val Ser Asn Ala Asp Phe Glu Lys Phe Val Asn Ser Thr Gly Tyr Leu
    130                 135                 140 aca gag gct gag aag ttt gga gac tct ttc gtc ttt gaa ggc atg ttg       481
Thr Glu Ala Glu Lys Phe Gly Asp Ser Phe Val Phe Glu Gly Met Leu
145                 150                 155                 160 agc gag caa gtg aaa acg cat atc cac cag gca gtt gca gct gct cca       529
Ser Glu Gln Val Lys Thr His Ile His Gln Ala Val Ala Ala Ala Pro
                165                 170                 175 tgg tgg ttg cct gtc aag gga gct aat tgg aga cac cca gag ggt ccg       577
Trp Trp Leu Pro Val Lys Gly Ala Asn Trp Arg His Pro Glu Gly Pro
            180                 185                 190 gac tcc agt att ctg cac agg tca aat cat ccg gtt ctc cat gtt tcc       625
Asp Ser Ser Ile Leu His Arg Ser Asn His Pro Val Leu His Val Ser
        195                 200                 205 tgg aac gat gct gtt gcc tac tgc aca tgg gcg ggc aag agg ttg cct       673
Trp Asn Asp Ala Val Ala Tyr Cys Thr Trp Ala Gly Lys Arg Leu Pro
    210                 215                 220 act gag gca gag tgg gaa tac agc tgt aga gga ggc ctg cag aac agg       721
Thr Glu Ala Glu Trp Glu Tyr Ser Cys Arg Gly Gly Leu Gln Asn Arg
225                 230                 235                 240 ctt ttc ccc tgg ggc aac aaa ctg cag ccc aaa gga cag cat tat gcc       769
Leu Phe Pro Trp Gly Asn Lys Leu Gln Pro Lys Gly Gln His Tyr Ala
                245                 250                 255
```

```
aac atc tgg cag ggc aag ttt cct gtg agc aac act ggc gag gat ggc      817
Asn Ile Trp Gln Gly Lys Phe Pro Val Ser Asn Thr Gly Glu Asp Gly
        260                 265                 270 ttc caa gga act gcc ccc gtt gat gcc ttt cct ccc aat ggc tat ggc      865
Phe Gln Gly Thr Ala Pro Val Asp Ala Phe Pro Pro Asn Gly Tyr Gly
            275                 280                 285 tta tac aac ata gtg ggg aat gtg tgg gag tgg acc tca gac tgg tgg      913
Leu Tyr Asn Ile Val Gly Asn Val Trp Glu Trp Thr Ser Asp Trp Trp
290                 295                 300 act gtt cac cat tct gtt gag gaa acg ttc aac cca aag ggt ccc act      961
Thr Val His His Ser Val Glu Glu Thr Phe Asn Pro Lys Gly Pro Thr
305                 310                 315                 320 tct ggg aaa gac cga gtg aag aag ggt gga tcc tac atg tgc cat aag     1009
Ser Gly Lys Asp Arg Val Lys Lys Gly Gly Ser Tyr Met Cys His Lys
                325                 330                 335 tcc tat tgc tat agg tac cgc tgt gca gct cga agc cag aac aca cca     1057
Ser Tyr Cys Tyr Arg Tyr Arg Cys Ala Ala Arg Ser Gln Asn Thr Pro
            340                 345                 350 gat agc tct gca tcc aac ctg gga ttc cga tgt gca gcc gac cac ctg     1105
Asp Ser Ser Ala Ser Asn Leu Gly Phe Arg Cys Ala Ala Asp His Leu
        355                 360                 365 ccc acc gca gac tgacagccaa gaggagcttt ccagattca agaaggcgtt          1157
Pro Thr Ala Asp
    370 tcttactcgc agctggcctc ccctggaaat ctgaactgat ctcatgtaaa gtattcccat   1217 ctacggagga ttccatgtcc acccagtggc caaaggaact gtctcgcgtg accaaatggc   1277 tggcgagtgt cagcacgtgt gctttattgt gtggtgtatc tttggggatc atcgccatgt   1337 tttactttga aagcctttg aagaggagag agccgagaac caggaagtcc tggccagact    1397 ctgccacagg gtcagaccct ggagtccagc accttgtctg ccttgacctc tgtctcctca   1457 tgaaatgagg gatggtcaac gtgatctttg aggctctctc caactctatt tgaactagca   1517 gattctattc gaactagcag agtgtattgt gattgcatag tgagaattta tgacagatta   1577 tttttttagct attttttttgc catgtgtgaa tcttgagtaa tactaatcat ataaggcgag  1637 agttatctta catattattt tcagaaaagg gtggggtttg agtcttttat attcatactg   1697 cactttgttc tttcaaggaa atcagtgtct tttacattgt tgtgacaaat cccattggga   1757 cagcgagggg acacttaagt ttggagttct gaacacacag gaatgcctgt ggagtgactc   1817 tactgtcctt tttctttga cattaagtgc ctttggctca gagggacagt ttgaagcctt    1877 gtttccccct tgcccccaag ccttcaaaga atgtgaaata tgtactaatt agggaaacca   1937 tttaattcta ggtctttggg tgttgaggtt ttgtcagatg gtatgaattg tattgtaatg   1997 ctaaatctgg tacctgaagg tctaggcctg tgagtgaatt ctcacattta caagattttg   2057 ttgtgcaaac cttgttcctt aatttaaaac tattggttaa ataaaattgg ctacagccaa   2117 ttactggagg gattagaggt aggtgggttt tgagtgtggt tgggtatgga gagagagagg   2177 agagatcaag gagagaagca ggaagaagag gataggagga gctgccatga agaagatgga   2237 ccataagcct ttgtccagag gaaactccca agtatctggg aacaccgctg tgaggcaacc   2297 aggccagcag ttagaaaagt agattagggg ctaccccag taattgtcaa agccaaataa    2357 aatatcaaaa aaaaaaaaaa aaaaaaaaaa aaaaaaaaaa aaaaaaaaaa aacaaaaaaa   2417 aaaaaaaaa                                                          2426

<210> SEQ ID NO 40
<211> LENGTH: 1119
```

-continued

```
<212> TYPE: DNA
<213> ORGANISM: Mus musculus

<400> SEQUENCE: 40
atggctgcgc ccgcgcgaga gccggctctc cgctgctgca tcagactggc gcgagtcttc      60
ttgctgctgg tgttggcgtg cgaggtggcg ggaagcgatg aggccgaggc cagggaaggt     120
gcggcgtccc ttgcgggctc gtgcggctgc ggaacgcccc agagggccgg ggcccatggc     180
agctcggcgc cggcgcagcg ctactcccgg gaggcgaacg ccccgggcct gacctcaggc     240
ccgcgaccgc tcgcgctcac caagatggtc cccattcctg ctggagtatt cacaatgggc     300
actgatgatc ctcagatcag gcaggatgga gaagcccctg ccaggagagt cactgttgat     360
ggcttttaca tggacgccta tgaagtcagc aatgcggatt ttgagaagtt tgtgaactcg     420
actggctatt tgacagaggc tgagaagttt ggagactctt tcgtctttga aggcatgttg     480
agcgagcaag tgaaaacgca tatccaccag gcagttgcag ctgctccatg gtggttgcct     540
gtcaagggag ctaattggag acacccagag ggtccggact ccagtattct gcacaggtca     600
aatcatccgg ttctccatgt ttcctggaac gatgctgttg cctactgcac atgggcgggc     660
aagaggttgc ctactgaggc agagtgggaa tacagctgta gaggaggcct gcagaacagg     720
cttttcccct ggggcaacaa actgcagccc aaaggacagc attatgccaa catctggcag     780
ggcaagtttc ctgtgagcaa cactggcgag gatggcttcc aaggaactgc cccgttgat      840 gcctttcctc ccaatggcta tggcttatac aacatagtgg ggaatgtgtg ggagtggacc     900
tcagactggt ggactgttca ccattctgtt gaggaaacgt tcaacccaaa gggtcccact     960
tctgggaaag accgagtgaa gaagggtgga tcctacatgt gccataagtc ctattgctat    1020
aggtaccgct gtgcagctcg aagccagaac acaccagata gctctgcatc caacctggga    1080
ttccgatgtg cagccgacca cctgcccacc gcagactga                           1119

<210> SEQ ID NO 41
<211> LENGTH: 372
<212> TYPE: PRT
<213> ORGANISM: Mus musculus
<220> FEATURE:
<221> NAME/KEY: SIGNAL
<222> LOCATION: (1)...(31)

<400> SEQUENCE: 41

Met Ala Ala Pro Ala Arg Glu Pro Ala Leu Arg Cys Cys Ile Arg Leu
    -30                 -25                 -20

Ala Arg Val Phe Leu Leu Val Leu Ala Cys Glu Val Ala Gly Ser
-15                 -10                  -5                   1

Asp Glu Ala Glu Ala Arg Glu Gly Ala Ala Ser Leu Ala Gly Ser Cys
                5                  10                  15

Gly Cys Gly Thr Pro Gln Arg Ala Gly Ala His Gly Ser Ser Ala Ala
            20                  25                  30

Ala Gln Arg Tyr Ser Arg Glu Ala Asn Ala Pro Gly Leu Thr Ser Gly
        35                  40                  45

Pro Arg Pro Leu Ala Leu Thr Lys Met Val Pro Ile Pro Ala Gly Val
50                  55                  60                  65

Phe Thr Met Gly Thr Asp Asp Pro Gln Ile Arg Gln Asp Gly Glu Ala
                70                  75                  80

Pro Ala Arg Arg Val Thr Val Asp Gly Phe Tyr Met Asp Ala Tyr Glu
            85                  90                  95

Val Ser Asn Ala Asp Phe Glu Lys Phe Val Asn Ser Thr Gly Tyr Leu
```

```
            100                 105                 110
Thr Glu Ala Glu Lys Phe Gly Asp Ser Phe Val Phe Glu Gly Met Leu
    115                 120                 125

Ser Glu Gln Val Lys Thr His Ile His Gln Ala Val Ala Ala Ala Pro
130                 135                 140                 145

Trp Trp Leu Pro Val Lys Gly Ala Asn Trp Arg His Pro Glu Gly Pro
                150                 155                 160

Asp Ser Ser Ile Leu His Arg Ser Asn His Pro Val Leu His Val Ser
                165                 170                 175

Trp Asn Asp Ala Val Ala Tyr Cys Thr Trp Ala Gly Lys Arg Leu Pro
                180                 185                 190

Thr Glu Ala Glu Trp Glu Tyr Ser Cys Arg Gly Gly Leu Gln Asn Arg
    195                 200                 205

Leu Phe Pro Trp Gly Asn Lys Leu Gln Pro Lys Gly Gln His Tyr Ala
210                 215                 220                 225

Asn Ile Trp Gln Gly Lys Phe Pro Val Ser Asn Thr Gly Glu Asp Gly
                230                 235                 240

Phe Gln Gly Thr Ala Pro Val Asp Ala Phe Pro Pro Asn Gly Tyr Gly
                245                 250                 255

Leu Tyr Asn Ile Val Gly Asn Val Trp Glu Trp Thr Ser Asp Trp Trp
                260                 265                 270

Thr Val His His Ser Val Glu Glu Thr Phe Asn Pro Lys Gly Pro Thr
    275                 280                 285

Ser Gly Lys Asp Arg Val Lys Lys Gly Gly Ser Tyr Met Cys His Lys
290                 295                 300                 305

Ser Tyr Cys Tyr Arg Tyr Arg Cys Ala Ala Arg Ser Gln Asn Thr Pro
                310                 315                 320

Asp Ser Ser Ala Ser Asn Leu Gly Phe Arg Cys Ala Ala Asp His Leu
                325                 330                 335

Pro Thr Ala Asp
        340

<210> SEQ ID NO 42
<211> LENGTH: 341
<212> TYPE: PRT
<213> ORGANISM: Mus musculus

<400> SEQUENCE: 42

Ser Asp Glu Ala Glu Ala Arg Glu Gly Ala Ala Ser Leu Ala Gly Ser
  1               5                  10                  15

Cys Gly Cys Gly Thr Pro Gln Arg Ala Gly Ala His Gly Ser Ser Ala
                20                  25                  30

Ala Ala Gln Arg Tyr Ser Arg Glu Ala Asn Ala Pro Gly Leu Thr Ser
            35                  40                  45

Gly Pro Arg Pro Leu Ala Leu Thr Lys Met Val Pro Ile Pro Ala Gly
        50                  55                  60

Val Phe Thr Met Gly Thr Asp Asp Pro Gln Ile Arg Gln Asp Gly Glu
65                  70                  75                  80

Ala Pro Ala Arg Arg Val Thr Val Asp Gly Phe Tyr Met Asp Ala Tyr
                85                  90                  95

Glu Val Ser Asn Ala Asp Phe Glu Lys Phe Val Asn Ser Thr Gly Tyr
                100                 105                 110

Leu Thr Glu Ala Glu Lys Phe Gly Asp Ser Phe Val Phe Glu Gly Met
            115                 120                 125
```

-continued

```
Leu Ser Glu Gln Val Lys Thr His Ile His Gln Ala Val Ala Ala
    130                 135                 140
Pro Trp Trp Leu Pro Val Lys Gly Ala Asn Trp Arg His Pro Glu Gly
145                 150                 155                 160
Pro Asp Ser Ser Ile Leu His Arg Ser Asn His Pro Val Leu His Val
                165                 170                 175
Ser Trp Asn Asp Ala Val Ala Tyr Cys Thr Trp Ala Gly Lys Arg Leu
            180                 185                 190
Pro Thr Glu Ala Glu Trp Glu Tyr Ser Cys Arg Gly Leu Gln Asn
                195                 200                 205
Arg Leu Phe Pro Trp Gly Asn Lys Leu Gln Pro Lys Gly Gln His Tyr
    210                 215                 220
Ala Asn Ile Trp Gln Gly Lys Phe Pro Val Ser Asn Thr Gly Glu Asp
225                 230                 235                 240
Gly Phe Gln Gly Thr Ala Pro Val Asp Ala Phe Pro Pro Asn Gly Tyr
                245                 250                 255
Gly Leu Tyr Asn Ile Val Gly Asn Val Trp Glu Trp Thr Ser Asp Trp
            260                 265                 270
Trp Thr Val His His Ser Val Glu Thr Phe Asn Pro Lys Gly Pro
    275                 280                 285
Thr Ser Gly Lys Asp Arg Val Lys Lys Gly Ser Tyr Met Cys His
    290                 295                 300
Lys Ser Tyr Cys Tyr Arg Tyr Arg Cys Ala Ala Arg Ser Gln Asn Thr
305                 310                 315                 320
Pro Asp Ser Ser Ala Ser Asn Leu Gly Phe Arg Cys Ala Ala Asp His
                325                 330                 335
Leu Pro Thr Ala Asp
            340
```

<210> SEQ ID NO 43
<211> LENGTH: 31
<212> TYPE: PRT
<213> ORGANISM: Mus musculus
<220> FEATURE:
<221> NAME/KEY: SIGNAL
<222> LOCATION: (1)...(31)

<400> SEQUENCE: 43

```
Met Ala Ala Pro Ala Arg Glu Pro Ala Leu Arg Cys Cys Ile Arg Leu
    -30                 -25                 -20
Ala Arg Val Phe Leu Leu Leu Val Leu Ala Cys Glu Val Ala Gly
-15                 -10                  -5
```

<210> SEQ ID NO 44
<211> LENGTH: 2811
<212> TYPE: DNA
<213> ORGANISM: Homo sapiens
<220> FEATURE:
<221> NAME/KEY: CDS
<222> LOCATION: (3)...(2567)

<400> SEQUENCE: 44

```
ct cgg ccc gct cgg cgc gcc cct tcc cag ccg ccc ttc cgt acc ggc        47
   Arg Pro Ala Arg Arg Ala Pro Ser Gln Pro Pro Phe Arg Thr Gly
   1               5                   10                  15 tct cgg gct ctt ccg gtc tcc ggc cgc ccc tta cct gca ggc tct tct    95
Ser Arg Ala Leu Pro Val Ser Gly Arg Pro Leu Pro Ala Gly Ser Ser
                20                  25                  30 ccc gcc gcg gcc cgg cgc tct ccg agt cgc ccc tgc gga ctg gtc tcg   143
Pro Ala Ala Ala Arg Arg Ser Pro Ser Arg Pro Cys Gly Leu Val Ser
```

```
                Pro Ala Ala Arg Arg Ser Pro Ser Arg Pro Cys Gly Leu Val Ser
                         35                  40                  45 cac agt gcc tgg gca ccg ggc gcc aga cag aca ctg gcc atg acg agc      191
His Ser Ala Trp Ala Pro Gly Ala Arg Gln Thr Leu Ala Met Thr Ser
         50                  55                  60 ggc gca acc agg tac cgg ctg agc tgc tcg ctc cgg ggc cac gag ctg      239
Gly Ala Thr Arg Tyr Arg Leu Ser Cys Ser Leu Arg Gly His Glu Leu
 65                  70                  75 gac gta cgg ggc ctg gtg tgc tgc gcc tat ccg ccg gga gcc ttt gtg      287
Asp Val Arg Gly Leu Val Cys Cys Ala Tyr Pro Pro Gly Ala Phe Val
 80                  85                  90                  95 tcc gtg tcc cga gac cgc acc acc cgc ctc tgg gcc cca gac agt cca      335
Ser Val Ser Arg Asp Arg Thr Thr Arg Leu Trp Ala Pro Asp Ser Pro
                100                 105                 110 aac agg agc ttt aca gaa atg cac tgt atg agt ggc cat tcc aat ttt      383
Asn Arg Ser Phe Thr Glu Met His Cys Met Ser Gly His Ser Asn Phe
             115                 120                 125 gta tct tgt gta tgc atc ata ccc tca agt gac atc tac cct cat ggc      431
Val Ser Cys Val Cys Ile Ile Pro Ser Ser Asp Ile Tyr Pro His Gly
         130                 135                 140 cta att gcc acc ggt gga aat gac cac aat ata tgc att ttc tca ctg      479
Leu Ile Ala Thr Gly Gly Asn Asp His Asn Ile Cys Ile Phe Ser Leu
145                 150                 155 gac agt cca atg cca ctt tat att cta aaa ggc cac aaa aat act gtt      527
Asp Ser Pro Met Pro Leu Tyr Ile Leu Lys Gly His Lys Asn Thr Val
160                 165                 170                 175 tgt agt cta tca tct gga aaa ttt ggg aca tta ctt agt ggt tca tgg      575
Cys Ser Leu Ser Ser Gly Lys Phe Gly Thr Leu Leu Ser Gly Ser Trp
                180                 185                 190 gac acc act gct aaa gtc tgg ctg aat gac aag tgc atg atg acc ttg      623
Asp Thr Thr Ala Lys Val Trp Leu Asn Asp Lys Cys Met Met Thr Leu
             195                 200                 205 cag ggt cat aca gct gca gtg tgg gcg gta aag atc tta cct gaa cag      671
Gln Gly His Thr Ala Ala Val Trp Ala Val Lys Ile Leu Pro Glu Gln
         210                 215                 220 ggc tta atg ttg act gga tca gca gac aag act gtt aaa ctg tgg aag      719
Gly Leu Met Leu Thr Gly Ser Ala Asp Lys Thr Val Lys Leu Trp Lys
225                 230                 235 gct gga aga tgt gag agg act ttt tca ggg cat gaa gac tgt gta aga      767
Ala Gly Arg Cys Glu Arg Thr Phe Ser Gly His Glu Asp Cys Val Arg
240                 245                 250                 255 ggt ttg gca att ttg agt gaa aca gaa ttt ctt tcc tgt gca aat gat      815
Gly Leu Ala Ile Leu Ser Glu Thr Glu Phe Leu Ser Cys Ala Asn Asp
                260                 265                 270 gct agt att aga agg tgg caa atc act ggc gag tgt ctt gaa gta tat      863
Ala Ser Ile Arg Arg Trp Gln Ile Thr Gly Glu Cys Leu Glu Val Tyr
             275                 280                 285 tat gga cat aca aat tat att tat agc ata tcc gtt ttt cca aat tgt      911
Tyr Gly His Thr Asn Tyr Ile Tyr Ser Ile Ser Val Phe Pro Asn Cys
         290                 295                 300 aga gac ttt gtg aca aca gca gag gac aga tct ctg aga atc tgg aaa      959
Arg Asp Phe Val Thr Thr Ala Glu Asp Arg Ser Leu Arg Ile Trp Lys
305                 310                 315 cat ggg gaa tgt gct caa act atc cga ctt cca gct cag tct ata tgg     1007
His Gly Glu Cys Ala Gln Thr Ile Arg Leu Pro Ala Gln Ser Ile Trp
320                 325                 330                 335 tgc tgc tgt gtg ctc gac aat ggt gac att gtg gtt ggt gcg agt gat     1055
Cys Cys Cys Val Leu Asp Asn Gly Asp Ile Val Val Gly Ala Ser Asp
                340                 345                 350
```

-continued

```
ggc att att aga gtg ttt aca gaa tca gaa gat cga aca gca agt gct        1103
Gly Ile Ile Arg Val Phe Thr Glu Ser Glu Asp Arg Thr Ala Ser Ala
            355                 360                 365 gaa gaa atc aag gct ttt gaa aaa gaa ctg tct cac gca acc att gat        1151
Glu Glu Ile Lys Ala Phe Glu Lys Glu Leu Ser His Ala Thr Ile Asp
    370                 375                 380 tct aaa act ggc gat tta ggg gac atc aat gct gag cag ctt cct ggg        1199
Ser Lys Thr Gly Asp Leu Gly Asp Ile Asn Ala Glu Gln Leu Pro Gly
385                 390                 395 agg gaa cat ctt aat gaa cct ggt act aga gaa gga cag act cgt cta        1247
Arg Glu His Leu Asn Glu Pro Gly Thr Arg Glu Gly Gln Thr Arg Leu
400                 405                 410                 415 atc aga gat ggg gag aaa gtc gaa gcc tat cag tgg agt gtt agt gaa        1295
Ile Arg Asp Gly Glu Lys Val Glu Ala Tyr Gln Trp Ser Val Ser Glu
                420                 425                 430 ggg agg tgg ata aaa att ggt gat gtt gtt ggc tca tct ggt gct aat        1343
Gly Arg Trp Ile Lys Ile Gly Asp Val Val Gly Ser Ser Gly Ala Asn
            435                 440                 445 cag caa aca tct gga aaa gtt tta tat gaa ggg aaa gaa ttt gat tat        1391
Gln Gln Thr Ser Gly Lys Val Leu Tyr Glu Gly Lys Glu Phe Asp Tyr
    450                 455                 460 gtt ttc tca att gat gtc aat gaa ggt gga cca tca tat aaa ttg cca        1439
Val Phe Ser Ile Asp Val Asn Glu Gly Gly Pro Ser Tyr Lys Leu Pro
465                 470                 475 tat aat acc agt gat gac cct tgg tta act gca tac aac ttc tta cag        1487
Tyr Asn Thr Ser Asp Asp Pro Trp Leu Thr Ala Tyr Asn Phe Leu Gln
480                 485                 490                 495 aag aat gat ttg aat cct atg ttt ctg gat caa gta gct aaa ttt att        1535
Lys Asn Asp Leu Asn Pro Met Phe Leu Asp Gln Val Ala Lys Phe Ile
                500                 505                 510 att gat aac aca aaa ggt caa atg ttg gga ctt ggg aat ccc agc ttt        1583
Ile Asp Asn Thr Lys Gly Gln Met Leu Gly Leu Gly Asn Pro Ser Phe
            515                 520                 525 tca gat cca ttt aca ggt ggt ggt cgg tat gtt ccg ggc tct tcg gga        1631
Ser Asp Pro Phe Thr Gly Gly Gly Arg Tyr Val Pro Gly Ser Ser Gly
    530                 535                 540 tct tct aac aca cta ccc aca gca gat cct ttt aca ggt gct ggt cgt        1679
Ser Ser Asn Thr Leu Pro Thr Ala Asp Pro Phe Thr Gly Ala Gly Arg
545                 550                 555 tat gta cca ggt tct gca agt atg gga act acc atg gcc gga gtt gat        1727
Tyr Val Pro Gly Ser Ala Ser Met Gly Thr Thr Met Ala Gly Val Asp
560                 565                 570                 575 cca ttt aca ggg aat agt gcc tac cga tca gct gca tct aaa aca atg        1775
Pro Phe Thr Gly Asn Ser Ala Tyr Arg Ser Ala Ala Ser Lys Thr Met
                580                 585                 590 aat att tat ttc cct aaa aaa gag gct gtc aca ttt gac caa gca aac        1823
Asn Ile Tyr Phe Pro Lys Lys Glu Ala Val Thr Phe Asp Gln Ala Asn
            595                 600                 605 cct aca caa ata tta ggt aaa ctg aag gaa ctt aat gga act gca cct        1871
Pro Thr Gln Ile Leu Gly Lys Leu Lys Glu Leu Asn Gly Thr Ala Pro
    610                 615                 620 gaa gag aag aag tta act gag gat gac ttg ata ctt ctt gag aag ata        1919
Glu Glu Lys Lys Leu Thr Glu Asp Asp Leu Ile Leu Leu Glu Lys Ile
625                 630                 635 ctg tct cta ata tgt aat agt tct tca gaa aaa ccc aca gtc cag caa        1967
Leu Ser Leu Ile Cys Asn Ser Ser Ser Glu Lys Pro Thr Val Gln Gln
640                 645                 650                 655 ctt cag att ttg tgg aaa gct att aac tgt cct gaa gat att gtc ttt        2015
Leu Gln Ile Leu Trp Lys Ala Ile Asn Cys Pro Glu Asp Ile Val Phe
                660                 665                 670
```

```
cct gca ctt gac att ctt cgg ttg tca att aaa cac ccc agt gtg aat     2063
Pro Ala Leu Asp Ile Leu Arg Leu Ser Ile Lys His Pro Ser Val Asn
            675                 680                 685 gag aac ttc tgc aat gaa aag gaa ggg gct cag ttc agc agt cat ctt     2111
Glu Asn Phe Cys Asn Glu Lys Glu Gly Ala Gln Phe Ser Ser His Leu
            690                 695                 700 atc aat ctt ctg aac cct aaa gga aag cca gca aac cag ctg ctt gct     2159
Ile Asn Leu Leu Asn Pro Lys Gly Lys Pro Ala Asn Gln Leu Leu Ala
705                 710                 715 ctc agg act ttt tgc aat tgt ttt gtt ggc cag gca gga caa aaa ctc     2207
Leu Arg Thr Phe Cys Asn Cys Phe Val Gly Gln Ala Gly Gln Lys Leu
720                 725                 730                 735 atg atg tcc cag agg gaa tca ctg atg tcc cat gca ata gaa ctg aaa     2255
Met Met Ser Gln Arg Glu Ser Leu Met Ser His Ala Ile Glu Leu Lys
            740                 745                 750 tca ggg agc aat aag aac att cac att gct ctg gct aca ttg gcc ctg     2303
Ser Gly Ser Asn Lys Asn Ile His Ile Ala Leu Ala Thr Leu Ala Leu
            755                 760                 765 aac tat tct gtt tgt ttt cat aaa gac cat aac att gaa ggg aaa gcc     2351
Asn Tyr Ser Val Cys Phe His Lys Asp His Asn Ile Glu Gly Lys Ala
            770                 775                 780 caa tgt ttg tca cta att agc aca atc ttg gaa gta gta caa gac cta     2399
Gln Cys Leu Ser Leu Ile Ser Thr Ile Leu Glu Val Val Gln Asp Leu
785                 790                 795 gaa gcc act ttt aga ctt ctt gtg gct ctt gga aca ctt atc agt gat     2447
Glu Ala Thr Phe Arg Leu Leu Val Ala Leu Gly Thr Leu Ile Ser Asp
800                 805                 810                 815 gat tca aat gct gta caa tta gcc aag tct tta ggt gtt gat tct caa     2495
Asp Ser Asn Ala Val Gln Leu Ala Lys Ser Leu Gly Val Asp Ser Gln
                820                 825                 830 ata aaa aag tat tcc tca gta tca gaa cca gct aaa gta agt gaa tgc     2543
Ile Lys Lys Tyr Ser Ser Val Ser Glu Pro Ala Lys Val Ser Glu Cys
                835                 840                 845 tgt aga ttt atc cta aat ttg ctg tagcagtggg aagagggac ggatatttt      2597
Cys Arg Phe Ile Leu Asn Leu Leu
            850                 855 aattgattag tgttttttc ctcacatttg acatgactga taacagataa ttaaaaaaag    2657
agaatacggt ggattaagta aaattttaca tcttgtaaag tggtggggag gggaaacaga   2717
aataaaattt ttgcactgct gaaaaaaaaa aaaaaaaaa aaaaaaaaa aaaaaaaaa      2777 aaaaaaaaa aaaaaaaaa aaaaaaaaa aaaa                                  2811

<210> SEQ ID NO 45
<211> LENGTH: 855
<212> TYPE: PRT
<213> ORGANISM: Homo sapiens

<400> SEQUENCE: 45

Arg Pro Ala Arg Arg Ala Pro Ser Gln Pro Pro Phe Arg Thr Gly Ser
1               5                   10                  15

Arg Ala Leu Pro Val Ser Gly Arg Pro Leu Pro Ala Gly Ser Ser Pro
                20                  25                  30

Ala Ala Ala Arg Arg Ser Pro Ser Arg Pro Cys Gly Leu Val Ser His
            35                  40                  45

Ser Ala Trp Ala Pro Gly Ala Arg Gln Thr Leu Ala Met Thr Ser Gly
        50                  55                  60

Ala Thr Arg Tyr Arg Leu Ser Cys Ser Leu Arg Gly His Glu Leu Asp
65                  70                  75                  80
```

-continued

```
Val Arg Gly Leu Val Cys Cys Ala Tyr Pro Pro Gly Ala Phe Val Ser
                85                  90                  95
Val Ser Arg Asp Arg Thr Thr Arg Leu Trp Ala Pro Asp Ser Pro Asn
            100                 105                 110
Arg Ser Phe Thr Glu Met His Cys Met Ser Gly His Ser Asn Phe Val
        115                 120                 125
Ser Cys Val Cys Ile Ile Pro Ser Ser Asp Ile Tyr Pro His Gly Leu
    130                 135                 140
Ile Ala Thr Gly Gly Asn Asp His Asn Ile Cys Ile Phe Ser Leu Asp
145                 150                 155                 160
Ser Pro Met Pro Leu Tyr Ile Leu Lys Gly His Lys Asn Thr Val Cys
                165                 170                 175
Ser Leu Ser Ser Gly Lys Phe Gly Thr Leu Leu Ser Gly Ser Trp Asp
            180                 185                 190
Thr Thr Ala Lys Val Trp Leu Asn Asp Lys Cys Met Met Thr Leu Gln
        195                 200                 205
Gly His Thr Ala Ala Val Trp Ala Val Lys Ile Leu Pro Glu Gln Gly
    210                 215                 220
Leu Met Leu Thr Gly Ser Ala Asp Lys Thr Val Lys Leu Trp Lys Ala
225                 230                 235                 240
Gly Arg Cys Glu Arg Thr Phe Ser Gly His Glu Asp Cys Val Arg Gly
                245                 250                 255
Leu Ala Ile Leu Ser Glu Thr Glu Phe Leu Ser Cys Ala Asn Asp Ala
            260                 265                 270
Ser Ile Arg Arg Trp Gln Ile Thr Gly Glu Cys Leu Glu Val Tyr Tyr
        275                 280                 285
Gly His Thr Asn Tyr Ile Tyr Ser Ile Ser Val Phe Pro Asn Cys Arg
    290                 295                 300
Asp Phe Val Thr Thr Ala Glu Asp Arg Ser Leu Arg Ile Trp Lys His
305                 310                 315                 320
Gly Glu Cys Ala Gln Thr Ile Arg Leu Pro Ala Gln Ser Ile Trp Cys
                325                 330                 335
Cys Cys Val Leu Asp Asn Gly Asp Ile Val Val Gly Ala Ser Asp Gly
            340                 345                 350
Ile Ile Arg Val Phe Thr Glu Ser Glu Asp Arg Thr Ala Ser Ala Glu
        355                 360                 365
Glu Ile Lys Ala Phe Glu Lys Glu Leu Ser His Ala Thr Ile Asp Ser
    370                 375                 380
Lys Thr Gly Asp Leu Gly Asp Ile Asn Ala Glu Gln Leu Pro Gly Arg
385                 390                 395                 400
Glu His Leu Asn Glu Pro Gly Thr Arg Glu Gly Gln Thr Arg Leu Ile
                405                 410                 415
Arg Asp Gly Glu Lys Val Glu Ala Tyr Gln Trp Ser Val Ser Glu Gly
            420                 425                 430
Arg Trp Ile Lys Ile Gly Asp Val Gly Ser Ser Gly Ala Asn Gln
        435                 440                 445
Gln Thr Ser Gly Lys Val Leu Tyr Glu Gly Lys Glu Phe Asp Tyr Val
    450                 455                 460
Phe Ser Ile Asp Val Asn Glu Gly Gly Pro Ser Tyr Lys Leu Pro Tyr
465                 470                 475                 480
Asn Thr Ser Asp Asp Pro Trp Leu Thr Ala Tyr Asn Phe Leu Gln Lys
                485                 490                 495
```

```
Asn Asp Leu Asn Pro Met Phe Leu Asp Gln Val Ala Lys Phe Ile Ile
            500                 505                 510

Asp Asn Thr Lys Gly Gln Met Leu Gly Leu Gly Asn Pro Ser Phe Ser
        515                 520                 525

Asp Pro Phe Thr Gly Gly Arg Tyr Val Pro Gly Ser Ser Gly Ser
    530                 535                 540

Ser Asn Thr Leu Pro Thr Ala Asp Pro Phe Thr Gly Ala Gly Arg Tyr
545                 550                 555                 560

Val Pro Gly Ser Ala Ser Met Gly Thr Thr Met Ala Gly Val Asp Pro
                565                 570                 575

Phe Thr Gly Asn Ser Ala Tyr Arg Ser Ala Ala Ser Lys Thr Met Asn
            580                 585                 590

Ile Tyr Phe Pro Lys Lys Glu Ala Val Thr Phe Asp Gln Ala Asn Pro
        595                 600                 605

Thr Gln Ile Leu Gly Lys Leu Lys Glu Leu Asn Gly Thr Ala Pro Glu
    610                 615                 620

Glu Lys Lys Leu Thr Glu Asp Asp Leu Ile Leu Leu Glu Lys Ile Leu
625                 630                 635                 640

Ser Leu Ile Cys Asn Ser Ser Glu Lys Pro Thr Val Gln Gln Leu
                645                 650                 655

Gln Ile Leu Trp Lys Ala Ile Asn Cys Pro Glu Asp Ile Val Phe Pro
            660                 665                 670

Ala Leu Asp Ile Leu Arg Leu Ser Ile Lys His Pro Ser Val Asn Glu
        675                 680                 685

Asn Phe Cys Asn Glu Lys Glu Gly Ala Gln Phe Ser Ser His Leu Ile
    690                 695                 700

Asn Leu Leu Asn Pro Lys Gly Lys Pro Ala Asn Gln Leu Leu Ala Leu
705                 710                 715                 720

Arg Thr Phe Cys Asn Cys Phe Val Gly Gln Ala Gly Gln Lys Leu Met
                725                 730                 735

Met Ser Gln Arg Glu Ser Leu Met Ser His Ala Ile Glu Leu Lys Ser
            740                 745                 750

Gly Ser Asn Lys Asn Ile His Ile Ala Leu Ala Thr Leu Ala Leu Asn
        755                 760                 765

Tyr Ser Val Cys Phe His Lys Asp His Asn Ile Glu Gly Lys Ala Gln
    770                 775                 780

Cys Leu Ser Leu Ile Ser Thr Ile Leu Glu Val Val Gln Asp Leu Glu
785                 790                 795                 800

Ala Thr Phe Arg Leu Leu Val Ala Leu Gly Thr Leu Ile Ser Asp Asp
                805                 810                 815

Ser Asn Ala Val Gln Leu Ala Lys Ser Leu Gly Val Asp Ser Gln Ile
            820                 825                 830

Lys Lys Tyr Ser Ser Val Ser Glu Pro Ala Lys Val Ser Glu Cys Cys
        835                 840                 845

Arg Phe Ile Leu Asn Leu Leu
    850                 855

<210> SEQ ID NO 46
<211> LENGTH: 57
<212> TYPE: PRT
<213> ORGANISM: Mus musculus

<400> SEQUENCE: 46

Gly Gln Asn Val Ser Leu Ser Cys Ser Thr Lys Asn Thr Ser Val Asp
```

```
                 1               5                  10                 15
Ile Thr Tyr Ser Leu Phe Trp Gly Thr Lys Tyr Leu Glu Ser Lys Arg
                      20                  25                 30

Arg Arg Gly Gly Ala Val Asp Phe His Leu Arg Ile Ser Asn Ala Asn
             35                  40                  45

Glu Ser Gly Pro Tyr Lys Cys Lys Val
         50                  55

<210> SEQ ID NO 47
<211> LENGTH: 252
<212> TYPE: PRT
<213> ORGANISM: Homo sapiens

<400> SEQUENCE: 47

Thr Glu Ser Glu Asp Arg Thr Ala Ser Ala Glu Glu Ile Lys Ala Phe
 1               5                  10                  15

Glu Lys Glu Leu Ser His Ala Thr Ile Asp Ser Lys Thr Gly Asp Leu
                 20                  25                  30

Gly Asp Ile Asn Ala Glu Gln Leu Pro Gly Arg Glu His Leu Asn Glu
             35                  40                  45

Pro Gly Thr Arg Glu Gly Gln Thr Arg Leu Ile Arg Asp Gly Glu Lys
         50                  55                  60

Val Glu Ala Tyr Gln Trp Ser Val Ser Glu Gly Arg Trp Ile Lys Ile
65                  70                  75                  80

Gly Asp Val Val Gly Ser Ser Gly Ala Asn Gln Gln Thr Ser Gly Lys
                 85                  90                  95

Val Leu Tyr Glu Gly Lys Glu Phe Asp Tyr Val Phe Ser Ile Asp Val
                100                 105                 110

Asn Glu Gly Gly Pro Ser Tyr Lys Leu Pro Tyr Asn Thr Ser Asp Asp
            115                 120                 125

Pro Trp Leu Thr Ala Tyr Asn Phe Leu Gln Lys Asn Asp Leu Asn Pro
        130                 135                 140

Met Phe Leu Asp Gln Val Ala Lys Phe Ile Ile Asp Asn Thr Lys Gly
145                 150                 155                 160

Gln Met Leu Gly Leu Gly Asn Pro Ser Phe Ser Asp Pro Phe Thr Gly
                165                 170                 175

Gly Gly Arg Tyr Val Pro Gly Ser Ser Gly Ser Ser Asn Thr Leu Pro
            180                 185                 190

Thr Ala Asp Pro Phe Thr Gly Ala Gly Arg Tyr Val Pro Gly Ser Ala
        195                 200                 205

Ser Met Gly Thr Thr Met Ala Gly Val Asp Pro Phe Thr Gly Asn Ser
    210                 215                 220

Ala Tyr Arg Ser Ala Ala Ser Lys Thr Met Asn Ile Tyr Phe Pro Lys
225                 230                 235                 240

Lys Glu Ala Val Thr Phe Asp Gln Ala Asn Pro Thr
                245                 250

<210> SEQ ID NO 48
<211> LENGTH: 231
<212> TYPE: PRT
<213> ORGANISM: Homo sapiens

<400> SEQUENCE: 48

Ser Asp Pro Phe Thr Gly Gly Arg Tyr Val Pro Gly Ser Ser Gly
 1               5                  10                  15

Ser Ser Asn Thr Leu Pro Thr Ala Asp Pro Phe Thr Gly Ala Gly Arg
```

```
                 20                  25                  30
Tyr Val Pro Gly Ser Ala Ser Met Gly Thr Thr Met Ala Gly Val Asp
             35                  40                  45

Pro Phe Thr Gly Asn Ser Ala Tyr Arg Ser Ala Ala Ser Lys Thr Met
 50                  55                  60

Asn Ile Tyr Phe Pro Lys Lys Glu Ala Val Thr Phe Asp Gln Ala Asn
 65                  70                  75                  80

Pro Thr Gln Ile Leu Gly Lys Leu Lys Glu Leu Asn Gly Thr Ala Pro
                 85                  90                  95

Glu Glu Lys Lys Leu Thr Glu Asp Asp Leu Ile Leu Leu Glu Lys Ile
                100                 105                 110

Leu Ser Leu Ile Cys Asn Ser Ser Glu Lys Pro Thr Val Gln Gln
             115                 120                 125

Leu Gln Ile Leu Trp Lys Ala Ile Asn Cys Pro Glu Asp Ile Val Phe
        130                 135                 140

Pro Ala Leu Asp Ile Leu Arg Leu Ser Ile Lys His Pro Ser Val Asn
145                 150                 155                 160

Glu Asn Phe Cys Asn Glu Lys Glu Gly Ala Gln Phe Ser Ser His Leu
                165                 170                 175

Ile Asn Leu Leu Asn Pro Lys Gly Lys Pro Ala Asn Gln Leu Leu Ala
            180                 185                 190

Leu Arg Thr Phe Cys Asn Cys Phe Val Gly Gln Ala Gly Gln Lys Leu
        195                 200                 205

Met Met Ser Gln Arg Glu Ser Leu Met Ser His Ala Ile Glu Leu Lys
    210                 215                 220

Ser Gly Ser Asn Lys Asn Ile
225                 230

<210> SEQ ID NO 49
<211> LENGTH: 88
<212> TYPE: PRT
<213> ORGANISM: Homo sapiens

<400> SEQUENCE: 49

Met His Cys Met Ser Gly His Ser Asn Phe Val Ser Cys Val Cys Ile
  1               5                  10                  15

Ile Pro Ser Ser Asp Ile Tyr Pro His Gly Leu Ile Ala Thr Gly Gly
                 20                  25                  30

Asn Asp His Asn Ile Cys Ile Phe Ser Leu Asp Ser Pro Met Pro Leu
             35                  40                  45

Tyr Ile Leu Lys Gly His Lys Asn Thr Val Cys Ser Leu Ser Ser Gly
 50                  55                  60

Lys Phe Gly Thr Leu Leu Ser Gly Ser Trp Asp Thr Thr Ala Lys Val
 65                  70                  75                  80

Trp Leu Asn Asp Lys Cys Met Met
                 85

<210> SEQ ID NO 50
<211> LENGTH: 35
<212> TYPE: PRT
<213> ORGANISM: Homo sapiens

<400> SEQUENCE: 50

Lys Ala Gly Arg Cys Glu Arg Thr Phe Ser Gly His Glu Asp Cys Val
  1               5                  10                  15

Arg Gly Leu Ala Ile Leu Ser Glu Thr Glu Phe Leu Ser Cys Ala Asn
```

```
                    20                  25                  30
Asp Ala Ser
        35

<210> SEQ ID NO 51
<211> LENGTH: 60
<212> TYPE: PRT
<213> ORGANISM: Artificial Sequence
<220> FEATURE:
<223> OTHER INFORMATION: consensus sequence
<221> NAME/KEY: VARIANT
<222> LOCATION: 20
<223> OTHER INFORMATION: Xaa = Val or Leu
<221> NAME/KEY: VARIANT
<222> LOCATION: (1)...(60)
<223> OTHER INFORMATION: Xaa = any amino acid

<400> SEQUENCE: 51

Gly His Xaa Xaa Xaa Xaa Xaa Xaa Xaa Val Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Asp Xaa Xaa Xaa Xaa Xaa Xaa Xaa Xaa Trp
        50                  55                  60
```

What is claimed is:

1. An isolated polypeptide selected from the group consisting of:
   a) a polypeptide comprising an amino acid sequence that has at least 95% amino acid sequence identity with SEQ ID NO:21, wherein the polypeptide is capable of modulating phospholipase A enzyme activation;
   b) a polypeptide comprising the amino acid sequence of a fragment of SEQ ID NO:21 comprising at least 740 contiguous amino acids, wherein the polypeptide is capable of modulating phospholipase A enzyme activation;
   c) a polypeptide which has an amino acid sequence that is encoded by a nucleic acid molecule comprising a nucleotide sequence which has at least 92% nucleotide sequence identity with the nucleotide sequence of SEQ ID NO:19, wherein the polypeptide is capable of modulating phospholipase A enzyme activation;
   d) a polypeptide encoded by a nucleic acid molecule comprising a nucleotide sequence which has at least 93% nucleotide sequence identity with the nucleotide sequence of SEQ ID NO:20, wherein the polypeptide is capable of modulating phospholipase A enzyme activation;
   e) a polypeptide comprising an amino acid sequence that has at least 95% amino acid sequence identity with the amino acid sequence encoded by the cDNA insert of the plasmid encoding TANGO 243 deposited with the ATCC under Accession Number 207116, wherein the polypeptide is capable of modulating phospholipase A enzyme activation; and
   f) a polypeptide comprising an amino acid sequence encoded by a fragment of the cDNA insert of the plasmid encoding TANGO 243 deposited with the ATCC under Accession Number 207116, wherein the fragment encodes at least 740 contiguous amino acids and wherein the polypeptide is capable of modulating phospholipase A enzyme activation;

wherein percent nucleotide sequence identity and percent amino acid sequence identity are determined over the full length of SEQ ID NO:19, 20 or 21 or over the full length of the cDNA insert of the plasmid encoding TANGO 243 deposited with the ATCC under Accession Number 207116 using the algorithm of Myers and Miller (CABIOS 4:11–17 (1988)).

2. The isolated polypeptide of claim 1, wherein said polypeptide comprises the amino acid sequence of SEQ ID NO:21 or a fragment of SEQ ID NO:21 comprising at least 740 contiguous amino acids.

3. The polypeptide of claim 1 further comprising a heterologous amino acid sequence.

4. An isolated polypeptide selected from the group consisting of:
   a) a polypeptide comprising the amino acid sequence of SEQ ID NO:45; and
   b) a polypeptide comprising an amino acid sequence which has at least 95% amino acid sequence identity with SEQ ID NO:45, wherein the polypeptide is capable of modulating phospholipase A enzyme activation and wherein amino acid sequence identity is determined over the full length of SEQ ID NO:45 using the algorithm of Myers and Miller (CABIOS 4:11–17 (1988)).

5. An isolated polypeptide selected from the group consisting of:
   a) a polypeptide comprising the amino acid sequence of SEQ ID NO:21;
   b) a polypeptide comprising a fragment of the amino acid sequence SEQ ID NO:21, wherein the fragment comprises at least 740 contiguous amino acids of SEQ ID NO:21 and wherein the polypeptide is capable of modulating phospholipase A enzyme activation;

c) a polypeptide comprising an amino acid sequence encoded by the cDNA insert of the plasmid encoding TANGO 243 deposited with the ATCC under Accession Number 207116; and d) a polypeptide comprising an amino acid sequence comprising at least 740 contiguous amino acids encoded by the cDNA insert of the plasmid encoding TANGO 243 deposited with the ATCC under Accession Number 207116, wherein the polypeptide is capable of modulating phospholipase A enzyme activation.

6. An isolated polypeptide comprising an amino acid sequence that has at least 95% amino acid sequence identity with SEQ ID NO:21, wherein the polypeptide is capable of modulating phospholipase A enzyme activation and wherein percent amino acid sequence identity is determined over the full length of SEQ ID NO:21 using the algorithm of Myers and Miller (CABIOS 4:11–17 (1988)).

7. An isolated polypeptide selected from the group consisting of:

a) a polypeptide which has an amino acid sequence that is encoded by a nucleic acid molecule comprising a nucleotide sequence which has at least 95% nucleotide sequence identity with the nucleotide sequence of SEQ ID NO:19, wherein the polypeptide is capable of modulating phospholipase A enzyme activation; and b) a polypeptide encoded by a nucleic acid molecule comprising a nucleotide sequence which has at least 95% nucleotide sequence identity with the nucleotide sequence of SEQ ID NO:20, wherein the polypeptide is capable of modulating phospholipase A enzyme activation;

wherein percent nucleotide sequence identity is determined over the full length of SEQ ID NO:19 or 20 using the algorithm of Myers and Miller (CABIOS 4:11–17 (1988)).

* * * * *